United States Patent
Moellering et al.

(10) Patent No.: US 11,046,979 B2
(45) Date of Patent: Jun. 29, 2021

(54) RECOMBINANT ALGAL MICROORGANISMS HAVING INCREASED LIPID PRODUCTION, AND METHODS OF MAKING AND USING THE SAME

(71) Applicant: Synthetic Genomics, Inc., La Jolla, CA (US)

(72) Inventors: Eric R. Moellering, San Diego, CA (US); Tom Carlson, La Jolla, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 16/518,360

(22) Filed: Jul. 22, 2019

(65) Prior Publication Data

US 2020/0024623 A1    Jan. 23, 2020

Related U.S. Application Data

(60) Provisional application No. 62/702,253, filed on Jul. 23, 2018.

(51) Int. Cl.
| | |
|---|---|
| C12P 7/64 | (2006.01) |
| C12N 9/04 | (2006.01) |
| C12N 9/02 | (2006.01) |
| C12N 9/88 | (2006.01) |

(52) U.S. Cl.
CPC .............. *C12P 7/64* (2013.01); *C12N 9/001* (2013.01); *C12N 9/0006* (2013.01); *C12N 9/88* (2013.01); *C12Y 101/01211* (2013.01); *C12Y 103/03006* (2013.01); *C12Y 401/03001* (2013.01); *C12Y 402/01017* (2013.01)

(58) Field of Classification Search
None
See application file for complete search history.

(56) References Cited

U.S. PATENT DOCUMENTS

| | | | | |
|---|---|---|---|---|
| 10,689,676 | B2 * | 6/2020 | Ajjawi | .................. C07K 14/405 |
| 2014/0162330 | A1 * | 6/2014 | Allen | ....................... C12N 15/74 |
| | | | | 435/134 |
| 2017/0121742 | A1 * | 5/2017 | Ajjawi | ..................... C12P 7/649 |
| 2017/0240908 | A1 | 8/2017 | Isaacs et al. | |

OTHER PUBLICATIONS

Chica et al. Curr Opin Biotechnol. Aug. 2005;16(4):378-84 (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession EWM19975. Feb. 14, 2014. (Year: 2014).*
Ajjawi et al. Nat Biotechnol. Jul. 2017;35(7):647-652. Epub Jun. 19, 2017. (Year: 2017).*
Mocellin et al. Journal of Translational Medicine 2004, 2:39, pp. 1-6 (Year: 2004).*
Accession K8YVC4. Feb. 6, 2013 (Year: 2013).*
Ijist, Lodewijk et al.: "*Common Missense Mutation G1528C in Longchain 3-Hydroxyacyl-Coa Dehydrogenase Deficiency. Characterization and Expression of the Mutant Protein, Mutation Analysis on Genomic DNA and Chromosomal Localization of the Mitochondrial Trifunctional Protein Alpha Subunit Gene*"; J. Clin. Invest. 1996, vol. 98, No. 4, 1028-1033.
International Search Report dated Oct. 18, 2019, regarding PCT/US2019/042768.
Salem, Mohamed et al.: "*Effect of Sexual Maturation on Muscle Gene Expression of Rainbow Trout: RNA-Seq Approach*"; Physiol Rep, 2013, vol. 1, No. 5, e00120; pp. 1-15; DOI: 10.1002/phy2.120.

* cited by examiner

*Primary Examiner* — Christian L Fronda
(74) *Attorney, Agent, or Firm* — DLA Piper LLP (US)

(57) ABSTRACT

The present invention provides a mutant algal microorganism that has a mutation that causes attenuated expression of TrifuncB and/or TrifuncA and as a result produces more lipids than a control algal microorganism. The mutant algal microorganism can further include a mutation in a gene encoding a peroxisomal beta-oxidation pathway protein, such as an ACO1 or PXA1 gene, or a glyoxylate pathway protein, such as an ICL1 gene, that results in attenuated expression and further increased lipid production. Furthermore, provided herein are methods of producing lipids using the mutant algal microorganisms and methods of making the mutant microorganisms.

23 Claims, 6 Drawing Sheets

Specification includes a Sequence Listing.

SEQUENCE LISTING

<160> NUMBER OF SEQ ID NOS: 57

<210> SEQ ID NO 1
<211> LENGTH: 756
<212> TYPE: PRT
<213> ORGANISM: Nannochloropsis gaditana
<220> FEATURE:
<221> NAME/KEY: misc_feature
<223> OTHER INFORMATION: TrifuncA amino acid sequence

<400> SEQUENCE: 1

Met Leu Arg Leu Ala Ser Ala Arg Ala Ser Leu Arg Leu Asn Gly Leu
1               5                   10                  15

Gly Ala Phe Gln Gly Thr Ala Thr Cys Pro Ser Phe Leu Lys Arg Ala
            20                  25                  30

Ser Leu Ser Thr Arg Gly Gln Tyr Phe Ala Pro Val Glu Val Lys Asp
        35                  40                  45

Gly Val Ala Ile Ile Arg Ile Asp Gly Pro Gly Lys Met Asn Thr Ile
    50                  55                  60

Asp Asp Asn Phe Arg Gln Glu Ile Asp Ala Leu Trp Thr Asp Lys Val
65                  70                  75                  80

Ala Asn Asp Ala Ser Val Lys Ala Ala Val Ile Ile Ser Ala Lys Pro
                85                  90                  95

Asp Asn Phe Ile Ala Gly Ala Asp Ile Lys Phe Ile Asp Ser Val Glu
            100                 105                 110

Asp Phe Ala Ser Leu Lys Asp Val Cys Leu Lys Gly His Ala Thr Phe
        115                 120                 125

Gln Lys Ile Arg Lys Ala Asn Lys Pro Leu Val Ala Ala Ile His Gly
    130                 135                 140

Pro Ala Leu Gly Gly Gly Leu Glu Val Ala Leu Tyr Cys Asp Tyr Arg
145                 150                 155                 160

Ile Val Thr Ser Ser Pro Lys Thr Val Leu Gly Leu Pro Glu Val Lys
                165                 170                 175

Leu Gly Leu Leu Pro Gly Phe Gly Gly Thr Gln Asn Leu His Pro Ile
            180                 185                 190

Val Gly Leu Gln Ala Ala Leu Asp Met Thr Leu Thr Gly Lys Asn Ile
        195                 200                 205

Arg Pro Asp Lys Ala Lys Lys Met Gly Leu Ala Asp Val Val Val Asp
    210                 215                 220

Pro Ala Ala Leu Glu Thr Val Ala Val Glu Thr Ala Arg Ala Leu Ala
225                 230                 235                 240

Glu Gly Ser Leu Lys Gly Lys Arg Lys Gly Lys Gly Leu Leu Gln Lys
                245                 250                 255

Val Leu Glu Asp Thr Ser Met Gly Arg Ser Ile Val Tyr Gly Gln Thr
            260                 265                 270

Glu Lys Met Val Ala Lys Asn Thr Gly Gly His Tyr Pro Ala Pro Thr
        275                 280                 285

```
Ala Ile Leu Asp Thr Ile Lys Tyr Gly Phe Thr His Ser Lys Pro Gln
            290                 295                 300

Ala Leu Glu Tyr Glu Ala Thr Arg Phe Ala Glu Leu Ala Ala Thr Ser
305                 310                 315                 320

Val Ser Ala Ala Leu Arg Gly Ile Phe Thr Gly Thr Thr Ala Leu Lys
                325                 330                 335

Gln Ser Lys Tyr Gly Lys Pro Ala Asn Pro Val Glu Thr Val Ala Val
                340                 345                 350

Val Gly Ala Gly Leu Met Gly Ala Gly Ile Ala Gln Val Thr Ala Glu
            355                 360                 365

Lys Gly Tyr Arg Val Leu Leu Lys Asp Lys Asp Leu Ala Gly Val Ser
370                 375                 380

Arg Gly Glu Lys Tyr Ile Ser Asp Asn Leu Lys Gly Lys Met Lys Lys
385                 390                 395                 400

Lys Arg Met Thr Lys Tyr Ala Tyr Asp Thr Thr Thr Ser Arg Val Val
                405                 410                 415

Gly Leu Thr Asp Glu Ser Ala Asn Trp Gly Lys Gln Phe Gly Lys Ala
            420                 425                 430

Asp Met Val Ile Glu Ala Val Phe Glu Asp Leu Ser Leu Lys His Lys
                435                 440                 445

Val Ile Gln Gln Leu Glu Glu His Leu Pro Pro His Ala Val Phe Ala
450                 455                 460

Ser Asn Thr Ser Ala Ile Pro Ile Ala Arg Ile Ala Glu Ala Ser Gln
465                 470                 475                 480

Arg Pro Glu Asn Val Ile Gly Met His Tyr Phe Ser Pro Val Pro Gln
                485                 490                 495

Met Pro Leu Leu Glu Ile Ile Pro His Lys Gly Thr Ser Lys Glu Ala
            500                 505                 510

Ala Ala Ala Ala Phe Glu Val Gly Lys Lys Gln Gly Lys Thr Val Ile
            515                 520                 525

Phe Val Lys Asp Val Pro Gly Phe Tyr Val Asn Arg Cys Leu Gly Pro
530                 535                 540

Tyr Leu Val Glu Thr Gly Ala Leu Met Glu Ala Gly Val Pro Leu Glu
545                 550                 555                 560

Gln Leu Asp Lys Ala Ile Lys Ala Tyr Gly Phe Pro Val Gly Pro Ile
                565                 570                 575

Thr Leu Ala Asp Glu Val Gly Val Asp Val Ala Ala His Val Gln Ala
            580                 585                 590

Phe Leu Ser Lys Ala Asp Leu Gly Val Arg Met Gly Gly Ser Asp Gly
            595                 600                 605

Pro Ile Leu Asp Ala Leu Leu Lys Ala Lys Leu Leu Gly Arg Lys Ala
610                 615                 620

Gly Lys Gly Phe Tyr Thr Tyr Pro Ala Gly Gly Lys Lys Glu Lys Gly
625                 630                 635                 640

Pro Lys Thr Leu Asn Pro Glu Ala Thr Ser Leu Val Gln Lys His Val
                645                 650                 655

Lys Gly Glu Ser Lys Leu Thr Asp Glu Glu Val Gln Asn Arg Leu Val
            660                 665                 670

Ser Arg Phe Val Asn Glu Ala Val Phe Ala Leu Gln Asp Gly Val Ile
            675                 680                 685

Ala Ser Pro Val Glu Gly Asp Ile Gly Ala Val Phe Gly Ile Gly Phe
690                 695                 700
```

```
Pro Pro Phe Leu Gly Gly Pro Phe Arg Leu Ile Asp Ala Leu Gly Ala
705                 710                 715                 720
Gly Lys Tyr Cys Ser Met Leu Glu Gly Phe Ala Gly Tyr Gly Glu
            725                 730                 735
Gln Phe Ala Pro Ala Pro Leu Leu Val Glu His Ala Lys Ser Gly Lys
            740                 745                 750
Lys Phe His Gln
        755

<210> SEQ ID NO 2
<211> LENGTH: 2271
<212> TYPE: DNA
<213> ORGANISM: Nannochloropsis gaditana
<220> FEATURE:
<221> NAME/KEY: misc_feature
<223> OTHER INFORMATION: TrifuncA cDNA

<400> SEQUENCE: 2
atgctccgct tggcgtcggc acgggcatcg ctgcggctga atggcttggg tgcttttcaa      60
ggcaccgcca cgtgcccctc cttcttgaaa cgcgccagtc tctccacgcg cgggcagtat     120
ttcgcgcccg tggaagtgaa ggacggggtc gcaatcattc gtattgatgg ccgggggaag     180
atgaacacga ttgacgacaa ttttcgccaa gagatcgatg cattgtggac ggacaaggtt     240
gcaaatgacg cgagtgtcaa gcggccgtg ataatttctg caaagcccga caatttcatc      300
gcaggagccg atatcaaatt catcgactcg gtggaagact cgcgagcct aaagacgtc       360
tgcctcaagg acacgccac cttccagaag attcgaaagg ccaacaagcc cttggttgcc     420
gccattcatg ggcccgccct tggcggcggt ctggaagtgg ccctgtactg cgactaccgc    480
atcgtcacct cctcccccaa gacggtgctg ggtctccccg aggtgaagct cggcctcttg    540
ccgggcttcg ggggcactca gaacctccac cctatcgtcg gcttgcaggc ggccctggac   600
atgacgctga cagggaagaa catccgcccg gacaaggcca agaagatggg cctggcggac   660
gtggtggtgg accccgccgc gttggagacc gtggcggttg agacggcccg cgccttggcc   720
gagggttcgc tgaaagggaa gaggaagggc aaggggctcc tccagaaggt tctggaagac   780
acctcgatgg gacggtcgat cgtgtacggg cagacggaga gatggttgc caagaacacg    840
ggtggccatt atcccgcacc gacggcgata ttggatacga tcaagtacgg tttcacccac   900
agcaagcccc aagccctaga gtacgaggcg acgcgctttg cggagctggc ggccacgagt   960
gtgagcgccg ccctgcgagg catttcacg ggcacgactg ccctgaaaca aagcaagtac   1020
gggaagcccg ctaatcccgt ggagacggtg gctgtggtgg gtgcaggatt gatgggcgcg   1080
ggtattgccc aggtgacggc ggagaaaggg taccgggtgc tcctgaagga caaggacctc  1140
gccgggtca gtcgcggcga gaaatacatt tcggacaact taaagggaaa gatgaagaag   1200
aagaggatga cgaagtacgc ctacgacacc accaccagcc gggtggtggg tttgacggac  1260
gagagcgcga actgggggaa gcaatttggg aaggcggaca tggtgataga ggcagtcttc  1320
gaggacctga gcctcaagca taaggtcatt cagcagttgg aggagcattt gcctccccac  1380
gccgtctttg ccagcaacac cagcgctatc cccatcgctc ggattgccga ggcgagccag  1440
cgaccggaga atgtgattgg catgcattat ttctcccccgg tgccccagat gcctcttctc  1500
gagatcattc gcacaaagg gaccagcaaa gaggccgcgg cggctgcttt cgaagtgggg   1560
aagaaacagg gcaaaacggt gattttcgtg aaagacgtgc caggctttta cgtgaatcgg  1620
tgcctggggc cctacctggt ggagacgggg gcgctcatgg aagccggcgt gccctcgaa  1680
```

| | |
|---|---|
| cagctggaca aggccatcaa ggcctacggt ttccccgtgg ggcccatcac cctcgccgac | 1740 |
| gaggtcggag tcgacgtcgc ggcccatgtt caagccttcc tatccaaagc cgacttgggc | 1800 |
| gtgcgaatgg gcgggagcga cggaccgatt ctggacgcgt tgctgaaggc caagcttttg | 1860 |
| ggccgtaagg ccggcaaagg cttctatacg taccccgcgg gggggaaaaa ggagaaaggg | 1920 |
| cccaagactt tgaatccgga agccacgtct ttggtccaga aacacgtgaa aggggagagc | 1980 |
| aagctcacgg acgaggaggt gcagaaccgg ctggtctcac gctttgtcaa cgaggcagtc | 2040 |
| ttcgccctcc aagatggagt gatcgcctcc cccgtcgagg gcgacattgg cgccgtcttt | 2100 |
| gggatcggat tcccgccttt cctgggggt ccttttccgcc tgatcgacgc attgggagca | 2160 |
| gggaagtact gttccatgct ggagggcttt gccggcaaat acgggagca attcgccccc | 2220 |
| gcgccactcc tggtcgagca cgcaaagagc gggaagaagt tccaccagta g | 2271 |

<210> SEQ ID NO 3
<211> LENGTH: 3820
<212> TYPE: DNA
<213> ORGANISM: Nannochloropsis gaditana
<220> FEATURE:
<221> NAME/KEY: misc_feature
<223> OTHER INFORMATION: TrifuncA gDNA sequence

<400> SEQUENCE: 3

| | |
|---|---|
| atgctccgct ggcgtcggc acgggcatcg ctgcggctga atggcttggg tgcttttcaa | 60 |
| ggtaagtctc gcggttttcc tcgagccctc gctctcagag ctcaactgct acaaggcata | 120 |
| ccattccttg ttcttacagg caggggagca tgagtcgttt gtattgcttt gacttaaaga | 180 |
| cggcctgatc accgtccatg cgtgaatttt ataatcgtcg gctcgtcttc cattttgatg | 240 |
| ttgcatgtat cttgggtgga ccgtttcctg gtcgtactcc tccgcttcaa ctacttcccc | 300 |
| ctcctcccct tgttctcggt gggctcccct tggtcccatg caatgattag aatatgcgtc | 360 |
| aacattcatg tctaccgtct caggatcagc atgcgcgctc acactgccat cattacgtct | 420 |
| tcttttgacc cgtaacaggc accgccacgt gcccctcctt cttgaaacgc gccagtctct | 480 |
| ccacgcgcgg gcagtatttc gcgcccgtgg aagtgaagga cggggtcgca atcattcgta | 540 |
| ttgatgggcc ggggaagatg aacacgattg acgacaattt tcgccaagag atcgatgcat | 600 |
| tgtggacggt aatgtcatgg aaagacaag ggatcgagac gggaaggggc acactccagc | 660 |
| ggttccttga ccttacgacc ccctggctga cgattcctc ctctcttata tatacaggac | 720 |
| aaggttgcaa atgacgcgag tgtcaaggcg gccgtgataa tttctgcaaa gcccgacaat | 780 |
| tcatcgcag agccgatat caaattcatc gactcggtgg aagacttcgc gagccttaaa | 840 |
| gacggtatgt gcgcctgact agacacgttc cccgtgctcg aatgtccttt ccacgtcctt | 900 |
| gcaaggctgc tgcttgtgtg cgcttgaata tgggccggca cctggtgcct gtggcctggt | 960 |
| ggtgtctcat tggggaccta tgacccttgt gactgcctca cacactctgc ggccgagggc | 1020 |
| atcgccacga gagggtttc cctctgccaa caagagaaac gaccacgcct tcaacgcaca | 1080 |
| gctttcactc atcctctttc ttgctttccc actctccatc cggcttgtcc cccctctct | 1140 |
| cggtcagtct gcctcaaggg acacgccacc ttccagaaga ttcgaaaggc caacaagccc | 1200 |
| ttggttgccg ccattcatgg gcccgccctt ggcggcggtc tggaagtggc cctgtactgc | 1260 |
| gactaccgca tcgtcacctc ctcccccaag acggtgctgg gtctccccga ggtgaagctc | 1320 |
| ggcctcttgc cgggcttcgg gggcactcag aacctccacc ctatcgtcgg cttgcaggcg | 1380 |
| gccctggaca tgacgctgac aggtgcgggg gggaggggtg ggaaggaagg aaggagggag | 1440 |

```
ggagggaggg agggagggag ggaggaaggg aaaaaggcgg gatcgtcgga cgggagggtc    1500
aggagataac ggtggcggga tgccagcatg tgttcccaac gtccagagct ttcctatccc    1560
gtataccatg caagtcatcc tcctttaatg tcactttgtc acctccacat cgcagggaag    1620
aacatccgcc cggacaaggc caagaagatg ggcctggcgg acgtggtggt ggaccccgcc    1680
gcgttggaga ccgtggcggt tgagacggcc cgcgccttgg ccgagggttc gctgaaaggg    1740
aagaggaagg gcaaggggct cctccagaag gttctggaag acacctcgat gggacggtcg    1800
atcgtgtacg ggcagacgga gaagatggtt gccaagaaca cgggtggcca ttatcccgca    1860
ccgacgcgca tattgggtgc gttcagacgg ggttttttaa aaatcaaaaa ataacgqatg    1920 tgttgcgcgt ggactcacga ttttccatca tcacctctga ttccctcgtg tgtccagata    1980
cgatcaagta cggtttcacc cacagcaagc cccaagccct agagtacgag gcgacgcgct    2040
ttgcggagct ggcggccacg agtgtgagcg ccgccctgcg aggcattttc acgggcacga    2100
ctgccctgaa acaaagcaag tacgggaagc ccgctaatcc cgtggagacg gtggctgtgg    2160
tgggtgcagg attgatgggc gcgggtattg cccaggtgac ggcggagaaa gggtaaggag    2220
ggggagggga gaaagggagg gagggagggg agaggacaag agcaagaagg cgattatgtc    2280
gcgcataaag aagaatgagg ttgttgatgg acagtgtagg gagggagaga gggaggaagg    2340
gaaggaggaa gggagggagg aagggaggga gggagggagg gagggagggg cagggtttgg    2400
gcggagcttg gtgggtttgt tggtgcgtga agggttatgt ttcctgtctc ttcgtatcgg    2460
aaatctccct gctcccttcg agtcacgaaa tagcgcatga cccgcttccc ctcgttcagg    2520
taccgggtgc tcctgaagga caaggacctc gccggggtca gtcgcggcga gaaatacatt    2580
tcggacaact taagggaaa gatgaagaag aagaggatga cgaagtacgc ctacgacacc    2640
accaccagcc gggtggtggg tttgacggac gagagcgcga actgggggaa gcaatttggg    2700
aaggcggaca tggtgataga ggcagtcttc gaggacctga gcctcaagca taaggtcatt    2760
cagcagttgg aggagcattt gcctcccccac gccgtctttg ccagcaacac cagcgctatc    2820
cccatcgctc ggattgccga ggcgagccag cgaccggaga atgtgattgg catgcattat    2880
ttctccccgg tgccccagat gcctcttctc gagatcattc cgcacaaagg gaccagcaaa    2940
gaggccgcgg cggctgcttt cgaagtgggg aagaaacagg gcaaaacggt gattttcgtg    3000
aaagacgtgc caggctttta cgtgaatcgg tgcctggggc cctacctggt ggagacgggg    3060
gcgctcatgg aaggtgcgtt ggttgcgagt ctggggatcg gttgtctcgc gtggttactc    3120
tcgccacgtt tgaaaatttg aacctttgac agtgcacact tacttacctt ttgattctca    3180
ttatttcctc gcgttgttcc accgggaccc agccggcgtg cccctcgaac agctggacaa    3240
ggccatcaag gcctacggtt tccccgtggg gcccatcacc ctcgccgacg aggtcggagt    3300
cgacgtcgcg gcccatgttc aagccttcct atccaaagcc gacttgggcg tgcgaatggg    3360
cgggagcgac ggaccgattc tggacgcgtt gctgaaggcc aagcttttgg gccgtaaggc    3420
cggcaaaggc ttctatacgt accccgcggg ggggaaaaag gagaaagggc caagactttt    3480
gaatccggaa gccacgtctt tggtccagaa acacgtgaaa ggggagagca agctcacgga    3540
cgaggaggtg cagaaccggc tggtctcacg cttttgtcaac gaggcagtct tcgcccctcca    3600 agatggagtg atcgcctccc ccgtcgaggg cgacattggc gccgtctttg ggatcggatt    3660
cccgcctttc ctgggggtc ctttccgcct gatcgacgca ttgggagcag ggaagtactg    3720
ttccatgctg gagggctttg ccggcaaata cggggagcaa ttcgcccccg cgccactcct    3780
ggtcgagcac gcaaagagcg ggaagaagtt ccaccagtag                         3820
```

<210> SEQ ID NO 4
<211> LENGTH: 826
<212> TYPE: PRT
<213> ORGANISM: Thalassiosira oceanica
<220> FEATURE:
<221> NAME/KEY: misc_feature
<223> OTHER INFORMATION: Trifunctional Protein A

<400> SEQUENCE: 4

```
Met Ile Leu Ser Ser Ala Val Gln Arg Ala Ile Leu Ser Gln Ser Arg
1               5                   10                  15

Ala Ala Ala Gly Ala Ala Arg Gln Ile Asn Ser Leu Ser Arg Arg Pro
            20                  25                  30

Ala Ser Ala Leu Ala Ala Cys Gln Gly Gly Ala Ser Ser Ala Thr Gly
        35                  40                  45

Val Val Ser Ile Gly Asp Ala His Ala Ala Asp Phe Asn Asn His Pro
    50                  55                  60

Arg Arg Arg Arg Ala Phe Ser Thr Ala Ala Val Arg Asp Glu Pro Ala
65                  70                  75                  80

Pro Ser Pro Thr Pro Ser Glu His Thr Ala Ala Asp Ser Ser Glu Lys
                85                  90                  95

Ser Phe Val Pro Ser Pro Gly Arg Lys Tyr Arg Phe Phe Arg Asn Val
            100                 105                 110

Glu Val Thr Pro Ala Gly Val Ala Val Ile Arg Phe Asp Asn Arg Glu
        115                 120                 125

Lys Lys Val Asn Thr Leu Ser Phe Glu Leu Met His Glu Ala Lys Ala
    130                 135                 140

Met Trp Asp Ala Glu Val His Ala Asn Ala Asp Val Lys Ser Val Val
145                 150                 155                 160

Phe Thr Ser Ala Lys Glu Ser Gly Phe Val Ala Gly Ala Asp Ile Phe
                165                 170                 175

Asp Ile Ser Ser Val Glu Asp Lys Ser Thr Leu Val Pro Val Ile Glu
            180                 185                 190

Glu Ala Leu Asp Phe Phe Leu His Met Lys Ser Lys Gly Ala Pro Met
        195                 200                 205

Val Ala Ala Ile His Gly Pro Ala Leu Gly Gly Gly Leu Glu Trp Ala
    210                 215                 220

Leu Trp Cys Asp Tyr Arg Ile Cys Thr Asp Ser Ser Ser Thr Lys Met
225                 230                 235                 240

Gly Leu Pro Glu Val Lys Leu Gly Leu Pro Gly Phe Gly Gly Thr
                245                 250                 255

Gln Asn Leu Pro Ala Leu Val Gly Val Gln Gly Ala Ile Asp Ile Met
            260                 265                 270

Leu Thr Gly Lys Asp Ile Arg Pro Lys Lys Ala Lys Gln Met Gly Leu
        275                 280                 285

Val Asp Leu Val Val Ala Pro Gln Ser Leu Glu Ala Val Ala Ile Glu
    290                 295                 300

Thr Ala Glu Gly Leu Ala Asn Gly Thr Val Arg Lys Ser Gly Pro Lys
305                 310                 315                 320

Lys Lys Ser Leu Val Asn Arg Leu Val Glu Asp Thr Pro Gly Arg
                325                 330                 335

His Val Met Trp Asn Gln Val Lys Lys Met Val Asp Lys Asn Thr Ala
            340                 345                 350

Gly Asn Tyr Pro Ala Pro Tyr Glu Ile Ile Asp Cys Val Lys Tyr Gly
```

```
            355                 360                 365
Leu Ala Asn Pro Asp Gly Leu Gly Lys Tyr Lys His Glu Arg Glu Gly
370                 375                 380

Phe Ala Lys Leu Ala Ala Thr Ser Glu Ser Glu Ser Leu Ile Gly Ile
385                 390                 395                 400

Phe Asp Gly Met Asn Lys Leu Lys Lys His Asp Ser Asp Ala Ser Pro
                405                 410                 415

Val Pro Val Arg Lys Val Ala Val Met Gly Ala Gly Leu Met Gly Ala
                420                 425                 430

Gly Ile Ala Gln Val Thr Ala Glu Lys Gly Tyr Asp Val Leu Leu Lys
                435                 440                 445

Asp Arg Asp Asp Ala Ser Leu Gly Arg Gly Val Ser Tyr Met Thr Asp
                450                 455                 460

Asn Trp Ser Lys Lys Thr Lys Arg Arg Met Thr Gln Tyr Gln Asn
465                 470                 475                 480

Asn Leu Asn Gln Ser Arg Val Thr Pro Leu Ser Asp Ala Thr Pro Ser
                485                 490                 495

Trp Pro Arg His Phe Ala Gly Ala Asp Leu Val Ile Glu Ala Val Phe
                500                 505                 510

Glu Asn Leu Glu Leu Lys Arg Lys Ile Ile Ser Gln Val Glu Glu Val
                515                 520                 525

Thr Pro Asp His Cys Val Phe Ala Thr Asn Thr Ser Ala Ile Pro Ile
                530                 535                 540

Ala Asp Ile Ala Ala Pro Gly Pro Glu Val Ser Arg Pro Gln Asn Val
545                 550                 555                 560

Val Gly Met His Tyr Phe Ser Pro Val Pro Ser Met Pro Leu Leu Glu
                565                 570                 575

Ile Ile Pro His Glu Gly Thr Ser Glu Glu Ala Thr Ala Thr Ala Phe
                580                 585                 590

Ala Val Gly Thr Lys Gln Gly Lys Thr Cys Val Val Lys Asp Val
                595                 600                 605

Pro Gly Phe Tyr Val Asn Arg Cys Leu Gly Pro Val Leu Val Glu Thr
                610                 615                 620

Ser Ala Leu Val Lys Glu Gly Val Pro Leu Glu Lys Met Asp Lys Ala
625                 630                 635                 640

Met Lys Ser Phe Gly Met Pro Val Gly Pro Ile Thr Leu Met Asp Glu
                645                 650                 655

Val Gly Ile Asp Val Gly Ser Lys Val Ala Ser Tyr Leu Ser Gly Ala
                660                 665                 670

Asp Leu Asp Val Arg Met Thr Gly Gly Asp Ile Ser Leu Met Ser Thr
                675                 680                 685

Met Val Asp Lys Gly Trp Leu Gly Lys Lys Ser Gly Lys Gly Phe Tyr
                690                 695                 700

Thr Tyr Ser Gly Lys Lys Gly Lys Lys Ile Gly Pro Glu Met Arg Ala
705                 710                 715                 720

Phe Leu Thr Glu Phe Thr Gly Gly Ala Thr Ser Asp Leu Ala Glu Thr
                725                 730                 735

Asp Ile Gln Asp Arg Ile Thr Ala Arg Leu Val Asn Glu Ala Ala Lys
                740                 745                 750

Cys Leu Glu Asp Gly Ile Ile Ala Asp Pro Val Ala Gly Asp Ile Gly
                755                 760                 765

Leu Val Phe Gly Ile Gly Phe Ala Pro Phe Arg Gly Gly Pro Phe Arg
770                 775                 780
```

-continued

```
Tyr Leu Asp Thr Val Gly Val Thr Ser Phe Val Asp Arg Met Asn Gly
785                 790                 795                 800

Phe Ala Asp Ala His Gly Gln Phe Glu Pro Cys Gln Leu Leu Lys
            805                 810                 815

Asp Tyr Ala Ala Ser Gly Lys Arg Phe His
            820                 825

<210> SEQ ID NO 5
<211> LENGTH: 683
<212> TYPE: PRT
<213> ORGANISM: Thalassiosira pseudonana
<220> FEATURE:
<221> NAME/KEY: misc_feature
<223> OTHER INFORMATION: Trifunctional Protein A

<400> SEQUENCE: 5

Met Trp Glu Ser Asp Val His Gly Asn Asp Ser Val Lys Ser Ile Val
1               5                   10                  15

Phe Thr Ser Ala Lys Glu Thr Gly Phe Ile Ala Gly Ala Asp Ile Phe
            20                  25                  30

Asp Ile Ser Gln Val Glu Asp Lys Ala Gln Leu Val Pro Val Ile Glu
        35                  40                  45

Glu Ala Leu Asn Phe Phe Leu Lys Met Lys Ser Lys Gly Val Pro Met
50                  55                  60

Val Ala Ala Ile His Gly Pro Ala Leu Gly Gly Leu Glu Trp Ala
65                  70                  75                  80

Leu Trp Cys Asp Tyr Arg Ile Cys Thr Asp Ser Ser Thr Lys Leu
            85                  90                  95

Gly Leu Pro Glu Val Lys Leu Gly Leu Pro Gly Phe Gly Gly Thr
            100                 105                 110

Gln Asn Leu Pro Lys Leu Val Gly Ile Gln Gly Gly Met Asp Met Met
        115                 120                 125

Leu Thr Gly Lys Asp Ile Arg Pro Pro Lys Ala Lys Lys Met Gly Leu
    130                 135                 140

Val Asp Leu Val Val Ala Pro Gln Ser Leu Glu Ser Val Ala Ile Gln
145                 150                 155                 160

Ser Ala Glu Gly Leu Ala Asn Gly Thr Val Lys Lys Ser Lys Pro Lys
                165                 170                 175

Glu Lys Ser Leu Met Asn Arg Leu Ile Glu Asp Thr Pro Pro Gly Gln
            180                 185                 190

Tyr Leu Met Trp Asp Lys Val Lys Lys Met Val Asp Lys Asn Thr Gly
        195                 200                 205

Gly Asn Tyr Pro Ala Pro Tyr Ala Ile Ile Asp Cys Val Lys Tyr Gly
    210                 215                 220

Leu Ala His Pro Ser Gly Asn Asp Lys Phe Lys His Glu Arg Glu Glu
225                 230                 235                 240

Phe Ala Lys Leu Ala Ala Thr Lys Glu Ser Glu Ala Leu Ile Gly Ile
                245                 250                 255

Phe Asp Gly Met Asn Gln Met Lys Lys Leu Ser Ser Ser Ala Ala Pro
            260                 265                 270

Ile Asp Val Lys Lys Val Ala Val Met Gly Ala Gly Leu Met Gly Ala
        275                 280                 285

Gly Ile Ala Gln Val Thr Ala Glu Lys Gly Tyr Asp Val Leu Leu Lys
    290                 295                 300

Asp Arg Asp Ala Ala Ser Leu Gly Arg Gly Leu Ser Tyr Met Thr Glu
```

```
            305                 310                 315                 320
Asn Trp Glu Lys Lys His Lys Arg Lys Arg Met Thr Thr Tyr Gln Leu
                325                 330                 335

Asn Leu Asn Thr Ser Arg Val Thr Pro Leu Ala Asp Asp Thr Glu Ser
                340                 345                 350

Trp Lys Arg His Phe Ala Gly Ala Asp Leu Val Ile Glu Ala Val Phe
                355                 360                 365

Glu Asn Leu Asp Leu Lys Arg Lys Ile Val Gln Gln Val Glu Glu Val
        370                 375                 380

Thr Ser Asp His Cys Val Phe Ala Thr Asn Thr Ser Ala Ile Pro Ile
385                 390                 395                 400

Ala Asp Ile Ala Ala Pro Gly Pro Asp Ile Lys Arg Pro Glu Asn Ile
                405                 410                 415

Val Gly Met His Tyr Phe Ser Pro Val Pro Ser Met Pro Leu Leu Glu
                420                 425                 430

Ile Ile Pro His Ala Gly Thr Ser Asp Glu Ala Leu Ala Thr Ala Phe
                435                 440                 445

Ala Val Gly Thr Lys Gln Gly Lys Thr Cys Val Val Val Lys Asp Val
        450                 455                 460

Pro Gly Phe Tyr Val Asn Arg Cys Leu Gly Pro Ile Leu Val Glu Val
465                 470                 475                 480

Ser Ala Leu Val Lys Glu Gly Val Pro Leu Glu Thr Leu Asp Lys Ala
                485                 490                 495

Met Lys Lys Phe Gly Met Pro Val Gly Pro Ile Thr Leu Ile Asp Glu
                500                 505                 510

Val Gly Val Asp Val Ala Ala Lys Val Ser Thr Phe Leu Ser Asp Ala
                515                 520                 525

Asp Leu Gly Val Arg Met Gly Gly Gly Asp Leu Ser Leu Met Thr Asn
        530                 535                 540

Met Val Glu Lys Gly Trp Leu Gly Arg Lys Ser Asn Gln Gly Phe Tyr
545                 550                 555                 560

Thr Tyr Ala Gly Lys Lys Gly Lys Thr Ile Gly Ser Glu Val Thr Ala
                565                 570                 575

Tyr Leu Lys Glu Phe Thr Gly Gly Lys Val Ser Asn Leu Ser Glu Lys
                580                 585                 590

Asp Ile Gln Asp Arg Ile Ala Ser Arg Leu Val Asn Glu Ala Ala Lys
        595                 600                 605

Cys Leu Glu Asp Ile Ile Glu Asn Pro Val Ala Gly Asp Ile Gly
        610                 615                 620

Leu Val Phe Gly Ile Gly Phe Ala Pro Phe Lys Gly Pro Phe Arg
625                 630                 635                 640

Tyr Leu Asp Ala Val Gly Val Ser Ser Tyr Val Asp Arg Met Asn Gly
                645                 650                 655

Phe Ala Asp Thr Leu Gly Glu Gln Phe Glu Pro Cys Gln Leu Leu Lys
                660                 665                 670

Asp Tyr Ala Thr Ser Gly Lys Lys Phe His Gly
                675                 680

<210> SEQ ID NO 6
<211> LENGTH: 684
<212> TYPE: PRT
<213> ORGANISM: Phaeodactylum tricornutum
<220> FEATURE:
<221> NAME/KEY: misc_feature
<223> OTHER INFORMATION: Trifunctional Protein A
```

<400> SEQUENCE: 6

```
Met Ala Glu Glu Ala Lys Lys Leu Trp Lys Asp Glu Ile Ala Ser Asn
1               5                   10                  15

Ser Asp Val Lys Ala Val Val Phe Ser Ser Ala Lys Pro Asp Met Phe
            20                  25                  30

Ile Ala Gly Ala Asp Ile Phe Asp Ile Lys Ala Val Glu Asn Lys Gln
        35                  40                  45

Asp Leu Ile Pro Phe Ile Ala Asp Gly Val Lys Phe Phe Gln Asp Met
    50                  55                  60

Arg Gly Lys Gly Val Pro Leu Val Ala Ile Asp Gly Pro Ala Leu
65                  70                  75                  80

Gly Gly Gly Leu Glu Trp Ala Leu Trp Cys Asp Tyr Arg Ile Cys Thr
                85                  90                  95

Asp Ser Ser Lys Thr Lys Met Gly Leu Pro Glu Val Lys Leu Gly Leu
            100                 105                 110

Leu Pro Gly Phe Gly Gly Thr Gln Asn Leu His Pro Val Val Gly Leu
        115                 120                 125

Gln Asn Ala Met Asp Met Met Leu Thr Gly Lys Asp Ile Arg Pro His
130                 135                 140

Gln Ala Lys Lys Met Gly Leu Val Asp Leu Val Val Ala Gln Ala Ser
145                 150                 155                 160

Leu Glu Arg Val Ala Ile Asp Ser Ala Ala Leu Ala Asn Gly Ser
                165                 170                 175

Leu Lys Ala Lys Arg Lys Ser Lys Ser Met Phe Asn Lys Ile Leu Glu
            180                 185                 190

Asp Asn Ser Ile Gly Arg Asn Val Ile Trp Asn Gln Ile Asp Lys Met
        195                 200                 205

Val Gln Lys Asn Thr Asn Gly Lys Tyr Pro Ala Pro Tyr Ala Ile Ile
    210                 215                 220

Asp Cys Val Lys Phe Gly Leu Asp Asn Pro Ser Gln Lys Tyr Gln His
225                 230                 235                 240

Glu Arg Glu Glu Phe Ala Lys Leu Ala Ala Thr Pro Glu Ser Glu Ala
                245                 250                 255

Leu Ile Gly Ile Phe Asp Gly Met Thr Gln Met Lys Lys His Ser Phe
            260                 265                 270

Gly Ala Asp Ala Ala Ile Pro Val Lys Thr Val Ala Val Met Gly Ala
        275                 280                 285

Gly Leu Met Gly Ala Gly Ile Ala Gln Val Thr Ala Glu Lys Gly Ile
    290                 295                 300

Lys Val Leu Leu Lys Asp Arg Asn Asp Glu Ala Val Gly Arg Gly Gln
305                 310                 315                 320

Ser Tyr Met Thr Glu Asn Trp Ser Lys Lys Leu Lys Arg Lys Arg Met
                325                 330                 335

Thr Gln Tyr Gln Tyr Asn Leu Asn Thr Ser Asn Val Thr Ala Leu Thr
            340                 345                 350

Asp Asp Ser Pro Thr Trp Gln Arg His Phe Gly Asn Ala Asp Met Val
        355                 360                 365

Ile Glu Ala Val Phe Glu Asp Leu Asp Leu Lys Arg Lys Ile Val Ala
    370                 375                 380

Asn Val Glu Ser Val Thr Lys Asp His Cys Ile Phe Ala Thr Asn Thr
385                 390                 395                 400

Ser Ala Ile Pro Ile Ala Asp Ile Ala Gln Gly Ala Ser Arg Pro Glu
```

```
                    405                 410                 415
Asn Ile Ile Gly Met His Tyr Phe Ser Pro Val Pro Ser Met Pro Leu
            420                 425                 430

Leu Glu Ile Ile Pro His Thr Gly Thr Ser Asp Thr Ala Thr Ala Thr
            435                 440                 445

Ala Phe Glu Ile Gly Ser Lys Gln Gly Lys Thr Cys Ile Val Val Lys
            450                 455                 460

Asp Val Pro Gly Phe Tyr Val Asn Arg Cys Leu Gly Pro Tyr Leu Val
465                 470                 475                 480

Glu Val Ser Ala Leu Val Arg Asp Gly Val Pro Leu Glu Ala Leu Asp
                485                 490                 495

Lys Ser Leu Lys Asn Phe Gly Met Pro Val Gly Pro Ile Thr Leu Ala
            500                 505                 510

Asp Glu Val Gly Ile Asp Val Ser Ser His Val Ala Lys Phe Leu Ser
            515                 520                 525

Asn Ala Asp Leu Gly Val Arg Met Glu Gly Gly Asp Val Ser Leu Met
            530                 535                 540

Glu Gln Met Ile Gly Lys Gly Trp Leu Gly Lys Lys Ser Gly Gln Gly
545                 550                 555                 560

Phe Tyr Thr Tyr Lys Gly Lys Lys Thr Ile Asn Glu Glu Val Gln
                565                 570                 575

Lys Tyr Val Lys Asp Phe Ala Thr Arg Asp Leu Lys Leu Asp Glu Lys
                580                 585                 590

Glu Ile Gln Asp Arg Ile Val Ser Arg Phe Val Asn Glu Ala Ala Lys
            595                 600                 605

Cys Leu Glu Asp Glu Ile Ile Glu Asn Pro Val Val Gly Asp Ile Gly
610                 615                 620

Leu Val Phe Gly Thr Gly Phe Ala Pro Phe Arg Gly Gly Pro Phe Arg
625                 630                 635                 640

Tyr Leu Asp Gln Val Gly Val Ala Ser Tyr Val Asp Arg Met Asn Thr
                645                 650                 655

Phe Thr Asp Lys Tyr Gly Pro Gln Phe Glu Pro Cys Gln Leu Leu Lys
                660                 665                 670

Asp Tyr Ala Ala Thr Asp Lys Lys Phe His Lys Arg
                675                 680

<210> SEQ ID NO 7
<211> LENGTH: 771
<212> TYPE: PRT
<213> ORGANISM: Fragilariopsis cylindrus
<220> FEATURE:
<221> NAME/KEY: misc_feature
<223> OTHER INFORMATION: Trifunctional Protein A

<400> SEQUENCE: 7

Met Thr Ala Phe Tyr Ser Ala Arg Tyr Gln Ser Thr Ala Ser Ser Ala
1               5                   10                  15

Val Leu Glu Glu Lys Pro Thr Asp Pro Ser Pro Ser Ala Ala Ala Ala
            20                  25                  30

Ser Ser Thr Ala Thr Asn Asn Glu Glu Gly Ser Lys Leu Phe Val Pro
            35                  40                  45

Thr Ala Asp Arg Lys Tyr Glu Tyr Phe Thr Asn Val Glu Phe Thr Lys
            50                  55                  60

Glu Gly Val Ala Ile Ile Arg Phe Asp Cys Pro Asn Lys Val Asn Thr
65                  70                  75                  80
```

```
Ile Ser Phe Ala Leu Ser Asp Glu Ala Arg Gln Leu Trp Lys Gly Glu
                85                  90                  95

Ile Glu Asn Asn Ser Asp Val Lys Ala Val Val Phe Ser Ser Ala Lys
                100                 105                 110

Pro Asp Met Phe Ile Ala Gly Ala Asp Ile Phe Asp Ile Lys Arg Ile
                115                 120                 125

Glu Asn Lys Asn Asp Leu Val Gly Leu Ile Glu Gly Val Thr Phe
                130                 135                 140

Phe Gln His Met Arg Glu Lys Lys Val Pro Leu Val Cys Ala Ile Asn
145                 150                 155                 160

Gly Pro Ala Leu Gly Gly Leu Glu Trp Ala Met Trp Cys Asp Tyr
                165                 170                 175

Arg Val Cys Ser Asp Ser Pro Lys Thr Lys Leu Gly Leu Pro Glu Val
                180                 185                 190

Lys Leu Gly Leu Leu Pro Gly Phe Gly Gly Thr Gln Asn Leu His Glu
                195                 200                 205

Leu Val Gly Leu Gln Asn Ala Met Asp Met Met Leu Thr Gly Lys Asp
                210                 215                 220

Ile Arg Pro His Lys Ala Lys Lys Met Gly Leu Val Asp Leu Val Val
225                 230                 235                 240

Ser Ser Gln Ser Val Glu Lys Asp Ala Ile Gln Ser Ala Val Asp Ile
                245                 250                 255

Ile Asn Gly Lys Leu Lys Pro Lys Lys Ala Lys Ser Leu Met Asn
                260                 265                 270

Arg Leu Leu Glu Asp Thr Ser Ile Gly Gln Lys Ile Ile Trp Asn Gln
                275                 280                 285

Ile Asn Lys Met Val Gln Lys Asn Thr Asn Gly Asn Tyr Pro Ala Pro
                290                 295                 300

Asn Ala Ile Ile Arg Cys Val Gln His Gly Ile Ala Asn Arg Ser Thr
305                 310                 315                 320

Arg Phe Glu Asn Glu Arg Glu Glu Phe Ala Lys Leu Ala Ala Thr Asp
                325                 330                 335

Glu Ser Glu Ala Leu Ile Gly Ile Phe Asp Gly Met Thr Gln Met Lys
                340                 345                 350

Lys Asn Pro Phe Asp Asn Thr Val Ala Val Pro Val Lys Thr Val Ala
                355                 360                 365

Val Met Gly Ala Gly Leu Met Gly Ala Gly Ile Ala Gln Ile Thr Ala
                370                 375                 380

Glu Lys Gly Met Ser Val Leu Leu Lys Asp Arg Asn Asp Ala Ala Ile
385                 390                 395                 400

Glu Arg Gly Gly Ser Tyr Met Arg Asp Asn Trp Asp Lys Lys Leu Lys
                405                 410                 415

Arg Lys Arg Met Thr Lys Phe Gln His Asn Leu Asn Ser Ser Asn Val
                420                 425                 430

Val Gly Leu Thr Asp Asp Asn Pro Asn Leu Val Glu Lys His Phe Gly
                435                 440                 445

Asn Thr Asp Met Ile Ile Glu Ala Val Phe Glu Asp Leu Asp Leu Lys
                450                 455                 460

Arg Lys Ile Val Ala Asp Ile Glu Lys Ile Thr Pro Asp His Cys Val
465                 470                 475                 480

Phe Ala Thr Asn Thr Ser Ala Ile Pro Ile Gly Ala Ile Ala Glu Gly
                485                 490                 495

Ser Lys Arg Pro Glu Asn Ile Ile Gly Met His Tyr Phe Ser Pro Val
```

```
                500             505             510
Pro Ser Met Pro Leu Glu Ile Ile Pro His Glu Gly Thr Asn Glu
        515             520             525
Ala Thr Arg Ala Thr Ala Phe Asn Val Gly Thr Lys Gln Gly Lys Thr
        530             535             540
Cys Ile Val Val Lys Asp Val Pro Gly Phe Tyr Val Asn Arg Cys Leu
545             550             555             560
Gly Pro Phe Leu Val Glu Val Ser Ala Leu Ile Arg Asp Gly Val Ser
                565             570             575
Leu Glu Lys Leu Asp Arg Ser Val Leu Asp Phe Gly Met Pro Val Gly
        580             585             590
Pro Val Thr Leu Ala Asp Glu Val Gly Ile Asp Val Thr Ser His Val
        595             600             605
Ala Thr Phe Leu Ser Lys Ala Asp Leu Gly Val Arg Met Asp Gly Gly
        610             615             620
Asp Ile Thr Leu Met Glu Lys Met Ile Asp Lys Gly Trp Leu Gly Lys
625             630             635             640
Lys Ser Gly Gln Gly Phe Tyr Thr Tyr Ser Asn Lys Lys Gly Lys
                645             650             655
Thr Ile Ser Pro Glu Val Gln Ala Tyr Val Lys Thr Phe Val Lys Gln
                660             665             670
Asp Leu Asn Leu Asp Lys Glu Glu Ile Gln Asn Arg Ile Ile Ser Arg
        675             680             685
Phe Val Asn Glu Ala Ala Lys Cys Leu Glu Asp Glu Ile Ile Asp Asn
        690             695             700
Pro Val Val Gly Asp Ile Gly Leu Val Phe Gly Thr Gly Phe Ala Pro
705             710             715             720
Phe Arg Gly Gly Pro Phe Arg Tyr Leu Asp Gln Ile Gly Val Ala Asn
                725             730             735
Tyr Val Asp Met Met Asn Ser Phe Ala Asp Lys Tyr Gly Gly Gln Phe
                740             745             750
Glu Pro Cys Gln Leu Leu Lys Asp Tyr Ala Ala Thr Asp Lys Lys Phe
        755             760             765
Tyr Asn Asn
        770

<210> SEQ ID NO 8
<211> LENGTH: 766
<212> TYPE: PRT
<213> ORGANISM: Aureococcus anophagefferens
<220> FEATURE:
<221> NAME/KEY: misc_feature
<223> OTHER INFORMATION: Trifunctional Protein A

<400> SEQUENCE: 8

Met Ser Ser Leu Leu Arg Tyr Ser Ala Arg Gln Val Ala Val Ala Gly
1               5               10              15
Arg Arg Arg Leu Ser Ala Gln Pro Val Ala Ser Glu Gly Ser Arg Ser
                20              25              30
Trp Glu Phe Phe Ala Gly Asp Pro Glu Val Thr Ala Asp Gly Val Ala
        35              40              45
Ile Val Arg Leu Asp Ala Lys Lys Ala Lys Met Asn Thr Leu Asn Pro
        50              55              60
Ala Leu Gln Ala Glu Ala Gln Glu Met Trp Ser Glu Leu Met Glu Ala
65              70              75              80
```

```
Arg Gly Asn Asp Val Lys Ala Ala Val Phe Ile Ser Ala Lys Pro Asp
                85                  90                  95

Asn Phe Ile Ala Gly Ala Asp Ile Ser Met Leu Ala Ala Lys Lys Ala
            100                 105                 110

Ser Gly Asp Glu Asp Ser Leu Glu Ala Ile Cys Leu Ser Gly His Thr
            115                 120                 125

Met Phe Ala Glu Leu Lys Ala Thr Asn Ile Pro Ile Val Ala Ala Ile
130                 135                 140

His Gly Ala Cys Leu Gly Gly Gly Leu Glu Trp Ala Leu Lys Cys Asp
145                 150                 155                 160

Tyr Arg Val Ala Ser Thr Ser Pro Lys Thr Lys Leu Gly Leu Pro Glu
                165                 170                 175

Val Lys Leu Gly Leu Leu Pro Gly Trp Gly Gly Thr Tyr Ala Leu Pro
            180                 185                 190

Lys Leu Ile Gly Leu Thr Glu Ala Leu Pro Met Ile Leu Gln Gly Lys
            195                 200                 205

Glu Val Lys Ala Asp Lys Ala Lys Lys Leu Gly Leu Val Asp Ala Val
210                 215                 220

Cys Asp Pro Ala Ala Leu Glu Arg Leu Ala Val Ala Lys Ala Ala Ala
225                 230                 235                 240

Leu Gly Asn Gly Ser Leu Lys Leu Lys Glu Lys Lys Ser Trp Met
                245                 250                 255

Arg Trp Ala Thr Glu Asp Val Ser Phe Gly Arg Asp Phe Val Phe Lys
                260                 265                 270

Lys Ala Lys Glu Thr Val Asp Lys Thr Thr Arg Gly Lys Tyr Pro Ala
            275                 280                 285

Ala Tyr Glu Ile Met Asp Cys Val Lys His Gly Leu Gly Lys Ser Pro
290                 295                 300

Glu Glu Ala Phe Ala Phe Glu Ala Lys Ala Phe Val Arg Leu Ala Lys
305                 310                 315                 320

Thr Pro Glu Ser Ser Ala Leu Ile Gly Leu Phe Asp Gly Ile Thr Ala
                325                 330                 335

Ser Lys Lys Asn Arg Tyr Gly Asn Ala Ser Asp Pro Ala Thr Leu Lys
            340                 345                 350

Ala Leu Asp Thr Val Ala Val Leu Gly Ala Gly Leu Met Gly Ala Gly
            355                 360                 365

Ile Ala Gln Val Ser Ala Glu Lys Gly Leu Asn Val Leu Leu Lys Asp
            370                 375                 380

Ala Ser Pro Glu Gly Leu Ala Lys Gly Val Asp Tyr Val Gly Gly Asn
385                 390                 395                 400

Leu Ala Lys Lys Val Lys Arg Arg Met Thr Asp Tyr Thr Arg Asn
                405                 410                 415

Thr Ile Thr Ser Lys Val Met Gly Tyr His Asp Gly Pro Gly Gly Gly
            420                 425                 430

Gly Asp Ala Ala Trp Leu Arg Lys Ala Ala Thr Ala Asp Val Val Val
            435                 440                 445

Glu Ala Val Phe Glu Asp Leu Asp Leu Lys His Lys Val Phe Gln Ser
450                 455                 460

Val Glu Pro Leu Val Ser Glu Ala Cys Val Leu Ala Thr Asn Thr Ser
465                 470                 475                 480

Ala Ile Pro Ile Ala Lys Val Ala Ala Gly Ala Ala Lys Pro Glu Arg
                485                 490                 495

Val Leu Gly Met His Tyr Phe Ser Pro Val Pro Gln Met Gln Leu Leu
```

```
                500                 505                 510
Glu Ile Ile Pro His Ala Gly Thr Asp Pro Lys Ala Met Ala Ala Ala
            515                 520                 525

Phe Ala Val Gly Ile Lys Gln Gly Lys Phe Cys Ile Glu Val Lys Asp
        530                 535                 540

Val Pro Gly Phe Tyr Val Asn Arg Cys Leu Ala Pro Met Met Ala Glu
545                 550                 555                 560

Leu Ala Pro Leu Phe Gln Asp Gly Val Glu Pro Lys Gln Leu Asp Glu
                565                 570                 575

Ala Ile Leu Asp Leu Gly Met Pro Val Gly Pro Val Thr Leu Ile Asp
            580                 585                 590

Glu Val Gly Ala Asp Val Gly Leu His Val Gln Arg Thr Met Leu Ala
        595                 600                 605

Asp Glu Thr Met Gly Gly Arg Met Ala Gly Ala Asp Pro Ala Met Leu
610                 615                 620

Gln Ala Val Val Asp Lys Gly Trp Leu Gly Arg Lys Ser Gly Lys Gly
625                 630                 635                 640

Phe Phe Val Tyr Asp Gly Lys Lys Thr Pro Asn Ala Glu Ala Asn
                645                 650                 655

Ala Tyr Val Glu Ser Glu Val Lys Arg Arg Asp Ala Gly Leu Ser Val
            660                 665                 670

Glu Thr Ile Gln Asp Arg Tyr Leu Thr Arg Phe Val Asn Glu Ala Ala
        675                 680                 685

Val Cys Leu Gln Glu Gly Ile Leu Lys Thr Pro Ala Asp Gly Asp Leu
690                 695                 700

Gly Ala Val Phe Gly Val Gly Phe Leu Pro Phe Thr Gly Gly Pro Phe
705                 710                 715                 720

Arg Met Leu Asp Ala Val Gly Ala Ala Thr Tyr Val Asp Lys Met Asn
                725                 730                 735

Arg Leu Ala Asp Glu Tyr Gly Asp Arg Phe Ala Pro Cys Asp Leu Leu
            740                 745                 750

Val Asp His Ala Asn Ser Gly Lys Lys Phe Tyr Pro Ser Lys
        755                 760                 765

<210> SEQ ID NO 9
<211> LENGTH: 739
<212> TYPE: PRT
<213> ORGANISM: Ectocarpus siliculosus
<220> FEATURE:
<221> NAME/KEY: misc_feature
<223> OTHER INFORMATION: Trifunctional Protein A

<400> SEQUENCE: 9

Met Pro Met Glu Asp Pro Ala Ser Val Glu Ser Thr Ser Asp Lys Ser
1               5                   10                  15

Pro Arg Phe Phe Gln Pro Val Glu Lys Leu Asp Asn Gly Val Ala Ile
            20                  25                  30

Ile Arg Ile Asp Gly Pro Glu Lys Met Asn Thr Ile Ser Gly Asp Phe
        35                  40                  45

Arg Gln Glu Ile Glu Asp Ile Trp Ser Gly Gln Ile Ala Glu Asp Pro
    50                  55                  60

Ser Val Lys Ala Val Val Phe Ile Ser Gly Lys Pro Asp Asn Tyr Ile
65                  70                  75                  80

Ala Gly Ala Asp Ile Arg Met Ile Ser Ala Thr Glu Asp Lys Ala Asp
                85                  90                  95
```

-continued

```
Leu Lys Gln Ile Cys Met Asp Gly His Ala Thr Phe Asp Ile Leu Ala
            100                 105                 110
Lys Lys Gly Ile Pro Val Ile Ala Ala Ile Asn Gly Ala Cys Leu Gly
        115                 120                 125
Gly Gly Leu Glu Trp Ala Leu His Cys Asp Tyr Arg Leu Ala Thr Thr
    130                 135                 140
Ser Pro Lys Thr Val Leu Gly Leu Pro Glu Val Lys Leu Gly Leu Leu
145                 150                 155                 160
Pro Gly Trp Gly Gly Thr Gln Leu Leu His Pro Leu Val Gly Leu Gln
                165                 170                 175
Ala Ala Leu Asp Met Ile Leu Thr Gly Lys Asn Ile Arg Pro His Lys
            180                 185                 190
Ala Leu Lys Met Gly Leu Val Asp Gln Leu Val Asp Ala Ala Ser Leu
        195                 200                 205
Glu Ala Val Ala Val Glu Ala Ala Ser Leu Ala Asp Gly Ser Leu
    210                 215                 220
Lys Ser Lys Arg Lys Pro Lys Ala Leu Met Asn Lys Ile Ile Glu Asp
225                 230                 235                 240
Thr Pro Met Gly Arg Ser Ile Met Trp Lys Lys Val Gly Glu Lys Val
                245                 250                 255
Ala Lys Ser Thr Gly Gly Asn Tyr Pro Asn Ala Thr Ala Ile Val Asp
            260                 265                 270
Cys Ile Lys Phe Gly Leu Ser Ser Lys Gln Ala Ala Leu Glu Tyr
        275                 280                 285
Glu Ala Gln Arg Phe Ser Glu Met Ala Ala Thr Pro Glu Ser Glu Ser
    290                 295                 300
Leu Ile Gly Leu Phe Glu Gly Ser Thr Ala Leu Lys Lys Asn Arg Phe
305                 310                 315                 320
Gly Lys Pro Ala Lys Lys Val Glu Lys Val Ala Val Leu Gly Ala Gly
                325                 330                 335
Leu Met Gly Ala Gly Ile Ala Gln Val Ser Ala Glu Lys Gly Met Thr
            340                 345                 350
Val Leu Leu Lys Asp Arg Asp Ser Ala Ser Val Gly Lys Gly Thr Ser
        355                 360                 365
Tyr Ile Met Asp Asn Ala Ala Ala Lys Leu Lys Lys Arg Arg Met Thr
    370                 375                 380
Lys Tyr Glu Met Asp Thr Val Gly Ser Arg Val Ile Pro Leu Thr Asp
385                 390                 395                 400
Glu Gly Asp Leu Trp Lys Arg His Phe Gly Ser Ala Glu Met Val Ile
                405                 410                 415
Glu Ala Val Pro Glu Asn Leu Asp Leu Lys His Arg Val Ile Gln Gln
            420                 425                 430
Ala Glu Gln Phe Leu Pro Glu Asp Cys Val Phe Ala Thr Asn Thr Ser
        435                 440                 445
Ala Leu Pro Ile Arg Asp Ile Ala Lys Ala Ser Lys Arg Pro Gln Asn
    450                 455                 460
Val Val Gly Met His Tyr Phe Ser Pro Val Pro Met Met Pro Leu Leu
465                 470                 475                 480
Glu Ile Ile Pro His Asp Gly Thr Ser Asp Ala Ala Ala Ala Ala
                485                 490                 495
Val Asp Val Gly Gly Arg Gln Gly Lys Thr Cys Ile Val Val Lys Asp
            500                 505                 510
Val Pro Gly Phe Tyr Val Asn Arg Cys Leu Gly Pro Phe Leu Val Glu
```

```
            515                 520                 525
Thr Cys Ala Leu Val Glu Ala Gly Val Gly Leu Glu Gln Leu Asp Lys
        530                 535                 540

Val Met Lys Ser Tyr Gly Leu Pro Val Gly Pro Ile Thr Leu Ala Asp
545                 550                 555                 560

Glu Val Gly Ile Asp Ile Gly Phe His Val Gln Ser Phe Leu Ser Glu
                565                 570                 575

Ala Asp Met Gly Val Arg Met Thr Gly Gly Asn Val Ala Val Met Gly
            580                 585                 590

Asp Met Val Glu Lys Gly Phe Leu Gly Arg Lys Ser Gly Lys Gly Phe
        595                 600                 605

Tyr Leu Tyr Pro Lys Gly Lys Gly Asn Lys Gly Gly Lys Glu Leu
    610                 615                 620

Asn Pro Glu Ala Val Ser Leu Ile Lys Ala His Gln Ala Ala Gly Gly
625                 630                 635                 640

Ala Gly Ala Ser Leu Ala Asn Asp Val Ile Gln Asp Arg Met Met Cys
                645                 650                 655

Arg Phe Val Asn Glu Ala Ala Leu Cys Leu Gln Glu Gly Ile Ile Ser
            660                 665                 670

Ser Pro Val Asp Gly Asp Ile Gly Ala Val Phe Gly Met Gly Phe Pro
        675                 680                 685

Pro Phe Arg Gly Gly Pro Phe Arg Leu Leu Asp Gln Arg Gly Ala Gly
    690                 695                 700

Ala Tyr Ala Asp Met Met Asn Arg Leu Ala Asp Glu His Gly Glu Gln
705                 710                 715                 720

Phe Arg Pro Cys Gln Leu Leu Met Asp His Ala Arg Gly Asp Lys Lys
                725                 730                 735

Phe His Thr

<210> SEQ ID NO 10
<211> LENGTH: 433
<212> TYPE: PRT
<213> ORGANISM: Nannochloropsis gaditana
<220> FEATURE:
<221> NAME/KEY: misc_feature
<223> OTHER INFORMATION: TrifuncB cDNA sequence

<400> SEQUENCE: 10

Met Asp Thr Gly Cys Thr Ile Val Val Glu Arg Met Leu Arg Ser Ser
1               5                   10                  15

Thr Leu Leu Arg Gly Leu Ala Ser Lys Ala Ala Gly Ala Gly Lys Lys
            20                  25                  30

Pro Thr Val Val Phe Val Asp Gly Ala Arg Ile Pro Phe Ala Gln Ser
        35                  40                  45

Ser Thr Val Tyr Asn Asp Tyr Leu Gly Val Asp Leu Gln Lys Phe Ala
    50                  55                  60

Tyr Lys Gly Leu Val Asp Lys Thr Ala Leu Asp Pro Lys Glu Ile Asp
65                  70                  75                  80

Tyr Ile Leu Gly Gly Asn Val Ile Gln Glu Val Arg Thr Ser Asn Ile
                85                  90                  95

Ala Arg Glu Ala Ala Met Ala Ala Gly Leu Pro Thr Asp Ile Pro Ala
            100                 105                 110

His Thr Val Val Leu Ala Cys Ile Ser Ser Asn Val Gly Ile Cys Ser
        115                 120                 125

Ala Ala Glu Lys Val Leu Thr Glu His Ala Ser Leu Val Leu Ala Leu
```

```
        130                 135                 140
Ile Thr Leu Pro Lys Ala Met Lys Lys Gly Pro Leu Gly Val Phe Lys
145                 150                 155                 160

His Leu Ala Lys Leu Asn Phe Lys Asp Leu Gly Leu Glu Thr Pro Ala
                165                 170                 175

Ile Ala Asn Tyr Thr Thr Gly Glu Val Met Gly His Ser Ser Asp Arg
            180                 185                 190

Leu Ser Ala Lys Phe Gly Val Ser Arg Arg Glu Gln Asp Glu Phe Ala
        195                 200                 205

Ala Leu Ser His Gln Arg Ala Ala Lys Ala His Lys Asp Gly Ile Tyr
    210                 215                 220

Lys Asp Glu Ile Ile Pro Val Asp Gly Asn Thr Gly Glu Asn Gly Ile
225                 230                 235                 240

Lys Gly Glu Ser Thr Ala Asp Thr Leu Ala Lys Leu Lys Pro Ala Phe
                245                 250                 255

Val Lys Pro His Gly Thr His Thr Ala Ala Asn Ser Ser Phe Leu Ser
            260                 265                 270

Asp Gly Ala Ser Ala Ser Leu Ile Ala Ser Glu Glu Lys Ala Leu Ser
        275                 280                 285

Leu Gly Leu Lys Pro Lys Ala Phe Leu Arg Ala Trp Glu Phe Val Ala
    290                 295                 300

Val Asp Pro Phe Glu Gln Leu Leu Leu Gly Pro Thr Tyr Ala Thr Ala
305                 310                 315                 320

Lys Val Leu Ser Ala Ala Gly Leu Thr Leu Ala Asp Ile Asp Val Ile
                325                 330                 335

Glu Ile His Glu Ala Phe Ala Gly Gln Val Leu Ser Asn Ile Arg Ala
            340                 345                 350

Met Gly Ser Asp Lys Phe Ala Gln Glu Tyr Leu Asn Arg Ser Thr Lys
        355                 360                 365

Val Gly Asp Ile Asp Met Ala Lys Thr Asn Leu His Gly Gly Ser Leu
    370                 375                 380

Ser Leu Gly His Pro Phe Ala Thr Gly Asn Arg Leu Val Thr Thr
385                 390                 395                 400

Ala Ala Asn Arg Leu His Arg Glu Gly Gly Arg Tyr Ala Leu Val Thr
                405                 410                 415

Ala Cys Ala Asp Gly Gly Leu Gly His Ala Cys Ile Ile Glu Lys Tyr
            420                 425                 430

Glu

<210> SEQ ID NO 11
<211> LENGTH: 1173
<212> TYPE: DNA
<213> ORGANISM: Nannochloropsis gaditana
<220> FEATURE:
<221> NAME/KEY: misc_feature
<223> OTHER INFORMATION: TrifuncB cDNA sequence

<400> SEQUENCE: 11
atgccttcga cagtatttga cgcctttgtt gtggcattga gtgcaggatg cgcgcgggac      60
tttggctgca caattgtcgt ggagagaatg ctgcggtcct ctacgctcct ccggggcttg     120
gcgtccaaag ccgccggcgc cgggaagaaa cccaccgttg tattcgtcga cggagctcgc     180
atccctttcg cccaatcctc caccgtgtac aacgactacc tgggcgtgga cctacagaaa     240
ttcgcctaca agggtctggt ggataaaacg gcgttggacc cgaaggaaat cgactacatc     300
```

| | |
|---|---:|
| ctgggcggga acgttatcca agaagtccgt accagcaaca tcgccaggga agccgccatg | 360 |
| gccgctggcc tccccaccga catccccgcc cacaccgtcg tcctggcctg tatttcctcc | 420 |
| aacgtgggca tctgctccgc cgcggagaaa gtcttgactg agcacgccag cctggtcttg | 480 |
| gtggggggg tggagacctt ctcggacgtg cctatccgcc tcacccgccc cctccgccag | 540 |
| gccctcataa ccctgcccaa ggcgatgaag aagggccctc tgggcgtctt caagcacctg | 600 |
| gcgaagctca acttcaagga tctgggcttg gagaccccg ccatcgccaa ctacaccacc | 660 |
| ggggaggtga tgggccactc ctcggaccga cttttcggcaa aattcggggt ttctcggcgg | 720 |
| gaacaggacg aatttgcggc cctctctcac caacgcgcag ccaaggcgca caaggacggc | 780 |
| atctacaagg acgagatcat ccccgtggac ggcaatacgg gcgagaacgg gatcaagggc | 840 |
| gagtctaccg cagatacccct cgccaagctc aaaccggcct ttgtgaagcc tcacggcacc | 900 |
| cacaccgccg ccaacagctc cttcctctcg gacggcgcct cggcttccct ggagtacctg | 960 |
| aaccgatcca ccaaggtggg cgacatcgac atggcaaaga ccaatctgca cggaggctcc | 1020 |
| ctctccctcg gccacccctt cgccgctacc ggaaaccgat tggtgacgac ggcggcgaat | 1080 |
| cgcctgcacc gggagggagg gaggtacgcc ctggtcactg cctgcgcgga tggcggtttg | 1140 |
| ggccacgcct gtatcatcga gaaatatgag tga | 1173 |

<210> SEQ ID NO 12
<211> LENGTH: 3517
<212> TYPE: DNA
<213> ORGANISM: Nannochloropsis gaditana
<220> FEATURE:
<221> NAME/KEY: misc_feature
<223> OTHER INFORMATION: TrifuncB gDNA sequence
<220> FEATURE:
<221> NAME/KEY: misc_feature
<222> LOCATION: (2249)..(2997)
<223> OTHER INFORMATION: n is a, c, g, or t

<400> SEQUENCE: 12

| | |
|---|---:|
| atgccttcga cagtatttga cgcctttgtt gtggcattga gtgcaggatg cgcgcgggac | 60 |
| tttggtaaat atggacttag tttcaccatc gtgttccaag catgaagtgg cggctctccc | 120 |
| ccctcgaata cgtcggctag gacgtggggc tcttcccct tcctgatcat tcgctttacc | 180 |
| cctttcgtct tcacacacat ggacacaggc tgcacaattg tcgtggagag aatgctgcgg | 240 |
| tcctctacgc tcctccgggg cttggcgtcc aaagccgccg cgccgggaa gaaacccacc | 300 |
| gttgtattcg tcgacggagc tcgcatcccct ttcgcccaat cctccaccgt gtacaacgac | 360 |
| tacctgggcg tggacctaca gaaattcgcc tacaagggtc tggtggataa aacggcgttg | 420 |
| gacccgaagg aaatcgacta catcctgggc gggaacggta agcctgaagc aagggggggg | 480 |
| gggagatcgt gctggcatgt atactcaaag atcaagcccct ctcaatgata atcacgagtt | 540 |
| ttcctgctcg ggccttgtcc aatgatactc actaactccc ggccctttc tccgctcgaa | 600 |
| ggatgatggg gagggaagtg atgaggacg aggagtctca caaccgtgtg atggggaggg | 660 |
| acgagagagg gcaacccccg aggcctcaag cctcgctcgt gccggtcctg gtccgcttcc | 720 |
| gccttctcaa ggcttacatc ctttcccttc ctccctccct tcttccctcc ccccctcctt | 780 |
| ccctccctcc ccatctcagt tatccaagaa gtccgtacca gcaacatcgc cagggaagcc | 840 |
| gccatggccg ctggcctccc caccgacatc cccgcccaca ccgtcgtcct ggcctgtatt | 900 |
| tcctccaacg tgggcatctg ctccgccgcg gtaggtcct ccctccccgt cctccggccc | 960 |
| gaagccctgt ctttgcctgc cctccctccc tccctccctc cctccctccc tcctccctc | 1020 |

```
cctccctccc tccctccctc cctccctccc tccctccctc tccctccctc           1080
cctccctccc tccctgcctg cctcgctcct cccctcctct ctcccctcca agctcagagg  1140
aaatcttgat tccccttccc cccttcctttt ctccctcgct ccctccctcc ctccctcccc  1200
agagaaagtc ttgactgagc acgccagcct ggtcttggtg ggggggggtgg agaccttctc  1260 ggacgtgcct atccgcctca cccgccccct ccgccaggcc ctcataaccc tgcccaaggc  1320
gatgaagaag ggccctctgg gcgtcttcaa gcacctggcg aagctcaact tcaaggtgcg  1380
tgttgtcttc tccttaagct gttcgggtca gacctccccc ccttcctttt cccatcaccg  1440
attttgctca aacacatgta ccaaggagag gttgtgaagg atggttactg gagaggcata  1500
ttttttcatg gagtcgccct cctttcttcc attctcttcc tccgcctctc cctcctcccc  1560
atgcctttgt tcatcttccc tcccttcctc cctccttccc tccttcccct gctaggatct  1620
gggcttggag accccgcca tcgccaacta caccaccggg gaggtgatgg ccactcctc  1680 ggaccgactt tcggcaaaat tcggggtttc tcggcgggaa cagggtaggg gggaggggag  1740
agggaaggga gctagggaga agcagaggga cgagaagagg ggccggggg gggcgggggt  1800 tattactcac cacacgtccc tatggatgtt tctcgcttcc tcttgacgcg cagacgaatt  1860
tgcggccctc tctcaccaac gcgcagccaa ggcgcacaag gacggcatct acaaggacgt  1920
gcgtcctccc tccctccttc cctccctcct tccctcctac cttcccttct accttccctc  1980
cctgcttcct atttcgccat ttatcgtgca gcgcagtcgt tcgtgccctc aggtcacctc  2040
ctcccttcct ccctccctcc ctccctcccct cctccctca ggagatcatc cccgtggacg  2100
gcaatacggg cgagaacggg atcaagggcg agtctaccgc agatacctc gccaagctca  2160 aaccggcctt tgtgaagcct cacggcaccc acaccgccgc caacagctcc ttcctctcgg  2220
acggcgcctc ggcttccctg gtgagggann nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnnnnnnnn  2580
nnnnnnnnnn nnnnnnnnnn nnnnnnnnnn nnnnnnnnnn nnnnnnnnnn nnnnnnnnnn  2640
nnnnnnnnnn nnnnnnnnnn nnnnnnnnnn nnnnnnnnnn nnnnnnnnnn nnnnnnnnnn  2700
nnnnnnnnnn nnnnnnnnnn nnnnnnnnnn nnnnnnnnnn nnnnnnnnnn nnnnnnnnnn  2760
nnnnnnnnnn nnnnnnnnnn nnnnnnnnnn nnnnnnnnnn nnnnnnnnnn nnnnnnnnnn  2820
nnnnnnnnnn nnnnnnnnnn nnnnnnnnnn nnnnnnnnnn nnnnnnnnnn nnnnnnnnnn  2880
nnnnnnnnnn nnnnnnnnnn nnnnnnnnnn nnnnnnnnnn nnnnnnnnnn nnnnnnnnnn  2940
nnnnnnnnnn nnnnnnnnnn nnnnnnnnnn nnnnnnnnnn nnnnnnnnnn nnnnnntca  3000 ttccttcagg agtacctgaa ccgatccacc aaggtgggcg acatcgacat ggcaaagacc  3060
aatctgcacg gaggctccct ctccctcggc cacccttcg ccgctaccgg tagggaggga  3120
gggagggagg gagggacaga tgatccccga cgaaatagtt gttggcttcc tcgttcagcc  3180
cgtcatggcg tatcggcact tccttgtgat tttcttccac gctcatcgtc tttcatcgat  3240
gcggccatgc gcgtgcgtcc ctgctgtctg tccccaaacc cttctccctc cgttctcatc  3300
acatttgatc aaagtattcc ctttgtttat ggagcttacc ttgccattcc tctctctttg  3360 tcggggaaa aatccaaatc ctccaaatcc atcaggaaac cgattggtga cgacggcggc  3420
```

```
gaatcgcctg caccgggagg gagggaggta cgccctggtc actgcctgcg cggatggcgg    3480
tttgggccac gcctgtatca tcgagaaata tgagtga                             3517
```

<210> SEQ ID NO 13
<211> LENGTH: 472
<212> TYPE: PRT
<213> ORGANISM: Thalassiosira pseudonana
<220> FEATURE:
<221> NAME/KEY: misc_feature
<223> OTHER INFORMATION: CCMP1335 TrifuncB

<400> SEQUENCE: 13

```
Met Ile Thr Ala Arg Leu Leu Lys Gln Gly Met Ser Ser Pro Ser Ser
1               5                   10                  15

Ser Ser Ser Ser Ser Arg Leu Ala Ala Ile Thr Ser Arg Ala Ala Thr
            20                  25                  30

Ser Leu Val Thr Ser Asn Ser Phe Ser Thr Thr Ser Thr Lys Leu Lys
        35                  40                  45

Asn Pro Lys Thr Asn Val Val Ile Val Asp Gly Ile Arg Leu Pro Phe
    50                  55                  60

Ala Gln Thr Thr Thr Ile Tyr Gln Asp Gln Leu Ala Val Asp Leu Gln
65                  70                  75                  80

Arg Leu Ala Tyr Gln Gly Leu Ile Thr Lys Thr Ala Leu Asp Lys Lys
                85                  90                  95

Asp Val Asp Tyr Val Met Ala Gly Thr Val Ile Gln Glu Val Arg Thr
            100                 105                 110

Ser Asn Leu Ala Arg Glu Ala Ala Ile Asn Ala Gly Phe Pro Ala Ser
        115                 120                 125

Ile Gly Ala His Thr Val Ala Met Ala Cys Ile Ser Ser Ser Val Ala
    130                 135                 140

Ile Thr Ser Ala Ala Glu Lys Ile Leu Ser Gly His Ala Ser Ile Val
145                 150                 155                 160

Ile Ala Gly Gly Ala Glu Thr Phe Ser Asp Val Pro Ile Arg Leu Thr
                165                 170                 175

Arg Pro Ile Arg Gln Lys Leu Ile Thr Met Pro Lys Ala Met Lys Lys
            180                 185                 190

Gly Gly Ala Leu Gly Ala Ile Arg His Leu Thr Lys Gly Leu Lys Met
        195                 200                 205

Lys Asp Ile Ser Leu Glu Thr Pro Ala Ile Ala Asn Tyr Thr Thr Gly
    210                 215                 220

Glu Val Met Gly Val Ser Ser Asp Arg Leu Ser Ala Lys Phe Gly Ile
225                 230                 235                 240

Thr Arg Leu Glu Gln Asp Glu Phe Thr Thr Asp Gly Leu Pro Arg Val
                245                 250                 255

Val Val Ser Ser Trp Tyr Asp Gly Glu Ile Val Pro Tyr Lys Gly Ser
            260                 265                 270

Thr Glu Glu Asn Gly Ile Lys Ala Asp Ser Thr Ile Glu Ser Val Ser
        275                 280                 285

Lys Leu Lys Pro Ala Phe Val Lys Pro His Gly Thr His Thr Ala Ala
    290                 295                 300

Asn Ser Ser Phe Leu Thr Asp Gly Ala Ser Ala Ser Leu Ile Met Ser
305                 310                 315                 320

Glu Glu Arg Ala Leu Glu Leu Gly Tyr Lys Pro Leu Ala Tyr Leu Arg
                325                 330                 335
```

```
Asp Trp Ser Phe Lys Ala Cys Asp Pro Phe Glu Glu Leu Leu Gly
            340                 345                 350

Pro Thr Tyr Cys Ser Gln Glu Val Leu Ser Arg Asn Asn Leu Asn Leu
            355                 360                 365

Glu Thr Asp Ile Gly Val Phe Glu Ile His Glu Ala Phe Ala Gly Gln
        370                 375                 380

Ile Leu Ser Asn Leu Thr Ala Met Asn Ser Gln Lys Phe Ala Asp Glu
385                 390                 395                 400

Lys Phe Gly Gly Lys Lys Val Gly Glu Ile Asp Met Arg Lys Met Asn
                405                 410                 415

Thr Lys Gly Gly Ser Leu Ala Leu Gly His Pro Phe Gly Ala Thr Gly
            420                 425                 430

Ser Arg Leu Val Thr Thr Ala Ser Arg Arg Leu Gln Leu Glu Asn Gln
            435                 440                 445

Arg Phe Ala Leu Ile Ala Ala Cys Ala Asp Gly Gly Leu Gly His Ala
        450                 455                 460

Cys Ile Leu Glu Arg Tyr Asp Asn
465                 470

<210> SEQ ID NO 14
<211> LENGTH: 457
<212> TYPE: PRT
<213> ORGANISM: Phaeodactylum tricornutum
<220> FEATURE:
<221> NAME/KEY: misc_feature
<223> OTHER INFORMATION: CCAP 1055/1 TrifuncB

<400> SEQUENCE: 14

Met Leu Ser Thr Ser Val Arg Ala Ile Ser Arg Gly Ser Pro Leu Val
1               5                   10                  15

Gln Thr Ala Ala Arg Arg Ser Leu Ala Ser Leu Ala Leu Thr Pro Asn
            20                  25                  30

Asp Pro Val Val Val Ser Gly Val Arg Leu Pro Phe Ala Met Thr
        35                  40                  45

Ser Thr Ile Tyr Glu Asp Gln Leu Ala Val Asp Leu Gln Arg Leu Ala
    50                  55                  60

Ile Gln Gly Leu Leu Thr Gln Thr Ala Leu Pro Lys Ser Glu Val Asp
65                  70                  75                  80

Tyr Val Ile Ala Gly Asn Val Ile Gln Glu Val Arg Thr Ser Asn Ile
                85                  90                  95

Ala Arg Glu Ala Ser Ile Asn Ala Gly Leu Pro Leu His Val Gly Ala
            100                 105                 110

His Thr Ile Ala Gln Ala Cys Ile Ser Ala Asn Ala Ala Ile Cys Ala
        115                 120                 125

Gly Ala Glu Lys Ile Leu Thr Gly His Ala Ser Val Val Ile Ala Gly
130                 135                 140

Gly Cys Glu Thr Phe Ser Asp Val Pro Ile Arg Leu Thr Arg Pro Ile
145                 150                 155                 160

Arg Gln Lys Leu Ile Thr Met Asn Lys Ala Met Lys Lys Gly Gly Met
                165                 170                 175

Val Gly Gly Ile Ser His Leu Leu Lys Gly Leu Ser Leu Lys Asp Val
            180                 185                 190

Ser Val Glu Thr Pro Ala Ile Ala Asn Tyr Thr Thr Gly Glu Val Met
        195                 200                 205

Gly Val Ser Ser Asp Arg Leu Ala Ala Lys Phe Gly Val Ser Arg His
    210                 215                 220
```

Asp Gln Asp Ala Phe Thr Val Arg Ser His Thr Met Ala Ala Lys Ala
225                 230                 235                 240

His Thr Asp Gly Phe Tyr Lys Asn Glu Val Val Pro Tyr Lys Gly Ser
            245                 250                 255

Thr Gln Glu Asn Gly Ile Lys Gly Asp Ser Thr Ile Glu Ser Val Ala
        260                 265                 270

Lys Leu Lys Pro Ala Phe Val Lys Pro His Gly Thr His Thr Ala Ala
    275                 280                 285

Asn Ser Ser Phe Leu Thr Asp Gly Ala Ala Thr Leu Ile Met Ser
290                 295                 300

Glu Ser Lys Ala Lys Glu Leu Gly Tyr Lys Pro Leu Ala Tyr Leu Arg
305                 310                 315                 320

Asp Trp Ser Phe Lys Ala Cys Asp Pro Phe Glu Glu Leu Leu Leu Gly
            325                 330                 335

Pro Thr Tyr Cys Ser Gln Glu Ile Leu Ala Arg Asn Lys Leu Gln Met
        340                 345                 350

Ser Asp Met Gly Val Leu Glu Ile His Glu Ala Phe Ala Gly Gln Ile
    355                 360                 365

Leu Ala Asn Leu Thr Ala Met Glu Ser Gln Thr Phe Ala Asp Lys Asn
370                 375                 380

Phe Gly Gly Lys Ile Val Gly Lys Val Asp Val Asp Lys Met Asn Thr
385                 390                 395                 400

Lys Gly Gly Ser Leu Ala Leu Gly His Pro Phe Gly Ala Thr Gly Ser
            405                 410                 415

Arg Leu Val Ser Thr Ala Ser Arg Arg Leu Gln His Glu Gly Ala Arg
        420                 425                 430

Phe Ala Leu Leu Ala Ala Cys Ala Asp Gly Gly Met Gly His Ala Cys
    435                 440                 445

Leu Leu Glu Arg Tyr Asp Asn Asp Asn
450                 455

<210> SEQ ID NO 15
<211> LENGTH: 450
<212> TYPE: PRT
<213> ORGANISM: Fragilariopsis cylindrus
<220> FEATURE:
<221> NAME/KEY: misc_feature
<223> OTHER INFORMATION: CCMP1102 TrifuncB

<400> SEQUENCE: 15

Met Ile Ser Ser Gln Lys Leu Val Arg Pro Leu Leu Thr Ala Gln Arg
1               5                   10                  15

Arg Leu Phe Ser Leu Arg Pro Ile Ala Gly Gly Arg Asp Val Val Ile
            20                  25                  30

Val Ser Gly Val Arg Leu Pro Phe Ala Gln Ala Ser Thr Ile Tyr Gln
        35                  40                  45

Asp Glu Met Ala Val Asp Leu Gln Arg Leu Ala Ile Lys Gly Leu Ile
    50                  55                  60

Asp Gln Thr Ala Leu Pro Lys Asp Ala Ile Asp Tyr Val Val Cys Gly
65                  70                  75                  80

Asn Val Ile Gln Glu Val Lys Thr Ser Asn Ile Ala Arg Glu Ala Ala
                85                  90                  95

Ile Asn Ala Gly Leu Pro Tyr Asn Ile Pro Ser His Thr Ile Ala Gln
            100                 105                 110

Ala Cys Ile Ser Ala Asn Ala Ala Ile Ala Thr Gly Ala Ala Ala Ile

```
            115                 120                 125
Gln Ser Gly His Ala Asp Val Ile Ala Gly Gly Val Glu Thr Phe
    130                 135                 140

Ser Asp Val Pro Ile Arg Leu Ser Arg Pro Ile Arg Gln Lys Leu Ile
145                 150                 155                 160

Thr Leu Pro Lys Ala Met Lys Lys Gly Gly Pro Ile Gly Ala Val Arg
                165                 170                 175

His Met Leu Lys Gly Leu Lys Met Lys Asp Leu Ser Leu Glu Thr Pro
            180                 185                 190

Ala Ile Ala Asn Phe Thr Thr Gly Glu Val Met Gly Val Ser Ser Asp
        195                 200                 205

Lys Leu Ser Ala Lys Phe Gly Ile Ser Arg Gln Gln Asp Glu Phe
    210                 215                 220

Thr Val Arg Ser His Thr Leu Ala His Lys Ala His Asp Asp Gly Phe
225                 230                 235                 240

Tyr Lys Asp Glu Ile Ile Pro Tyr Arg Gly Ser Ile Ala Glu Asn Gly
                245                 250                 255

Ile Lys Gly Asn Ser Ser Tyr Glu Ser Val Ser Lys Leu Lys Ala Ala
            260                 265                 270

Phe Val Lys Pro Asn Gly Thr His Thr Ala Ala Asn Ser Ser Phe Leu
        275                 280                 285

Thr Asp Gly Ala Ala Ala Thr Leu Ile Met Ser Glu Glu Lys Ala Lys
    290                 295                 300

Glu Leu Gly Tyr Lys Pro Leu Ala Tyr Leu Arg Asp Trp Ser Phe Lys
305                 310                 315                 320

Ser Cys Asp Pro Trp Glu Glu Leu Leu Leu Gly Pro Thr Tyr Cys Thr
                325                 330                 335

Gln Asp Ile Leu Gln Arg Asn Ser Met Ser Ile Asn Asp Phe Gly Val
            340                 345                 350

Phe Glu Ile His Glu Ala Phe Ala Gly Gln Ile Leu Ser Asn Leu Ala
        355                 360                 365

Ala Met Asp Ser Asp Ile Phe Ala Lys Glu Lys Gly Trp Ser Lys Lys
    370                 375                 380

Val Gly Ala Ile Asp Phe Asp Lys Met Asn Ile Lys Gly Gly Ser Leu
385                 390                 395                 400

Ser Ile Gly His Pro Phe Gly Ala Thr Gly Ser Arg Leu Val Thr Thr
                405                 410                 415

Ala Ala Arg Arg Leu Gln Glu Glu Gly Gln Gln Phe Ala Leu Ile Ala
            420                 425                 430

Ala Cys Ala Asp Gly Gly Leu Gly His Ala Cys Leu Leu Glu Arg Tyr
        435                 440                 445

Asp Asn
    450

<210> SEQ ID NO 16
<211> LENGTH: 451
<212> TYPE: PRT
<213> ORGANISM: Emiliania huxleyi
<220> FEATURE:
<221> NAME/KEY: misc_feature
<223> OTHER INFORMATION: CCMP1516 TrifuncB

<400> SEQUENCE: 16

Met Leu Gln Leu Ser Thr Arg Leu Arg Ala Val Arg Pro Ala Ile Val
1               5                   10                  15
```

Arg Ala Arg Ala Arg Ser Thr Ala Ala Ser Thr Gly Gln Lys Lys Val
                20                  25                  30

Val Leu Val Asp Gly Cys Arg Ile Pro Phe Gln Pro Ser Arg Gly Glu
            35                  40                  45

Tyr Phe Asp Leu Met Ser Tyr Asp Leu Thr Arg Leu Ala Met His Gly
        50                  55                  60

Leu Leu Thr Lys Thr Ala Val Asp Pro Lys Ala Ile Asp Tyr Val Leu
65                  70                  75                  80

Trp Gly Lys Val Ile Gln Glu Pro Lys Thr Ser Asn Ile Ala Arg Asp
                85                  90                  95

Ala Ala Phe Ala Ala Gly Ile Pro Arg Gly Val Pro Ala His Thr Val
            100                 105                 110

Thr Gln Ala Cys Ile Ser Ser Asn Gln Ala Ile Cys Thr Gly Ala Ser
        115                 120                 125

Gln Ile Leu Ser Gly Gln Ala Glu Val Val Leu Ala Gly Gly Val Glu
    130                 135                 140

Thr Phe Ser Asp Ala Pro Ile Arg Tyr Ser Arg Pro Ile Arg Lys Lys
145                 150                 155                 160

Leu Ile Lys Met Ser Lys Ala Lys Ser Pro Gly Gln Met Ala Ser Ile
                165                 170                 175

Phe Phe Lys Gly Leu Lys Met Lys Asp Leu Ala Pro Glu Gln Pro Ala
            180                 185                 190

Ile Ala Asn Phe Leu Thr Gly Glu Val Met Gly His Asn Ala Asp Arg
        195                 200                 205

Leu Ser Asp Arg Phe Gly Val Ser Arg Arg Glu Gln Glu Glu Phe Ala
    210                 215                 220

Leu Arg Ser His Leu Asn Ala Ala Asn Ala His Ala Asp Gly Phe Tyr
225                 230                 235                 240

Asp Gly Glu Val Ile Ala Gly Pro Gly Gly Lys Thr Leu Glu Asp Gly
                245                 250                 255

Pro Arg Ala Asp Ser Ser Leu Glu Lys Met Ala Thr Leu Lys Pro Ala
            260                 265                 270

Phe Val Lys Pro His Gly Thr Val Thr Ala Ala Ser Ala Ser Pro Phe
        275                 280                 285

Thr Asp Gly Ala Ser Ala Thr Leu Leu Met Ser Asp Gly Lys Ala Ser
    290                 295                 300

Glu Leu Gly Leu Ser Pro Lys Ala Glu Leu Leu Ala Tyr Ala Phe Val
305                 310                 315                 320

Ala Cys Asp Pro Phe Glu Glu Leu Leu Leu Gly Pro Thr Tyr Gly Ala
                325                 330                 335

Ser Lys Val Leu Arg Met Ala Gly Leu Ser Leu Lys Asp Ile Asp Val
            340                 345                 350

Ile Glu Phe His Glu Ala Phe Ala Gly Gln Val Leu Ser Asn Leu Val
        355                 360                 365

Ala Met Asp Ser Asp Lys Phe Phe Ala Glu Asn Leu Pro Gly Val Asp
    370                 375                 380

Lys Val Gly Ser Val Asp Met Thr Lys Leu Asn Thr Lys Gly Gly Ser
385                 390                 395                 400

Leu Ser Ile Gly His Pro Phe Gly Ala Thr Gly Ala Arg Leu Val Thr
                405                 410                 415

Thr Ala Ala Asn Arg Leu Val Lys Glu Gly Gly Thr Tyr Ala Leu Val
            420                 425                 430

Ala Ala Cys Ala Asp Gly Gly Leu Gly His Ala Cys Ile Leu Lys Arg 435                 440                 445

Tyr Gly Ala
        450

<210> SEQ ID NO 17
<211> LENGTH: 451
<212> TYPE: PRT
<213> ORGANISM: Emiliania huxleyi
<220> FEATURE:
<221> NAME/KEY: misc_feature
<223> OTHER INFORMATION: CCMP1516 TrifuncB

<400> SEQUENCE: 17

Met Leu Gln Leu Ser Thr Arg Leu Arg Ala Val Arg Pro Ala Ile Val
1               5                   10                  15

Arg Ala Arg Ala Arg Ser Thr Ala Ala Ser Thr Gly Gln Lys Lys Val
            20                  25                  30

Val Leu Val Asp Gly Cys Arg Ile Pro Phe Gln Pro Ser Arg Gly Glu
        35                  40                  45

Tyr Phe Asp Leu Met Ser Tyr Asp Leu Thr Arg Leu Ala Met His Gly
    50                  55                  60

Leu Leu Thr Lys Thr Ala Val Asp Pro Lys Ala Ile Asp Tyr Val Leu
65                  70                  75                  80

Trp Gly Lys Val Ile Gln Glu Pro Lys Thr Ser Asn Ile Ala Arg Asp
                85                  90                  95

Ala Ala Phe Ala Ala Gly Ile Pro Arg Gly Val Pro Ala His Thr Val
            100                 105                 110

Thr Gln Ala Cys Ile Ser Ser Asn Gln Ala Ile Cys Thr Gly Ala Ser
        115                 120                 125

Gln Ile Leu Ser Gly Gln Ala Glu Val Val Leu Ala Gly Gly Val Glu
    130                 135                 140

Thr Phe Ser Asp Ala Pro Ile Arg Tyr Ser Arg Pro Ile Arg Lys Lys
145                 150                 155                 160

Leu Ile Lys Met Ser Lys Ala Lys Ser Pro Gly Gln Met Ala Ser Ile
                165                 170                 175

Phe Phe Lys Gly Leu Lys Met Lys Asp Leu Ala Pro Glu Gln Pro Ala
            180                 185                 190

Ile Ala Asn Phe Leu Thr Gly Glu Val Met Gly His Asn Ala Asp Arg
        195                 200                 205

Leu Ser Asp Arg Phe Gly Val Ser Arg Arg Glu Gln Glu Glu Phe Ala
    210                 215                 220

Leu Arg Ser His Leu Asn Ala Ala Asn Ala His Ala Asp Gly Phe Tyr
225                 230                 235                 240

Asp Gly Glu Val Ile Ala Gly Pro Gly Gly Lys Thr Leu Glu Asp Gly
                245                 250                 255

Pro Arg Ala Asp Ser Ser Leu Glu Lys Met Ala Thr Leu Lys Pro Ala
            260                 265                 270

Phe Val Lys Pro His Gly Thr Val Thr Ala Ala Ser Ala Ser Pro Phe
        275                 280                 285

Thr Asp Gly Ala Ser Ala Thr Leu Leu Met Ser Asp Gly Lys Ala Ser
    290                 295                 300

Glu Leu Gly Leu Ser Arg Lys Ala Glu Leu Leu Ala Tyr Ala Phe Val
305                 310                 315                 320

Ala Trp Asp Pro Leu Glu Glu Leu Leu Leu Gly Pro Thr Tyr Gly Ala
                325                 330                 335

-continued

```
Ser Lys Val Leu Arg Met Pro Gly Leu Ser Leu Lys Asp Ile Asp Val
                340                 345                 350

Ile Glu Phe His Glu Ala Phe Ala Gly Gln Val Leu Ser Asn Leu Val
            355                 360                 365

Ala Met Asp Ser Asp Lys Phe Phe Ala Glu Asn Leu Pro Gly Val Asp
        370                 375                 380

Lys Val Gly Ser Val Asp Met Thr Lys Leu Asn Thr Lys Gly Gly Ser
385                 390                 395                 400

Leu Ser Ile Gly His Pro Phe Gly Ala Thr Gly Ala Arg Leu Val Thr
                405                 410                 415

Thr Ala Ala Asn Arg Leu Val Lys Glu Gly Gly Thr Tyr Ala Leu Val
            420                 425                 430

Ala Ala Cys Ala Asp Gly Gly Leu Gly His Ala Cys Ile Leu Lys Arg
        435                 440                 445

Tyr Gly Ala
    450

<210> SEQ ID NO 18
<211> LENGTH: 449
<212> TYPE: PRT
<213> ORGANISM: Aureococcus anophagefferens
<220> FEATURE:
<221> NAME/KEY: misc_feature
<223> OTHER INFORMATION: TrifuncB

<400> SEQUENCE: 18

Met Leu Gly Leu Lys Ser Leu Ser Ser Arg Ala Leu Ser Arg Ala
1               5                   10                  15

Arg Ser Leu Ser Thr Gly Gly Lys Asn Val Val Ile Val Asp Gly Val
            20                  25                  30

Arg Ile Pro Phe Ala Leu Ser Gln Thr Ile Tyr Gln Asp Val Met Ala
        35                  40                  45

Val Asp Leu Ala Lys Met Ser Leu Thr Gly Leu Met Gln Lys Thr Gly
    50                  55                  60

Leu Asp Ala Ser Leu Val Asp Tyr Val Leu Tyr Gly Thr Val Ile Gln
65                  70                  75                  80

Glu Ser Arg Thr Ser Asn Ile Ala Arg Glu Ala Ala Met His Ala Gly
                85                  90                  95

Tyr Pro Ile Asp Val Pro Ala His Thr Val Thr Leu Ala Cys Val Ser
            100                 105                 110

Ser Asn Ala Ala Ile Cys Gln Gly Ala Glu Lys Ile Leu Ala Gly Gln
        115                 120                 125

Ala Asp Val Val Val Ala Gly Gly Cys Glu Thr Phe Ser Asp Val Pro
    130                 135                 140

Ile Arg Tyr Ser Arg Pro Val Arg Lys Arg Leu Leu Gly Ala Ala Lys
145                 150                 155                 160

Ala Leu Lys Lys Gly Pro Ala Gly Ala Leu Gly Leu Lys Gly Leu
                165                 170                 175

Lys Leu Lys Asp Leu Ala Pro Glu Ala Pro Ser Ile Ser Asn Phe Thr
            180                 185                 190

Thr Gly Glu Val Met Gly His Ser Ser Asp Arg Leu Ala Ala Lys Phe
        195                 200                 205

Gly Ile Ser Arg Lys Asp Gln Asp Tyr Thr Leu Met Ser His Thr
    210                 215                 220

Arg Ala Gln Gln Ala His Asp Asp Gly Leu Tyr Ala Glu Glu Leu Val
225                 230                 235                 240
```

-continued

```
Pro Gly Val Gln Gly Ala Asp Leu Ser Glu Asn Gly Ile Lys Ala Gly
                245                 250                 255

Ser Thr Pro Glu Lys Leu Ala Lys Leu Lys Pro Ala Phe Ile Lys Asn
            260                 265                 270

Glu Thr Gly Thr His Thr Ala Ala Asn Ser Ser Phe Leu Thr Asp Gly
        275                 280                 285

Ala Ala Ala Thr Leu Val Met Ser Glu Glu Lys Ala Leu Ala Leu Gly
    290                 295                 300

Phe Lys Pro Lys Ala Tyr Leu Arg His Trp Thr Phe Ala Ala Val Asp
305                 310                 315                 320

Pro Phe Glu Glu Leu Leu Leu Gly Pro Thr Tyr Ala Val Ser Lys Val
                325                 330                 335

Leu Asn Asp Ala Lys Leu Asp Leu Lys Asp Val Gly Val Val Glu Met
            340                 345                 350

His Glu Ala Phe Ala Gly Gln Val Leu Ser Asn Phe Ala Ala Met Asn
        355                 360                 365

Ser Asp Lys Phe Ala Ala Asp Phe Leu Pro Asn Arg Thr Gln Lys Leu
    370                 375                 380

Gly Glu Met Asp Phe Ala Lys Val Asn Thr Gln Gly Gly Ser Leu Ser
385                 390                 395                 400

Leu Gly His Pro Phe Gly Ala Thr Gly Ser Arg Ile Val Thr Thr Ala
                405                 410                 415

Ser Asn Arg Leu Gln Arg Ser Gly Glu Gln Phe Ala Leu Val Ala Ala
            420                 425                 430

Cys Ala Asp Gly Gly Ile Gly His Ser Cys Leu Leu Glu Arg Tyr Pro
        435                 440                 445

Asn

<210> SEQ ID NO 19
<211> LENGTH: 472
<212> TYPE: PRT
<213> ORGANISM: Ectocarpus siliculosus virus
<220> FEATURE:
<221> NAME/KEY: misc_feature
<223> OTHER INFORMATION: Acetyl-CoA acetyltransferase subunit, putative
      mitochondrial presursor Acetyl-CoA

<400> SEQUENCE: 19

Met Val His Gln Gly Val Thr Ala Thr Met Arg Ser Ala Arg Ala Ala
1               5                   10                  15

Met Val Ser Ser Arg Ala Ala Ala Ala Ala Arg Ala Ser Cys
            20                  25                  30

Gly Arg Arg Ala Asn Ser Ser Ala Ser Ser Ser Ser Ser Ser
        35                  40                  45

Ser Arg Lys Pro Val Phe Val Asp Gly Ala Arg Ile Pro Phe Val Leu
    50                  55                  60

Ser Gly Thr Thr Tyr Lys Asp Leu Leu Ala Val Asp Leu Gly Lys Leu
65                  70                  75                  80

Ala Leu Arg Gly Leu Leu Asn Arg Asn Pro Glu Leu Asp Pro Lys Asp
                85                  90                  95

Val Asp Tyr Leu Leu Phe Gly Thr Val Ile Gln Glu Ser Arg Thr Ser
            100                 105                 110

Asn Ile Ala Arg Glu Ala Gly Met Gly Ala Gly Ile Pro Val Ser Val
        115                 120                 125

Pro Ser His Thr Val Ser Gln Ala Cys Ile Ser Ala Asn Gln Ala Met
```

```
            130                 135                 140

Cys Asn Gly Ala Glu Lys Ile Leu Ala Gly Thr Ala Asp Val Val Leu
    145                 150                 155                 160

Ala Gly Gly Val Glu Thr Phe Ser Asp Leu Pro Ile Arg Phe Ser Arg
                    165                 170                 175

Pro Ile Arg Asn Arg Leu Leu Asn Leu Gly Lys Ala Lys Lys Lys Gly
                180                 185                 190

Leu Pro Gly Val Leu Gly Leu Lys Gly Leu Lys Leu Lys Asp Ile
            195                 200                 205

Ala Pro Glu Thr Pro Ala Ile Ala Asn Tyr Thr Thr Gly Glu Val Met
        210                 215                 220

Gly His Ser Ser Asp Arg Leu Ser Gly Arg Phe Gly Ile Ser Arg Gln
    225                 230                 235                 240

Glu Gln Asp Glu Phe Ala Leu Arg Ser His Gln Asn Ala Ala Lys Ala
                    245                 250                 255

His Ala Asp Gly Ile Tyr Asp Gln Glu Ile Ile Pro Val Asp Gly Ser
                260                 265                 270

Thr Asp Glu Asn Gly Val Lys Gly Glu Ser Thr Leu Glu Lys Leu Gly
            275                 280                 285

Ser Leu Lys Pro Ala Phe Val Lys Pro His Gly Thr His Thr Ala Ala
        290                 295                 300

Asn Ser Ser Phe Leu Ser Asp Gly Ala Ser Ala Leu Ile Met Ser
    305                 310                 315                 320

Glu Gly Arg Ala Leu Glu Met Gly Leu Ala Pro Arg Ser Ser Phe Lys
                    325                 330                 335

Ser Trp Ala Phe Val Ala Leu Asp Pro Phe Glu Asp Leu Leu Leu Gly
                340                 345                 350

Pro Ala Phe Gly Ala Ala Lys Val Leu Asp Asp Ala Gly Leu Thr Leu
            355                 360                 365

Ser Asp Ile Asp Val Phe Glu Ile His Glu Ala Phe Ala Gly Gln Val
        370                 375                 380

Leu Ser Asn Leu Ala Ala Met Asn Ser Thr Asp Phe Ala Gln Lys Ser
    385                 390                 395                 400

Met Gly Arg Ser Ala Lys Leu Gly Glu Val Pro Met Glu Lys Leu Asn
                    405                 410                 415

Ile His Gly Gly Ser Leu Ser Leu Gly His Pro Phe Gly Ala Thr Gly
                420                 425                 430

Val Arg Leu Val Ala Thr Ala Thr Asn Arg Leu His Arg Glu Gly Gly
            435                 440                 445

Arg Tyr Ala Leu Val Ala Ala Cys Ala Asp Gly Gly Leu Gly His Ala
        450                 455                 460

Cys Ile Val Glu Arg Tyr Asp Ser
    465                 470

<210> SEQ ID NO 20
<211> LENGTH: 843
<212> TYPE: PRT
<213> ORGANISM: Nannochloropsis gaditana
<220> FEATURE:
<221> NAME/KEY: misc_feature
<223> OTHER INFORMATION: PXA amino acid

<400> SEQUENCE: 20

Met Ala Pro Ser Phe Ser His Arg Gly Gln Lys Arg His Asp Asn Val
1               5                  10                  15
```

Val Ser Ala Phe Phe Asn Ser Phe Met Ser Ala Gly Glu Gln Lys Phe
            20                  25                  30

Thr Val Val Ser Ser Leu Phe Ser Ser Gly Leu Phe Leu Val Ala Leu
        35                  40                  45

Ala Leu Val Lys Gln Leu Ser Ser Leu Gln Glu Gln Glu Glu Lys Val
50                  55                  60

Ala Ala Ser Leu Glu Arg Gln Asp Pro Ser Lys Glu Gly Gly Ser Leu
65                  70                  75                  80

Ala Ala Pro Leu Pro Gln Pro Asp Gly Arg Cys Gln Thr Pro Gln Pro
                85                  90                  95

Pro Pro Pro Ser Pro Pro Ser Ala Ser Pro Ser Ser Phe Ser Ala
                100                 105                 110

Thr Ser Thr Ala Arg Thr Arg Ser Pro Asn Ala Asp Ala Leu Thr Arg
        115                 120                 125

Ser Gly Arg Asp Ala Ala Gly His Gly Glu Arg Gly Ser Gly Gly Met
        130                 135                 140

Arg Arg Pro Gly Gly Pro Pro Leu Pro Gln Glu Gly Gln Arg Val Ala
145                 150                 155                 160

Leu Asp Asp Glu Phe Gly Arg Gln Leu Leu Ser Leu Leu His Lys Leu
                165                 170                 175

Ile Pro Ser Trp Lys Thr Arg Glu Ala Ala Cys Leu Gly Gly Met Val
                180                 185                 190

Phe Leu Leu Leu Ala Arg Ser Ala Cys Asp Leu Arg Met Ile Asn Leu
            195                 200                 205

Val Val Gly Ala Glu Lys Ala Ile Val Leu Gly Asn Arg Pro Ala Phe
210                 215                 220

Arg Ile Ser Leu Ala Arg Phe Leu Arg Phe Met Val Pro Val Ala Cys
225                 230                 235                 240

Val Asn Ala Leu Leu Lys Tyr Thr Thr Arg Glu Leu Ser Leu Gly Leu
                245                 250                 255

Arg Gln Arg Leu Thr Glu His Leu Gln Ser Lys Tyr Met Lys Gly Phe
            260                 265                 270

Thr Phe Tyr Ser Met Ala Val Met Glu Gly His Ala Arg Glu Ile Glu
        275                 280                 285

Gln Leu Met Thr Val Asp Val Asp Lys Phe Ser Leu Cys Ile Thr Glu
290                 295                 300

Leu Ala Ser Asn Leu Leu Lys Pro Thr Leu Asp Ile Leu Leu Tyr Ala
305                 310                 315                 320

Thr Lys Leu Gln Thr Ser Val Gly Pro Leu Ile Pro Leu Ala Met Ala
                325                 330                 335

Ser Tyr Leu Phe Ser Ser Gly Thr Ala Leu Thr Arg Leu Arg Arg Pro
            340                 345                 350

Ala Ala Glu Tyr Thr Ala Ala Ile Gln Arg Arg Glu Gly Asp Tyr Arg
        355                 360                 365

Phe Val Thr Asn Arg Met Val Ala His Ala Glu Ile Ala Phe Tyr
        370                 375                 380

Asp Gly Val Gly Arg Glu Lys Asn Tyr Leu Gln Gln Ile Phe Gly Ser
385                 390                 395                 400

Leu Leu Gly Thr Ile Arg Arg Gly Ser Arg Phe Arg His Ala Met Asp
                405                 410                 415

Ile Leu Asp Ser Val Met Ala Lys Tyr Ile Ala Thr Ala Leu Gly Trp
            420                 425                 430

Val Leu Leu Asn Arg Ala Ala Gln Gln Gln Lys Gln Glu Ala Leu Pro

```
                435                 440                 445
Val Pro Ser Pro Ala Leu Pro Pro Ser Pro Ala Ala Ser Ser Tyr Asp
450                 455                 460
Ser Phe His Gln Ser Ala Arg Met Met Phe Asn Phe Ala Gln Ala Leu
465                 470                 475                 480
Ser Ala Ile Val Leu Ala Gly Arg Glu Ala Thr Arg Leu Ala Gly Tyr
                485                 490                 495
Thr Ser Arg Val Thr Arg Leu Glu Arg Leu Ile Asp Asp Leu Glu Arg
                500                 505                 510
Glu Asp Glu Ala Arg Ser Thr Ala Ser Glu Phe Leu Glu Lys Lys Asp
                515                 520                 525
Val Ile Glu Leu Gln Gly Val Pro Ile Val Ala Pro Val Val Gly Asn
                530                 535                 540
Gly Arg Lys Asp Ser Asp Gly Arg Gly Arg Lys Gly Arg Glu
545                 550                 555                 560
Gly Gly Arg Val Arg Arg Leu Thr Ser Pro Leu Thr Leu Arg Ile Glu
                565                 570                 575
Pro Gly Met His Val Leu Val Thr Gly Pro Asn Gly Ser Gly Lys Ser
                580                 585                 590
Ser Leu Phe Arg Met Ile Cys Gly Leu Trp Pro Val Ser Glu Gly Arg
                595                 600                 605
Leu Ile Lys Pro Pro Arg Ser Gln Leu Phe Tyr Ile Pro Gln Arg Pro
610                 615                 620
Tyr Leu Pro Leu Gly Ser Leu Arg Asp Gln Val Ile Tyr Pro His Ser
625                 630                 635                 640
Gln Ala Glu Met Ala Ala Leu Gly Arg Thr Asp Ala Asp Val Leu Ala
                645                 650                 655
Leu Leu Asp Glu Val Gln Leu Ser Phe Leu Ala Pro Pro Arg Val Val
                660                 665                 670
Gly Pro Glu Ser Asn Ala Ser Asp Ala Leu Pro Ser Leu Pro Ser Ser
                675                 680                 685
Leu Pro Ser Ser Leu Pro Ser Ser Leu Pro Ser Phe Pro Ser Phe
690                 695                 700
Ser Ser Leu Ala Gln Val Leu Thr Arg Pro Ser Pro Thr Thr Pro Glu
705                 710                 715                 720
Glu Glu Glu Gly Arg Glu Gly Gly Arg Glu Gly Gly Arg Glu Gly Gly
                725                 730                 735
Leu Glu Arg Val Cys Asp Trp Gly Glu Thr Leu Ser Gly Gly Glu Lys
                740                 745                 750
Gln Arg Leu Ala Phe Ala Arg Leu Tyr Tyr His Arg Pro Arg Phe Ala
                755                 760                 765
Ile Leu Asp Glu Cys Thr Ser Ala Val Ser Ser Asp Val Glu Asp His
                770                 775                 780
Leu Tyr Arg Gln Ala Gln Ala Leu Gly Ile Thr Leu Leu Thr Val Ala
                785                 790                 795                 800
His Arg Gln Ala Leu Trp Lys His His Glu Tyr Leu Leu Met Leu Asp
                805                 810                 815
Gly Lys Gly Gly Trp Ser Phe Arg Pro Met Gln Thr Leu Glu Pro Glu
                820                 825                 830
Ala Ala Glu Gly Asp Gly Asp Ile Lys Tyr Thr
                835                 840

<210> SEQ ID NO 21
```

<211> LENGTH: 2532
<212> TYPE: DNA
<213> ORGANISM: Nannochloropsis gaditana
<220> FEATURE:
<221> NAME/KEY: misc_feature
<223> OTHER INFORMATION: PXA coding sequence

<400> SEQUENCE: 21

| | | | | | |
|---|---|---|---|---|---|
| atggcccctt | ccttctccca | tcgcggtcaa | aaacggcacg | acaatgtggt | ttctgctttt | 60 |
| ttcaactcct | ttatgtccgc | tggcgagcaa | aaattcacgg | tggtctcatc | tcttttctcg | 120 |
| agcgggttgt | tcctagttgc | cttagccctc | gtgaaacagc | tgtcgagcct | acaagagcaa | 180 |
| gaagaaaagg | ttgctgcgtc | cctagaacgc | aagacccaa | gcaaggaagg | aggaagtctg | 240 |
| gcggcaccct | tgccccagcc | tgacggcagg | tgccagaccc | ccagcctcc | cctccctca | 300 |
| cccccaccct | ccgcctcgcc | ctcctccttc | tcagcgacct | ccacagcccg | gactaggagt | 360 |
| cccaatgccg | atgctttgac | gaggtcgggg | agggatgctg | ccggccatgg | agaaagaggg | 420 |
| agcggggggca | tgaggagacc | aggcggccct | ccgctaccgc | aggaagggca | gagggtggct | 480 |
| ctggacgatg | aattcggaag | gcagctctta | agccttctcc | acaaattaat | ccccagctgg | 540 |
| aagacgcgtg | aagccgcctg | cctaggaggc | atggttttcc | tcctcctggc | tcgcagcgcc | 600 |
| tgtgacttgc | gaatgataaa | cctggtggtg | ggggcggaga | aggcgatcgt | gttgggcaat | 660 |
| cggcccgcct | tcaggatctc | tttggcgcgc | ttttaagat | tcatggtgcc | tgtgcctgt | 720 |
| gtgaatgccc | tgctcaagta | cacaacgaga | gagctctctc | ttggcctccg | tcaacgactc | 780 |
| acagagcatc | ttcagtctaa | atacatgaaa | ggctttacct | tctactctat | ggcggtcatg | 840 |
| gaagggcatg | cgagggaaat | cgagcagctt | atgaccgtgg | acgtggacaa | gttctccctg | 900 |
| tgcattacgg | agctggcctc | aaacctccta | agccaaccc | ttgatattct | tctttacgca | 960 |
| acaaaattac | aaacctcggt | cggtcctctg | atcccgttag | ccatggctag | ctacctcttc | 1020 |
| tcctctggca | cagccttgac | gcgcctgcga | agacctgccg | cagagtatac | ggccgcgatc | 1080 |
| caacggcgcg | agggcgacta | cagatttgtg | acgaatagaa | tggtcgcgca | cgccgaagag | 1140 |
| atcgctttct | acgatggagt | ggggagggaa | aaaaactacc | tgcagcagat | cttcggttct | 1200 |
| ttgttgggaa | cgatccggcg | cggctcccgg | ttccgccacg | cgatggacat | cctcgatagt | 1260 |
| gtcatggcca | agtacatagc | caccgctctt | ggctgggtgc | ttttgaatcg | cgcggctcag | 1320 |
| caacagaaac | aagaagcgct | tcctgtcccc | tctcccgccc | tcccaccctc | cccgctgcc | 1380 |
| tcttcctacg | actctttcca | tcaatccgct | cgcatgatgt | tcaactttgc | acaggccctc | 1440 |
| tccgccatcg | tcctggcggg | cagggaggcg | acgcgtctgg | caggctatac | ctctcgggtc | 1500 |
| acgcgcctcg | aacgcctcat | tgatgacctg | gagcgcgaag | acgaagcaag | atccaccgca | 1560 |
| tcggagtttt | tggagaagaa | agatgtgata | gagctccagg | gtgtgcccat | cgtcgctccg | 1620 |
| gtcgtcggca | atggccgcaa | ggacagcgac | ggcgggaggg | gagggagaaa | aggaagggaa | 1680 |
| ggagggaggg | tacggcgatt | gacatctcct | ctgaccctga | gaattgagcc | aggcatgcac | 1740 |
| gtcctcgtca | caggaccgaa | tggaagtggg | aaatcgtctc | ttttccgaat | gatctgtggc | 1800 |
| ctctggcctg | tctccgaagg | gcgcctcatc | aaacctcctc | gatcccagct | cttctacata | 1860 |
| ccccaacgac | cctacctccc | gcttggaagc | ttgcgggatc | aggtgattta | ccctcactcc | 1920 |
| caggccgaga | tggcggcact | agggaggacg | gatgcagatg | tgctggcgct | tttggatgag | 1980 |
| gttcaactct | ccttccttgc | ccccccccgg | gtggtaggac | cggagagcaa | cgccagcgat | 2040 |
| gctctgccct | ccctcccttc | ctccctccct | tcctccctcc | cttcctccct | tcctcccctcc | 2100 |

-continued

```
tttccgtcttt tctcctccttt ggcccaagtc ctcacccggc catcgcctac gaccccggaa    2160
gaggaggaag ggagggaggg agggagggag ggagggaggg agggagggtt ggagcgagtc    2220
tgcgactggg gcgagacatt gtcgggggc gagaagcagc ggctggcttt tgcccgtctc     2280
tattaccacc gaccgcgctt tgccatcttg gacgagtgca cgagcgccgt gtcgagcgat    2340
gtggaggacc atctgtacag acaggcgcag gcactcggca tcaccttgct cacagtggcg    2400
catcggcagg ccttgtggaa acatcatgaa tatctgctga tgctggatgg gaaaggggc     2460 tggtctttta ggcccatgca gacactggaa ccggaagctg ccgaagggga cggagatata    2520
aagtacacct ga                                                        2532
```

<210> SEQ ID NO 22
<211> LENGTH: 716
<212> TYPE: PRT
<213> ORGANISM: Nannochloropsis gaditana
<220> FEATURE:
<221> NAME/KEY: misc_feature
<223> OTHER INFORMATION: Acyl-CoA oxidase amino acid

<400> SEQUENCE: 22

```
Met Thr Thr Ala Asn Ala Arg Leu Ser Arg Leu Lys Asp His Leu Ala
1               5                   10                  15

Glu Thr Gly Ala Val Ala Arg Ala Pro Ile Ser Ser Ser Ala Ile Asn
            20                  25                  30

Ala Thr Pro Phe Ala Ala Arg Thr Thr His Thr Met Glu Arg Met Ala
        35                  40                  45

Arg Glu Arg Ala Lys Ala Ser Phe Pro Val Arg Asp Met Thr Tyr Phe
    50                  55                  60

Leu Asp Gly Gly Arg Ser Met Thr Glu Val Lys Glu Gly Met Met Ala
65                  70                  75                  80

Asp Leu Ala Ala Asn Pro Val Phe Thr Asp Pro Glu Trp Asn Asp Leu
                85                  90                  95

Asn Arg Asp Gln Ile Arg Glu Arg Thr Ile Ser Arg Leu Arg Ala Ala
            100                 105                 110

Tyr Lys Leu Leu Ile Arg Asp Gly Ala Asp Val Ser Arg Arg Asn Ala
        115                 120                 125

Arg Leu Glu Ile His Ala Leu His Asp Leu Gly Trp Tyr Val Arg Gln
    130                 135                 140

Gly Val His Phe Gly Leu Phe Met Gly Ala Leu Ala Gly Gln Gly Ser
145                 150                 155                 160

Asp Glu Gln Arg Ala Glu Trp Leu Pro Arg Thr Met Met Cys Glu Ile
                165                 170                 175

Tyr Gly Cys Phe Gly Met Thr Glu Leu Gly His Gly Ser Phe Leu Arg
            180                 185                 190

Gly Leu Glu Thr Thr Ala Met Tyr Asp Lys Asp Thr Gln Glu Phe Val
        195                 200                 205

Ile Asn Ser Pro Thr Asp Thr Ser Thr Lys Trp Trp Ile Gly Ala Ala
    210                 215                 220

Gly Gln Thr Ala Thr His Ser Val Val Phe Ala Arg Leu Leu Leu Pro
225                 230                 235                 240

Ser Gly Asp Asp Met Gly Val His Asn Phe Ile Ile Pro Leu Arg Asp
                245                 250                 255

Met Glu Thr His Leu Pro Leu Pro Gly Ile His Ile Gly Asp Leu Gly
            260                 265                 270

Ala Lys Met Gly Leu Asn Gly Ile Asp Asn Gly Trp Met Gln Phe Asp
```

```
              275                 280                 285
His Val Arg Val Pro Arg Asp Asn Met Leu Cys Arg Tyr Ala Gln Val
290                 295                 300

Thr Pro Glu Gly Lys Tyr Ile Arg Pro Arg Lys Glu Met Ala Tyr
305                 310                 315                 320

Gly Ala Leu Ile Gly Thr Arg Ala Ala Leu Val Lys Thr Ala Val Asp
                    325                 330                 335

Phe Gln Lys Lys Ala Leu Met Ile Gly Ile Arg Tyr Thr Ala Leu Arg
            340                 345                 350

Thr Gln Gly Val Val Glu Glu Gly Gln Arg Glu Glu Thr Ala Ile Ile
                355                 360                 365

Asp Tyr Pro Ile His Arg Asp Lys Leu Leu Lys Leu Leu Ala Ala Ala
370                 375                 380

Tyr Ala Trp His Phe Gln Ala Ala Tyr Val Leu His Leu Asn Asp Ser
385                 390                 395                 400

Leu Glu Glu Gly Leu Glu Ala Gly Asp Leu Ser Ile Leu Lys Asp Val
                    405                 410                 415

His Gly Thr Met Ala Gly Leu Lys Ala Phe Gly Thr Trp Phe Thr Tyr
                420                 425                 430

Asn Thr Ile Glu Ala Cys Arg Gln Val Cys Gly Gly His Gly Tyr Ser
                435                 440                 445

Lys Tyr Asn Gly Leu Ser Asn Thr Leu Gln Asp Phe Ala Val Met Cys
450                 455                 460

Thr Trp Glu Gly Asp Asn Thr Val Met Ala Leu Gln Thr Ala Arg Tyr
465                 470                 475                 480

Leu Val Arg Ser Tyr Glu Lys Ala Lys Arg Gly Gly Glu Thr Leu Ala
                485                 490                 495

Gly Ser Val Ser Tyr Leu Gln Asp Ala His Pro Pro Ala Trp Arg Ala
                500                 505                 510

Arg Ser Ala Glu Asp Leu Met Asn Met Glu Val Gln Met Glu Ala Trp
                515                 520                 525

Arg Ala Leu Leu Ala Ala Lys Val Ser Arg Ala Ser Glu Arg Val Leu
                530                 535                 540

Ala Arg Gln Ala Ala Leu Arg Gly Asn Glu Ala Gln Ala Phe Asn Glu
545                 550                 555                 560

His Gln Val Glu Leu Phe Glu Cys Ala Lys Thr His Val Tyr Phe Asn
                565                 570                 575

Val Ala Ala Arg Phe Ala Glu Ala Val Val Glu Ala Gly Thr Thr His
                580                 585                 590

Pro Ala Leu Ala Pro Val Leu Ala Arg Leu Cys His Leu Phe Ser Leu
                595                 600                 605

Ser Ser Leu Leu Glu Asp Glu Ala Ser Leu Leu Ala Ser Gly Phe Ala
                610                 615                 620

Ser Ala Gly Gln Met Gln Leu Ile Arg Glu Ala Val Gly Ala Leu Leu
625                 630                 635                 640

Leu Ala Leu Arg Pro Asp Ala Val Ala Leu Val Asp Ala Phe Asn Tyr
                645                 650                 655

Ser Asp Glu Val Leu Asn Ser His Leu Gly Thr Ala Asn Gly Asp Ile
                660                 665                 670

Tyr Thr Gly Tyr Leu Gln Gln Val Gln Arg Leu Val Pro Glu Asn Lys
                675                 680                 685

Leu Ala Val Ala Pro Tyr Ile Met Arg Glu Val Lys Pro Leu Met Gln
690                 695                 700
```

Gly Ala Asp Leu Ile Ser Thr Asp Glu Glu Glu Asp
705                 710                 715

<210> SEQ ID NO 23
<211> LENGTH: 2151
<212> TYPE: DNA
<213> ORGANISM: Nannochloropsis gaditana
<220> FEATURE:
<221> NAME/KEY: misc_feature
<223> OTHER INFORMATION: Acyl-CoA oxidase cDNA

<400> SEQUENCE: 23

| | | | | | |
|---|---|---|---|---|---|
| atgacgaccg | ccaatgcccg | tttgtcgagg | ctcaaagatc | atttagcaga | gacgggggct | 60 |
| gtggcgcgcg | cgccgattag | ctcctctgcc | atcaatgcca | cgccttttgc | ggcgaggacg | 120 |
| acgcatacca | tggagcgcat | ggcaagggaa | cgagccaagg | cctccttccc | cgtccgagac | 180 |
| atgacgtact | tcttggacgg | cgggaggagc | atgaccgagg | tcaaggaggg | catgatggcg | 240 |
| gacttggcgg | cgaatccggt | ctttacggac | ccagaatgga | acgacttgaa | cagagatcag | 300 |
| atccgtgaac | gcaccatctc | tcgactgaga | gctgcgtaca | agctcctgat | ccgagacggt | 360 |
| gccgatgtca | gccgccggaa | tgcccggctt | gagattcacg | ccctccatga | cttggggtgg | 420 |
| tacgtgcggc | agggtgtgca | tttcggcctc | tttatgggcg | ccttggccgg | gcaggggagc | 480 |
| gacgaacaac | gcgctgagtg | gctgcccagg | accatgatgt | gtgagatcta | cggggtgcttc | 540 |
| gggatgacgg | agttggggca | cggctcattc | ttgcggggcc | tggagaccac | agcgatgtac | 600 |
| gacaaggaca | cgcaagaatt | tgtaatcaat | tcccccactg | acacaagcac | caaatggtgg | 660 |
| atcggtgcgg | ccgggcagac | ggccacacat | tcggtggttt | tcgcccgcct | cctccttccc | 720 |
| tcaggggacg | acatgggtgt | gcacaacttc | atcataccCc | tccgggatat | ggaaacgcac | 780 |
| ttgccCctcc | ctggcatcca | cattggcgat | tggggggcca | gatgggcttt | gaatggcatc | 840 |
| gacaacgggt | ggatgcaatt | tgaccacgtc | cgcgtgcccc | gggacaacat | gctttgtcgc | 900 |
| tacgcacagg | tcaccccgga | ggggaaatac | atccgtcctc | caggaaggaa | gatggcttac | 960 |
| ggcgctctca | tcggcactcg | ggcggctctg | tcaagacag | ccgtggactt | tcaaaaaaag | 1020 |
| gccctcatga | tcgggatccg | ctacaccgcc | ctccggacac | agggcgtggt | ggaggaaggc | 1080 |
| caaagggaag | agaccgccat | catcgactac | cccatccacc | gggacaaact | cctgaaactc | 1140 |
| ttggcggccg | cctacgcctg | gcacttccaa | gccgcctacg | ttctccacct | gaacgattcc | 1200 |
| ttggaggagg | ggctcgaggc | gggggacctc | tccatcctca | aggatgtgca | tgggaccatg | 1260 |
| gctggcctca | aggctttcgg | aacctggttc | acgtacaaca | cgatcgaggc | ctgccggcaa | 1320 |
| gtgtgcgggg | ccacgggtag | cagcaagtac | aacggcctct | ccaacaccct | ccaggacttt | 1380 |
| gctgtcatgt | gcacctggga | gggcgacaac | accgtgatgg | ctctacagac | ggcgcggtat | 1440 |
| ctagttcggt | cctacgagaa | ggcgaagcgg | ggggcgaga | ccctggcagg | ctccgtctca | 1500 |
| tacctgcagg | atgcgcatcc | cccggcttgg | cgggcgaggc | ctgcggagga | cttgatgaac | 1560 |
| atggaagtgc | agatggaggc | ctggcgggcc | ctcctagccg | ccaaggtctc | cagagcctca | 1620 |
| gagcgggtct | tggcaaggca | ggcggcgttg | cgggggaacg | aggcgcaggc | cttcaacgag | 1680 |
| catcaggtgg | agcttttcga | gtgcgccaag | acccatgtct | acttcaatgt | ggcggcgcgg | 1740 |
| tttgccgagg | cggtcgtgga | ggccggcacc | acccacccg | ccctggcccc | tgtcctcgcc | 1800 |
| cgcctctgcc | acctcttctc | tctctcgagc | cttctagaag | acgaagcctc | cctgctcgcc | 1860 |
| agcggtttcg | cctccgcggg | gcagatgcag | ctcattcgcg | aggccgtggg | cgccctcctc | 1920 |

```
ctcgccctcc gcccggacgc ggtggcccct gtcgacgcct tcaactattc cgacgaagtt    1980
ttgaactcac atttaggcac cgccaacggc gatatttata cgggctacct ccaacaggtg    2040
cagcgcctcg tccctgagaa caagctggcc gtcgccccct acatcatgag ggaggtgaag    2100
cctttaatgc aaggagcaga cctgatctcc acggacgagg aggaggactg a             2151
```

<210> SEQ ID NO 24
<211> LENGTH: 607
<212> TYPE: PRT
<213> ORGANISM: Nannochloropsis gaditana
<220> FEATURE:
<221> NAME/KEY: misc_feature
<223> OTHER INFORMATION: Isocitrate Lyase

<400> SEQUENCE: 24

```
Met Tyr Trp Lys Arg Thr Cys Cys Asp Cys Leu Gly Leu His Phe Arg
1               5                   10                  15

Thr Leu Ile Leu Asp Leu Phe Pro Cys Ser Ala Gly Ala Leu His Ser
            20                  25                  30

Asn Pro Tyr Arg Leu Ser Val Arg Lys Pro Ile Lys Ile Thr Ile Thr
        35                  40                  45

Thr Arg Thr Met Glu Glu Thr Arg Leu Tyr His Glu Asp Val Ala Ala
50                  55                  60

Thr Glu His Phe Phe Arg Asn Pro Arg Phe Ala Gln Thr Val Arg Pro
65                  70                  75                  80

Tyr Ser Ala Gln Asp Val Val Ala Leu Arg Ser Ser Leu Leu Val Glu
                85                  90                  95

Pro Ala Ser Asn Arg Gln Ala Gln Lys Leu Trp Ser Leu Leu Thr Gly
            100                 105                 110

Leu Ala Gly Gln Gly Lys Cys Ser Tyr Thr Phe Gly Ala Leu Asp Pro
        115                 120                 125

Val Gln Val Val Gln Met Ala Pro His Val Ser Thr Ile Tyr Val Ser
130                 135                 140

Gly Trp Gln Cys Ser Ser Thr Ala Ser Thr Ser Asn Glu Pro Gly Pro
145                 150                 155                 160

Asp Phe Ala Asp Tyr Pro Met Asp Thr Val Pro Asn Lys Val His Gln
                165                 170                 175

Leu Phe Ser Ala Gln Leu Phe His Asp Arg Arg Gln Gln Glu Ala Arg
            180                 185                 190

Ala Arg Met Thr Asp Ala Ser Lys Val Ala Glu Pro Pro Val Asp Tyr
        195                 200                 205

Leu Arg Pro Ile Ile Ala Asp Gly Asp Thr Gly His Gly Gly Leu Thr
210                 215                 220

Ala Val Met Lys Leu Thr Lys Met Phe Ile Glu Arg Gly Ala Ala Gly
225                 230                 235                 240

Ile His Phe Glu Asp Gln Lys Pro Gly Thr Lys Lys Cys Gly His Met
                245                 250                 255

Gly Gly Lys Val Leu Val Ser Val Gln Glu His Ile Asp Arg Leu Thr
            260                 265                 270

Ala Ala Arg Leu Gln Ala Asp Val Met Gly Ala Gln Thr Ile Ile Val
        275                 280                 285

Ala Arg Thr Asp Gly Glu Ala Ala Ser Leu Leu Asp Thr Asn Ile Asp
290                 295                 300

Ala Arg Asp His Pro Phe Ile Leu Gly Ala Thr Val Pro Gly Thr Arg
305                 310                 315                 320
```

```
Ala Leu Asn Glu Val Val Glu Ala Arg Ala Gln Gly Val Thr Gly
                325                 330                 335

Ala Glu Leu Asp Arg Ile Thr Asp Gln Trp Thr Ala Ala Asn Leu
            340                 345                 350

Arg Arg Phe Pro Glu Ala Val Cys Asp Ala Leu Ser Thr Leu Pro Asn
        355                 360                 365

Pro Ala Pro Lys Leu Ala Val Trp Lys Ala Gln Ala Tyr Asn Leu Ser
    370                 375                 380

Leu Pro Gln Ala Arg Ala Leu Ala Lys Glu Leu Met Gly Arg Glu Val
385                 390                 395                 400

Tyr Phe Asp Trp Glu Ala Pro Arg Ser Arg Glu Gly Tyr Tyr Arg Ile
                405                 410                 415

Lys Gly Gly Val Asp Tyr Cys Val Ala Arg Ala Val Ala Tyr Ala Pro
            420                 425                 430

His Ala Asp Leu Ile Trp Met Glu Thr Ala Lys Pro Asp Leu Ser Glu
        435                 440                 445

Ala Arg Glu Phe Ala Gln Gly Val Arg Ala Ala Val Pro Gly Lys Met
    450                 455                 460

Leu Ala Tyr Asn Leu Ser Pro Ser Phe Asn Trp Asp Val Ala Gly Leu
465                 470                 475                 480

Ser Pro Gln Glu Met Glu His Phe Asn Ser Ser Leu Ala Ala Met Gly
                485                 490                 495

Phe Val Trp Gln Phe Ile Thr Leu Ala Gly Phe His Ala Asn Gly Leu
            500                 505                 510

Met Thr Thr Met Phe Ala Arg Glu Tyr Gly Lys Arg Gly Val Val Ala
        515                 520                 525

Tyr Val Glu Met Ile Gln Arg Lys Glu Arg Glu Gln Glu Val Asp Met
    530                 535                 540

Leu Thr His Gln Lys Trp Ser Gly Ala Ala Leu Leu Asp Lys Gln Met
545                 550                 555                 560

Gln Thr Val Thr Gly Gly Met Ser Ser Thr Ser Ser Met Gly Lys Gly
                565                 570                 575

Val Thr Glu Ala Gln Phe Gly Ala Lys Gly Pro Gly Ala Ala Gly Val
            580                 585                 590

Ser Ser Gly Ala Gly Ala Ala Arg Ala Gly Ala Ile Ser Arg Leu
        595                 600                 605
```

<210> SEQ ID NO 25
<211> LENGTH: 1824
<212> TYPE: DNA
<213> ORGANISM: Nannochloropsis gaditana
<220> FEATURE:
<221> NAME/KEY: misc_feature
<223> OTHER INFORMATION: Isocitrate Lyase cDNA

<400> SEQUENCE: 25

| | | | | | |
|---|---|---|---|---|---|
| atgtattgga | agaggacgtg | ttgtgactgt | ctagggcttc | atttccggac | cctcattctc | 60 |
| gacctcttcc | cttgctctgc | tggcgcccct | cattccaacc | cttacagact | ttcggtgcgc | 120 |
| aagccgatca | agatcacaat | caccacaagg | acaatggagg | aaacacgcct | atatcatgaa | 180 |
| gatgttgctg | cgacagagca | ttttttccgc | aaccgcgct | tgcccaaac | tgttcggccc | 240 |
| tattcggcgc | aggacgtcgt | cgcactccgg | tccagcctcc | tggtcgaacc | tgcctccaat | 300 |
| cgacaggccc | agaagctctg | gtccctcctg | accgggctgg | ccggtcaagg | aaagtgctcg | 360 |
| tacaccttcg | gcgccctcga | ccccgttcag | gtggtgcaga | tggcccccca | cgtctccacc | 420 |

```
atttacgtga gtggctggca gtgctcctcc acggcctcca ctagcaacga gcccggccca    480
gactttgcag attaccccat ggacacggtc cccaacaagg tgcaccaact cttctccgcc    540
caactcttcc acgaccgccg ccagcaagag gcgcgagccc gcatgacgga cgcgagcaag    600
gtggcggaac cccctgtcga ctacctccgg cccatcatcg ccgacggcga cacgggccac    660
ggcggtctga ccgcggtgat gaagctgacc aagatgttca ttgagcgagg ggcggcgggg    720
attcacttcg aggatcagaa accaggcact aagaagtgcg ggcacatggg cgggaaggtg    780
ttggtgtccg tccaagagca cattgaccgg ttgacagccg cacggctgca ggcggacgtg    840 atggggcgc aaaccatcat tgtggcgcgt actgacgggg aggcggccag tcttttggac     900
accaacatcg acgcgcgcga ccatccttc atcttggggg ccacggtccc tggcacccgc     960
gccctgaatg aggtggtggc cgaggcgagg gcccagggg tgacgggcgc ggagttggac     1020
cgcattacgg accaatggac ggcggccgcc aatttgcgtc gctttccgga agctgtctgc    1080
gacgccttgt ccacgctacc caatccggcc ccgaagctcg ccgtctggaa ggctcaggcc    1140
tacaacctct ccctgccgca ggcgcgtgcg ctcgcgaagg aactgatggg ccggaggtg    1200 tacttcgact gggaggcgcc gcgttccgc gaggggtatt accgcatcaa gggtgggtg     1260 gactactgtg tagcccgggc ggtggcgtac gcgccgcacg cggatttgat ttggatggag    1320
acggcgaaac cggatctttc cgaagctagg gagttcgctc aaggggtgcg ggcggccgtg    1380
cctggtaaga tgctcgccta caacctctct ccttccttta actgggacgt ggccggcttg    1440
tccccgcagg agatggagca tttcaactcg tccctggcgg ccatgggctt cgtctggcag    1500
ttcattacct tggcgggctt ccacgcgaac gggctcatga ccaccatgtt tgcgcgcgag    1560
tacggaaagc gggggtggt ggcctacgtg gagatgatcc agcggaagga gcgggagcag    1620
gaggtggaca tgctcaccca ccagaagtgg tcaggagccg cgttactcga caagcagatg    1680
cagacggtga cgggcggcat gtcctccacg tcctccatgg gcaagggcgt gacagaggcc    1740
cagtttggcg ccaagggacc gggagcggcc ggtgtctcat cgggagcagg agcggcgcgt    1800 gcggggcga tttctcggtt gtaa                                           1824
```

<210> SEQ ID NO 26  
<211> LENGTH: 11263  
<212> TYPE: DNA  
<213> ORGANISM: Artificial Sequence  
<220> FEATURE:  
<223> OTHER INFORMATION: Synthetic  
<220> FEATURE:  
<221> NAME/KEY: misc_feature  
<223> OTHER INFORMATION: pSGE-6206 vector

<400> SEQUENCE: 26

```
gcggccgccg tatggtcgac ggttgctcgg atggggggg cggggagcga tggagggagg     60
aagatcaggt aaggtctcga cagactagag aagcacgagt gcaggtataa gaaacagcaa    120
aaaaaagtaa tgggcccagg cctggagagg gtatttgtct tgttttctt tggccaggaa     180 cttgttctcc tttcttcgtt tctaggaccc cgatccccgc tcgcatttct ctcttcctca    240
gccgaagcgc agcggtaaag catccatttt atcccaccga aagggcgctc ccagccttcg    300
tcgagcggaa ccggggttac agtgcctcaa ccctcccaga cgtagccaga gggaagcaac    360
tccctgatgc caaccgctgt gggctgccca tcggaatctt tgacaattgc cttgatcccc    420
gggtgcaagt caagcagcac ctgccgacat cgcccgcacg gagacagaat gccgcggttt    480
tcgttcccga tggccactat gcacgtcaga tttccggcag cagccgcagc ggccgttccg    540
```

-continued

| | | |
|---|---|---|
| aggaccacga gctccgcgca tggccctccg gtgaaatgat atacattcac gccggtaaag | 600 |
| atccgaccgt cggacgagag ggctgcactg gccaccgagt agtcctcgct aataggtatg | 660 |
| ctgttgatgg tcgcagttgc acgttcgatc agcgtggatt cctcttggga taaaggcttg | 720 |
| gccatcgagc tcggtacccg gggatccatg attgttgtat tatgtaccta tgtttgtgat | 780 |
| gagacaataa atatgagaag agaacgttgc ggccactttt ttctccttcc ttcgcgtgct | 840 |
| catgttggtg gtttgggagg cagaagatgc atggagcgcc acacattcgg taggacgaaa | 900 |
| cagcctcccc cacaaaggga ccatgggtag ctaggatgac gcacaagcga gttcccgctc | 960 |
| tcgaagggaa acccaggcat ttccttcctc ttttcaagcc acttgttcac gtgtcaacac | 1020 |
| aattttggac taaaatgccc ctcggaactc ggcaggcctc cctctgctcc gttgtcctgg | 1080 |
| tcgccgagaa cgcgagaccg tgccgcatgc catcgatctg ctcgtctgta ctactaatcg | 1140 |
| tgtgcgtgtt cgtgcttgtt tcgcacgaaa ttgtcctcgt tcggccctca caacggtgga | 1200 |
| aatcggtgct agaataaagt gaggtggctt atttcaatgg cggccgtcat catgcgggat | 1260 |
| caactgaagt acgcgggtt ctcgagattt catcgtgctc gtccagagca ggtgttttgc | 1320 |
| ctgcagctct tcatgtttag gggtcatgat ttcatctgat atgccgtaag aaaaccaata | 1380 |
| ttcacttctc aattttccat ggaaaggtga aggcctaggt tgtgtgcgag caacgactg | 1440 |
| gggagggatc gcaacattct tgctaacctc ccctctatct tggccgctgt gaatcggcat | 1500 |
| atttaccggg ctgaattgag aaagtgtttt gagggaatta aaaggtggct gtcttgcaag | 1560 |
| cttggcttca gtgcctgctt aattcgaacc gatccagctt gtgatgaggc cttcctaagc | 1620 |
| ctggtagtca gaagcgacat ggcgctataa atttcgtctc agttggagag tagaaaagca | 1680 |
| tgattcgaac acggttttca actgccaaag atatctccat tgtttccttc aatctgtaca | 1740 |
| cctgcacggt gcaccagttg gtacggcata ttatggttta ataagcatac atcatatgaa | 1800 |
| tacaattcag cttaaattta tcatacaaag atgtaagtgc agcgtgggtc tgtaacgatc | 1860 |
| gggcgtaatt taagataatg cgagggaccg ggggaggttt tggaacggaa tgaggaatgg | 1920 |
| gtcatggccc ataataataa tatgggtttg gtcgcctcgc acagcaaccg tacgtgcgaa | 1980 |
| aaaggaacag atccatttaa taagttgaac gttattcttt cctatgcaat gcgtgtatcg | 2040 |
| gaggcgagag caagtcatag gtggctgcgc acaataattg agtctcagct gagcgccgtc | 2100 |
| cgcgggtggt gtgagtggtc atcctcctcc cggcctatcg ctcacatcgc ctctcaatgg | 2160 |
| tggtggtggg gcctgatatg acctcaatgc cgacccatat taaaacccag taaagcattc | 2220 |
| accaacgaac gaggggctct tttgtgtgtg ttttgagtat gattttacac ctctttgtgc | 2280 |
| atctctctgg tcttccttgg ttcccgtagt ttgggcatca tcactcacgc ttccctcgac | 2340 |
| cttcgttctt cctttacaac cccgacacag gtcagagttg gagtaatcaa aaagggtg | 2400 |
| cacgaatgag atacattaga ttttgacaga tatccttta ctggagaggg ttcaagggat | 2460 |
| caaatgaaca gcgggcgttg gcaatctagg gagggatcgg aggttggcag cgagcgaaag | 2520 |
| cgtgtccatc cttttggctg tcacacctca cgaaccaact gttagcaggc cagcacagat | 2580 |
| gacatacgag aatctttatt atatcgtaga ccttatgtgg atgacctttg gtgctgtgtg | 2640 |
| tctggcaatg aacctgaagg cttgataggg aggtggctcc cgtaaaccct ttgtcctttc | 2700 |
| cacgctgagt ctcccccgca ctgtccttta tacaaattgt tacagtcatc tgcaggcggt | 2760 |
| ttttctttgg caggcaaaga tgcccaagaa aaagcggaag gtcggcgact acaaggatga | 2820 |
| cgatgacaag ttggagcctg gagagaagcc ctacaaatgc cctgagtgcg gaaagagctt | 2880 |
| cagccaatct ggagccttga cccggcatca acgaacgcat acacgagaca agaagtactc | 2940 |

```
catcgggctg gacatcggga cgaactccgt gggatgggcc gtgatcacag acgaatacaa    3000
ggtgccttcc aagaagttca aggtgctggg gaacacggac agacactcca tcaagaagaa    3060
cctcatcggg gccttgctct tcgactccgg agaaaccgcc gaagcaacgc gattgaaaag    3120
aaccgccaga agacgataca cacgacgaaa gaaccgcatc tgctacctcc aggagatctt    3180
cagcaacgag atggccaagg tggacgactc gttctttcat cgcctggagg agagcttcct    3240
ggtggaggaa gacaagaaac atgagcgcca cccgatcttc gggaacatcg tggacgaagt    3300
ggcctaccac gagaaatacc ccacgatcta ccacttgcgc aagaaactcg tggactccac    3360
ggacaaagcg gacttgcggt tgatctactt ggccttggcc cacatgatca aatttcgggg    3420
ccacttcctg atcgagggcg acttgaatcc cgacaattcc gacgtggaca agctcttcat    3480
ccagctggtg cagacctaca accagctctt cgaggagaac cccatcaatg cctccggagt    3540
ggacgccaaa gccatcttgt ccgcccgatt gtccaaatcc agacgcttgg agaacttgat    3600
cgcacaactt cctggcgaga agaagaacgg cctcttcggc aacttgatcg cgctgtcgct    3660
gggattgacg cctaacttca gtccaacttc gacttggcc gaggacgcca gttgcaact    3720 gtccaaggac acctacgacg acgacctcga caacctgctg gcccaaattg gcgaccaata    3780
cgcggacttg ttttttggcgg ccaagaactt gagcgacgcc atcttgttga gcgacatctt    3840
gcgcgtgaat acggagatca ccaaagcccc tttgtccgcc tctatgatca agcggtacga    3900
cgagcaccac caagacttga ccctgttgaa agccctcgtg cggcaacaat tgcccgagaa    3960
gtacaaggag atcttcttcg accagtccaa gaacgggtac gccggctaca tcgacggagg    4020
agcctcccaa gaagagttct acaagttcat caagcccatc ctggagaaga tggacggcac    4080
cgaggagttg ctcgtgaagc tgaaccgcga agacttgttg cgaaaacagc ggacgttcga    4140
caatggcagc atcccccacc aaatccattt gggagagttg cacgccatct gcgacggca    4200 agaggacttc tacccgttcc tgaaggacaa ccgcgagaaa atcgagaaga tcctgacgtt    4260
cagaatcccc tactacgtgg acccttggc ccgaggcaat tcccggtttg catggatgac    4320
gcgcaaaagc gaagagacga tcacccctg gaacttcgaa gaagtggtcg acaaaggagc    4380
atccgcacag agcttcatcg agcgaatgac gaacttcgac aagaacctgc caacgagaa    4440 ggtgttgccc aagcattcgc tgctgtacga gtacttcacg gtgtacaacg agctgaccaa    4500
ggtgaagtac gtgaccgagg gcatgcgcaa acccgcgttc ctgtcgggag agcaaaagaa    4560
ggccattgtg gacctgctgt tcaagaccaa ccggaaggtg accgtgaaac agctgaaaga    4620
ggactacttc aagaagatcg agtgcttcga ctccgtggag atctccggcg tggaggaccg    4680
attcaatgcc tccttgggaa cctaccatga cctcctgaag atcatcaagg acaaggactt    4740
cctggacaac gaggagaacg aggacatcct ggaggacatc gtgctgaccc tgaccctgtt    4800
cgaggaccga gagatgatcg aggaacggtt gaaaacgtac gcccacttgt cgacgacaa    4860 ggtgatgaag cagctgaaac gccgccgcta caccggatgg ggacgattga ccgcaaact    4920 gattaatgga attcgcgaca agcaatccgg aaagaccatc ctggacttcc tgaagtccga    4980
cgggttcgcc aaccgcaact tcatgcagct catccacgac gactccttga ccttcaagga    5040
ggacatccag aaggcccaag tgtccggaca aggagactcc ttgcacgagc acatcgccaa    5100
tttggccgga tccccgcaa tcaaaaaagg catcttgcaa accgtgaaag tggtcgacga    5160
actggtgaag gtgatgggac ggcacaagcc cgagaacatc gtgatcgaaa tggcccgcga    5220
gaaccaaacc acccaaaaag gacagaagaa ctcccgagag cgcatgaagc ggatcgaaga    5280
```

```
gggcatcaag gagttgggct cccagatcct gaaggagcat cccgtggaga atacccaatt   5340
gcaaaacgag aagctctacc tctactacct ccagaacggg cgggacatgt acgtcgacca   5400
agagctggac atcaaccgcc tctccgacta cgatgtggat catattgtgc cccagagctt   5460
cctcaaggac gacagcatcg acaacaaggt cctgacgcgc agcgacaaga accggggcaa   5520
gtctgacaat gtgccttccg aagaagtcgt gaagaagatg aagaactact ggcggcagct   5580
gctcaacgcc aagctcatca cccaacggaa gttcgacaac ctgaccaagg ccgagagagg   5640
aggattgtcc gagttggaca agccggctt cattaaacgc caactcgtgg agacccgcca   5700
gatcacgaag cacgtggccc aaatcttgga ctcccggatg aacacgaaat acgacgagaa   5760
tgacaagctg atccgcgagg tgaaggtgat cacgctgaag tccaagctgg tgagcgactt   5820
ccggaaggac ttccagttct acaaggtgcg ggagatcaac aactaccatc acgcccatga   5880
cgcctacctg aacgccgtgg tcggaaccgc cctgatcaag aaatacccca agctggagtc   5940
cgaattcgtg tacggagatt acaaggtcta cgacgtgcgg aagatgatcg cgaagtccga   6000
gcaggagatc ggcaaagcca ccgccaagta cttcttttac tccaacatca tgaacttctt   6060
caagaccgag atcacgctcg ccaacggcga gatccgcaag cgcccctga tcgagaccaa   6120 cggcgagacg ggagagattg tgtgggacaa aggaagagat tttgccacag tgcgcaaggt   6180
gctgtccatg cctcaggtga acatcgtgaa gaagaccgag gtgcaaacag gagggttttc   6240
caaagagtcc attttgccta agaggaattc cgacaagctc atcgcccgca gaaggactg   6300 ggaccccaag aagtacgggg gcttcgactc ccccacggtg gcctactccg tgttggtggt   6360
ggccaaagtg gagaaaggga agagcaagaa gctgaaatcc gtgaaggagt tgctcggaat   6420
cacgatcatg gaacgatcgt cgttcgagaa aaaccccatc gacttcctcg aagccaaagg   6480
gtacaaagag gtgaagaagg acctgatcat caagctgccc aagtactccc tgttcgagct   6540
ggagaacggc cgcaagcgga tgctggcctc cgccgggaa ctgcagaaag gaacgaatt   6600 ggccttgccc tccaaatacg tgaacttcct ctacttggcc tcccattacg aaaagctcaa   6660
aggatcccct gaggacaatg agcagaagca actcttcgtg gaacaacaca agcactacct   6720
ggacgagatc atcgagcaga tcagcgagtt ctccaagcgc gtgatcctcg ccgacgccaa   6780
cctggacaag gtgctctccg cctacaacaa gcaccgcgac aagcctatcc gcgagcaagc   6840
cgagaatatc attcacctgt ttaccctgac gaatttggga gcccctgccg cctttaaata   6900
ctttgacacc accatcgacc gcaaaagata cacctccacc aaggaagtct ggacgccac   6960 cctcatccac cagtccatca cgggcctcta cgagacgcgc atcgacctct cccaattggg   7020
cggcgactaa agtgatgcgg cctttaggaa acaccacaaa agtaattgac aatctcagga   7080
acgatctgcg tgtttacagc ttcccaaata acaattatac cacgtaccaa aagggtta    7140 atgtatctca caaattcttc taataggtac agcttctcaa attgggtgta tgatgtgaca   7200
cttcgtctca cacacgtcac gataattcag cgtatggctt cccttcatca cattcacgca   7260
aacttctaca caaccctggg catatttctt gtgttggcaa cactcccgaa atcgattctg   7320
cacacaatgg ttcattcaat gattcaagta cgttttagac ggactaggca gtttaattaa   7380
aaacatctat cctccagatc accagggcca gtgaggccgg cataaaggac ggcaaggaaa   7440
gaaaagaaag aaagaaaagg acacttatag catagtttga agttataagt agtcgcaatc   7500
tgtgtgcagc cgacagatgc tttttttttc cgtttggcag gaggtgtagg gatgtcgaag   7560
accagtccag ctagtatcta tcctacaagt caatcatgct gcgacaaaaa tttctcgcac   7620
gaggcctctc gataaacaaa actttaaaag cacacttcat tgtcatgcag agtaataact   7680
```

```
cttccgcgtc gatcaattta tcaatctcta tcatttccgc cccttteett gcatagagca    7740 agaaaagcga cccggatgag gataacatgt cctgcgccag tagtgtggca ttgcctgtct    7800
ctcatttaca cgtactgaaa gcataatgca cgcgcatacc aatattttte gtgtacggag    7860 atgaagagac gcgacacgta agatcacgag aaggcgagca cggttgccaa tggcagacgc    7920
gctagtctcc attatcgcgt tgttcggtag cttgctgcat gtcttcagtg cactatatc    7980 cactctgcct cgtcttctac acgagggcca catcggtgca agttcgaaaa atcatatctc    8040
aatcttcaga tcctttccag aaacggtgct caggcgggaa agtgaaggtt ttctactcta    8100
gtggctaccc caattctctc cgactgtcgc agacggtcct tcgttgcgca cgcaccgcgc    8160
actacctctg aaattcgaca accgaagttc aattttacat ctaacttctt tcccattctc    8220
tcaccaaaag cctagcttac atgttggaga gcgacgagag cggcctgccc gccatggaga    8280
tcgagtgccg catcaccggc accctgaacg gcgtggagtt cgagctggtg ggcggcggag    8340
agggcacccc cgagcagggc cgcatgacca acaagatgaa gagcaccaaa ggcgccctga    8400
ccttcagccc ctacctgctg agccacgtga tgggctacgg cttctaccac ttcggcacct    8460
accccagcgg ctacgagaac cccttcctgc acgccatcaa caacggcggc tacaccaaca    8520
cccgcatcga gaagtacgag gacggcggcg tgctgcacgt gagcttcagc taccgctacg    8580
aggccggccg cgtgatcggc gacttcaagg tgatgggcac cggcttcccc gaggacagcg    8640
tgatcttcac cgacaagatc atccgcagca acgccaccgt ggagcacctg cacccatgg    8700 gcgataacga tctggatggc agcttcaccc gcaccttcag cctgcgcgac ggcggctact    8760
acagctccgt ggtggacagc cacatgcact tcaagagcgc catccacccc agcatcctgc    8820
agaacggggg ccccatgttc gccttccgcc gcgtggagga ggatcacagc aacaccgagc    8880
tgggcatcgt ggagtaccag cacgccttca agaccccgga tgcagatgcc ggtgaagaat    8940
aagggtggga aggagtcggg gagggtcctg gcagagcggc gtcctcatga tgtgttggag    9000
acctggagag tcgagagctt cctcgtcacc tgattgtcat gtgtgtatag gttaaggggg    9060
cccactcaaa gccataaaga cgaacacaaa cactaatctc aacaaagtct actagcatgc    9120
cgtctgtcca tctttatttc ctggcgcgcc tatgcttgta aaccgttttg tgaaaaaatt    9180
tttaaaataa aaaaggggac ctctagggtc cccaattaat tagtaatata atctattaaa    9240
ggtcattcaa aaggtcatcc agacgaaagg gcctcgtgat acgcctattt ttataggtta    9300
atgtcatgat aataatggtt tcttagacgt caggtggcac ttttcgggga aatgtgcgcg    9360 gaaccectat ttgtttattt ttctaaatac attcaaatat gtatccgctc atgagacaat    9420
aaccctgata aatgcttcaa taatattgaa aaaggaagag tatgagtatt caacatttcc    9480
gtgtcgccct tattccettt tttgcggcat tttgccttcc tgtttttgct cacccagaaa    9540
cgctggtgaa agtaaaagat gctgaagatc agttgggtgc acgagtgggt tacatcgaac    9600
tggatctcaa cagcggtaag atccttgaga gttttcgccc cgaagaacgt tttccaatga    9660
tgagcacttt taaagttctg ctatgtggcg cggtattatc ccgtattgac gccgggcaag    9720
agcaactcgg tcgccgcata cactattctc agaatgactt ggttgagtac tcaccagtca    9780
cagaaaagca tcttacggat ggcatgacag taagagaatt atgcagtgct gccataacca    9840
tgagtgataa cactgcggcc aacttacttc tgacaacgat cggaggaccg aaggagctaa    9900 ccgcttttt gcacaacatg ggggatcatg taactcgcct tgatcgttgg aaccggagc    9960 tgaatgaagc cataccaaac gacgagcgtg acaccacgat gcctgtagca atggcaacaa   10020
```

```
cgttgcgcaa actattaact ggcgaactac ttactctagc ttcccggcaa caattaatag    10080
actggatgga ggcggataaa gttgcaggac cacttctgcg ctcggccctt ccggctggct    10140
ggtttattgc tgataaatct ggagccggtg agcgtgggtc tcgcggtatc attgcagcac    10200
tggggccaga tggtaagccc tcccgtatcg tagttatcta cacgacgggg agtcaggcaa    10260
ctatggatga acgaaataga cagatcgctg agataggtgc ctcactgatt aagcattggt    10320
aactgtcaga ccaagtttac tcatatatac tttagattga tttaaaactt cattttttaat   10380 ttaaaaggat ctaggtgaag atccttttg ataatctcat gaccaaaatc ccttaacgtg     10440
agttttcgtt ccactgagcg tcagaccccg tagaaaagat caaaggatct tcttgagatc    10500 cttttttct gcgcgtaatc tgctgcttgc aaacaaaaaa accaccgcta ccagcggtgg     10560
tttgtttgcc ggatcaagag ctaccaactc ttttccgaa ggtaactggc ttcagcagag     10620
cgcagatacc aaatactgtc cttctagtgt agccgtagtt aggccaccac ttcaagaact    10680
ctgtagcacc gcctacatac ctcgctctgc taatcctgtt accagtggct gctgccagtg    10740
gcgataagtc gtgtcttacc gggttggact caagacgata gttaccggat aaggcgcagc    10800
ggtcgggctg aacggggggt tcgtgcacac agcccagctt ggagcgaacg acctacaccg    10860
aactgagata cctacagcgt gagctatgag aaagcgccac gcttcccgaa gggagaaagg    10920
cggacaggta tccggtaagc ggcagggtcg gaacaggaga gcgcacgagg gagcttccag    10980
ggggaaacgc ctggtatctt tatagtcctg tcgggtttcg ccacctctga cttgagcgtc    11040
gatttttgtg atgctcgtca gggggcgga gcctatggaa aaacgccagc aacgcggcct     11100
ttttacggtt cctggccttt tgctggcctt ttgctcacat gttctttcct gcgttatccc    11160
ctgattctgt ggataaccgt attaccgcct ttgagtgagc tgataccgct cgccgcagcc    11220
gaacgaccga gcgcagcgag tcagtgagcg aggaagcgga aga                     11263
```

<210> SEQ ID NO 27
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: S. pyogenes CAS9 gene codon optimized for
      Nannochloropsis

<400> SEQUENCE: 27

```
gacaagaagt actccatcgg gctggacatc gggacgaact ccgtgggatg ggccgtgatc      60
acagacgaat acaaggtgcc ttccaagaag ttcaaggtgc tggggaacac ggacagacac     120
tccatcaaga agaacctcat cggggccttg ctcttcgact ccggagaaac cgccgaagca    180
acgcgattga aagaaccgc cagaagacga tacacacgac ggaagaaccg catctgctac     240
ctccaggaga tcttcagcaa cgagatggcc aaggtggacg actcgttctt catcgcctg     300 gaggagagct tcctggtgga ggaagacaag aaacatgagc gccacccgat cttcgggaac    360
atcgtggacg aagtggccta ccacgagaaa taccccacga tctaccactt gcgcaagaaa    420
ctcgtggact ccacgacaa agcggacttg cggttgatct acttggcctt ggcccacatg    480
atcaaatttc ggggccactt cctgatcgag ggcgacttga tcccgacaa ttccgacgtg    540 gacaagctct tcatccagct ggtgcagacc tacaaccagc tcttcgagga accccatc     600 aatgcctccg gagtggacgc caagccatc ttgtccgccc gattgtccaa atccagacgc    660
ttggagaact tgatcgcaca acttcctggc gagaagaaga acggcctctt cggcaacttg    720
```

```
atcgcgctgt cgctgggatt gacgcctaac ttcaagtcca acttcgactt ggccgaggac    780
gccaagttgc aactgtccaa ggacacctac gacgacgacc tcgacaacct gctggcccaa    840
attggcgacc aatacgcgga cttgttttg gcggccaaga acttgagcga cgccatcttg     900
ttgagcgaca tcttgcgcgt gaatacggag atcaccaaag ccccttttgtc cgcctctatg   960
atcaagcggt acgacgagca ccaccaagac ttgaccctgt tgaaagccct cgtgcggcaa   1020
caattgcccg agaagtacaa ggagatcttc ttcgaccagt ccaagaacgg gtacgccggc   1080
tacatcgacg gaggagcctc ccaagaagag ttctacaagt tcatcaagcc catcctggag   1140
aagatggacg gcaccgagga gttgctcgtg aagctgaacc gcgaagactt gttgcgaaaa   1200
cagcggacgt tcgacaatgg cagcatcccc caccaaatcc atttgggaga gttgcacgcc   1260
atcttgcgac ggcaagagga cttctacccg ttcctgaagg acaaccgcga gaaaatcgag   1320
aagatcctga cgttcagaat cccctactac gtgggaccct tggcccgagg caattcccgg   1380
tttgcatgga tgacgcgcaa aagcgaagag acgatcaccc cctggaactt cgaagaagtg   1440
gtcgacaaag gagcatccgc acagagcttc atcgagcgaa tgacgaactt cgacaagaac   1500
ctgcccaacg agaaggtgtt gcccaagcat tcgctgctgt acgagtactt cacggtgtac   1560
aacgagctga ccaaggtgaa gtacgtgacc gagggcatgc gcaaaccgc gttcctgtcg    1620
ggagagcaaa agaaggccat tgtggacctg ctgttcaaga ccaaccggaa ggtgaccgtg   1680
aaacagctga agaggactac cttcaagaag atcgagtgct cgactccgt ggagatctcc    1740
ggcgtggagg accgattcaa tgcctccttg ggaacctacc atgacctcct gaagatcatc   1800
aaggacaagg acttcctgga caacgaggag aacgaggaca tcctggagga catcgtgctg   1860
accctgaccc tgttcgagga ccgagagatg atcgaggaac ggttgaaaac gtacgcccac   1920
ttgttcgacg acaaggtgat gaagcagctg aaacgccgcc gctacaccgg atggggacga   1980
ttgagccgca aactgattaa tggaattcgc gacaagcaat ccggaaagac catcctggac   2040
ttcctgaagt ccgacgggtt cgccaaccgc aacttcatgc agctcatcca cgacgactcc   2100
ttgaccttca aggaggacat ccagaaggcc caagtgtccg acaaggaga ctccttgcac    2160
gagcacatcg ccaatttggc cggatccccc gcaatcaaaa aaggcatctt gcaaaccgtg   2220
aaagtggtcg acgaactggt gaaggtgatg ggacggcaca gcccgagaa catcgtgatc    2280
gaaatggccc gcgagaacca aaccaccaa aaaggacaga agaactcccg agagcgcatg    2340
aagcggatcg aagagggcat caaggagttg gctcccaga tcctgaagga gcatcccgtg    2400
gagaatacc aattgcaaaa cgagaagctc tacctctact acctccagaa cgggcggac    2460
atgtacgtcg accaagagct ggacatcaac cgcctctccg actacgatgt ggatcatatt   2520
gtgccccaga gcttcctcaa ggacgacagc atcgacaaca aggtcctgac gcgcagcgac   2580
aagaaccggg gcaagtctga caatgtgcct tccgaagaag tcgtgaagaa gatgaagaac   2640
tactggcggc agctgctcaa cgccaagctc atcacccaac ggaagttcga caacctgacc   2700
aaggccgaga gaggaggatt gtccgagttg acaaagccg gcttcattaa cgccaactc     2760
gtggagaccc gccagatcac gaagcacgtg gcccaaatct tggactcccg gatgaacacg   2820
aaatacgacg agaatgacaa gctgatccgc gaggtgaagg tgatcacgct gaagtccaag   2880
ctggtgagcg acttccggaa ggacttccag ttctacaagg tgcgggagat caacaactac   2940
catcacgccc atgacgccta cctgaacgcc gtggtcggaa ccgccctgat caagaaatac   3000
cccaagctgg agtccgaatt cgtgtacgga gattacaagg tctacgacgt gcggaagatg   3060
```

| | |
|---|---|
| atcgcgaagt ccgagcagga gatcggcaaa gccaccgcca agtacttctt ttactccaac | 3120 |
| atcatgaact tcttcaagac cgagatcacg ctcgccaacg gcgagatccg caagcgcccc | 3180 |
| ctgatcgaga ccaacggcga gacgggagag attgtgtggg acaaaggaag agattttgcc | 3240 |
| acagtgcgca aggtgctgtc catgcctcag gtgaacatcg tgaagaagac cgaggtgcaa | 3300 |
| acaggagggt tttccaaaga gtccattttg cctaagagga attccgacaa gctcatcgcc | 3360 |
| cgcaagaagg actgggaccc caagaagtac gggggcttcg actcccccac ggtgccctac | 3420 |
| tccgtgttgg tggtggccaa agtggagaaa gggaagagca agaagctgaa atccgtgaag | 3480 |
| gagttgctcg gaatcacgat catggaacga tcgtcgttcg agaaaaaccc catcgacttc | 3540 |
| ctcgaagcca aagggtacaa agaggtgaag aaggacctga tcatcaagct gcccaagtac | 3600 |
| tccctgttcg agctggagaa cggccgcaag cggatgctgg cctccgccgg ggaactgcag | 3660 |
| aaagggaacg aattggcctt gccctccaaa tacgtgaact tcctctactt ggcctcccat | 3720 |
| tacgaaaagc tcaaaggatc ccctgaggac aatgagcaga agcaactctt cgtggaacaa | 3780 |
| cacaagcact acctggacga gatcatcgag cagatcagcg agttctccaa gcgcgtgatc | 3840 |
| ctcgccgacg ccaacctgga caaggtgctc tccgcctaca acaagcaccg cgacaagcct | 3900 |
| atccgcgagc aagccgagaa tatcattcac ctgtttaccc tgacgaattt gggagcccct | 3960 |
| gccgccttta aatactttga caccaccatc gaccgcaaaa gatacacctc caccaaggaa | 4020 |
| gtcttggacg ccaccctcat ccaccagtcc atcacgggcc tctacgagac gcgcatcgac | 4080 |
| ctctcccaat gggcggcga c | 4101 |

<210> SEQ ID NO 28
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes NLS, FLAG tag, linker

<400> SEQUENCE: 28

| | |
|---|---|
| atgcccaaga aaaagcggaa ggtcggcgac tacaaggatg acgatgacaa gttggagcct | 60 |
| ggagagaagc cctacaaatg ccctgagtgc ggaaagagct tcagccaatc tggagccttg | 120 |
| acccggcatc aacgaacgca tacacga | 147 |

<210> SEQ ID NO 29
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 29

| | |
|---|---|
| aataagcata catcatatga atacaattca gcttaaattt atcatacaaa gatgtaagtg | 60 |
| cagcgtgggt ctgtaacgat cgggcgtaat ttaagataat gcgagggacc gggggaggtt | 120 |
| ttggaacgga atgaggaatg ggtcatggcc cataataata atatgggttt ggtcgcctcg | 180 |
| cacagcaacc gtacgtgcga aaaaggaaca gatccattta ataagttgaa cgttattctt | 240 |
| tcctatgcaa tgcgtgtatc ggaggcgaga gcaagtcata ggtggctgcg cacaataatt | 300 |
| gagtctcagc tgagcgccgt ccgcgggtgg tgtgagtggt catcctcctc ccggcctatc | 360 |
| gctcacatcg cctctcaatg gtggtggtgg ggcctgatat gacctcaatg ccgacccata | 420 |

```
ttaaaacccca gtaaagcatt caccaacgaa cgaggggctc ttttgtgtgt gttttgagta    480
tgattttaca cctctttgtg catctctctg gtcttccttg gttcccgtag tttgggcatc    540
atcactcacg cttccctcga ccttcgttct tcctttacaa ccccgacaca ggtcagagtt    600
ggagtaatca aaaaggggt gcacgaatga gatacattag attttgacag atatcctttt     660
actggagagg gttcaaggga tcaaatgaac agcgggcgtt ggcaatctag ggagggatcg    720
gaggttggca gcgagcgaaa gcgtgtccat ccttttggct gtcacacctc acgaaccaac    780
tgttagcagg ccagcacaga tgacatacga gaatctttat tatatcgtag accttatgtg    840
gatgaccttt ggtgctgtgt gtctggcaat gaacctgaag gcttgatagg gaggtggctc    900
ccgtaaaccc tttgtccttt ccacgctgag tctcccccgc actgtccttt atacaaattg    960
ttacagtcat ctgcaggcgg tttttctttg gcaggcaaag                         1000
```

<210> SEQ ID NO 30
<211> LENGTH: 317
<212> TYPE: DNA
<213> ORGANISM: Nannochloropsis gaditana
<220> FEATURE:
<221> NAME/KEY: misc_feature
<223> OTHER INFORMATION: Bidirectional terminator 2

<400> SEQUENCE: 30

```
agtgatgcgg cctttaggaa acaccacaaa agtaattgac aatctcagga acgatctgcg     60
tgtttacagc ttcccaaata acaattatac cacgtaccaa aagggggttta atgtatctca   120 caaattcttc taataggtac agcttctcaa attgggtgta tgatgtgaca cttcgtctca   180
cacacgtcac gataattcag cgtatggctt cccttcatca cattcacgca aacttctaca   240
caaccctggg catatttctt gtgttggcaa cactcccgaa atcgattctg cacacaatgg   300
ttcattcaat gattcaa                                                 317
```

<210> SEQ ID NO 31
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Aspergillus terreus BLAST gene codon optimized
    for N. gaditana

<400> SEQUENCE: 31

```
atggccaagc ctttatccca gaggaatcc acgctgatcg aacgtgcaac tgcgaccatc     60
aacagcatac ctattagcga ggactactcg gtggccagtg cagccctctc gtccgacggt   120
cggatcttta ccggcgtgaa tgtatatcat ttcaccggag ggccatgcgc ggagctcgtg   180
gtcctcggaa cggccgctgc ggctgctgcc ggaaatctga cgtgcatagt ggccatcggg   240
aacgaaaacc gcggcattct gtctccgtgc gggcgatgtc ggcaggtgct gcttgacttg   300
cacccgggga tcaaggcaat tgtcaaagat tccgatgggc agcccacagc ggttggcatc   360
agggagttgc ttccctctgg ctacgtctgg gagggttga                          399
```

<210> SEQ ID NO 32
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 32

| | | | | | |
|---|---|---|---|---|---|
| cgtgcaggtg | tacagattga | aggaaacaat | ggagatatct | ttggcagttg | aaaaccgtgt | 60 |
| tcgaatcatg | cttttctact | ctccaactga | gacgaaattt | atagcgccat | gtcgcttctg | 120 |
| actaccaggc | ttaggaaggc | ctcatcacaa | gctggatcgg | ttcgaattaa | gcaggcactg | 180 |
| aagccaagct | tgcaagacag | ccaccttta | attccctcaa | aacactttct | caattcagcc | 240 |
| cggtaaatat | gccgattcac | agcggccaag | atagagggga | ggttagcaag | aatgttgcga | 300 |
| tccctcccca | gtcgttgcct | cgcacacaac | ctaggccttc | acctttccat | ggaaaattga | 360 |
| gaagtgaata | ttggttttct | tacggcatat | cagatgaaat | catgaccct | aaacatgaag | 420 |
| agctgcaggc | aaaacacctg | ctctggacga | gcacgatgaa | atctcgagaa | cccgccgtac | 480 |
| ttcagttgat | cccgcatgat | gacggccgcc | attgaaataa | gccacctcac | tttattctag | 540 |
| caccgattc | caccgttgtg | agggccgaac | gaggacaatt | tcgtgcgaaa | caagcacgaa | 600 |
| cacgcacacg | attagtagta | cagacgagca | gatcgatggc | atgcggcacg | gtctcgcgtt | 660 |
| ctcggcgacc | aggacaacgg | agcagaggga | ggcctgccga | gttccgaggg | gcattttagt | 720 |
| ccaaaattgt | gttgacacgt | gaacaagtgg | cttgaaaaga | ggaaggaaat | gcctgggttt | 780 |
| cccttcgaga | gcgggaactc | gcttgtgcgt | catcctagct | acccatggtc | cctttgtggg | 840 |
| ggaggctgtt | tcgtcctacc | gaatgtgtgg | cgctccatgc | atcttctgcc | tcccaaacca | 900 |
| ccaacatgag | cacgcgaagg | aaggagaaaa | aagtggccgc | aacgttctct | tctcatattt | 960 |
| attgtctcat | cacaaacata | ggtacataat | acaacaatc | | | 999 |

<210> SEQ ID NO 33
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 33

| | | | | | |
|---|---|---|---|---|---|
| ggcactgtaa | ccccggttcc | gctcgacgaa | ggctgggagc | gccctttcgg | tgggataaaa | 60 |
| tggatgcttt | accgctgcgc | ttcggctgag | gaagagagaa | atgcgagcgg | ggatcggggt | 120 |
| cctagaaacg | aagaaaggag | aacaagttcc | tggccaaaga | aaaacaagac | aaataccctc | 180 |
| tccaggcctg | ggcccattac | tttttttgc | tgtttcttat | acctgcactc | gtgcttctct | 240 |
| agtctgtcga | gaccttacct | gatcttcctc | cctccatcgc | tccccgcccc | cccatccga | 300 |
| gcaaccgtcg | accatacg | | | | | 318 |

<210> SEQ ID NO 34
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP gene codon optimized for N. gaditana

<400> SEQUENCE: 34

| | | | | | |
|---|---|---|---|---|---|
| atgttggaga | gcgacgagag | cggcctgccc | gccatggaga | tcgagtgccg | catcaccggc | 60 |
| accctgaacg | gcgtggagtt | cgagctggtg | ggcggcggag | agggcacccc | cgagcagggc | 120 |
| cgcatgacca | acaagatgaa | gagcaccaaa | ggcgccctga | ccttcagccc | ctacctgctg | 180 |

```
agccacgtga tgggctacgg cttctaccac ttcggcacct accccagcgg ctacgagaac    240
cccttcctgc acgccatcaa caacggcggc tacaccaaca cccgcatcga gaagtacgag    300
gacggcggcg tgctgcacgt gagcttcagc taccgctacg aggccggccg cgtgatcggc    360
gacttcaagg tgatgggcac cggcttcccc gaggacagcg tgatcttcac cgacaagatc    420
atccgcagca acgccaccgt ggagcacctg cacccatgg gcgataacga tctggatggc    480
agcttcaccc gcaccttcag cctgcgcgac ggcggctact acagctccgt ggtggacagc    540
cacatgcact tcaagagcgc catccacccc agcatcctgc agaacggggg ccccatgttc    600
gccttccgcc gcgtggagga ggatcacagc aacaccgagc tgggcatcgt ggagtaccag    660
cacgccttca agaccccgga tgcagatgcc ggtgaagaat aa                       702
```

```
<210> SEQ ID NO 35
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4A-III promoter

<400> SEQUENCE: 35
ggcataaagg acggcaagga aagaaaagaa agaaagaaaa ggacacttat agcatagttt     60
gaagttataa gtagtcgcaa tctgtgtgca gccgacagat gcttttttt tccgtttggc    120 aggaggtgta gggatgtcga agaccagtcc agctagtatc tatcctacaa gtcaatcatg    180
ctgcgacaaa aatttctcgc acgaggcctc tcgataaaca aaactttaaa agcacacttc    240
attgtcatgc agagtaataa ctcttccgcg tcgatcaatt tatcaatctc tatcatttcc    300 gccccttcc ttgcatagag caagaaaagc gaccccgatg aggataacat gtcctgcgcc    360
agtagtgtgg cattgcctgt ctctcattta cacgtactga aagcataatg cacgcgcata    420
ccaatatttt tcgtgtacgg agatgaagag acgcgacacg taagatcacg agaaggcgag    480
cacggttgcc aatggcagac gcgctagtct ccattatcgc gttgttcggt agcttgctgc    540
atgtcttcag tggcactata tccactctgc ctcgtcttct acacgagggc cacatcggtg    600
caagttcgaa aaatcatatc tcaatcttca gatccttcc agaaacggtg ctcaggcggg    660
aaagtgaagg ttttctactc tagtggctac cccaattctc tccgactgtc gcagacggtc    720
cttcgttgcg cacgcaccgc gcactacctc tgaaattcga caaccgaagt tcaattttac    780
atctaacttc tttcccattc tctcaccaaa agcctagctt ac                       822
```

```
<210> SEQ ID NO 36
<211> LENGTH: 200
<212> TYPE: DNA
<213> ORGANISM: Nannochloropsis gaditana
<220> FEATURE:
<221> NAME/KEY: misc_feature
<223> OTHER INFORMATION: bidirectional terminator 5

<400> SEQUENCE: 36
gggtgggaag gagtcgggga gggtcctggc agagcggcgt cctcatgatg tgttggagac     60
ctggagagtc gagagcttcc tcgtcacctg attgtcatgt gtgtataggt taagggggcc    120
cactcaaagc cataaagacg aacacaaaca ctaatctcaa caaagtctac tagcatgccg    180
tctgtccatc tttatttcct                                                200
```

```
<210> SEQ ID NO 37
```

<211> LENGTH: 2346
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HygR Cassette

<400> SEQUENCE: 37

| | | | | | |
|---|---|---|---|---|---|
| tcataatcaa | agatgagcca | gccacgaagc | taccggagaa | ttctgtaaga | aaaatgttta | 60 |
| aagttgaaaa | tgctaacagt | gaagtgatat | cctttttttaa | tggagtgttg | aggtgaagtc | 120 |
| tagcatcgta | ggggaaaaca | ggattctgtg | tcttccattc | tactccttga | taaagcgaag | 180 |
| aaatccgaca | aaaccaaaga | gattgttcaa | gtttaagatt | tgtaagcgta | caactatgaa | 240 |
| cttcttctct | ttgtaggcct | gagtggtcgt | atgcatacga | ttcatgaagt | gaatcagtat | 300 |
| cgctggattt | tgcttaggag | taaagcacaa | ctaagaaaat | atgctgcctg | gcaggcatcc | 360 |
| tgagacatga | ggcaagcgac | gtagcaattg | aatcctaatt | taagccaggg | catctgtatg | 420 |
| actctgttag | ttaattgatg | aaccaatgag | ctttaaaaaa | aaatcgttgc | gcgtaatgta | 480 |
| gttttaattc | tccgccttga | ggtgcggggc | catttcggac | aaggttcttt | ggacggagat | 540 |
| ggcagcatgt | gtcccttctc | caaattggtc | cgtgtggtag | ttgagatgct | gccttaaaat | 600 |
| tctgctcggt | catcctgcct | tcgcattcac | tcctttcgag | ctgtcgggtt | cctcacgagg | 660 |
| cctccgggag | cggattgcgc | agaaaggcga | cccggagaca | cagagaccat | acaccgacta | 720 |
| aattgcactg | gacgatacgg | catggcgacg | acgatggcca | agcattgcta | cgtgattatt | 780 |
| cgccttgtca | ttcagggaga | atgatgaca | tgtgtgggac | ggtctttaca | tgggaagagg | 840 |
| gcatgaaaat | aacatggcct | ggcgggatgg | agcgtcacac | ctgtgtatgc | gttcgatcca | 900 |
| caagcaactc | accatttgcg | tcggggcctg | tctccaatct | gctttaggct | acttttctct | 960 |
| aatttagcct | attctataca | gacagagaca | cacagggatc | atggggaaga | aaccggaact | 1020 |
| gaccgctacg | tccgtggaga | aattcccttat | tgagaagttc | gactctgtct | ccgacttgat | 1080 |
| gcaactgagc | gagggagagg | agagtagggc | gttctcgttt | gacgtagggg | gtcggggata | 1140 |
| cgtgttgagg | gttaatagtt | gtgcggacgg | gttctacaag | gatcggtatg | tctaccgtca | 1200 |
| tttcgcctcc | gccgctctcc | ccataccaga | ggtactggac | attggggagt | ttagcgaatc | 1260 |
| tctcacgtac | tgcatctcgc | gccgagccca | gggagtgacg | ttgcaagatc | tgcccgaaac | 1320 |
| tgaattgcct | gccgttttgc | aacccgtggc | cgaggccatg | gacgcgatcg | ctgccgcaga | 1380 |
| tctgtctcag | acgtccggct | ttggacccttt | tgggccccag | ggcatcgggc | agtcacgac | 1440 |
| ctggcgagac | ttcatctgcg | ccattgccga | tcctcacgtc | tatcattggc | agacagtcat | 1500 |
| ggatgacacc | gtgtctgcat | ccgtggccca | agcactggac | gaactcatgt | tgtgggccga | 1560 |
| ggattgccct | gaggtcaggc | acctggtgca | cgcggatttc | ggcagcaata | acgtacttac | 1620 |
| agacaatggt | cggattactg | ctgtcatcga | ctggtccgaa | gcgatgtttg | gtgatagcca | 1680 |
| atacgaagtg | gcgaacatat | tcttctggcg | tccctggttg | gcgtgcatgg | agcagcagac | 1740 |
| acgctacttt | gaacggaggc | acccggagct | ggccggctcc | ccacgactcc | gcgcctatat | 1800 |
| gttgcgtatc | ggactcgatc | agctttacca | gtctctcgtc | gacggcaact | tcgacgacgc | 1860 |
| cgcgtgggcg | cagggccgct | gcgacgcgat | agtccgcagc | ggggctggga | cggtgggtcg | 1920 |
| gacccaaatc | gcacgccggt | cggctgcggt | gtggacagac | ggctgtgttg | aggtgcttgc | 1980 |
| ggactcgggc | aaccgtaggc | cgagcacccg | accgcgtgca | aaggagtgat | tgaatcattg | 2040 |

| aatgaaccat tgtgtgcaga atcgatttcg ggagtgttgc caacacaaga aatatgccca | 2100 |
| gggttgtgta gaagtttgcg tgaatgtgat gaagggaagc catacgctga attatcgtga | 2160 |
| cgtgtgtgag acgaagtgtc acatcataca cccaatttga gaagctgtac ctattagaag | 2220 |
| aatttgtgag atacattaaa cccctttgg tacgtggtat aattgttatt tgggaagctg | 2280 |
| taaacacgca gatcgttcct gagattgtca attactttg tggtgtttcc taaaggccgc | 2340 |
| atcact | 2346 |

<210> SEQ ID NO 38
<211> LENGTH: 23
<212> TYPE: DNA
<213> ORGANISM: Nannochloropsis gaditana
<220> FEATURE:
<221> NAME/KEY: misc_feature
<223> OTHER INFORMATION: Target sequence of guide targeting TrifuncB

<400> SEQUENCE: 38

| ggcttggcgt ccaaagccgc cgg | 23 |

<210> SEQ ID NO 39
<211> LENGTH: 1029
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hygromycin resistance gene, codon optimized for
      Nannochloropsis

<400> SEQUENCE: 39

| atggggaaga aaccggaact gaccgctacg tccgtggaga aattccttat tgagaagttc | 60 |
| gactctgtct ccgacttgat gcaactgagc gagggagagg agagtagggc gttctcgttt | 120 |
| gacgtagggg gtcggggata cgtgttgagg gttaatagtt gtgcggacgg gttctacaag | 180 |
| gatcggtatg tctaccgtca tttcgcctcc gccgctctcc ccataccaga ggtactggac | 240 |
| attggggagt ttagcgaatc tctcacgtac tgcatctcgc gccgagccca gggagtgacg | 300 |
| ttgcaagatc tgcccgaaac tgaattgcct gccgttttgc aacccgtggc cgaggccatg | 360 |
| gacgcgatcg ctgccgcaga tctgtctcag acgtccggct ttggaccttt tgggccccag | 420 |
| ggcatcgggc agtacacgac ctggcgagac ttcatctgcg ccattgccga tcctcacgtc | 480 |
| tatcattggc agacagtcat ggatgacacc gtgtctgcat ccgtggccca agcactggac | 540 |
| gaactcatgt tgtgggccga ggattgccct gaggtcaggc acctggtgca cgcggatttc | 600 |
| ggcagcaata acgtacttac agacaatggt cggattactg ctgtcatcga ctggtccgaa | 660 |
| gcgatgtttg tgatagcca atacgaagtg gcgaacatat tcttctggcg tccctggttg | 720 |
| gcgtgcatgg agcagcagac acgctacttt gaacggaggc acccggagct ggccggctcc | 780 |
| ccacgactcc gcgcctatat gttgcgtatc ggactcgatc agctttacca gtctctcgtc | 840 |
| gacggcaact tcgacgacgc cgcgtgggcg cagggccgct gcgacgcgat agtccgcagc | 900 |
| ggggctggga cggtgggtcg gacccaaatc gcacgccggt cggctgcggt gtggacagac | 960 |
| ggctgtgttg agtgcttgc ggactcgggc aaccgtaggc cgagcacccg accgcgtgca | 1020 |
| aaggagtga | 1029 |

<210> SEQ ID NO 40
<211> LENGTH: 1000
<212> TYPE: DNA

<213> ORGANISM: Nannochloropsis gaditana
<220> FEATURE:
<221> NAME/KEY: misc_feature
<223> OTHER INFORMATION: EIF3 promoter

<400> SEQUENCE: 40

```
tcataatcaa agatgagcca gccacgaagc taccggagaa ttctgtaaga aaaatgttta      60
aagttgaaaa tgctaacagt gaagtgatat ccttttttaa tggagtgttg aggtgaagtc     120
tagcatcgta ggggaaaaca ggattctgtg tcttccattc tactccttga taaagcgaag    180
aaatccgaca aaaccaaaga gattgttcaa gtttaagatt tgtaagcgta caactatgaa    240
cttcttctct tgtaggcct gagtggtcgt atgcatacga ttcatgaagt gaatcagtat    300
cgctggattt tgcttaggag taaagcacaa ctaagaaaat atgctgcctg gcaggcatcc    360
tgagacatga ggcaagcgac gtagcaattg aatcctaatt taagccaggg catctgtatg    420
actctgttag ttaattgatg aaccaatgag ctttaaaaaa aaatcgttgc gcgtaatgta    480
gttttaattc tccgccttga ggtgcgggc catttcggac aaggttcttt ggacggagat    540
ggcagcatgt gtcccttctc caaattggtc cgtgtggtag ttgagatgct gccttaaaat    600
tctgctcggt catcctgcct tcgcattcac tcctttcgag ctgtcgggtt cctcacgagg    660
cctccgggag cggattgcgc agaaaggcga cccggagaca cagagaccat acaccgacta    720
aattgcactg gacgatacgg catggcgacg acgatggcca agcattgcta cgtgattatt    780
cgccttgtca ttcagggaga aatgatgaca tgtgtgggac ggtctttaca tgggaagagg    840
gcatgaaaat aacatggcct ggcgggatgg agcgtcacac ctgtgtatgc gttcgatcca    900
caagcaactc accatttgcg tcggggcctg tctccaatct gctttaggct acttttctct    960
aatttagcct attctataca gacagagaca cacagggatc                         1000
```

<210> SEQ ID NO 41
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5'ID sequence

<400> SEQUENCE: 41

```
tccacagccc gaacccatga gagagaa                                         27
```

<210> SEQ ID NO 42
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3'ID sequence

<400> SEQUENCE: 42

```
gcccgaatcg agttgatggc ccgcaaa                                         27
```

<210> SEQ ID NO 43
<211> LENGTH: 2400
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: HygR Cassette with flanking ID sequences

<400> SEQUENCE: 43

```
tccacagccc gaacccatga gagagaatca taatcaaaga tgagccagcc acgaagctac      60
cggagaattc tgtaagaaaa atgtttaaag ttgaaaatgc taacagtgaa gtgatatcct     120
ttttaatgg agtgttgagg tgaagtctag catcgtaggg gaaaacagga ttctgtgtct      180
tccattctac tccttgataa agcgaagaaa tccgacaaaa ccaaagagat tgttcaagtt     240
taagatttgt aagcgtacaa ctatgaactt cttctctttg taggcctgag tggtcgtatg     300
catacgattc atgaagtgaa tcagtatcgc tggattttgc ttaggagtaa agcacaacta     360
agaaaatatg ctgcctggca ggcatcctga gacatgaggc aagcgacgta gcaattgaat     420
cctaatttaa gccagggcat ctgtatgact ctgttagtta attgatgaac caatgagctt     480
taaaaaaaaa tcgttgcgcg taatgtagtt ttaattctcc gccttgaggt gcgggccat      540
ttcggacaag gttctttgga cggagatggc agcatgtgtc ccttctccaa attggtccgt     600
gtggtagttg agatgctgcc ttaaaattct gctcggtcat cctgccttcg cattcactcc     660
tttcgagctg tcgggttcct cacgaggcct ccgggagcgg attgcgcaga aaggcgaccc     720
ggagacacag agaccataca ccgactaaat tgcactggac gatacggcat ggcgacgacg     780
atggccaagc attgctacgt gattattcgc cttgtcattc agggagaaat gatgacatgt     840
gtgggacggt ctttacatgg gaagagggca tgaaaataac atggcctggc gggatggagc     900
gtcacacctg tgtatgcgtt cgatccacaa gcaactcacc atttgcgtcg ggcctgtct      960
ccaatctgct ttaggctact tttctctaat ttagcctatt ctatacagac agagacacac    1020
agggatcatg gggaagaaac cggaactgac cgctacgtcc gtggagaaat tccttattga    1080
gaagttcgac tctgtctccg acttgatgca actgagcgag ggagaggaga gtagggcgtt    1140
ctcgtttgac gtaggggggtc ggggatacgt gttgagggtt aatagttgtg cggacgggtt    1200
ctacaaggat cggtatgtct accgtcattt cgcctccgcc gctctcccca taccagaggt    1260
actggacatt ggggagttta gcgaatctct cacgtactgc atctcgcgcc gagcccaggg    1320
agtgacgttg caagatctgc ccgaaactga attgcctgcc gttttgcaac ccgtggccga    1380
ggccatggac gcgatcgctg ccgcagatct gtctcagacg tccggctttg gacctttgg    1440
gccccagggc atcgggcagt acacgacctg gcgagacttc atctgcgcca ttgccgatcc    1500
tcacgtctat cattggcaga cagtcatgga tgacaccgtg tctgcatccg tggcccaagc    1560
actgacgaa ctcatgttgt gggccgagga ttgccctgag gtcaggcacc tggtgcacgc     1620
ggatttcggc agcaataacg tacttacaga caatggtcgg attactgctg tcatcgactg    1680
gtccgaagcg atgtttggtg atagccaata cgaagtggcg aacatattct tctggcgtcc    1740
ctggttggcg tgcatggagc agcagacacg ctactttgaa cggaggcacc cggagctggc    1800
cggctcccca cgactccgcg cctatatgtt gcgtatcgga ctcgatcagc tttaccagtc    1860
tctcgtcgac ggcaacttcg acgacgccgc gtgggcgcag ggccgctgcg acgcgatagt    1920
ccgcagcggg gctgggacgg tgggtcggac ccaaatcgca cgccggtcgg ctgcggtgtg    1980
gacagacggc tgtgttgagg tgcttgcgga ctcgggcaac cgtaggccga gcacccgacc    2040
gcgtgcaaag gagtgattga atcattgaat gaaccattgt gtgcagaatc gatttcggga    2100
gtgttgccaa cacaagaaat atgcccaggg ttgtgtagaa gtttgcgtga atgtgatgaa    2160
gggaagccat acgctgaatt atcgtgacgt gtgtgagacg aagtgtcaca tcatacaccc    2220
```

```
aatttgagaa gctgtaccta ttagaagaat ttgtgagata cattaaaccc cttttggtac   2280
gtggtataat tgttatttgg gaagctgtaa acacgcagat cgttcctgag attgtcaatt   2340
acttttgtgg tgtttcctaa aggccgcatc actgcccgaa tcgagttgat ggcccgcaaa   2400
```

```
<210> SEQ ID NO 44
<211> LENGTH: 23
<212> TYPE: DNA
<213> ORGANISM: Nannochloropsis gaditana
<220> FEATURE:
<221> NAME/KEY: misc_feature
<223> OTHER INFORMATION: Target sequence of guide targeting PXA1

<400> SEQUENCE: 44
ggggtctggc acctgccgtc agg                                             23

<210> SEQ ID NO 45
<211> LENGTH: 23
<212> TYPE: DNA
<213> ORGANISM: Nannochloropsis gaditana
<220> FEATURE:
<221> NAME/KEY: misc_feature
<223> OTHER INFORMATION: Target sequence of guide targeting ACO1

<400> SEQUENCE: 45
ggcgaggacg acgcatacca tgg                                             23

<210> SEQ ID NO 46
<211> LENGTH: 23
<212> TYPE: DNA
<213> ORGANISM: Nannochloropsis gaditana
<220> FEATURE:
<221> NAME/KEY: misc_feature
<223> OTHER INFORMATION: Target sequence of guide targeting ICL

<400> SEQUENCE: 46
ggcaggttcg accaggaggc tgg                                             23

<210> SEQ ID NO 47
<211> LENGTH: 23
<212> TYPE: DNA
<213> ORGANISM: Nannochloropsis gaditana
<220> FEATURE:
<221> NAME/KEY: misc_feature
<223> OTHER INFORMATION: Forward primer to detect donor fragment
      insertion at TrifuncB locus

<400> SEQUENCE: 47
ggcttggcgt ccaaagccgc cgg                                             23

<210> SEQ ID NO 48
<211> LENGTH: 22
<212> TYPE: DNA
<213> ORGANISM: Nannochloropsis gaditana
<220> FEATURE:
<221> NAME/KEY: misc_feature
<223> OTHER INFORMATION: Reverse primer to detect donor fragment
      insertion at TrifuncB locus

<400> SEQUENCE: 48
ggcgaatttc tgtaggtcca cg                                              22

<210> SEQ ID NO 49
<211> LENGTH: 27
<212> TYPE: DNA
<213> ORGANISM: Nannochloropsis gaditana
<220> FEATURE:
```

```
<221> NAME/KEY: misc_feature
<223> OTHER INFORMATION: Forward primer to detect donor fragment
      insertion at PXA1 locus

<400> SEQUENCE: 49
gcttgtgtag gtcgtgacct ggaaggc                                          27

<210> SEQ ID NO 50
<211> LENGTH: 22
<212> TYPE: DNA
<213> ORGANISM: Nannochloropsis gaditana
<220> FEATURE:
<221> NAME/KEY: misc_feature
<223> OTHER INFORMATION: Reverse primer to detect donor fragment
      insertion at PXA1 locus

<400> SEQUENCE: 50
ccgacctcgt caaagcatcg gc                                               22

<210> SEQ ID NO 51
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Forward primer to detect donor fragment
      insertion at AOC1 locus

<400> SEQUENCE: 51
tcaaagatca tttagcagag a                                                21

<210> SEQ ID NO 52
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Reverse primer to detect donor fragment
      insertion at AOC1 locus

<400> SEQUENCE: 52
agtcgagaga tggtgcgttc a                                                21

<210> SEQ ID NO 53
<211> LENGTH: 25
<212> TYPE: DNA
<213> ORGANISM: Nannochloropsis gaditana
<220> FEATURE:
<221> NAME/KEY: misc_feature
<223> OTHER INFORMATION: Forward primer to detect donor fragment
      insertion at ICL locus

<400> SEQUENCE: 53
ggactttcca tgcgacatag ctttc                                            25

<210> SEQ ID NO 54
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer to detect donor fragment
      insertion at ICL locus

<400> SEQUENCE: 54
catctgcacc acctgaacgg                                                  20
```

```
<210> SEQ ID NO 55
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bleomycin resistance gene, codon optimized for
      Nannochloropsis

<400> SEQUENCE: 55
atggccaagc tgaccagcgc cgttccggtg ctcaccgcgc gcgacgtcgc cggagcggtc      60
gagttctgga ccgaccggct cgggttctcc cggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca actgcgtgca cttcgtggcc     360
gaggagcagg actaa                                                      375

<210> SEQ ID NO 56
<211> LENGTH: 1000
<212> TYPE: DNA
<213> ORGANISM: Phaeodactylum tricornutum
<220> FEATURE:
<221> NAME/KEY: misc_feature
<223> OTHER INFORMATION: GAPDH promoter

<400> SEQUENCE: 56
ggatttgcct cccatgcgcg gaaagtttgc acagagccag ctacagcaat gtcaatttct      60
tttgcagtgg ttggcacggg ttgatgggct gcactatcga tattgctgtc aatggctgtg     120
ctttggtttg acatcggtgc tgtgcgacgt ttggccatgc gctcggccat tctgtttttt     180
cgaatatgca aagttgtctc ttcccgagat cgacgaccgt cttcagctga cacggtcttc     240
ttaaatgacg catcacgacg aggaactaaa gccgcccagg tatacaattg tggcattaga     300
gactgaatac aatgcctcga atagcggaga tactaagggc cgttatttcg tacctgcggc     360
gactagggtc atgattgtat ctctaagaac aacaagggaa atttctgatc aaggtcgacg     420
ggtaaaaggc ggaacaagaa taaaaggatg gtgatacgga acagagcaac gctacagaaa     480
agtgaggatc gccaaccatc aagttgtggc gatgcgatac ttttttgcgat aacgtctcgc     540 gctctatgat tttctttgtt atattaattt gttcaacatg agctaattaa ccgaaacctt     600
atgcctcaac tgccgactca gcacaagtac ctaactttgc aaggttttgt cgtatacgtc     660
tgtccataga acgttgacta atgtaagagg aagattttttg tggacgttgt gcgcttgaca     720
tccattggtt gatgtggttt tgctgatgtc acggcatcct gagtcccta acgtttcact     780 tggcgcctcg cagctgttg cagttcgctc ggtatctttt tctaggatct tccgcagatt     840
tgaagttcgc atcgaaacca ttcctgtcgt ggaaaaaagg cctggatcgc atcttgcagg     900
tgcaacgcta attcttctcc attcataaaa acagaactcg tagaaaacga ttcaaatctt     960 tttttcgcctt tctaaacatc agtaattcta tcaaattcta                         1000

<210> SEQ ID NO 57
<211> LENGTH: 479
<212> TYPE: DNA
<213> ORGANISM: Thalassiosira pseudonana
<220> FEATURE:
<221> NAME/KEY: misc_feature
```

-continued

```
<223> OTHER INFORMATION: alpha tubulin terminator

<400> SEQUENCE: 57
tcactctgtc gcgctgttgg cgccactact ttgggggtac gagtttaggc tgccttggct       60
gggataaaga atgataagtt tacataattt gtattggaaa tccatcgagt tttggattca      120
gttgacgtct cctgcgttac tatgtcttca ttctctccag tatcaatgcc tatggttcgt      180
cgacattgag cacatttctt tcatcagcgc gatgcatgca atcatcactt cgcaatcttg      240
acaaacatcc tcaatgattc ctccacctct cccaacaaag tcaatgcatt catccttgga      300
tcttctcctc caccgaacgg ccgtgaagcc gactccatta gtgcatccag tccatcaaaa      360
taccgtatga attcccgaaa agattcactt gccaagtact gtttgtcatc ctcctcttca      420
ggtatctcat caatgagtgc atttgcagct atacgaatct ttgactcgga aatcaatcc       479
```

RECOMBINANT ALGAL MICROORGANISMS HAVING INCREASED LIPID PRODUCTION, AND METHODS OF MAKING AND USING THE SAME

CROSS-REFERENCE TO RELATED APPLICATIONS

This application claims benefit of priority under 35 U.S.C. § 119(e) of U.S. Ser. No. 62/702,253, filed Jul. 23, 2018, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2190_1_Sequence_Listing, was created on Jul. 16, 2019, and is 162 kb. The file can be accessed using Microsoft Word on a computer that uses Windows OS.

FIELD OF THE INVENTION

The invention relates to mutant algal microorganisms having increased lipid productivity and methods of their use in producing lipids.

BACKGROUND INFORMATION

Various attempts to improve lipid productivity by increasing lipid biosynthesis have been made by attempting to manipulate genes encoding enzymes for nitrogen assimilation or lipid metabolism as well as genes encoding polypeptides involved in lipid storage. For example, US 2014/0162330 discloses a *Phaeodactylum tricornutum* strain in which expression of the nitrate reductase (NR) gene was attenuated by RNAi-based knockdown; Trentacoste et al. ((2013) *Proc. Natl. Acad. Sci. USA* 110: 19748-19753) disclose diatoms transformed with an RNAi construct targeting the Thaps3_264297 gene predicted to be involved in lipid catabolism; and WO2011127118 discloses transformation of *Chlamydomonas* with genes encoding oleosins (lipid storage proteins) as well as with genes encoding diacylglycerol transferase (DGAT) genes. Although in each case increased lipid production was asserted based on microscopy or staining with lipophilic dyes, no quantitation of lipid produced by the manipulated cells was provided, nor was the relationship between biomass and lipid productivities over time determined.

Daboussi et al. 2014 (*Nature Comm.* 5:3881) report that disruption of the UGPase gene in *Phaeodactylum triconornutum*, which is believed to provide precursors to laminarin (storage carbohydrate) synthesis, results in increased lipid accumulation. However, no biochemical data was shown to indicate that laminarin content was affected (or even present) and lipid and biomass productivities were not reported. Similarly, several groups have reported increases in lipid accumulation in *Chlamydomonas* starchless mutants (Wang et al. 2009 *Eukaryotic Cell* 8:1856-1868; Li et al. 2010 *Metab Eng.* 12:387-391) however, successive reports that actually measured lipid productivity concluded that these strains were impaired in growth when grown in phototrophic conditions (Siaut et al. (2011) *BMC Biotechnol.* 11: 7; Davey et al. 2014 *Eukaryot Cell* 13:392-400). These reports concluded that the highest lipid productivities (measured as TAG per liter per day) were actually achieved by the wild-type parental strain.

WO 2011/097261 and US 20120322157 report that a gene denoted "SN03" encoding an arrestin protein has a role in increasing lipid production under nutrient replete conditions when overexpressed in *Chlamydomonas*. However, overexpression of the SN03 gene was observed to result in the appearance of unidentified polar lipids (which were not quantified) and did not result in an increase in triglycerides (TAG). Another polypeptide identified as potentially regulating stress-induced lipid biosynthesis has been described by Boyle et al. ((2012) *J. Biol. Chem.* 287:15811-15825). Knockout of the NRR1 gene in *Chlamydomonas* encoding a "SQUAMOUSA" domain polypeptide resulted in a reduction of lipid biosynthesis with respect to wild type cells under nitrogen depletion; however, no mutants were obtained demonstrating increased lipid production. US 2010/0255550 recommends the overexpression of putative transcription factors ("TF1, TF2, TF3, TF4, and TF5") in algal cells to increase lipid production, but no mutants having enhanced lipid production are disclosed.

US 2017/005803 discloses a ZyCys regulator gene whose attenuation results in increased lipid productivity in mutant algae when cultured in a medium that includes nitrate. The mutant algae demonstrated growth in culture, accumulating biomass at a rate at least 80% that of wild type cells while producing up to twice as much lipid as the wild type progenitor strain. US 2017/0121742 discloses mutant algae having attenuated expression of a gene encoding a polypeptide having a Bromo domain and a TAZ zinc finger domain that demonstrate elevated lipid productivity with minimal reduction in biomass productivity with respect to wild type algae.

Fatty acid degradation occurs in the peroxisome of plants and fungi, while in animals the mitochondria have a major role in beta oxidation of fatty acids (Poirier et al. (2006) *Biochem Biophys Acta* 1763:1413-1426; Bartlett and Eaton (2004) *Eur. J. Biochem.* 271:462-469). Germain et al. (*Plant J.* 28:1-12, 2001) disclose that *Arabidopsis* seedlings mutated in the KAT2 gene encoding a peroxisomal 3-ketoacyl-CoA thiolase demonstrates persistence of lipid bodies and TAG in developing seedlings, and Slocombe et al. (*Plant Biotechnol. J.* 7:694-703, 2009) disclosed that *Arabidopsis* plants having mutated genes encoding peroxisomal transporters or a peroxisomal acyl-CoA oxidase had increased TAG accumulation in senescing leaves. US 2016/0097066 suggests attenuating expression of genes encoding components of the peroxisomal beta-oxidation pathway, including acyl-CoA oxidases, the multifunctional enzyme (including domains for hydroxyacyl-CoA dehydrogenase and enoyl-CoA hydratase), and oxyacyl-CoA thiolase in oleaginous yeasts such as *Yarrowia* to improve fatty acid production, although US 2016/0215308 discloses that disruption of the genes for a peroxisomal transporter (PXA2) and peroxisomal acyl-CoA oxidase (POX1) did not improve fatty acid production in a *Saccharomyces* strain engineered to overproduce fatty acids.

SUMMARY OF THE INVENTION

Provided herein in a first aspect is a mutant microorganism, such as an algal or heterokont microorganism, that has attenuated expression of at least one gene that encodes a polypeptide of the mitochondrial beta oxidation pathway. For example, the gene whose expression is attenuated can encode an acyl-CoA dehydrogenase, a trifunctional protein alpha subunit, or a trifunctional protein beta subunit. In some embodiments, the mutant microorganism includes a mutation that results in attenuated expression of mitochondrial trifunctional protein subunit B (TrifuncB) and/or mitochondrial trifunctional protein subunit A (TrifuncA). The expression of the gene encoding a polypeptide of the mitochondrial beta oxidation pathway is attenuated with respect to a control microorganism, for example, a microorganism of a strain from which the mutant microorganism was derived. Expression of the gene can be attenuated by genetic engineering or can be the result of a classical mutation. The microorganism that has attenuated expression of a gene encoding a polypeptide of the mitochondrial beta oxidation pathway can have higher lipid productivity and, for example, can accumulate more lipid on a daily basis than a control algal or fungal microorganism, e.g., a wild type microorganism or a microorganism from with the mutant microorganism was derived.

A mutant microorganism as provided herein that has attenuated expression of at least one gene that encodes a polypeptide of the mitochondrial beta oxidation pathway can optionally additionally have attenuated expression of at least one gene that encodes a polypeptide of the peroxisomal beta oxidation pathway. For example, the mutant microorganism can have, in addition to attenuated expression of a gene encoding an acyl-CoA dehydrogenase, TrifuncA, or TrifuncB, attenuated expression of a gene encoding an acyl-CoA oxidase, or a peroxisomal multifunctional enzyme having enoyl-CoA hydratase and hydroxyacyl-CoA dehydrogenase activity, or a ketoacyl-thiolase, or any combination thereof. Alternatively or in addition, a mutant microorganism as provided herein that has attenuated expression of at least one gene that encodes a polypeptide of the mitochondrial beta oxidation pathway can optionally additionally have attenuated expression of at least one gene that encodes a peroxisomal acyl-CoA transporter. Alternatively or in addition to any of the above, a mutant microorganism as provided herein that has attenuated expression of at least one gene that encodes a polypeptide of the mitochondrial beta oxidation pathway can optionally additionally have attenuated expression of at least one gene that encodes an enzyme of the glyoxylate pathway, such as for example isocitrate lyase. Thus, provided herein in a further aspect is a mutant microorganism that has attenuated expression of at least one gene that encodes a polypeptide that participates in the mitochondrial pathway of fatty acid oxidation and attenuated expression of at least one gene that encodes a polypeptide that participates in the peroxisomal pathway of fatty acid oxidation (including as an enzyme or as a transporter) or the glyoxylate pathway. The mutant microorganism can produce more lipids, such as fatty acid methyl ester-derivatizable lipids (FAME lipids), on a per volume or per area basis than a control microorganism of the same species as the mutant microorganism. The mutant microorganism can be an algal or heterokont microorganism.

A mutant microorganism as provided herein that has attenuated expression of at least one gene that encodes a polypeptide of the mitochondrial beta oxidation pathway and additionally has attenuated expression of one or more additional genes that encode any of an acyl-CoA transporter, a peroxisomal enzyme that functions in fatty acid catabolism, or an enzyme of the glyoxylate pathway can have higher lipid productivity and/or can accumulate more lipid on a daily basis than a control microorganism, e.g., a wild type microorganism or a microorganism from which the mutant having attenuated expression of a mitochondrial beta oxidation gene and at least one of a peroxisomal acyl-CoA transporter, a peroxisomal enzyme, and an enzyme of the glyoxylate pathway, was derived.

The microorganism that has attenuated expression of a mitochondrial beta oxidation pathway and optionally a peroxisomal beta oxidation pathway gene, peroxisomal acyl-CoA transporter, or a glyoxylate pathway enzyme can have one or more further genetic modifications, including but not limited to, modification in genes encoding regulators of lipid biosynthesis, photosynthetic efficiency, nitrogen metabolism, transporters, or resistance to herbicides or toxins. Such modifications can be the result of genetic engineering or classical mutagenesis. Genetic modifications in a mutant microorganism can also include introduced genes or mutations that increases expression of one or more genes such as, for example, genes affecting lipid biosynthesis, growth, herbicide or toxin resistance, photosynthetic efficiency, etc. The microorganism can be an algal or heterokont microorganism, for example, a microalga, such as a eukaryotic microalga that can be of the Bacillariophytes (diatoms), Eustigmatophytes, Xanthophytes, Phaeophytes, Chrysophytes, Raphidophytes, or Chlorophytes (for example, a member of the Chlorophyceae, Chlorodendrophyceae, Trebouxiophyceae, or Prasinophyceae), as nonlimiting examples. For example, the engineered or mutant microorganism may be an algal heterokont species belonging to, for example, the Bacillariophytes or the Eustigmatophytes. Alternatively, the microorganism can be a heterotrophic heterokont such as a Labyrinthulomycete, for example a member of the Labyrinthulids or Thraustochytrids.

Further included in the invention are a biomass comprising a mutant microorganism as provided herein and lysates or extracts of mutant microorganisms as provided herein. Products that include such biomass, lysates, or extracts are also considered, including food, feed, and biofuel feedstocks.

Yet another aspect of the invention is a method of producing lipid that includes culturing a mutant microorganism having attenuated expression of at least one gene that encodes a polypeptide of the mitochondrial beta oxidation pathway and isolating lipid from the culture. Also included is a method of producing lipid that includes culturing a mutant microorganism having attenuated expression of at least one gene that encodes a polypeptide of the mitochondrial beta oxidation pathway and attenuated expression of at least one gene that encodes any of an acyl-CoA transporter, a peroxisomal enzyme that functions in fatty acid catabolism, or an enzyme of the glyoxylate pathway and isolating a lipid from the culture.

A further aspect of the invention is a method of improving lipid accumulation or productivity of a microorganism where the method includes attenuating expression of at least one gene that encodes a polypeptide that functions in the peroxisomal fatty acid oxidation pathway and at least one enzyme that functions in the mitochondrial beta oxidation pathway.

These and other objects and features of the invention will become more fully apparent when the following detailed description of the invention is read in conjunction with the accompanying drawings.

DETAILED DESCRIPTION OF THE INVENTION

Definitions

Figure 1:
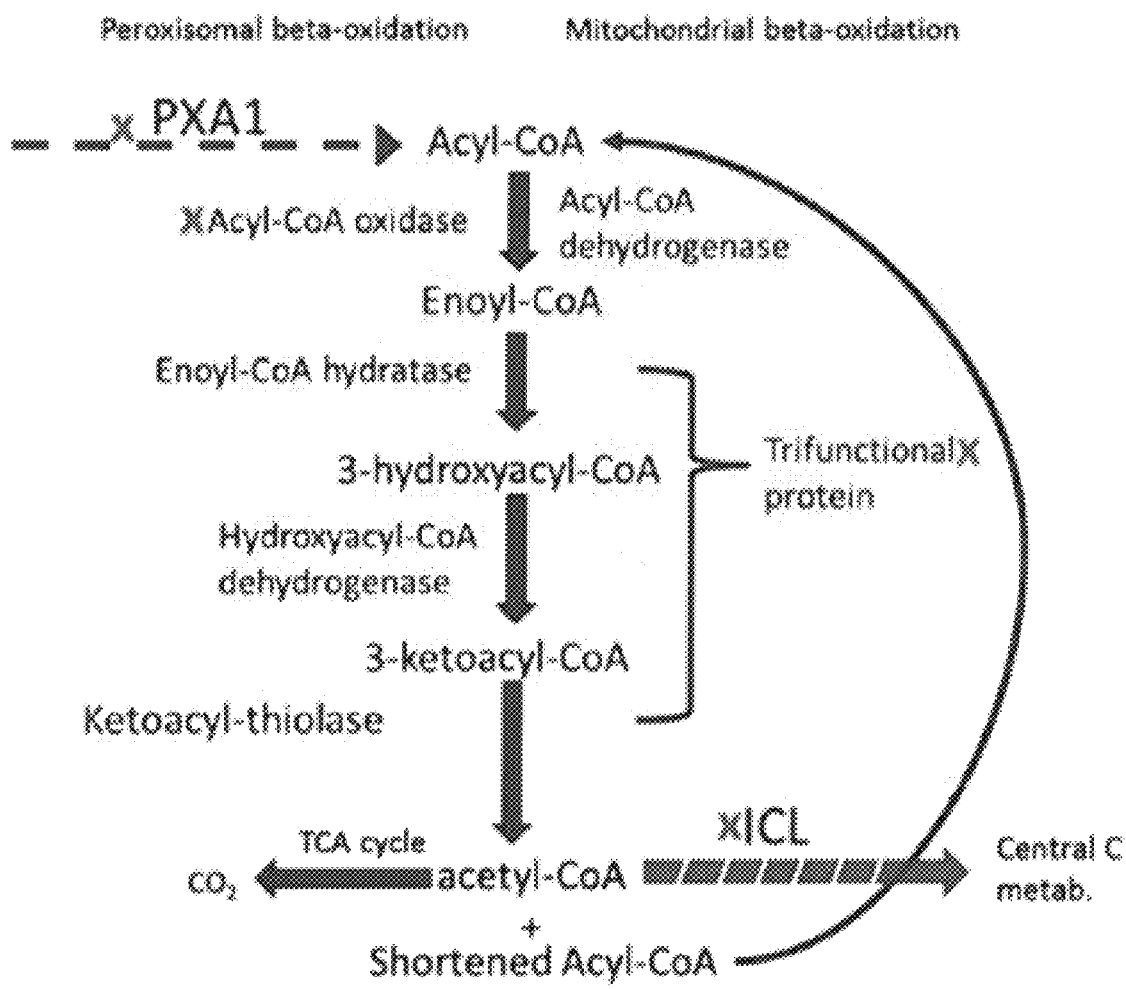
FIG. 1. Schematic depicting the metabolic pathways of mitochondrial and peroxisomal beta-oxidation as well as post-beta-oxidation in *Nannochloropsis gaditana* wild-type strain 3730 ("WT-3730"). Genes for which Cas9 mediated insertional mutations have been generated are indicated with X's, indicating the node of metabolism that has been defunctionalized.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All ranges provided within the application are inclusive of the values of the upper and lower ends of the range unless specifically indicated otherwise.

All publications, patents and other references mentioned herein are incorporated by reference in their entireties for all purposes as if each individual publication or patent application were specifically and individually indicated to be incorporated by reference.

All headings are for the convenience of the reader and do not limit the invention.

The term "and/or" as used in a phrase such as "A and/or B" herein is intended to include any of "A and B", "A or B", "A", and "B".

"About" means either within 10% of the stated value, or within 5% of the stated value, or in some cases within 2.5% of the stated value, or, "about" can mean rounded to the nearest significant digit.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene can be of any length and is preferably greater than 50 nucleotides in length, more preferably greater than 100 nucleotides in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid molecule that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence, or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As non-limiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of coding or noncoding sequences, including sequences 5' of the transcribed or translated region of the gene and sequences 3' of the transcribed or translated region of the gene, and may include, for example, gene regulatory sequences. An attenuated gene may also be a gene targeted by a nucleic acid molecule of construct that reduces expression of the gene, such as, for example, an antisense RNA, microRNA, RNAi molecule, or ribozyme. As used herein "mutant", such as "mutant organism", "mutant microorganism", "mutant alga" mutant algal microorganism, "mutant heterkont microorganism, "mutant cell" and the like refers to organisms and cells have on ore more alterations (insertions, deletions, substitutions, etc.) in the sequence of a gene or its adjacent 5' or 3' sequences and also refers to organism and cells that include exogenous nucleic acid molecules and/or genetic constructs that target a gene or its expression, such as, for example, antisense RNA molecules or constructs for expression antisense RNA molecules, RNAi constructs or RNAi molecules, ribozymes or constructs for producing ribozymes, etc. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide, or results in a polypeptide having amino acid substitution(s) that affect protein folding, protein complex assembly, and/or protein activity.

"Exogenous nucleic acid molecule", "exogenous nucleic acid", "exogenous DNA", or "exogenous gene" refers to a nucleic acid molecule or gene that has been introduced ("transformed") into a cell. A transformed cell may be referred to as a recombinant cell, into which additional exogenous gene(s) may optionally be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Thus non-native genes include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, gene replacement, and promoter replacement, deletion, or insertion, as well as introduction of transgenes or synthetic genes into the organism. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or CRISPR/Cas systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

A "control cell" or "control microorganism" is a cell or microorganism that is substantially identical to the manipulated, recombinant, or mutant cell referred to, with the exception that the control cell does not have the modification of the manipulated, recombinant, or mutant cell. A control cell can be a wild type cell, for example a wild type cell of the strain from which the manipulated, recombinant, or mutant cell is directly or indirectly derived. A control cell may be "substantially genetically identical" or "genetically essentially identical", meaning that it includes the same species or strain genome and the same introduced constructs or genetic alterations as the mutant or recombinant cell or organism, while taking into account there may be minor and inconsequential (for the purposes of the invention relating to lipid productivity) differences between the control and mutant microorganism in addition to the changes described herein. For example, there may be small nucleotide polymorphisms (SNPs) unrelated to any TrifuncA, TrifuncB, perosisomal transporter, acyl-CoA oxidase, and isocitrate lyase genes that differ in the control and mutant genomes.

Reference to properties that are "substantially the same" or "substantially identical", without further explanation of the intended meaning, is intended to mean the properties are within 10%, and preferably within 5%, and may be within 2.5%, within 1%, or within 0.5% of the reference value. Where the intended meaning of "substantially" in a particular context is not set forth, the term is used to include minor and irrelevant deviations that are not material to the characteristics considered important in the context of the invention.

Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

"The same conditions" or "the same culture conditions", as used herein, means substantially the same conditions, that is, any differences between the referenced conditions are minor and not relevant to the function or properties of the microorganism that are material to the invention, e.g., lipid production or biomass production.

The "protospacer adjacent motif" or "PAM" is a DNA sequence, typically two to eight nucleotides in length, for example, two to four nucleotides in length, immediately following or preceding the DNA sequence targeted by a Cas protein. PAM sequences are believed to be important for Cas proteins to bind to or cleave a target DNA sequence. Some mutations caused by Cas proteins in a microorganism will be upstream or downstream of the PAM sequence within a number of base pairs, such as within 5 base pairs, within 10 base pairs, within 15 base pairs, within 20 base pairs, within 25 base pairs, within 30 base pairs, within 35 base pairs, within 40 base pairs, within 45 base pairs, or within 50 base pairs.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene ID numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "Gene ID" is associated with nucleotide and amino acid sequences for the gene. Searching and obtaining nucleic acid or gene sequences or protein sequences based on Gene ID numbers is well known in the arts of, e.g., cell biology, biochemistry, molecular biology, and molecular genetics. In addition to the gene name, genes from the algae *Nannochloropsis gaditana* provided herein are also associated with a Naga number on the Worldwide web at nannochloropsis.org. These numbers refer to specific locations in the genome of *Nannochloropsis gaditana*. A skilled artisan will be able to use these numbers to search and obtain nucleic acid or gene sequences or protein sequences.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 60, less than about 50, less than about 40, less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150, at least 200 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, cas/CRISPR-mediated generation of mutations by non-homologous end joining DNA repair or insertion of a gene-disrupting nucleic acid sequence (donor fragment), or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest. Further, CRISPR-mediated mutations, such as but not limited to insertions of a donor fragment, in non-coding regions of a gene such as the promoter region, 5'UTR, or 3' UTR, can result in reduced expression of the targeted gene.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "down-regulated" or "down-regulation" includes a decrease in expression of a gene or nucleic acid molecule of interest or the activity of an enzyme, e.g., a decrease in gene expression (including without limitation by reduced transcription level, reduced RNA transcript stability, and reduced translation level) or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that can include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism. A mutant organism of interest will typically have a phenotype different than that of the corresponding wild type or progenitor strain that lacks the mutation, where the phenotype can be assessed by growth assays, product analysis (e.g. lipid and/or biomass analysis), photosynthetic properties, biochemical assays (e.g. lipid productivity), etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. As non-limiting examples, a mutant gene can be a gene that has an insertion within the promoter region, an intron, 3' UTR, or 5' UTR, that can either increase or decrease expression of the gene; can be a gene that has a deletion, resulting in production of a nonfunctional protein, truncated protein, dominant negative protein, or no protein; can be a gene that has one or more point mutations leading to a change in the amino acid of the encoded protein or results in aberrant splicing of the gene transcript, etc.

The term "Pfam" refers to a large collection of protein domains and protein families maintained by the Pfam Consortium and available at several sponsored world wide web sites, including: pfam.xfam.org/(European Bioinformatics Institute (EMBL-EBI). The latest release of Pfam is Pfam 29.0 (December 2015). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using the above-referenced website, protein sequences can be queried against the HMMs using HMMER homology search software (e.g., HMMER2, HMMER3, or a higher version, hmmer.org). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

Reference to properties that are "substantially the same" or "substantially identical" without further explanation of the intended meaning, is intended to mean the properties are within 10%, and preferably within 5%, and may be within 2.5%, of the reference value. Where the intended meaning of "substantially" in a particular context is not set forth, the term is used to include minor and irrelevant deviations that are not material to the characteristics considered important in the context of the invention.

"The same conditions" or "the same culture conditions", as used herein, means substantially the same conditions, that is, any differences between the referenced conditions are minor and not relevant to the function or properties of the microorganism that are material to the invention, e.g., lipid production or biomass production.

"Nitrogen replete" conditions, with respect to a particular cell type, are conditions under which the cell does not experience growth deficient due to insufficient nitrogen.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. As used herein, "fatty acid methyl ester lipids", "fatty acid methyl ester-derivatizable lipids", "FAME lipids", or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. Lipid productivity can be assessed as FAME productivity in milligrams per liter (mg/L) and for algae, may be reported as grams per meter2 per day (g/m2/day) (areal productivity). In the semi-continuous productivity assays (SCPAs) provided herein, mg/L values are converted to g/m2/day by taking into account the area of incident irradiance (the SCPA flask rack aperture of 1½"×33/8", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example, where the microorganisms are inoculated into a container of culture, allowed to grow for a length of time, and then harvested. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as total carbon ("TOC") productivity in milligrams per liter (mg/L) and for algae, may be reported as grams per meter2 per day (g/m2/day). In the semi-continuous assays provided herein, mg/L values are converted to g/m2/day by taking into account the area of incident irradiance (the SCPA flask rack aperture of 1½"×33/8", or 0.003145 m2) and the volume of the culture (550 ml). To obtain productivity values in g/m2/day, mg/L values are multiplied by the daily dilution rate (30%) and a conversion factor of 0.175. Where biomass is expressed as a percentage, the percentage is a weight percent unless indicated otherwise.

In the context of the invention, a "nitrogen source" is a source of nitrogen that can be taken up and metabolized by the subject microorganism and incorporated into biomolecules for growth. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium, ammonia, urea, or an amino acid that can be metabolized by the microorganism being cultured to provide a source of nitrogen for incorporation into biomolecules, thereby supporting growth. For example, in addition to ammonium/ammonia and urea, reduced nitrogen can include various amino acids where the amino acid(s) can serve as a nitrogen source to the subject microorganism. Examples of amino acids can include, without limitation, glutamate, glutamine, histidine, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen [in the culture medium]" is used interchangeably with "substantially the sole source of nitrogen" and indicates that no other nitrogen source is intentionally added to the culture medium, or that no other nitrogen source is present in an amount sufficient to significantly increase the growth of the microorganisms or cells cultured in the referenced medium. Throughout this application, for brevity, the terms "nitrate-only" and "urea-only" are used to characterize culture media in which nitrate is the only source of nitrogen that is available to the microorganisms for supporting growth or urea is the only source of nitrogen that is available to the microorganisms for supporting growth, respectively.

Similarly, "the sole source of carbon [in the culture medium]" is used interchangeably with "substantially the sole source of carbon" and indicates that no other carbon source is present in an amount sufficient to increase the productivity or growth of the microorganisms or cells cultured in the referenced medium or is not significantly incorporated into biomolecules such as lipids produced by the microorganisms or cells.

As used herein, the term "mitochondrial trifunctional protein" or "MTP" refers to a mitochondrial protein with the following enzymatic activities: 2-enoyl coenzyme A (CoA) hydratase, long-chain 3-hydroxy acyl-coA dehydrogenase, and long-chain 3-ketoacyl CoA thiolase (Eaton et al. (2000) Organisms, Organs, Cells, and Organelles 28:177-182). MTP is composed of the TrifuncA and TrifuncB subunits, which have different enzymatic activities within the MTP holoenzyme, as discussed herein. "Mitochondrial trifunctional protein subunit A" or "TrifuncA", also known as "hydroxyacyl-CoA dehydrogenase/3-ketoacyl-CoA thiolase/enoyl-CoA hydratase (trifunctional protein), alpha subunit" and sometimes referred to as "multifunctional fatty acid oxidation complex subunit alpha" refers to an enzyme that is localized to the mitochondria and is capable of catalyzing the second and third steps of mitochondrial beta-oxidation of long chain fatty acids, i.e., the 3-hydroxyacyl-CoA dehydrogenase and enoyl-CoA hydratase activities of the mitochondrial trifunctional protein holoenzyme. The enzyme converts medium- and long-chain 2-enoyl-CoA compounds into 3-ketoacyl-CoA when NAD is solely present and acetyl-CoA when NAD and CoA are present. TrifuncA is Uniprot W7TLR9 (see on the internet at uniprot.org) and includes those enzymes that correspond to Enzyme Commission Numbers 1.1.1.211 and 4.2.1.17. TrifuncA includes pfam domain PF00378 (ECH-1, Enoyl-CoA hydratase/isomerase; "crotonase family note='Crotonase/Enoyl-Coenzyme A (CoA) hydratase superfamily'") and also includes pfam domain PF02737 (3HCDH_N, 3-hydroxyacyl-CoA dehydrogenase, NAD binding domain) and pfam domain PF00725 (3HCDH, 3-hydroxyacyl-CoA dehydrogenase, C-terminal domain). TrifuncA includes the conserved domain "cl28491" also referred to as "FadJ Superfamily". Protein sequences can be searched to identify conserved domains at ncbi.nlm.nih (CDD or 'conserved domain database' of the BLAST menu).

An amino acid sequence of wild type *N. gaditana* TrifuncA is provided in SEQ ID NO:1. A nucleotide sequence of a cDNA encoding wild type *N. gaditana* TrifuncA is provided in SEQ ID NO:2. A nucleotide sequence of a genomic DNA of a wild type *N gaditana* TrifuncA gene is provided in SEQ ID NO:3. The *N gaditana* TrifuncA gene can be found at the chromosomal locus Naga_100466g3 or NG_scf06 (299664-304033) (see *Nannochloropsis* genome available on the Worldwide web at nannochloropsis.org). A skilled artisan can use this disclosure to identify a TrifuncA gene in other microbial species, such as algal or heterokont species, as a gene encoding a protein that has protein domains diagnostic of the TrifuncA polypeptide and/or when expressed has the enzymatic activity of TrifuncA, for example using genomic DNA or cDNA. Examples of genes from other species that are homologous to TrifuncA follow, and should aid a skilled artisan in the identification of a TrifuncA gene in other microbial species, such as algal or heterokont species: the hydroxyacyl-CoA dehydrogenase/3-ketoacyl-CoA thiolase/enoyl-CoA hydratase (trifunctional protein), alpha subunit genes in *Homo sapiens* (Official symbol: HADHA; Gene ID: 3030), Pan troglodytes (Official symbol: HADHA; Gene ID: 459079), *Macaca mulatta* (Official symbol: HADHA; Gene ID: 695975), *Canis lupus familiaris* (Official symbol: HADHA; Gene ID: 100856745), Bos taurus (Official symbol: HADHA; Gene ID: 281810), *Mus musculus* (Official symbol: Hadha; Gene ID: 97212), *Rattus norvegicus* (Official symbol: Hadha; Gene ID: 170670), *Gallus* (Official symbol: HADHA; Gene ID: 395929), and *Xenopus tropicalis* (Official symbol: hadha; Gene ID: 394832), the hydroxyacyl-Coenzyme A dehydrogenase/3-ketoacyl-Coenzyme A thiolase/enoyl-Coenzyme A hydratase, alpha subunit a and hydroxyacyl-Coenzyme A dehydrogenase/3-ketoacyl-Coenzyme A thiolase/enoyl-Coenzyme A hydratase, alpha subunit b genes in *Danio rerio* (Official symbol: hadhaa; Gene ID: 553401 and Official symbol: hadhab; Gene ID: 793834, respectively), the mitochondrial trifunctional protein alpha subunit gene in *Drosophila melanogaster* (Official symbol: Mtpalpha; Gene ID: 34276), the AGAP007784-PA gene in *Anopheles gambiae* str. PEST (Official symbol: AgaP_AGAP007784; Gene ID: 1278181), and the Enoyl-CoA Hydratase genes in *Caenorhabditis elegans* (Official symbol: ech-1.1; Gene ID: 180037 and Official symbol: exh-1.2; Gene ID: 172310).

TrifuncA polypeptides of heterokont and algal species include, for example, the polypeptide of GenBank accession EJK46802.1 (SEQ ID NO:4) of the diatom algal species *Thalassiosira oceanica*, the polypeptide of GenBank accession XP_002292674.1 (SEQ ID NO:5) of the diatom algal species *Thalassiosira pseudonana*, the polypeptide of Genbank XP_002179641.1 (SEQ ID NO:6) of the diatom species *Phaeodactylum tricornutum*, the polypeptide of GenBank accession OEU18702.1 (SEQ ID NO:7) of the diatom algal species *Fragilariopsis cylindrus*, the polypeptide of GenBank accession XP_009032222.1 (SEQ ID NO:8) of the heterokont alga *Aureococcus anophagefferens*, as well as the polypeptide of GenBank accession CBJ30498.1 (SEQ ID NO:9) of the brown alga *Ectocarpus silicus*.

As used herein, the term "mitochondrial trifunctional protein subunit B" or "TrifuncB", also known as "3-ketoa-cyl-CoA thiolase, acetyl 1-CoA acyltransferase" or "beta-ketothiolase", refers to an enzyme that is expressed at least in part in the mitochondria and is capable of catalyzing the final step of beta-oxidation, in which 3-ketoacyl CoA is cleaved by the thiol group of another molecule of Coenzyme A. The thiol is inserted between C-2 and C-3, which yields an acetyl CoA molecule and an acyl-CoA molecule that is two carbons shorter than the acyl-CoA entering the beta oxidation cycle. TrifuncB includes an enzyme that corresponds to Enzyme Commission Number 2.3.1.16. TrifuncB includes pfam domain PF00108 (Thiolase N, "Thiolase, N-terminal domain") and also includes pfam domain PF02803 (Thiolase C, "Thiolase, C-terminal domain"). TrifuncB includes the conserved domain "cd00751", the "thiolase" domain. Protein sequences can be searched to identify conserved domains at ncbi.nlm.nih (CDD or 'conserved domain database' of the BLAST menu).

An amino acid sequence of wild type *N. gaditana* TrifuncB is provided in SEQ ID NO:10. A nucleotide sequence of a cDNA encoding wild type *N. gaditana* TrifuncB is provided in SEQ ID NO:11. A nucleotide sequence of a genomic DNA of a wild type *N gaditana* TrifuncB gene is provided in SEQ ID NO: 12. The genomic location of the *N gaditana* TrifuncB gene is NG_contig02524 (74-597) or (Naga_102524g1) (*Nannochloropsis* genome available on the Worldwide web at nannochloropsis.org). A skilled artisan can use this disclosure to identify a TrifuncB gene in any microbial species, such as any algal or heterokont species, as a gene encoding a protein that has protein domains diagnostic of the TrifuncB polypeptide and/or when expressed has the enzymatic activity of TrifuncA, for example using genomic DNA or cDNA. TrifuncB genes from other species that are homologous to TrifuncB follow and should aid a skilled artisan in the identification of a homologous gene in any microbail species, such as an algal or heterokont species: the hydroxyacyl-CoA dehydrogenase/3-ketoacyl-CoA thiolase/enoyl-CoA hydratase (trifunctional protein), beta subunit genes in *Homo sapiens* (Official Symbol: HADHB; Gene ID: 3032), Pan troglodytes (Official Symbol: HADHB; Gene ID: 459080), *Macaca mulatta* (Official Symbol: HADHB; Gene ID: 698025), *Canis lupus familiaris* (Official Symbol: HADHB; Gene ID: 607926), Bos taurus (Official Symbol: HADHB; Gene ID: 281811), *Mus musculus* (Official Symbol: Hadhb; Gene ID: 231086), *Rattus norvegicus* (Official Symbol: Hadhb; Gene ID: 171155), *Gallus* (Official Symbol: HADHB; Gene ID: 421995), *Xenopus tropicalis* (Official Symbol: hadhb; Gene ID: 394747), and *Danio rerio* (Official Symbol: hadhb; Gene ID: 336606) and the thiolase gene in *Drosophila melanogaster* (Official Symbol: Thiolase; Gene ID: 37784), the AGAP011827-PA gene in *Anopheles gambiae* str. PEST (Official Symbol: AgaP_A-GAP011827; Gene ID: 1280821), and the hypothetical protein gene in *Caenorhabditis elegans* (Official Symbol: B0303.3; Gene ID: 176216).

TrifuncB polypeptides of algal and heterokont species include, for example, the polypeptide of GenBank accession XP_002288423.1 (SEQ ID NO:13) of the diatom algal species *Thalassiosira pseudonana*, the polypeptide of Genbank XP_002185619.1 (SEQ ID NO:14) of the diatom species *Phaeodactylum tricornutum*, the polypeptide of GenBank accession OEU17499.1 (SEQ ID NO: 15) of the diatom algal species *Fragilariopsis cylindrus*, the polypeptide of GenBank accession XP_005780946.1 (SEQ ID NO:16) of the heterokont alga *Emiliania huxleyi*, the polypeptide of GenBank accession XP_005771442.1 (SEQ ID NO:17) of the heterokont alga *Emiliania huxleyi*, the polypeptide of GenBank accession XP_009036682.1 (SEQ ID NO: 18) of the heterokont alga *Aureococcus anophageffer-ens*, as well as the polypeptide of GenBank accession CBJ26972.1 (SEQ ID NO: 19) of the brown alga *Ectocarpus silicus*.

As used herein, the term "peroxisomal ABC-type acyl-coenzyme A transporter" or "ATP-binding cassette long-chain fatty acid transporter" refers to an enzyme that is localized to the peroxisome and is capable of transporting acyl-coenzyme A into or out of the peroxisome in the presence of ATP. Peroxisomal ABC transporters belong to subfamily D of the ABC transporters, i.e., are ABCD proteins, and may be known as "PXA" (e.g., "PXA1" or "PXA2"), ALDP, ALDRP, ABCD (e.g., ABCD1, ABCD2), PMP (e.g., PMP69, PMP70, PMP1, PMP2, etc.), or CTS polypeptides, for example.

Peroxisomal ABC transporters correspond to Uniprot W7T9SO (See on the Internet at uniprot.org) and correspond to Enzyme Commission Number 3.6.3.47. The PXA polypeptide or "peroxisomal ABC-type acyl-CoA transporter" includes a cl26602 or "SunT Superfamily" or "ABC-type bacteriocin/antibiotic exporter" conserved domain; polypeptides can be queried against the CDD at ncbi.nlm.nih to determine the presence of the cl26602 domain. A peroxisomal ABC-type acyl-CoA transporter polypeptide includes pfam domain PF00005 (pfam ABC transporter or "ABC_trans") and/or pfam domain PF06472 (pfam ABC transporter transmembrane region 2 or "ABC_membrane_2" domain). For example, a peroxisomal ABC-type acyl-CoA transporter polypeptide can include pfam domain PF00005 (pfam ABC transporter or "ABC_trans") and pfam domain PF06472 (pfam ABC transporter transmembrane region 2 or "ABC_membrane_2" domain). An amino acid sequence of wild type *N. gaditana* peroxisomal ABC-type acyl-CoA transporter, referred to herein as *N. gaditana* PXA1, is provided in SEQ ID NO:20. A nucleotide sequence of a cDNA encoding wild type *N. gaditana* PXA1 is provided in SEQ ID NO:21. The genomic location of the *N gaditana* PXA1 gene is NG_chr16 (42141-43970), NG_chr16 (44127-45281), or NG_chr16 (46051-46789) (Naga_101131g2, Naga_101730g1, and Naga_102509g1, respectively). A skilled artisan can use this disclosure to identify a peroxisomal ABC-type acyl-CoA transporter gene in any microbial species, such as an algal or heterokont species, for example as a gene encoding a protein that has protein domains diagnostic of a peroxisomal ABC-type acyl-CoA transporter and/or when expressed has the activity of a peroxisomal ABC-type acyl-CoA transporter, for example using genomic DNA or cDNA. Peroxisomal ABC-type acyl-CoA transporter genes from other species follow and can aid a skilled artisan in the identification of a homologous gene in any microbial, e.g., algal or heterokont, species: the ATP-binding cassette, sub-family D (ALD), member 3 genes in *Homo sapiens* (Official Symbol: ABCD3; Gene ID: 5825), *Canis lupus familiaris* (Official Symbol: ABCD3; Gene ID: 479939), *Bos taurus* (Official Symbol: ABCD3; Gene ID: 526059), *Mus musculus* (Official Symbol: Abcd3; Gene ID: 19299), *Rattus norvegicus* (Official Symbol: Abcd3; Gene ID: 25270), *Gallus* (Official Symbol: ABCD3; Gene ID: 424487), and *Xenopus tropicalis* (Official Symbol: abcd3; Gene ID: 100489671), the ATP binding cassette subfamily D member 3 gene in *Macaca mulatta* (Official Symbol: ABCD3; Gene ID: 709188), the ATP-binding cassette, sub-family D (ALD), member 3a gene in *Danio rerio* (Official Symbol: abcd3a; Gene ID: 406803), the Pmp70 gene in *Drosophila melanogaster* (Official Symbol: Pmp70; Gene ID: 32992), the AGAP000440-PA gene in *Anopheles gambiae* str. PEST (Official Symbol: AgaP_AGAP000440; Gene ID: 1271802), the Peroxisomal Membrane Protein related genes in *Caenorhabditis elegans* (Official Symbol: pmp-1; Gene ID: 174126 and Official Symbol: pmp-2; Gene ID: 174127), and the ABC transporter D family member 1 genes in *Arabidopsis thaliana* (Official Symbol: PXA1; Gene ID: 830144) and *Oryza sativa* Japonica Group (Official Symbol: LOC4337574; Gene ID: 4337574). For brevity, a peroxisomal ABC-type acyl-CoA transporter of any species may be referred to herein as a PXA polypeptide (or simply "PXA"), and a peroxisomal ABC-type acyl-CoA transporter gene of any species may be referred to herein as a PXA gene.

As used herein, the term "acyl-CoA oxidase" or "ACO" (e.g., ACO1), also known as "fatty Acyl-CoA oxidase", "acyl coenzyme A oxidase", and "fatty acyl-coenzyme A oxidase" refers to an enzyme that is localized in peroxisomes and is capable of catalyzing the reaction of acyl-CoA with 02 to form trans-2,3-dehydroacyl-CoA and H2O2 as part of the peroxisomal beta-oxidation pathway. Acyl-CoA oxidase includes an enzyme that corresponds to Enzyme Commission Number 1.3.3.6, and may be designated "AOX", "AXO", "FAO" or "POX", for example. For brevity, an acyl-CoA oxidase polypeptide of any species may be referred to herein as an ACO polypeptide (or simply, "ACO") an acyl-CoA oxidase gene of any species may be referred to herein as a ACO gene. An amino acid sequence of wild type *N. gaditana* peroxisomal acyl-CoA oxidase, referred to herein as *N. gaditana* ACO1, is provided in SEQ ID NO:22 W. A nucleotide sequence of a cDNA encoding wild type *N. gaditana* ACO1 is provided in SEQ ID NO:23 X. A skilled artisan can use this disclosure to identify any gene that is orthologous to a peroxisomal acyl-CoA oxidase gene in any microbial species, such as an algal or heterokont species, for example as a gene encoding a protein that has protein domains diagnostic of a peroxisomal acyl-CoA oxidase and/or when expressed has the activity of a peroxisomal acyl-CoA oxidase, for example using genomic DNA or cDNA. Peroxisomal acyl-CoA oxidase genes from other microbial, e.g., algal or heterokont, species can be identified by homology of the encoded polypeptide to ACO1 (SEQ ID NO:22) to *Saccharomyces cerevisiae* peroxisomal acyl-CoA oxidase (Official Symbol: POX1; Gene ID: 852667), or to other peroxisomal acyl-CoA oxidases, as well as by the presence of known domains, e.g., the cl09933 (Acyl-CoA dehydrogenase) conserved domain (ncbi.nlim.nih.gov/structure/cdd), and can include the pfam domains PF14749 (Acyl-coenzyme A oxidase N-terminal), PF02770 (Acyl-CoA dehydrogenase, middle domain), and PF00441 (Acyl-CoA dehydrogenase, C-terminal domain), and/or pfam domain PF01756 (acyl-CoA oxidase) (pfam.xfam.org).

As used herein, the term "isocitrate lyase" or "ICL", also known as "isocitrase, isocitritase", "isocitratase", "threo-Ds-isocitrate glyoxylate-lyase", and "isocitrate glyoxylate-lyase", refers to an enzyme that is expressed at least in part in the mitochondria and/or peroxisome and/or the specialized peroxisomes known as glyoxysomes, and is capable of catalyzing the cleavage of isocitrate to succinate and glyoxylate as part of the glyoxylate pathway. ICL is Uniprot W7TRS4 (See on the Internet at uniprot.org) and includes an enzyme that corresponds to Enzyme Commission Number 4.1.3.1. An amino acid sequence of wild type *N. gaditana* ICL is provided in SEQ ID NO:24. A nucleotide sequence of a cDNA encoding wild type *N. gaditana* ICL is provided in SEQ ID NO:25. The genomic location of the *N gaditana* ICL gene is NG_chr09 (682258-685950) (Naga_100025g12). A skilled artisan can use this disclosure to identify an ICL gene in any microbial species, such as an algal or heterokont species, as a gene encoding a protein that is expressed in the microbial species and has a pfam PF00463 (isocitrate lyase) domain, and/or a cl21457 conserved domain (ICL/PEPM_KPHMT enzyme superfamily) or has the enzymatic activity of ICL. Conserved domains, including pfam domains, and ICL genes from other species follow and will aid a skilled artisan in the identification of a homologous gene in any microbial, e.g., algal or heterokont, species: the isocitrate lyase 1 gene in *Saccharomyces cerevisiae* (Official Symbol: ICL; Gene ID: 856794), the hypothetical protein gene in *Kluyveromyces lactis* NRRL Y-1140 (Official Symbol: KLLA0C08107g; Gene ID: 2892560), the ADL066Cp gene in *Ashbya gossypii* ATCC 10895 (Official Symbol: AGOS_ADL066C; Gene ID: 4620172), the isocitrate lyase gene in *Magnaporthe oryzae* 70-15 (Official Symbol: MGG_04895; Gene ID: 2675603), the acetate utilization-3 gene in *Neurospora crassa* OR74A (Official Symbol: acu-3; Gene ID: 3877001), and the isocitrate lyase genes in *Arabidopsis thaliana* (Official Symbol: ICL; Gene ID: 821726), *Oryza sativa* Japonica Group (Official Symbol: LOC4343441; Gene ID: 4343441), and *Acetobacter aceti*. (Official symbol: aceA).

Mutant Algal Microorganisms Having Increased Lipid Productivity

The beta-oxidation pathway is a catabolic process by which fatty acid molecules are broken down to generate acetyl-CoA. The general mechanism of the pathway occurs over four steps: 1) acyl-CoA dehydrogenase catalyzes the dehydrogenation of a long-chain fatty acid conjugated to coenzyme A (fatty acyl-CoA) to create a trans double bond between C2 and C3 and produce trans-delta 2-enoyl-CoA, 2) an enoyl-CoA hydratase catalyzes the hydration of trans-delta 2-enoyl-CoA at the double bond to produce L-3-hydroxyacyl-CoA, 3) a 3-hydroxyacyl-CoA dehydrogenase catalyzes the dehydrogenation of L-3-hydroxyacyl-CoA to create 3-ketoacyl-CoA, and 4) a thiolase catalyzes the breakage of the bond between C2 and C3 (alpha and beta carbons) of 3-ketoacyl-CoA by Coenzyme A to generate acetyl-CoA and a fatty acyl-CoA that is two carbons shorter than the acyl-CoA that was the initial substrate. The four-step process continues until all of the carbons in the fatty acid are converted to acetyl-CoA.

In plants and most fungi, the peroxisome is the sole compartment that participates in beta oxidation of fatty acids (Poirier et al. (2006) Biochim Biophys Acta 1763: 1413-1426), whereas in animal cells, beta oxidation of fatty acids occurs in both the peroxisome and the mitochondria. A key component of mitochondrial beta oxidation in animal cells is the Trifunctional protein that has three enzymatic functions: enoyl-CoA hydratase, hydroxyacyl-CoA dehydrogenase, and ketoacyl-CoA thiolase. The mammalian mitochondrial trifunctional protein is a heterodimer comprising an alpha subunit that includes the enoyl-CoA hydratase and hydroxyacyl-CoA dehydrogenase activities, and a beta subunit that includes the ketoacyl-CoA thiolase activity (Eaton et al. (2000) Biochem Soc Transactions 28:177-182).

The mitochondrial trifunctional protein (MTP), a heterooctamer composed of four mitochondrial trifunctional protein subunit A (TrifuncA) subunits and four mitochondrial trifunctional protein subunit B (TrifuncB) subunits, is able to catalyze the last three steps of the beta-oxidation pathway in certain organisms. These enzymatic functions of MTP are known as 2-enoyl coenzyme A (CoA) hydratase, long-chain 3-hydroxy acyl-coA dehydrogenase, and long-chain 3-ketoacyl CoA thiolase. As advantageously provided herein, attenuation of expression of the mitochondrial TrifuncB and/or TrifuncA proteins can lead to increased lipid productivity, for example in algal and heterokont microorganisms. Not to be limited by theory, it is believed that this increase in lipid production is the result of reduced levels of fatty acid catabolism resulting from the attenuation of expression of the TrifuncB and/or TrifuncA protein(s).

The catabolism of long chain fatty acids begins in the peroxisome in many organisms and these reactions are therefore known as the peroxisomal beta-oxidation pathway. In animal cells, fatty acids processed by peroxisomal beta-oxidation are eventually transferred to the mitochondria for beta-oxidation as octanoyl-CoA (a C8 fatty acid derivative). There are multiple steps involved in peroxisomal beta-oxidation beginning with the import of acyl-CoA into the peroxisome. This can be performed by the peroxisomal ABC-type acyl-coenzyme A transporter (often designated PXA, e.g., PXA1). Acyl-CoA oxidase (often designated ACO, e.g., ACO1) catalyzes the first step of beta-oxidation in the peroxisome, desaturating the imported acyl-CoAs to 2-trans-enoyl-CoAs for further processing in the next steps. As advantageously provided herein, attenuation of the expression of a peroxisomal ABC-type acyl-coenzyme A transporter and/or a peroxisomal acyl-CoA oxidase protein in mutant microorganisms that have attenuated expression of the mitochondrial TrifuncB and/or TrifuncA proteins can lead to further increased lipid productivity with respect to the lipid productivity of mutant microorganisms only that have attenuated expression of TrifuncB or TrifuncA. Not to be limited by theory, it is believed that this further increase in lipid productivity in mutant microorganisms that have attenuated expression of either or both of TrifuncB or TrifuncA as well as a peroxisomal ABC-type acyl-coenzyme A transporter and/or a peroxisomal acyl-CoA oxidase enzyme is the result of even further reduction in the levels of fatty acid catabolism in these mutants.

The glyoxylate pathway is an anabolic pathway in plants, bacteria, protists, and fungi whereby cells convert acetyl-CoA to succinate for the synthesis of carbohydrates by gluconeogenesis. One enzyme involved in this pathway, isocitrate lyase (ICL), catalyzes the cleavage of isocitrate to succinate and glyoxylate. As advantageously provided herein, attenuation of the expression of the ICL enzyme in mutant microorganisms that also have attenuated expression of the mitochondrial TrifuncB and/or TrifuncA proteins can lead to further increased lipid productivity with respect to the lipid productivity of mutant microorganisms that have attenuated expression of TrifuncB and/or TrifuncA only. Not to be limited by theory, it is believed that this further increase in lipid productivity in mutant microorganisms that have attenuated expression of both TrifuncB and/or TrifuncA as well as ICL is the result of reduced levels of gluconeogenesis from acyl-CoA leading to increased accumulation of lipids in cells.

Accordingly, provided herein are mutant microorganisms, such as algal or heterokont microorganisms, that have a mutation that causes attenuated expression of mitochondrial TrifuncB and/or TrifuncA and as a result produce (for example on a per volume or per area per day basis) more lipids, such as fatty acid methyl ester-derivatizable lipids (FAME lipids), and/or have a higher ratio of lipids to total biomass (which may be assessed as total organic carbon), than a control microorganism of the same species that does have attenuated expression of TrifuncB and/or TrifuncA. In related embodiments, provided herein are mutant microorganisms, such as algal or heterokont microorganisms, that have at least one mutation that attenuates expression of the TrifuncB and/or TrifuncA gene and results in increased lipid production, such as increased volumetric lipid productivity, and/or a higher ratio of lipids to total carbon, as compared to a control microorganism essentially genetically identical to the mutant microorganisms except for the mutation(s), when cultured under the same conditions. As used herein "mutation" encompasses mutations in the gene whose expression is attenuated, including regions 5' and 3' of the coding region and transcribed region of the gene, and also encompasses other genetic modification to the microorganism such as exogenous nucleic acid molecules or constructs in the mutant microorganism that attenuate (reduce or eliminate) gene expression, such as but not limited to antisense RNAs, ribozymes, micro RNAs, silencing RNAs, RNAi, short hairpin RNAs, guide RNAs, and constructs encoding such nucleic acid molecules. The TrifuncB and/or TrifuncA mutation can be a knockdown or, in illustrative examples, a knockout mutation. In illustrative embodiments the mutation in the mutant microorganism is in the TrifuncB gene and results in attenuated expression of the TrifuncB gene that causes the mutant microorganism to increase its lipid productivity as compared to a control microorganism essentially genetically identical to the mutant microorganism except for the mutation, when cultured under the same conditions.

A mutant microorganism as provided herein that has attenuated expression of a gene encoding a TrifuncB and/or TrifuncA polypeptide can in some embodiments be a microorganism that includes a genetic construct for attenuating expression of a TrifuncB and/or TrifuncA gene, such as, for example, a construct for expressing an antisense RNA, microRNA, RNAi molecule (e.g., a siRNA), or a ribozyme. The mutant microorganism can have attenuated expression of a gene that encodes a mitochondrial TrifuncB and/or TrifuncA polypeptide where the attenuated expression can result in production of more lipids, such as fatty acid methyl ester-derivatizable lipids (FAME lipids), and/or a higher ratio of lipids to total carbon, with respect to the production of lipids or ratio of lipid to carbon of a control microorganism of the same species that does not have the construct for attenuating expression of a TrifuncB and/or TrifuncA gene. In additional embodiments a mutant microorganism as provided herein that has attenuated expression of a gene encoding a TrifuncB and/or TrifuncA polypeptide can be a microorganism that has a disrupted or mutated TrifuncB and/or TrifuncA gene, such as, for example, a TrifuncB and/or TrifuncA gene that is disrupted by insertion of exogenous DNA or a mutation that results in a frameshift mutation and/or truncation of the encoded polypeptide. The disrupted gene can for example produce essentially no active polypeptide. The mutant microorganism can be a heterkont or algal microorganism.

A mutant microorganism provided herein that increases its lipid production over a control microorganism of the same species as a result of a mutation or construct that causes attenuation of expression of a TrifuncB and/or TrifuncA protein can further include a mutation in a gene encoding a peroxisomal beta-oxidation pathway protein and/or a glyoxylate pathway protein that results in attenuation of the expression of the peroxisomal beta-oxidation pathway protein and/or the glyoxylate pathway protein. In illustrative examples the mutated gene from the peroxisomal beta-oxidation pathway is a peroxisomal acyl-CoA oxidase gene, which may be referred to herein for brevity as an ACO gene, e.g., an ACO1 gene, and/or is a peroxisomal ABC-type acyl-CoA transporter gene, which may be referred to herein as a PXA gene, such as a PXA1 gene. As non-limiting examples, such mutant algal or heterokont microorganism can include a knockdown or knockout mutation in an ACO and/or PXA gene in addition to a knockdown or knockout mutation of TrifuncB and/or TrifuncA gene. Alternatively, a mutant algal or heterokont microorganism provided herein that increases its lipid production over a control algal microorganism of the same species as a result of a mutation or construct that causes attenuation of expression of a TrifuncB and/or TrifuncA protein can further include a genetic construct for attenuating expression of a gene encoding a peroxisomal beta-oxidation pathway protein or a glyoxylate pathway protein that results in attenuation of the expression of the peroxisomal beta-oxidation pathway protein or the glyoxylate pathway protein, including, but not limited to an ACO or PXA gene. The genetic construct can be, for example, a construct for expressing an antisense RNA, microRNA, RNAi molecule (e.g., a siRNA), or a ribozyme. A mutant algal microorganism that has a mutation or includes a genetic construct that results in attenuation of expression of TrifuncB and/or TrifuncA protein and that additionally has a mutation or includes a genetic construct that results in attenuation of expression of a peroxisomal beta-oxidation pathway protein can exhibit higher lipid productivity and/or increased ratio of lipid (e.g. FAME) to total organic carbon than a strain that does not include a mutation or genetic construct that results in attenuation of expression of a peroxisomal beta-oxidation pathway protein In further embodiments a mutant algal or heterokont microorganism provided herein that increases its lipid production due to attenuated expression of the TrifuncB and/or TrifuncA proteins, can in addition include a mutation in a gene encoding a glyoxylate pathway protein, for example the glyoxylate pathway protein isocitrate lyase (ICL). The glyoxylate pathway protein mutant (e.g. ICL mutant) can be, for example, a knockdown or knockout mutation with a knockdown or knockout mutation in TrifuncA and/or TrifuncB. The mutant algal or heterokont microorganism having attenuated expression of an ICL gene can include a genetic construct, e.g., a construct encoding an antisense RNA, microRNA, RNAi molecule (e.g., a siRNA), or a ribozyme, for attenuating expression of the ICL gene. The mutant algal or heterokont microorganism having attenuated expression of the TrifuncB and/or TrifuncA proteins and further having attenuated expression of an ICL gene can optionally further have at least one genetic alteration that results in attenuated expression of a peroxisomal beta-oxidation pathway gene, such as an ACO and/or PXA gene.

As indicated herein, the mutation in a TrifuncB, TrifuncA, PXA, ACO, and/or ICL gene can be a knockdown mutation or, as in illustrative embodiments, a knockout mutation. A knockout mutation can be, for example, a mutation in which the reading frame of the polypeptide is disrupted such that the functional protein is not produced, or only a portion of the target protein is produced that does not have one or more functions of the wild type protein. Knockdown mutations in certain examples are provided by expressing exogenous DNA, for example, a construct that encodes an interfering RNA, antisense RNA, or ribozyme that results in attenuated expression of the targeted gene. This exogenous DNA can optionally include a marker gene that is not found in the genome of the control algal microorganism. In various embodiments, the mutant algal microorganism has a mutation, such as but not limited to an insertion, in the promoter region or 5' untranslated region of the gene, e.g., upstream of the translational start site of the gene and/or upstream of the transcriptional start site of the gene. In some embodiments, the mutant algal microorganism has a mutation, such as but not limited to an insertion, in the 3' untranslated region of the gene, e.g., downstream of the translational stop site of the gene. In some embodiments, the mutant algal microorganism has a mutation, such as but not limited to an insertion, in an intron of the gene. Without limiting the invention to any particular mechanism, it can be that insertions, such as but not limited to cas-mediated insertions, into a noncoding region of a gene can reduce gene expression levels of the gene. In some embodiments, the mutant algal microorganism has a mutation in at least 1 or at least 2, 3, 4, or all 5 of the TrifuncB, TrifuncA, PXA1, ACO1, and ICL genes, and the mutations are all knockdown mutations, all knockout mutations, or the mutations are a combination of knockout and knockdown mutations. The mutations can occur in any portion of the target gene, and in some embodiments, are in a first, second, or third exon, or are in other than a last exon or other than a first from last exon. The term "mutation" encompasses constructs or nucleic acid molecules introduced into the microorganism that result in reduction of expression of a gene targeted by the construct or nucleic acid molecule, e.g., specifically includes alteration of gene expression by RNAi molecules, antisense RNA, micro RNAs, and ribozymes.

The mutant microorganism of the invention can be any microorganism that naturally expresses a mitochondrial TrifuncA or TrifuncB protein. The mutant microorganism can be an algal microorganism derived, for example, from any species of the following genera: *Achnanthes, Amphiprora, Amphora, Ankistrodesmus, Asteromonas, Aureococcus, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Cryptheco-dinium, Cryptomonas, Cyclotella, Desmodesmus, Dunaliella, Elipsoidon, Emiliania, Eremosphaera, Emodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phxodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the algal microorganism can be a member of the chlorophyes such as, without limitation, *Botryococcus, Chlorella, Eremosphaera, Franceia, Micractinium, Nannochloris, Oocystis, Parachlorella, Picochlorum, Prototheca*, or *Pseudochlorella*. In some aspects, the eukaryotic host cell can be a species belonging to the genus of *Auxenochlorella, Chlorella, Heveochlorella, Marinichlorella, Parachlorella, Pseudochlorella* or *Tetrachlorella*.

In some aspects the present disclosure provides a recombinant or classically-derived mutant alga, wherein the mutant alga is a heterokont alga. In some examples, the mutant heterokont alga belongs to the diatoms (Bacillariophytes), Eustigmatophytes, Xanthophytes, Pelagophytes, Phaeophytes, Chrysophytes, or Raphidophytes. In any of the embodiments provided herein, the mutant algal microorganism can be a heterokont alga, such as, for example, a Eustigmatophyte, or a diatom (e.g., Bacillariophyte). In some examples, the mutant heterokont alga is a diatom and in some embodiments belongs to a genus of diatoms selected from the group consisting of *Amphiprora, Amphora, Chaetoceros, Cyclotella, Fragilaria, Fragilaropsis, Hantzschia, Navicula, Nitzschia, Phæodactylum, Skeletonema*, and *Thalassiosira*. In some examples, the mutant alga is a Eustigmatophyte alga. In some examples, the Eustigmatophyte alga belongs to a genus selected from the group consisting of *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraëdriella*, and *Vischeria*. In some examples, the mutant alga cell is a *Nannochloropsis* species, e.g., *Nannochloropsis gaditana, Nannochloropsis granulata, Nannochloropsis limnetica Nannochloropsis oceanica, Nannochloropsis oculata*, and *Nannochloropsis salina*.

Heterokont species that can be mutant microorganisms of the invention also include, but are not limited to, Labyrinthulomycetes, e.g., Labrinthulids, and Thraustochytrids such as, for example, species of *Labryinthula, Labryinthuloides, Thraustochytrium, Schizochytrium, Aplanochytrium, Aurantiochytrium, Oblongichytrium, Japonochytrium, Diplophrys*, or *Ulkenia*.

Genes encoding enzymes of the mitochondrial beta oxidation pathway, such as TrifuncB and TrifuncA, genes encoding polypeptides that participate in the peroxisomal beta oxidation pathway, including peroxisomal ABC-type acyl-CoA transporters and peroxisomal acyl-CoA oxidase, and genes encoding enzymes of the glyoxylate pathway such as isocitrate lyase, can be identified by a skilled artisan using various methods well known in the art, including but not limited to cDNA expression libraries combined with antibody screening or activity assays, hybridization with probes from conserved regions of homologous genes of other species, PCR with degenerate primers designed to conserved gene regions, and genome sequencing and bioinformatic annotation. A homologous or orthologous gene from an algal or heterokont species other than *N. gaditana* typically has the same enzymatic activity and/or subcellular localization as provided herein for *N. gaditana* TrifuncB, TrifuncA, PXA1, ACO1, or ICL, and can have at least 30%, at least 35%, at least 40%, or at least 45%, and typically has at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to a contiguous stretch of at least 50%, at least 75%, at least 80%, at least 90%, at least 95%, or 100% of any of the amino acid sequences of *N. gaditana* TrifuncA (SEQ ID NO: 1) or other TrifuncA polypeptides identified herein, including for example, SEQ ID NO:4, SEQ ID NO:5, SEQ ID NO:6, SEQ ID NO:7, SEQ ID NO:8, or SEQ ID NO:9; to *N. gaditana* TrifuncB (SEQ ID NO: 10) or other TrifuncB genes identified herein, including for example, SEQ ID NO:3, SEQ ID NO:4, SEQ ID NO:5, SEQ ID NO:6, SEQ ID NO:7, SEQ ID NO:8, or SEQ ID NO:9; *N. gaditana* PXA1 (SEQ ID NO:20) or other peroxisomal ABC-type acyl-CoA transporters; *N. gaditana* ACO1 (SEQ ID NO:22) or other peroxisomal acyl-CoA oxidases, or *N. gaditana* ICL (SEQ ID NO:24) or other isocitrate lyases. A homologous or orthologous gene from an algal species other than *N. gaditana* can in some embodiments have a coding region having at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to any of the coding sequences of *N. gaditana* TrifuncA (SEQ ID NO:2), TrifuncB (SEQ ID NO:11), PXA1 (SEQ ID NO:21), ACO1 (SEQ ID NO:23), or ICL (SEQ ID NO:25).

Some species of microorganism (e.g., some species of algae or heterokonts) may have more than one copy of a TrifuncB, TrifuncA, peroxisomal ABC-type acyl-CoA transporter, peroxisomal acyl-CoA oxidase, and/or isocitrate lyase gene. A skilled artisan can identify and mutate such additional copies of genes encoding these target proteins using known methods and the teachings herein. For example, homologous genes in algal or heterokont microorganisms other than *Nannochloropsis*, or different species of *Nannochloropsis*, whether as a single copy or multiple copy gene in a particular species, can be identified using bioinformatic analysis and/or sequence information provided herein for each of the target genes. In a species having more than one copy of the TrifuncB, TrifuncA, peroxisomal ABC-type acyl-CoA transporter (such as PXA1), peroxisomal acyl-CoA oxidase (such as ACO1), and/or isocitrate lyase genes, multiple copies (e.g. all copies) of one or more of these target genes in any of the embodiments provided herein can be mutated, or one or more but less than all copies of one or more of the target gene can be mutated to achieve attenuated expression.

The mutant microorganisms provided herein can have greater partitioning of carbon to lipid (e.g., a higher FAME/TOC ratio) with respect to a control microorganism cultured under identical conditions, for example under batch, semi-continuous, or continuous culture conditions in nitrogen replete, nitrogen limited, or nitrogen deplete conditions that may, in the case of mutant algal microorganisms, be photoautotrophic conditions. A mutant having increased partitioning of carbon to lipid with respect to a control microorganism can have increased partitioning of carbon to total extractable lipid, to total neutral lipids, to triglycerides, and/or to FAME-derivatizable lipids. For example, a mutant microorganism as provided herein can have a ratio of the amount of FAME-derivatizable lipids ("FAME") produced to biomass (which can be measured as TOC or ash-free dry weight (AFDW), for example) produced that is at least 10% higher than that of a control microorganism. Lipid and biomass production and/or production can be assessed, for example, by gravimetric analysis as known in the art and demonstrated in the examples herein.

For example, a mutant microorganism, such as a mutant algal or heterokont microorganism, as provided herein that has attenuated expression of a TrifuncB and/or TrifuncA gene can have a ratio of FAME to TOC (FAME/TOC) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85, at least 90%, at least 95%, at least 100%, at least 110%, at least 120%, at least 130%, at least 140%, at least 150%, at least 160%, at least 170%, at least 180%, at least 190%, or at least 200% higher than the FAME/TOC ratio of a control microorganism. In some embodiments, a mutant microorganism as provided herein that has attenuated expression of a TrifuncB and/or TrifuncA gene can have a ratio of FAME to TOC (FAME/TOC) that is at least 5%, at least 10%, at least 15%, at least 20%, at least 25%, or at least 30%, higher than the FAME/TOC ratio of a control microorganism but may be less than 500%, 400%, or 300% higher than the FAME/TOC ratio of a control microorganism. In some embodiments, a mutant microorganism, such as a mutant algal or heterokont microorganism, as provided herein that has attenuated expression of a TrifuncB and/or TrifuncA gene can have a ratio of FAME to TOC (FAME/TOC) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85, at least 90%, at least 95%, at least 100%, at least 110%, at least 120%, at least 130%, at least 140%, at least 150%, at least 160%, at least 170%, at least 180%, at least 190%, or at least 200% higher than the FAME/TOC ratio of a control microorganism when both the mutant microorganism and the control microorganism are cultured under identical conditions. For example, in some embodiments a mutant microorganism, such as a mutant algal microorganism, as provided herein that has attenuated expression of a TrifuncB and/or TrifuncA gene can have a ratio of FAME to TOC (FAME/TOC) that is at least 10%, at least 15%, at least 20%, at least 25%, at least 30%, at least 40%, at least 50%, at least 60%, at least 70%, at least 80%, at least 90%, at least 100%, at least 120%, at least 140%, at least 150%, at least 170%, at least 180%, or at least 200% higher than the FAME/TOC ratio of a control microorganism when both the mutant microorganism and the control microorganism are cultured under conditions nitrogen replete or nitrogen-limited culture conditions.

In additional examples, a mutant microorganism as provided herein that has attenuated expression of a TrifuncB and/or TrifuncA gene can produce at least 10% more FAME while producing at least 50%, at least 60%, or at least 70% of the TOC produced by a control cell (such as a wild type cell) when cultured under identical conditions, and the FAME/TOC ratio of the mutant microorganism can be at least 20%, at least 30%, at least 35%, at least 40%, at least 50%, at least 60%, or at least 65% higher than the FAME/TOC of the control microorganism. The FAME/TOC ratio of the mutant microorganism can be, for example, at least 0.30 or at least 0.35 or at least about 0.40 during the lipid production period. The mutant microorganism can in some embodiments have attenuated expression of a gene encoding a polypeptide that functions in peroxisomal fatty acid oxidation or in the glyoxylate pathway in addition to having attenuated expression of a TrifuncB and/or TrifuncA gene. In some embodiments the mutant microorganism has attenuated expression of a gene encoding a mitochondrial TrifuncB and/or TrifuncA polypeptide and further has attenuated expression of a gene encoding a peroxisomal ABC-type acyl-CoA transporter, a peroxisomal acyl-CoA oxidase, and/or isocitrate lyase.

Mutant algal or heterokont microorganisms of the present invention can be spontaneous mutants, classically-derived mutants, or engineered mutants having attenuated expression of a TrifuncA and/or TrifuncB gene and optionally a gene from the peroxisomal beta-oxidation pathway or the glyoxylate pathway. In various examples, the mutant microorganism is an algal or heterokont species and has attenuated expression of a gene that encodes a polypeptide having at 50%, at least 55%, at least 60%, at least 65%, at least 70%, at least 75%, at least 80%, at least 85%, at least 90%, or at least 95%, at least 96%, at least 97%, at least 98%, at least 99% or 100% identity to a contiguous stretch of at least 50%, 75%, 80%, 90%, 95%, or 100% of any of the amino acid sequences of N. gaditana TrifuncB (SEQ ID NO:10), TrifuncA (SEQ ID NO:1), PXA1 (SEQ ID NO:20), ACO1 (SEQ ID NO:22), or ICL (SEQ ID NO:24), and/or has a coding sequence having at least 35%, at least 40%, at least 45%, at least 50%, at least 55%, at least 60%, at least 65%, at least 70%, at least 75%, at least 80%, at least 85%, at least 90%, at least 95%, at least 98%, or 100% identity to any of the coding sequences of N. gaditana TrifuncB (SEQ ID NO: 11), TrifuncA (SEQ ID NO:2), PXA1 (SEQ ID NO:21), ACO1 (SEQ ID NO:23), or ICL (SEQ ID NO:25). The mutated gene typically has the same enzymatic activity and/or subcellular localization as provided herein for TrifuncA, TrifuncB, peroxisomal ABC-type acyl-CoA transporter, peroxisomal acyl-CoA oxidase, or isocitrate lyase.

In some embodiments, a mutant microorganism as provided herein has attenuated expression of a gene encoding a TrifuncA subunit and produces more lipid in a batch, semi-continuous, or continuous assay system than is produced by a control microorganism that does not have attenuated expression of a TrifuncA subunit gene. In some embodiments, a mutant microorganism as provided herein has attenuated expression of a gene encoding a TrifuncB subunit and produces more lipid in a batch, semi-continuous, or continuous assay system than is produced by a control microorganism that does not have attenuated expression of a TrifuncB subunit gene. In various embodiments, a mutant microorganism as provided herein has attenuated expression of a gene encoding a TrifuncA subunit and/or a gene encoding a TrifuncB subunit, and further has attenuated expression of a gene encoding a polypeptide of a peroxisomal beta oxidation pathway (such as an enzyme or transporter) or a gene encoding an enzyme of the glyoxolate pathway. The mutant microorganism having attenuated expression of a TrifuncA and/or TrifuncB gene and attenuated expression of a peroxisomal beta oxidation pathway or glyoxate pathway gene can produce more lipid than a control microorganism that does not have attenuated expression of a TrifuncA and/or TrifuncB gene and attenuated expression of a peroxisomal beta oxidation pathway or glyoxate pathway gene. The mutant microorganism having attenuated expression of a TrifuncA and/or TrifuncB gene and attenuated expression of a peroxisomal beta oxidation pathway or glyoxate pathway gene can have a higher FAME/TOC ratio than a control microorganism that does not have attenuated expression of a TrifuncA and/or TrifuncB gene and attenuated expression of a peroxisomal beta oxidation pathway or glyoxate pathway gene. The attenuated genes are naturally-occurring genes of the host microorganism that are attenuated, for example, by classical mutation or genetic engineering, including, without limitation, one or more meganucleases, TALENs, RNA guided endonucleases (e.g., Cas proteins), homologous recombination, random insertion, RNAi constructs, ribozyme constructs, or antisense constructs. Attenuation can also include mutations that result in amino acid changes that reduce or eliminate the activity of the encoded protein. Where a microorganism is diploid or polyploid, gene mutations can be effected in one, some, or all of the genes encoding the targeted polypeptide.

In some embodiments, a mutant microorganism as provided herein has attenuated expression of a gene encoding a TrifuncA subunit and/or a TrifuncB subunit and further has attenuated expression of a gene encoding a polypeptide that participates in the peroxisomal beta oxidation pathway, such as, for example, a peroxisomal ABC-type acyl-CoA transporter or a peroxisomal acyl-CoA oxidase. For example, a mutant microorganism as provided herein can have attenuated expression of a naturally-occurring TrifuncA gene and a naturally-occurring gene encoding a peroxisomal ABC-type acyl-CoA transporter and can produce more lipid than a control microorganism that does not have attenuated expression of a naturally-occurring TrifuncA gene and a naturally-occurring peroxisomal ABC-type acyl-CoA transporter gene. In other examples, a mutant microorganism as provided herein can have attenuated expression of a naturally-occurring TrifuncB gene and a naturally-occurring gene encoding a peroxisomal ABC-type acyl-CoA transporter and can produce more lipid than a control microorganism that does not have attenuated expression of a naturally-occurring TrifuncB gene and a naturally-occurring peroxisomal ABC-type acyl-CoA transporter gene. In yet other examples, a mutant microorganism as provided herein can have attenuated expression of a naturally-occurring TrifuncA gene and a naturally-occurring gene encoding a peroxisomal acyl-CoA oxidase and can produce more lipid than a control microorganism that does not have attenuated expression of a naturally-occurring TrifuncA gene and a naturally-occurring peroxisomal acyl-CoA oxidase gene. In a further example, a mutant microorganism as provided herein can have attenuated expression of a naturally-occurring TrifuncB gene and a naturally-occurring gene encoding a peroxisomal acyl-CoA oxidase and can produce more lipid than a control microorganism that does not have attenuated expression of a naturally-occurring TrifuncB gene and a naturally-occurring peroxisomal acyl-CoA oxidase gene. In yet other examples, a mutant microorganism as provided herein can have attenuated expression of a naturally-occurring TrifuncA gene and a naturally-occurring gene encoding an isocitrate lyase and can produce more lipid than a control microorganism that does not have attenuated expression of a naturally-occurring TrifuncA gene and a naturally-occurring peroxisomal isocitrate lyase gene. In additional examples, a mutant microorganism as provided herein can have attenuated expression of a naturally-occurring TrifuncB gene and a naturally-occurring gene encoding an isocitrate lyase and can produce more lipid than a control microorganism that does not have attenuated expression of a naturally-occurring TrifuncB gene and a naturally-occurring peroxisomal isocitrate lyase gene. Any of the mutant microorganisms provided herein can produce more lipid in a batch, semi-continuous, or continuous assay system than is produced by a control microorganism The mutant algal or heterokont microorganism having attenuated expression of a TrifuncA and/or TrifuncB gene, and optionally having attenuated expression of a gene encoding a protein from the peroxisomal beta-oxidation pathway or the glyoxylate pathway can be a "knockout" mutant, for example, in which the reading frame of the polypeptide is disrupted such that the functional protein is not produced. For example, the gene can include an insertion where exogenous DNA is present in the gene, a deletion, or a mutation in the reading frame that results in no functional protein being made. The exogenous DNA present in the gene can be a marker gene that is not found in a wild type genome of the species of the algal microorganism. In other examples, the mutant algal microorganism can be a "knockdown" mutant in which expression of the gene is reduced with respect to a control algal microorganism. Knockdowns can be mutants in which a mutation, insertion, or deletion occurs in a non-coding region of the gene or exogenous DNA is present in the gene or can be effected by expressing constructs in the cells that attenuate expression of the targeted gene, such as antisense molecules, RNAi molecules, or ribozymes. The exogenous DNA present in the gene can comprise a marker gene that is not found in the genome of the control algal or heterokont microorganism. Furthermore, the mutant algal or heterokont microorganism can have a combination of knockout and knockdown mutations to attenuate one or more of the genes. Where the mutant has more than one copy of the attenuated gene, and attenuation is by means of mutation at the gene locus (e.g., mutation, whether insertion, deletion, or nucleotide changes that is generated by means such as one ore more RNA-guided nucleases (e.g., Cas9, Cpf1, Csm1, or Cms1 enzymes), TALENs, meganucleases, homologous recombination, or insertional mutagenesis), the mutation(s) can be effected at one, all, or a subset of the gene loci.

Certain embodiments of the invention include a mutant algal or heterokont microorganism that has a mutated TrifuncA and/or TrifuncB gene that attenuates expression of the gene(s) and results in increased lipid production and optionally a mutation in a gene encoding a polypeptide of the peroxisomal beta oxidation pathway, a peroxisomal transporter, or a glyoxylate pathway enzyme, such as, for example, a peroxisomal ABC-type acyl-CoA transporter gene, a peroxisomal acyl-CoA oxidase gene, and/or an isocitrate lyase gene, according to any of the embodiments disclosed herein, and one or more additional mutation(s)

known in the art that results in further increased lipid production. For example, a mutant algal or heterokont species as disclosed herein that has a mutated TrifuncA and/or TrifuncB gene that attenuates expression of the gene(s) and results in increased lipid production and optionally a mutation in a peroxisomal ABC-type acyl-CoA transporter, peroxisomal acyl-CoA oxidase, and/or isocitrate lyase gene can further have attenuated expression of a gene encoding a regulator of lipid biosynthesis such as the ZnCys-2845 regulator disclosed in US 2017/005803 or a homolog or ortholog thereof, or the Bromo-1091 regulator disclosed in copending and commonly owned US 2017/0121742, or a homolog or ortholog thereof.

A skilled artisan will recognize that other known methods for increased production of lipids in algae can be combined with the mutated algal microorganisms provided herein.

Methods of Making Mutants

Methods for mutating genes such as a TrifuncB, TrifuncA, peroxisomal ABC-type acyl-CoA transporter, peroxisomal acyl-CoA oxidase, and isocitrate lyase gene are known in the art and exemplified herein. Such methods can be used to make any of the mutant algal or heterokont microorganisms provided herein. Such methods themselves provide further embodiments of the invention. Furthermore, any mutated algal or heterokont microorganisms made using the methods of making provided herein, are themselves examples of mutated algal or heterokont microorganisms of the present invention.

Accordingly, a mutant algal or heterokont microorganism having attenuated expression of a TrifuncA and/or TrifuncB gene, and optionally a peroxisomal ABC-type acyl-CoA transporter, peroxisomal acyl-CoA oxidase, and/or isocitrate lyase gene, can be a mutant generated by any feasible method, including but not limited to UV irradiation, gamma irradiation, or chemical mutagenesis, and screening for mutants having increase lipid production, for example by staining with lipophilic dyes such as Nile Red or BODIPY (e.g., Cabanelas et al. (2015) Bioresource Technology 184: 47-52). Methods for generating classical mutants of microorganisms are well known. Mutations in a gene locus of interest can be confirmed by genome sequencing or sequencing of PCR products corresponding to the genomic locus.

In other examples, a mutant algal or heterokont microorganism as provided herein that produces more lipids than the control algal microorganism can be a genetically engineered mutant, for example, a mutant in which a gene such as TrifuncB, TrifuncA, a peroxisomal ABC-type acyl-CoA transporter gene, a peroxisomal acyl-CoA oxidase gene, and/or an isocitrate lyase gene has been targeted by homologous recombination, for example for knock-out, knock-in, or gene replacement (for example with a mutated form of the gene that may encode a polypeptide having reduced activity with respect to the polypeptide in a control algal microorganism). For example, a microorganism of interest may be engineered by site directed homologous recombination to insert a sequence into a genomic locus and thereby alter a gene and/or its expression, or to insert a promoter into a genetic locus of the host microorganism to affect the expression of a particular gene or set of genes at the locus. In other examples, a mutant algal or heterokont microorganism as provided herein can be a genetically engineered mutant, wherein expression of a TrifuncB and/or TrifuncA gene, and optionally expression of a PXA, ACO, or ICL gene, is attenuated using RNAi.

Gene and polypeptide sequences, searchable databases of conserved domains of proteins and search programs that identify such domains, and searching and sequence comparison software for genes, proteins, and conserved domains such as those disclosed herein are publicly available on the world wide web and their use is well-known to those of skill in the art. One of skill in the art can readily identify genes encoding mitochondrial beta oxidation enzymes, peroxisomal transporters, peroxisomal beta oxidation enzymes, and enzymes of the glyoxylate pathway in a microbial species of interest, such as an algal and heterokont species, using in silico methods and, if necessary, hybridization to genomic or cDNA libraries generated from a species of interest, antibody screening of such libraries, PCR using degenerate primers targeting conserved domains, genome walking, genome and/or RNA sequencing, etc. Included in the disclosure herein are examples of genes that may be targeted, the sequences of encoded proteins and the conserved domains of such proteins, as well as the sequences of homologs in a variety of species, including algal and heterokont species. One of skill in the art would not be burdened to identify and target the relevant genes in additional species of interest encoding polypeptides of the mitochondrial beta oxidation pathway, the peroxisomal beta oxidation pathway, peroxisomal transporters, or glyoxylate pathway enzymes based on the disclosure herein and the vast amount of bioinformatic information and tools available.

Accordingly, a method for making a mutant algal or heterokont microorganism having attenuated expression of, for example, a TrifuncA and/or TrifuncB gene, and optionally ACO, PXA, and/or ICL gene, can utilize, for example, homologous recombination; CRISPR systems, including guide RNAs, Cas enzymes, and optionally, donor fragments for insertion into the targeted site; RNAi constructs, including constructs for producting shRNAs, siRNAs, and microRNAs; antisense RNA molecules and constructs; ribozyme constructs; TALENS, Zinc Finger nucleases; and meganucleases. For example, a mutant algal or heterokont microorganism engineered to have attenuated expression of a gene encoding a protein from the beta-oxidation pathway, the peroxisomal beta-oxidation pathway, or the glyoxylate pathway can have a disrupted gene that includes at least one insertion, mutation, or deletion that reduces or abolishes expression of the gene such that a fully functional protein is not produced or is produced in lower amounts than is produced by a control algal microorganism that does not include the disrupted gene. The disrupted gene can be disrupted by, for example, an insertion or gene replacement mediated by homologous recombination and/or by the activity of a targeted nuclease such as meganuclease, zinc finger nuclease (Perez-Pinera et al. (2012) Curr. Opin. Chem. Biol. 16: 268-277), TALEN (WO 2014/207043; WO 2014/076571), or a Cas protein (e.g., a Cas9 protein) of a CRISPR system.

Gene knockout or replacement by homologous recombination can be performed by transformation of a nucleic acid (e.g., DNA) fragment that includes a sequence homologous to the region of the genome to be altered, such as a TrifuncA and/or TrifuncB gene, and optionally an ACO1, PXA1, and/or ICL gene, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knockin" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knockout or knockin construct can be an isolated or synthesized fragment, including but not limited to a PCR product. In some instances, a split marker system can be used to generate gene knockouts by homologous recombination, where two DNA fragments can be introduced that can regenerate a selectable marker and disrupt the gene locus of interest via three crossover events (Jeong et al. (2007) FEMS Microbiol Lett 273: 157-163)

Accordingly, provided herein is a method for making a mutant algal microorganism that includes inserting a recombinant nucleic acid molecule into a mitochondrial trifunctional protein subunit B (TrifuncB) gene or mitochondrial trifunctional protein subunit A (TrifuncA) gene using one or more of homologous recombination, clustered regulatory interspaced short palindromic repeat (CRISPR)/Cas-based RNA-guided DNA endonucleases, Transcription Activator-Like Effector Nucleases (TALENs), Zinc Finger Nucleases (ZFNs) or meganucleases. As provided herein, the mutation typically results in attenuated expression of the TrifuncB or TrifuncA protein, and the mutant produces more lipids, for example as demonstrated by more fatty acid methyl ester-derivatizable lipids (FAME lipids) on a per volume or per area per day basis and/or demonstrated by an increased fatty acid methyl ester-derivatizable lipids to total organic carbon (FAME/TOC) ratio, than a control wild type algal microorganism.

Mutating one copy of one of the genes can provide attenuated expression of the gene and result in increased lipid production as compared to a control microorganism grown under the same culture conditions. Furthermore, in species having more than one copy of the TrifuncB, TrifuncA, PXA1, ACO1, and/or ICL genes, multiple copies (e.g. all copies) of one or more of these target genes in any of the embodiments provided herein can be mutated, or one or more but less than all copies of one or more of the target gene can be mutated to achieve attenuated expression.

Any of the mutant algal microorganisms provided herein where mutations in a TrifuncA and/or TrifuncB gene, and optionally an ACO, PXA, and/or ICL gene result in attenuated expression, can be generated through the use of targeted nucleases including any CRISPR/Cas system. CRISPR systems, reviewed by Hsu et al. (Cell 157:1262-1278, 2014) and Zetsche et al. ( ) include, in addition to the Cas nuclease polypeptide or complex, a targeting RNA, often denoted "crRNA", that interacts with the genome target site by complementarity with a target site sequence, a trans-activating ("tracr") RNA that complexes with the Cas polypeptide and also includes a region that binds (by complementarity) the targeting crRNA.

Accordingly, in one embodiment the mutation that results in attenuated expression of a TrifuncA and/or TrifuncB gene, and optionally an ACO, PXA, and/or ICL gene is within 5, 10, 15, 20, 25, 30, 40, 45, or 50 base pairs upstream of a Cas PAM sequence, such as a Cas9 PAM sequence. As provided herein, in exemplary embodiments the mutation is the first or second exon of the TrifuncB gene that results from an insertion performed with CRISPR/Cas-based RNA-guided DNA endonucleases.

Mutant algal microorganisms provided herein can be generated using two RNA molecules (a "crRNA" and a "tracrRNA") that can be co-transformed into a host strain (or expressed in a host strain) that expresses or is transfected with a Cas protein for genome editing, or the use of a single guide RNA that includes a sequence complementary to a target sequence as well as a sequence that interacts with a Cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA." Alternatively, the DNA-targeting RNA can also include the trans-activating sequence for interaction with the Cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety. In some embodiments, the guide RNA of a CRISPR system includes, for example at least 17, at least 18, at least 19, at least 20, at least 21, at least 22, at least 23, at least 24, or at least 25 nucleotides of sequence of a naturally occurring TrifuncB, TrifuncA, ACO, PXA, or ICL gene.

Any Cas protein can be used in the methods herein, including but not limited to Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Csb1, Csb2, Csb3, Csm, Csx17, Csx14, Csx10, Csx16, CsaX, Csx3, Csx1, Csx15, Csf1, Csf2, Csf3, Csf4, any of MAD 1-20, homologs thereof, or modified versions thereof. The Cas protein can be a Cas9 protein, such as a Cas9 protein of *Staphylococcus pyogenes, S. thermophilus, S. pneumonia, S. aureus*, or *Neisseria meningitidis*, as non-limiting examples. Also considered are the Cas9 proteins provided as SEQ ID NOs:1-256 and 795-1346 in U.S. Patent Application Publication No. US 2014/0068797, and chimeric Cas9 proteins that may combine domains from more than one Cas9 protein, as well variants and mutants of identified Cas9 proteins. The Cas protein can be a Cpf1 protein, such as a Cpf1 protein of As or *Francisella novicida, Acidaminococcus, Prevotella*, or *Lachnospiraceae bacterium*, or a derivative or modified version thereof, as nonlimiting examples.

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") that may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc. The use of Cas systems for gene editing is well-known in the art and described in many patents and published patent applications such as for example, U.S. Pat. Nos. 10,000,772, 9,697,359, 8,697,359, 10,011,849, US 2017/0073695, and WO 2016/166340, each of which is incorporated herein in its entirety.

In some instances, cleavage of DNA by a site-directed modifying polypeptide (e.g., a Cas nuclease, zinc finger nuclease, meganuclease, TALEN, or other targeted nuclease) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a Cas nuclease along with a donor DNA, the subject methods may be used to add, i.e. insert or replace, nucleic acid material to a target DNA sequence (e.g. "knockout" by insertional mutagenesis), or "knockin" a nucleic acid that encodes a protein (e.g., a selectable marker and/or any protein of interest), an siRNA, a miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the target gene, such as a TrifuncA and/or TrifuncB gene, and optionally an ACO1, PXA1, and/or ICL gene. The donor DNA can include a sequence, such as for example a selectable marker or any convenient sequence that can interfere with the native promoter. The additional sequence inserted upstream of the initiating ATG of the open reading frame (e.g., in the 5'UTR or upstream of the transcriptional start site of the gene) can decrease or even eliminate expression of the endogenous gene encoding a protein from the beta-oxidation pathway, the peroxisomal beta-oxidation pathway, or the glyoxylate pathway. Alternatively, or in addition, the native gene encoding a protein from the beta-oxidation pathway, the peroxisomal beta-oxidation pathway, or the glyoxylate pathway can have its endogenous promoter wholly or partially replaced by a weaker or differently regulated promoter, or a non-promoter sequence.

In some examples, a nucleic acid molecule introduced into an algal host microorganism for generating a high efficiency genome editing cell line encodes a Cas9 enzyme that is mutated with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce off-target cleavage, as both strands must be accurately and specifically cleaved to achieve genome mutation.

In additional examples, a mutant Cas9 enzyme that is impaired in its ability to cleave DNA can be expressed in the microorganism, where one or more guide RNAs that target a sequence upstream of the transcriptional or translational start site of the targeted gene are also introduced. In this case, the Cas enzyme may bind the target sequence and block transcription of the targeted gene (Qi et al. (2013) Cell 152:1173-1183). This CRISPR interference of gene expression can be referred to as RNAi and is also described in detail in Larson et al. (2013) Nat. Protoc. 8: 2180-2196. In some cases, a Cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner").

Host microorganisms can be genetically engineered (e.g. transduced or transformed or transfected) with, for example, a vector construct that can be, for example, a vector for homologous recombination that includes nucleic acid sequences homologous to a portion of a TrifuncA, TrifuncB, ACO, PXA, and/or ICL gene of the host microorganism or to regions adjacent thereto, or can be an expression vector for the expression of any or a combination of: a Cas protein (e.g., a Cas9 protein), a CRISPR chimeric guide RNA, a crRNA, and/or a tracrRNA, an RNAi construct (e.g., an shRNA, an siRNA or a microRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host gene sequences encoding a protein from the beta-oxidation pathway, the peroxisomal beta-oxidation pathway, or the glyoxylate pathway (including sequences that are upstream and downstream of the genes encoding a protein from the beta-oxidation pathway, the peroxisomal beta-oxidation pathway, or the glyoxylate pathway sequences), as well as, optionally, a selectable marker or reporter gene, can be employed to transform an appropriate host to cause attenuation of a TrifuncA and/or TrifuncB gene, and optionally an ACO1, PXA1, and/or ICL gene.

A mutant algal or heterokont microorganism as provided herein can in some examples include a nucleic acid construct for attenuating the expression of a gene encoding a protein from the beta-oxidation pathway, the peroxisomal beta-oxidation pathway, or the glyoxylate pathway, such as, for example, a gene encoding a polypeptide having at least 55%, at least 60%, at least 65%, at least 70%, at least 75%, at least 80%, at least 85%, at least 90%, or at least 95% identity to any of the amino acid sequences of *N. gaditana* TrifuncB (SEQ ID NO:10), TrifuncA (SEQ ID NO:1), PXA1 (SEQ ID NO:20), ACO1 (SEQ ID NO:22), or ICL (SEQ ID NO:24). For example, a mutant algal or heterokont microorganism can include a construct for expressing an RNAi molecule, ribozyme, or antisense molecule that reduces expression of a gene encoding TrifuncA, TrifuncB, a PXA, a ACO, and/or ICL. For example, an antisense RNA construct that includes all or a portion of the transcribed region of a gene can be introduced into a microorganism to decrease gene expression (Shroda et al. (1999) The Plant Cell 11:1165-78; Ngiam et al. (2000) Appl. Environ. Microbiol. 66: 775-782; Ohnuma et al. (2009) Protoplasma 236: 107-112; Lavaud et al. (2012) PLoS One 7:e36806). Alternatively, or in addition, one or more RNAi constructs (for example, a construct encoding a short hairpin RNA) targeting a gene encoding a protein from the mitochondrial beta-oxidation pathway, the peroxisomal beta-oxidation pathway, and/or the glyoxylate pathway, such as TrifuncB, TrifuncA, a PXA, an ACO, and/or ICL, can be introduced into an algal microorganism for reducing expression of the gene(s) (see, for example, Cerruti et al. (2011) Eukaryotic Cell (2011) 10: 1164-1172; Shroda et al. (2006) Curr. Genet. 49:69-84). Such mutant algal or heterokont microorganism in some examples can have reduced but not abolished expression of the target gene and can have an increase in lipid production of from about 25% to about 200% or more, for example.

Accordingly, provided herein is a method for making a mutant algal or heterokont microorganism that includes introducing a recombinant nucleic acid molecule for expressing one or more of an RNAi molecule, a microRNA, an antisense molecule, or a ribozyme into a control algal microorganism, wherein the RNAi molecule, the antisense molecule, or the ribozyme targets a TrifuncA or TrifuncB gene of the algal microorganism. The mutant algal or heterokont microorganism typically demonstrates increased lipid production compared to the control algal or heterokont microorganism. In other embodiments, provided herein is a method for making a double mutant algal or heterokont microorganism that includes introducing a recombinant nucleic acid molecule for expressing one or more of an RNAi molecule, a microRNA, an antisense molecule, or a ribozyme into a mutant algal or heterokont microorganism, wherein the mutant algal or heterokont microorganism includes a mutation that results in attenuated expression of a mitochondrial trifunctional protein subunit B (TrifuncB) and/or a mitochondrial trifunctional protein subunit A (TrifuncA), and wherein the RNAi molecule, the antisense molecule, or the ribozyme targets a gene of the peroxisomal beta oxidation pathway or a gene of the glyoxylate pathway of the algal microorganism. Such a mutant algal or heterokont microorganism typically demonstrates further increased lipid production compared to the mutant algal microorganism. The double mutant algal microorganism in some examples can include the recombinant nucleic acid molecule for expressing the RNAi molecule, microRNA, antisense molecule, or ribozyme targeting a gene of the peroxisomal beta oxidation pathway or a gene of the glyoxylate pathway of the algal microorganism, and another recombinant nucleic acid molecule for expressing another RNAi molecule, microRNA, antisense molecule, or ribozyme targeting a TrifuncA gene or a TrifuncB gene. In illustrative embodiments, the peroxisomal beta-oxidation pathway protein is ACO1 or PXA1 and the glyoxylate pathway protein is ICL.

Ribozymes are RNA-protein complexes that cleave nucleic acids in a site-specific fashion. Ribozymes have specific catalytic domains that possess endonuclease activity. For example, U.S. Pat. No. 5,354,855 reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) Nature 334:585-591.

Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence, which is the cleavage site. For hammerhead ribozymes, the cleavage site is a dinucleotide sequence on the target RNA, e.g. a uracil (U) followed by either an adenine, cytosine, or uracil (A, C, or U) (Thompson et al., (1995) Nucl Acids Res 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme-directed RNA cleavage activity has been discussed in detail (Haseloff and Gerlach (1988) Nature 334:585-591; Symons (1992) Ann Rev Biochem 61: 641-71; Chowrira et al. (1994) J Biol Chem 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art.

The use of RNAi constructs is discussed in the literature cited above as well as in US2005/0166289 and WO 2013/016267, for example. A double stranded RNA with homology to the target gene is delivered to the cell or produced in the cell by expression of an RNAi construct, for example, an RNAi short hairpin (sh) construct (shRNA). The construct can include a sequence that is identical to the target gene (i.e. a TrifuncA, TrifuncB, ACO, PXA, and/or ICL gene), or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1000 bases of sequence homologous to the target gene. Expression vectors can be engineered using promoters selected for continuous or inducible expression of an RNAi construct, such as a construct that produces an shRNA.

A recombinant nucleic acid molecule for gene attenuation, e.g., a ribozyme, RNAi, or antisense construct can include at least 15, at least 20, at least 30, at least 40, at least 50, or at least 60 nucleotides having at least 80%, such as at least 85%, at least 90%, at least 95%, or at least 99%, identity or complementarity to at least a portion of the sequence of a target gene (i.e. a TrifuncA, TrifuncB, PXA, ACO, and/or ICL gene), of the microorganism to be engineered. A recombinant nucleic acid molecule for gene attenuation, e.g., a ribozyme, RNAi, or antisense construct can include at least 15, at least 20, at least 30, at least 40, at least 50, or at least 60 nucleotides having at least 80%, such as at least 95% or about 100%, identity or complementarity to the sequence of a naturally-occurring target gene, such as a gene encoding a polypeptide having at least 50%, at least 55%, at least 60%, at least 65%, at least 70%, at least 75%, at least 80% or at least 85%, at least 90%, or at least 95% sequence identity to an endogenous target gene (i.e. TrifuncA, TrifuncB, PXA, ACO, and/or ICL gene). For example, a recombinant nucleic acid molecule for gene attenuation, e.g., a ribozyme, RNAi, or antisense construct can include at least 15, at least 20, at least 30, at least 40, at least 50, or at least 60 nucleotides having at least 80% identity or complementarity to the sequence of a naturally-occurring target gene (e.g. TrifuncA, TrifuncB, PXA, ACO, and/or ICL gene). The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a recombinant nucleic acid molecule for gene attenuation, e.g., a ribozyme, RNAi, or antisense construct can include at least 15, at least 20, at least 30, at least 40, at least 50, at least 60, or at least 100 nucleotides having at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, or at least 95% identity or complementarity to an endogenous gene encoding a target protein (i.e. TrifuncA, TrifuncB, PXA, ACO, and/or ICL).

Promoters used in antisense RNA, RNAi, or ribozyme constructs can be any that are functional in the host algal microorganism and that are suitable for the levels of expression required for reducing expression of the target gene to a desired amount. Promoters functional in algae and heterokonts are known in the art. The construct can be transformed into algae using any feasible method, include any disclosed herein. A mutant algal microorganism transformed with a recombinant nucleic acid molecule for attenuating expression of a gene encoding a protein from the mitochondrial beta-oxidation pathway, the peroxisomal beta-oxidation pathway, and/or the glyoxylate pathway, such as but not limited to an antisense, RNAi, or ribozyme construct, can have the properties of a mutant as described herein, including, for example, increased lipid production as compared to a host microorganism that does not include the recombinant nucleic acid molecule(s) that results in attenuated gene expression.

A related aspect of the invention that itself forms an embodiment of the invention, is a recombinant nucleic acid molecule designed for attenuating expression of a gene encoding a TrifuncA, TrifuncB, ACO, PXA, and/or ICL. The recombinant nucleic acid molecule can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring gene encoding a protein from the mitochondrial beta-oxidation pathway, the peroxisomal beta-oxidation pathway, or the glyoxylate pathway as disclosed herein and/or sequences adjacent thereto in the genome of the algal microorganism from which the gene is derived such as at least a portion of an intron, at least a portion of a 5'UTR, at least a portion of the promoter region, and/or at least a portion of a 3' UTR of the gene. For example, the recombinant nucleic acid molecule can include at least a portion of a gene encoding a protein with a sequence homologous to at least a portion of a naturally-occurring gene that encodes a polypeptide at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to a contiguous stretch of at least 50%, at least 75%, at least 80%, at least 90%, at least 95%, or about 100% of any of the amino acid sequences of N. gaditana TrifuncB (SEQ ID NO:10), TrifuncA (SEQ ID NO: 1), PXA1 (SEQ ID NO:20), ACO1 (SEQ ID NO:22), or ICL (SEQ ID NO:24), and/or has a coding region having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to any of the coding sequences of N. gaditana TrifuncB (SEQ ID NO:11), TrifuncA (SEQ ID NO:2), PXA1 (SEQ ID NO:21), ACO1 (SEQ ID NO:23), or ICL (SEQ ID NO:25). Further, provided herein are recombinant nucleic acid molecules for homologous recombination that include at least one sequence from a TrifuncB, TrifuncA, PXA1, ACO1, or ICL gene locus of the genome of an algal or heterokont microorganism juxtaposed with a heterologous nucleic acid sequence that can be, in non-limiting examples, a selectable marker or detectable marker gene. In some examples a construct for homologous recombination includes two nucleic acid sequences from a TrifuncB, TrifuncA, PXA1, ACO1, or ICL gene locus of the genome of an alga where the two sequences flank a heterologous sequence for insertion into the TrifuncB, TrifuncA, PXA1, ACO1, or ICL gene locus. In addition, provided herein are antisense, ribozyme, or RNAi constructs that include at least a portion of a naturally-occurring gene having encoding a TrifuncB, TrifuncA, PXA1, ACO1, or ICL protein, for example a polypeptide having at least at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, or at least 95% identity to any of SEQ ID NOs:10, 1, 20, 22, or 24, in which a promoter, such as a heterologous promoter, is operably linked to the TrifuncB, TrifuncA, PXA1, ACO1, or ICL gene sequence and the TrifuncB, TrifuncA, PXA1, ACO1, or ICL gene sequence is in antisense orientation. In one embodiment the mutation is within 25 base pairs upstream of a Cas9 PAM sequence. In an exemplary embodiment the mutation is in the second exon of the TrifuncB gene. This mutation of the second exon of TrifuncB can be, for example, an insertion performed with CRISPR/Cas-based RNA-guided DNA endonucleases.

Increased Lipid Production

Mutant algal microorganisms provided herein typically exhibit increased lipid production. Methods of measuring the amount of lipid produced by microorganisms are well known in the art and illustrated in the examples herein. Total extractable lipid can be determined according to Folch et al. (1957) J. Biol. Chem. 226: 497-509; Bligh & Dyer (1959) Can. J. Biochem. Physiol. 37: 911-917; or Matyash et al. (2008) J. Lipid Res. 49:1137-1146, for example, and the percentage of biomass present as lipid can also be assessed using Fourier transform infrared spectroscopy (FT-IR) (Pistorius et al. (2008) Biotechnol & Bioengin. 103:123-129). Additional references for gravimetric analysis of FAME and TAGs are provided in U.S. Pat. No. 8,207,363 and WO 2011127118 for example, each incorporated herein by reference in its entirety. Once the amount of lipid is known in the mutant algal or heterokont microorganism and the control algal or heterokont microorganism, lipid production can be determined for each, for example, by determining volumetric lipid productivity, which can be assessed as the amount of lipid produced per volume per day or per area per day. As such, an increase in lipid production can be the result of an increase in lipid synthesis or a decrease in lipid metabolism. Not to be limited by theory, it is believed that the increased lipid production exhibited by the mutant algal and heterokont microorganisms provided herein, is the result of decreased lipid metabolism. Thus, more total carbon is partitioned into lipid and more lipid accumulates over time in the mutant algal or heterokont microorganism.

Biomass can be assessed by measuring total organic carbon (TOC) or by other methods, such as measuring ash-free dry weight (AFDW). Methods for measuring TOC are known in the art (e.g., U.S. Pat. No. 8,835,149) and are provided herein. Methods of measuring AFDW are also well known and can be found, for example, in U.S. Pat. No. 8,940,508, incorporated herein by reference in its entirety.

The properties of a mutant as provided herein having increased lipid production are compared to the same properties of a control algal microorganism that can be a wild type organism of the same species as the mutant, preferably the progenitor strain of the mutant. Alternatively, a control algal or heterokont microorganism can be a microorganism that is substantially identical to the mutant algal or heterokont microorganism with the exception that the control algal or heterokont microorganism does not have the mutation present in the mutant algal or heterokont microorganism. For example, a control algal or heterokont microorganism can be a genetically engineered microorganism or classically mutated organism that has been further mutated or engineered to generate a mutant having increased lipid productivity as disclosed herein.

In some examples, a control microorganism can be a microorganism that is substantially identical to the mutant microorganism, with the exception that the control microorganism does not have a mutation in a gene encoding a TrifuncA and/or TrifuncB protein, and optionally a peroxisomal beta oxidation pathway or glyoxylate pathway protein such as an ACO, PXA, and/or ICL protein. The properties of a mutant having a disrupted, attenuated, or otherwise directly or indirectly genetically manipulated gene or genes (resulting in altered structure or expression of a TrifuncA and/or TrifuncB gene, and optionally an ACO, PXA, and/or ICL gene) can also be compared with the same properties of a control microorganism that does not have a disrupted, attenuated, or otherwise directly or indirectly genetically manipulated gene or genes encoding a TrifuncA and/or TrifuncB, and optionally an ACO, PXA, and/or ICL (regardless of whether the microorganism is "wild-type"). For example, a control algal or heterokont microorganism may be a mutant algal or heterokont microorganism or an algal or heterokont microorganism mutated in a gene other than a TrifuncA and/or TrifuncB gene, and optionally an ACO, PXA, and/or ICL gene. In some examples, the control microorganism is a wild-type microorganism.

In some embodiments, a mutant algal or heterokont microorganism provided herein has increased productivity of FAME with respect to a control algal or heterokont microorganism when grown under identical conditions where the control algal or heterokont microorganism produces biomass. The FAME produced by any of the mutant algal or heterokont microorganisms provided herein can be, for example, at least 5%, at least 10%, at least 15%, at least 20%, at least 25% at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 120%, at least 140%, at least 160%, at least 180%, or at least 200% greater than the FAME produced by the control algal or heterokont microorganism when both the mutant algal or heterokont microorganism and the control algal or heterokont microorganism are cultured under conditions in which both the culture of the mutant algal or heterokont microorganism and the culture of the control algal or heterokont microorganism produce biomass. In certain examples, the FAME produced by a mutant algal or heterokont microorganism can be between 5, 10, 15, 20, 25, 30, 35, 40, 45, 50, 55, 60, 65, 70, 75, 80, 85, 90, 95, and 100% on the low end of the range and 20, 25, 30, 35, 40, 45, 50, 55, 60, 65, 70, 75, 80, 85, 90, 95, 100, 125, 150, 175, and 200% on the high end of the range greater than the FAME produced by the control algal or heterokont microorganism.

A mutant having increased lipid production can have increased partitioning of carbon to lipid with respect to a control microorganism, this increased partitioning can be expressed as partitioning of carbon to total extractable lipid, to total neutral lipids, to triglycerides, and/or to FAME-derivatizable lipids. For example, a mutant algal or heterokont microorganism as provided herein can have a ratio of the amount of FAME-derivatizable lipids ("FAME") produced to biomass (TOC or ash-free dry weight (AFDW), for example) produced that is higher than that of a control algal or heterokont microorganism. The FAME/TOC of a mutant algal or heterokont microorganism provided herein can be, for example, at least 5%, at least 10%, at least 15%, at least 20%, at least 25% at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 120%, at least 140%, at least 160%, at least 180%, or at least 200% higher than the FAME/TOC of the control algal or heterokont microorganism when both the mutant algal or heterokont microorganism and the control algal or heterokont microorganism are cultured under conditions in which both the culture of the mutant algal microorganism and the culture of the control algal microorganism produce biomass. In other examples, the FAME/TOC of a mutant algal microorganism can be between 5, 10, 15, 20, 25, 30, 35, 40, 45, 50, 55, 60, 65, 70, 75, 80, 85, 90, 95, and 100% on the low end of the range and 20, 25, 30, 35, 40, 45, 50, 55, 60, 65, 70, 75, 80, 85, 90, 95, 100, 125, 150, 175, and 200% on the high end of the range higher than the FAME/TOC of the control algal or heterokont microorganism.

In other examples, the FAME/TOC of a mutant as provided herein can be at least 0.10, at least 0.15, at least 0.20, at least 0.25, at least 0.30, at least 0.35, at least 0.40, at least 0.45, at least 0.50, at least 0.55, at least 0.60, at least 0.65, at least 0.7, or at least 0.75 when cultured under conditions in which the mutant algal or heterokont microorganism culture produces at least 50%, at least 60%, at least 65%, at least 70%, at least 75%, at least 80%, at least 85, at least 90%, at least 95%, or at least 100% as much biomass (e.g., TOC) as a control algal or heterokont microorganism culture, under conditions where both the control and mutant cultures produce biomass.

In these embodiments where a mutant algal or heterokont microorganism as provided herein produces higher amounts of FAME or exhibits a higher Fame/TOC with respect to a control algal or heterokont microorganism under culture conditions in which both the mutant and control algal or heterokont microorganism are producing biomass, the mutant algal microorganism can produce at least 50%, at least 55%, at least 60%, at least 65%, at least 70%, at least 75%, at least 80%, at least 85%, at least 90%, at least 95%, at least 100%, at least 120%, at least 140%, at least 160%, at least 180%, or at least 200% of the biomass produced by a control algal or heterokont microorganism on a daily basis.

In some specific examples, a mutant algal or heterokont microorganism as provided herein produces higher amounts of FAME with respect to a control algal microorganism and at least 50% of the biomass but less than 150% or less than 200% of the biomass produced by the control algal microorganism. A mutant algal or heterokont microorganism can produce, for example, at least 25% more FAME than a control algal microorganism and at least 50% as much biomass as the control algal microorganism. In additional examples, a mutant algal or heterokont microorganism can produce 50% more FAME than a control algal or heterokont microorganism and have at least 50% as much biomass as the control algal or heterokont microorganism, under conditions in which the control algal or heterokont microorganism is producing biomass. A mutant can in some examples produce less than 400% more lipid than a control algal or heterokont microorganism while accumulating at least 50% as much biomass as the control algal or heterokont microorganism.

In other specific examples, a mutant algal or heterokont microorganism as provided herein can produce at least 5%, at least 10%, at least 15%, at least 20%, at least 25%, at least 30%, at least 35%, at least 40%, at least 45%, at least 50%, at least 55%, at least 60%, at least 60%, at least 65%, at least 70%, at least 75%, at least 80%, at least 85%, at least 85%, at least 90%, at least 95%, or at least 100% more FAME while producing at least 70%, at least 75%, at least 80%, at least 85%, at least 90%, at least 95%, or at least 100% of the TOC produced by a control algal or heterokont microorganism when cultured under conditions in which both the control and mutant microorganism produce biomass, and the FAME/TOC of the mutant microorganism is at least 30%, at least 35%, at least 40%, at least 45%, at least 50%, at least 55%, at least 60%, at least 65%, at least 70%, or at least 75% higher than the FAME/TOC of the control microorganism. The FAME/TOC of the mutant algal or heterokont microorganism can be, for example, at least 0.30 or at least 0.35. In additional embodiments a mutant algal or heterokont microorganism as provided herein can produce at least 50%, at least 55%, at least 60%, at least 60%, at least 65%, at least 70%, at least 75%, at least 80%, at least 85%, at least 85%, at least 90%, at least 95%, or at least 100% of the TOC produced by a control algal or heterokont microorganism when cultured under conditions in which both control and mutant microorganism are producing biomass, and the FAME/TOC of the mutant algal or heterokont microorganism is at least 30%, at least 35%, at least 40%, at least 45%, at least 50%, at least 55%, at least 60%, at least 65%, at least 70%, at least 75%, at least 80%, at least 85%, at least 85%, at least 90%, at least 95%, or at least 100% greater than the FAME/TOC of the control algal or heterokont microorganism. The FAME/TOC of the mutant microorganism can be, for example, at least 0.35, at least 0.40, or at least 0.45.

In yet further specific examples a mutant algal microorganism as provided herein can produce at least 85%, at least 90%, at least 95%, at least 100%, at least 105%, at least 110%, at least 115%, at least 120%, at least 125%, at least 130%, at least 135%, at least 140%, at least 145%, or at least 150% more FAME than a control algal microorganism while producing at least 70%, at least 75%, at least 80%, or at least 85% of the TOC produced by a control algal microorganism when cultured under conditions in which both wild type and mutant algal microorganism are producing biomass, and the FAME/TOC of the mutant algal microorganism is at least 100%, at least 110%, at least 120%, at least 130%, at least 140%, at least 150%, at least 160%, at least 170%, or at least 180% greater than the FAME/TOC of the control algal microorganism.

Any of the embodiments of mutant algal microorganisms provided herein that have increased lipid productivity with respect to a control algal microorganism when both the mutant algal microorganism and control algal microorganism are cultured under identical conditions in which the control algal microorganism culture is producing biomass, can have lipid measurements performed for example, after a culture period of at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 60, at least 70, at least 80, at least 90, or at least 100 days, and/or fewer than 1, fewer than 2, fewer than 3, fewer than 4, fewer than 5, fewer than 6, fewer than 7, fewer than 8, fewer than 9, fewer than 10, fewer than 11, fewer than 12, fewer than 13, fewer than 14, fewer than 15, fewer than 20, fewer than 25, fewer than 30, fewer than 35, fewer than 40, fewer than 45, fewer than 50, fewer than 60, fewer than 70, fewer than 80, fewer than 90, fewer than 100, fewer than 120 or fewer than 180 days. In any of the embodiments, lipid measurements can be performed on the mutant and control algal microorganisms whether cultured in batch, semi-continuous, or continuous culture for the above lengths of time. In some examples, a mutant algal microorganism as provided herein has increased lipid productivity with respect to a control algal microorganism under culture conditions in which both the mutant and control algal microorganisms are producing biomass and actively dividing. The culture conditions under which any of the mutant algal microorganisms provided herein have increased lipid productivity as compared to a control algal microorganism can be nitrogen replete with respect to the control algal microorganism, that is, the culture conditions can be sufficient in nitrogen with respect to the control algal microorganism such that additional nitrogen does not increase the growth rate of the microorganism (where all other culture conditions and ingredients remain the same). The culture conditions for any of the embodiments provided herein can also be photoautotrophic, wherein the culture conditions only contain inorganic carbon.

Mutant algal microorganisms of the present invention result in increased overall lipid production. As illustrated in the Examples herein, such increased lipid production can include an increase in FAME with a specific profile. For example, in certain examples, mutant algal microorganisms provided herein exhibit increased lipid production with a FAME profile having an increase in 16 carbon fatty acids, such as 16:0 and/or 16:1 fatty acids and/or a decrease in 20 carbon fatty acids, such as 20:4 and/or 20:5 fatty acids compared to a fatty acid profile of lipid isolated from a control algal microorganism. A skilled artisan will identify methods that can be used to characterize lipid profiles, as illustrated in the Examples section herein, such as thin layer chromatography, liquid chromatography, including HPLC, gas chromatography and/or mass spectroscopy. Accordingly, provided herein as another embodiment of the invention, are lipid compositions, produced using any of the mutant algal microorganisms provided herein. Methods for producing and isolating such lipids are provided below. In specific examples, profiles of lipids provided by the mutant algal microorganisms herein can include an increase of at least 5, 10, 15, 20, or 25% in 16 carbon fatty acids, such as 16:0 and/or 16:1 fatty acids and/or a decrease of at least 5, 10, 15, 20, or 25% in 20 carbon fatty acids, such as 20:4 and/or 20:5 fatty acids. In related specific examples, profiles of lipids provided by the mutant algal microorganisms herein can include an increase of between 2.5, 5, and 10% on the low end of the range and 5, 10, 15, 20, or 25% on the high end of the range in 16 carbon fatty acids, such as 16:0 and/or 16:1 fatty acids and/or a decrease of between 2.5, 5, and 10% on the low end of the range and 5, 10, 15, 20, or 25% on the high end of the range in 20 carbon fatty acids, such as 20:4 and/or 20:5 fatty acids.

Methods of Producing Lipids

Provided herein in certain embodiments, are methods of producing lipid by culturing a mutant or recombinant algal microorganism as provided herein under effective conditions (i.e. in a suitable medium and for a sufficient time) to produce lipid; and isolating at least one lipid from the culture medium, or the microorganism, or both. The culture can be a photoautotrophic culture. Culturing can be done in batch, semi-continuous, or continuous mode.

Any of the mutant algal microorganisms of the invention, as disclosed herein, can be used in a method of producing lipids provided herein. The mutant microorganisms typically used in the methods of producing a lipid provided herein are recombinant or mutant algal microorganisms that include a mutation in the mitochondrial trifunctional protein subunit B (TrifuncB) and/or the mitochondrial trifunctional protein subunit A (TrifuncA) genes that result in attenuated expression of the mitochondrial trifunctional protein subunit B (TrifuncB) and/or the mitochondrial trifunctional protein subunit A (TrifuncA), respectively, as provided herein. The mutant or recombinant algal microorganism can additionally include a mutation in a peroxisomal beta-oxidation pathway protein or a glyoxylate pathway protein, wherein the mutation results in attenuated expression of the peroxisomal beta-oxidation pathway protein or the glyoxylate pathway protein. The peroxisomal beta-oxidation pathway protein can include, for example, Acyl-CoA oxidase or PXA1. The glyoxylate pathway protein can be, for example, isocitrate lyase.

The mutant algal microorganisms can be cultured in any suitable vessel(s), including flasks or bioreactors, where the algae may be exposed to artificial or natural light (or natural light supplemented with artificial light).

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. A microorganism as provided herein can be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically, "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as non-limiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

In some embodiments of the present invention, the microorganisms having increased lipid productivity can be cultured in a "photobioreactor" equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally, or alternately, a mutant algal microorganism provided herein, can be grown in ponds, canals, sea-based growth containers, trenches, raceways, channels, or the like, or combinations thereof. In such systems, the temperature may be unregulated, or various heating or cooling method or devices may be employed as with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO (carbon monoxide) in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The methods include culturing a mutant algal microorganism as provided herein, such as a mutant microorganism as provided herein that has increased lipid productivity and/or increased lipid partitioning with respect to a control cell while producing at least 50%, 60%, 70%, 75%, 80%, 90%, 95% or 100% percent of the biomass produced by a control cell under the same culture conditions to produce biomass or lipid. Lipids can be recovered from culture by recovery means known to those of ordinary skill in the art, such as by whole culture extraction, for example, using organic solvents or by first isolating biomass from which lipids are extracted (see, for example, Grima et al. (2003) Biotechnol. Advances 20:491-515). In some cases, recovery of fatty acid products can be enhanced by homogenization of the cells (Gunerken et al. (2015) Biotechnol. Advances 33:243-260). For example, lipids such as fatty acids, fatty acid derivatives, and/or triglycerides can be isolated from algae by extraction of the algae with a solvent at elevated temperature and/or pressure, as described in the co-pending, commonly-assigned U.S. Pat. No. 9,243,207 entitled "Solvent Extraction of Products from Algae", which is incorporated herein by reference in its entirety.

Biomass can be harvested, for example, by centrifugation or filtering. The biomass may be dried and/or frozen. Further products can be isolated from biomass, such as, for example, various lipids or one or more proteins.

As a specific, non-limiting example, lipid extraction can be performed using a monophasic ternary system of chloroform:methanol:water, a less hazardous solvent mixture of dichloromethane:methanol, an alternative solvent mixture of propan-2-ol:cyclohexane:water, direct saponification using KOH in ethanol, or supercritical CO2 extraction (Li et al. (2014) "A comparative study: the impact of different lipid extraction methods on current microalgal lipid research" Microbial Cell Factories 13:14). These extraction methods are representative extraction methods for *Tetraselmis*. A skilled artisan will understand that modifications of such methods, or different methods can be used for lipid isolation from other algal microorganisms.

In some embodiments, a method of producing lipid provided herein, can include culturing a microorganism under conditions in which the FAME to TOC (FAME/TOC) ratio of the microorganism is maintained between about 0.3 and about 0.8, and isolating lipid from the microorganism, the culture medium, or both. For example, the microorganisms can be cultured such that the FAME/TOC is maintained at between about 0.3 and about 0.8, between about 0.4 and about 0.7, between about 0.4 and about 0.6, or between about 0.45 and about 0.55. The ratio can be maintained at between about 0.3 and about 0.8, for example between about 0.4 and about 0.8, between about 0.4 and about 0.7, between about 0.4 and about 0.6, or between about 0.45 and about 0.55 for at least 3, at least 4, at least 5, at least 6, at least 7, at least 8, at least 9, at least 10, at least 11, at least 12, at least 13, at least 15, at least 20, at least 30 days, or at least 60 days. In these methods the microorganism can be cultured under continuous or semi-continuous conditions. For example, the microorganism can be a mutant algal microorganism having attenuated expression of a gene encoding a polypeptide having at least 55%, at least 65%, at least 75%, or at least 85% identity to any of the amino acid sequences of *N. gaditana* TrifuncB (SEQ ID NO:10), TrifuncA (SEQ ID NO:1), PXA1 (SEQ ID NO:20), ACO1 (SEQ ID NO:22), or ICL (SEQ ID NO:24). The FAME/TOC may be adjusted, for example, by the type and concentration of nitrogen source present in the culture medium.

Further Embodiments

In another embodiment, provided herein is a suspension of a mutant algal microorganism in a culture medium, where the culture medium can include an antibiotic or a cryopreservative and/or be nitrogen replete, and where the mutant algal microorganism can be any of the mutant microorganisms provided herein. In one embodiment, the suspension can include a mutant algal microorganism with a mutation in a TrifuncB and/or the TrifuncA gene that results in attenuated expression of the gene with or without a mutation in a gene encoding a protein from the peroxisomal beta-oxidation pathway or the glyoxylate pathway that results in attenuated expression of the peroxisomal or glyoxylate pathway gene and increased lipid production when compared to a control algal microorganism of the same species as the mutant algal microorganism when cultured under the same conditions.

In examples where a mutant algal microorganism of the invention is suspended in a cryopreservative, provided herein are cryopreserved mutant algal microorganism. Furthermore, in certain embodiments, provided herein are mutant algal microorganisms in a cryopreservative in a container, such as a cryovial that is positioned within a container at below 0 C. For example, the cryovial can be stored in liquid nitrogen at a temperature below −50 C, −60 C, −70 C, or −75 C, or at −80 C. The mutant algal microorganism can be suspended in a cryopreservative such as, not to be limiting, 5% methanol in culture medium or GeneArt® Cryopreservative Reagent B (ThermoFisher, Carlsbad, Calif.).

In another embodiment, provided herein is a solid media that includes a mutant algal microorganism of the invention. For example, provided herein is an agar media, such as an agar slant, that includes any of the mutant algal microorganisms of the invention thereon.

In another embodiment, provided herein is a biomass that includes any of the mutant algal microorganisms of the invention. In some examples, the biomass can include an antibiotic, such as a synthetic antibiotic. In one embodiment, the biomass can include a mutant algal microorganism with a mutation in a TrifuncB and/or the TrifuncA gene that results in attenuated expression of the gene with or without a mutation in a gene encoding a protein from a peroxisomal beta-oxidation pathway, or a glyoxylate pathway that results in attenuated expression of the peroxisomal or glyoxylate pathway gene and increased lipid production when compared to a control algal microorganism of the same species as the mutant algal microorganism when cultured under the same conditions.

Any of the mutant algae disclosed herein can be designed to be unequipped to live and proliferate outside of a select environment by any number or combination of biocontainment technologies. The algal microorganism can be controlled by including a mutation therein which prevents proliferation outside a select environment, or any combination which exerts a select behavioral, or temporal, or regional control on the mutant algal microorganism which acts as a method to control from surviving outside the select environment. Accordingly, provided herein in another embodiment, is a method for making any of the mutant algal microorganisms herein, a biocontainable mutant algal microorganism. In certain embodiments, the mutant algal microorganisms provided herein are mutated such that they are dependent on non-naturally occurring amino acids (Nature, 518, Issue 7537, pp. 55-60 (2015)). In other examples, the method can include inserting an exogenous non-algal nucleic acid encoding a gene for biocontainment into a mutant algal microorganism of the present invention. The mutant algal microorganism can include any of the mutant algal microorganisms provided herein, which typically includes a mutation that attenuates expression of TrifuncA and/or TrifuncB and results in increased lipid production.

In a related embodiment, provided herein is a biocontainable mutant algal microorganisms that includes a mutation in a TrifuncA and/or TrifuncB gene that results in attenuation of expression of TrifuncA and/or TrifuncB and increased lipid production, as provided herein, and an exogenous gene for biocontainment. The exogenous gene for biocontainment that is introduced into a mutant algal microorganism can be a "suicide gene" that will kill the mutant algal microorganism if it escapes from a select environment, such as a laboratory environment or a lipid production environment, such as a commercial lipid production environment. In certain embodiments, the biocontainment gene is a toxin gene (See e.g. U.S. Pat. No. 8,975,061, Bielinski et al., "Regulation of Toxin and Antitoxin Genes for Biological Containment"). Accordingly, the present invention includes a mutant algal microorganism as provided herein, that further includes an exogenous toxin gene (i.e. a toxin gene that is non naturally-occurring in the algae and that is toxic to the algae).

In one embodiment, the toxin gene is a Type II toxin gene, for example that is derived from a eubacterial or archaebacterial species, and optionally can be derived from a cyanobacterial species, for example, any of the aforementioned cyanobacterial species, and can be homologous or heterologous with respect to the recombinant prokaryotic host. The toxin in some additional embodiments can be an endoribonuclease that cleaves specific RNA sequences. In some further embodiments, the nucleotide sequence of the toxin gene can be designed to exclude endonuclease recognition sequences that render the encoded RNA susceptible to cleavage by the toxin.

The exogenous toxin gene can encode, in some alternative embodiments, a toxin of the CcdB toxin family, the RelE toxin family, the MazF toxin family, the ParE toxin family, the PIN toxin family, the Ahal toxin family, the MNT toxin family, the Doc toxin family, the VapC toxin family, the zeta toxin family, the HipA toxin family, or the HigB toxin family. For example, the Type II toxin may be a CcdB, RelE, MazF, ParE, PIN, Ahal, MNT, Doc, VapC, zeta, HipA, HigB, ChpI, StbE, Txe, YafQ, or YoeB toxin, or an ortholog or homolog of any of these toxins, or other Type II toxins.

Expression of the exogenous toxin gene can be driven by a heterologous promoter operably linked to the toxin gene. In an illustrative embodiment the promoter is a regulatable promoter, such as a promoter regulated by a compound that is present in the cell culture or cell environment, such as, as non-limiting examples, a sugar, an organic acid, a fatty acid, an amino acid or amino acid analog, a lipid, a hydrocarbon, phosphate, nitrate, ammonium, a metal, a quorum-sensing compound, a lactone, a vitamin, a secreted protein or peptide, or any combination thereof.

A skilled artisan will recognize that there are different mechanisms for controlling expression of an exogenous toxin gene in a mutant algal microorganism such that it is effective for biocontainment. For example, expression of the toxin gene can be under the control of a regulator that is present or absent from naturally occurring environments. For example, the toxin gene can be under the control of a regulatory element that is induced by a compound that is present in natural environments. Thus, escape of a mutant algal microorganism from its controlled environment can be prevented because the toxin gene will be expressed if the microorganism escapes its controlled environment. In another embodiment, expression of the toxin gene can be under the control of a compound that is not present in natural environments. As such, expression of the toxin gene can be inhibited by the presence of the compound. Controlled environments for culturing such mutant algal microorganism can include the compound, thereby inhibiting expression of the toxin. Escape of the mutant microorganism from the controlled environment will result in expression of the toxin and will kill the algae.

EXAMPLES

The Following Media are Used in the Examples

PM074 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM NaNO3, 0.361 mM NaH2PO4.H2O, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM124 medium is PM074 supplemented with 5 mM Ammonium and 10 mM HEPES pH 8.0. It is made by adding 10 mls of 1 M HEPES pH 8 and 5 mls of NH$_4$Cl to the PM074 recipe (final volume of 1 L).

Example 1

Knockout of Beta-Oxidation Genes in *Nannochloropsis*

Transgenic algal strains of *Nannochloropsis gaditana* were created where genes involved in beta-oxidation were functionally ablated or knocked out by targeted mutagenesis. The wild type *Nannochloropsis gaditana* strain is designated WT-3730. In order to create mutant algal microorganisms with increased lipid content, the mitochondrial trifunctional protein beta subunit or "subunit B" (TrifuncB) (hydroxyacyl-CoA dehydrogenase/3-ketoacyl-CoA thiolase/ enoyl-CoA hydratase (trifunctional protein), beta subunit, Naga_102524g1, see SEQ ID NO:10 for the amino acid sequence, and SEQ ID NO:11 for the cDNA sequence), which catalyzes the last three steps of beta-oxidation in the mitochondria (see FIG. 1), as well as enzymes involved in the peroxisomal beta-oxidation or glyoxylate pathways were targeted. The knockout mutants were generated using CRISPR technology.

To produce the knock-out mutants, a high efficiency *Nannochloropsis* Cas9 Editor line (*N. gaditana* strain GE-6791) was developed as disclosed in US 2017/0073695 "Compositions and Methods for High Efficiency In Vivo Genome Editing", filed Dec. 31, 2015, naming inventors John Verruto and Eric Moellering, incorporated herein by reference in its entirety. Engineered strain GE-6791, which expresses a gene encoding the *Streptococcus pyogenes* Cas9 nuclease, was used as a host for transformation with a chimeric guide RNA and donor DNA for insertional knockout. *Nannochloropsis* strain GE-6791 exhibited expression of the introduced Cas9 gene in close to 100% of the cell population of a growing culture. The vector pSGE-6206 (SEQ ID NO:26) was used to transform wild type *N. gaditana* strain WT-3730 and included the following three elements: 1) a Cas9 expression cassette which contained a Cas9 gene from *Streptococcus pyogenes* codon optimized for *N. gaditana* (SEQ ID NO:27) that included sequences encoding an N-terminal nuclear localization signal followed by a FLAG tag and peptide linker (together provided as SEQ ID NO:28), driven by the *N. gaditana* RPL24 promoter (SEQ ID NO:29) and terminated by the *N. gaditana* bidirectional terminator 2 (SEQ ID NO:30); 2) a selectable marker expression cassette, which contained the blasticidin S deaminase gene from *Aspergillus terreus* codon optimized for *N. gaditana* (SEQ ID NO:31), driven by the *N. gaditana* TCTP promoter (SEQ ID NO:32) and followed by the EIF3 terminator (SEQ ID NO:33); and 3) a GFP reporter expression cassette, which contained the TurboGFP gene (Evrogen, Moscow, Russia) codon optimized for *N. gaditana* (SEQ ID NO:34), driven by the *N. gaditana* 4A-III promoter (SEQ ID NO:35) and followed by the *N. gaditana* bidirectional terminator 5 (SEQ ID NO:36). Transformation was essentially as disclosed in published US 2014/0220638 ("Algal mutants having a locked-in high light acclimated phenotype," filed Dec. 6, 2013, incorporated herein by reference in its entirety).

The transformation mixture was plated onto PM074 agar medium containing 100 mg/L of blasticidin. Resulting colonies were patched onto selection media for analysis and archiving. A small amount of biomass was taken from the patches and completely resuspended in 300 µl of 1× Instant Ocean Salts solution (Aquatic Eco Systems; Apopka, Fla.). Care was taken to not add too much biomass so that a light green resuspension was obtained. This suspension was directly analyzed by flow cytometry using a BD Accuri C6 flow cytometer (BD Biosciences, San Diego, Calif.), using a 488 nm laser and 530/10 nm filter to measure GFP fluorescence per cell. 10,000-30,000 events were recorded for each sample using the slow fluidics setting. A strain having a single fluorescence peak that was shifted to a fluorescence level higher than that demonstrated by wild-type cells and also demonstrating Cas9 protein expression by Western, designated strain GE-6791, was selected as a Cas9 Editor strain and used in mutant generation by CRISPR/Cas9 genome editing as disclosed herein.

Figure 2:
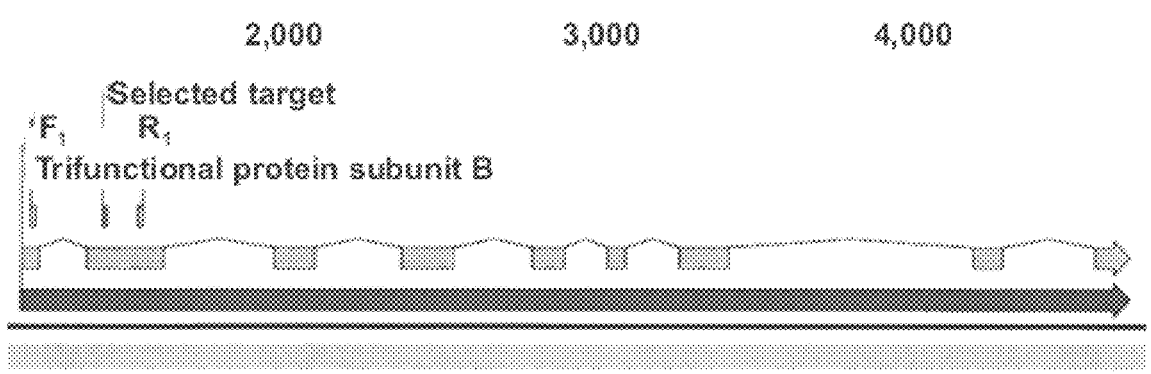
FIG. 2. Schematic depicting the TrifuncB gene locus in *N. gaditana* WT-3730 and the region selected for Cas9 mediated insertion of a minimal HygR cassette ("selected target"). Solid blocks denote exons and introns are depicted as lines. The positions of sequencing primers used to confirm insertional mutagenesis are also shown.

The TrifuncB encoding gene (SEQ ID NO: 11) was targeted for disruption using Cas9-mediated genome editing. Briefly, a Hygromycin resistance expression cassette (SEQ ID NO:37) was targeted to insert into the second exon of the TrifuncB gene (FIG. 2). For targeting of the TrifuncB gene for disruption, a DNA construct was made (SGI-DNA, La Jolla, Calif.) for producing a guide RNA in which the DNA molecule included the sequence of a chimeric guide engineered downstream of a T7 promoter. The chimeric guide sequence included a 23 bp target sequence (SEQ ID NO:38) homologous to a sequence within the second exon TrifuncB gene sequence (that included an *S. pyogenes* Cas9 PAM sequence (NGG)), and also included the transactivating CRISPR RNA (tracr) sequence. The chimeric guide sequence was synthesized as disclosed in US 2017/0073695 (see, for example, Examples 2, 5, 9, and 10) by first making a DNA template made up of complementary DNA oligonucleotides that were annealed to create a double-stranded DNA template in which the target sequence and tracr sequences were downstream of a T7 promoter sequence. The double-stranded DNA guide template that included a T7 promoter was used in in vitro transcription reactions using the MEGAshortscript™ T7 Kit (Life Technologies, Carlsbad, Calif. #AM1354M) according to the manufacturer's instructions to synthesize the guide RNA. The resulting RNA was purified using Zymo-Spin™ V-E columns (Zymo Research #C1024-25) according to the manufacturer's protocol.

The donor fragment for insertion into the targeted TrifuncB locus (SEQ ID NO: 12) included a selectable marker cassette that included the hygromycin resistance gene (HygR, SEQ ID NO:39) downstream of the *N. gaditana* EIF3 promoter (SEQ ID NO:40) and followed by *N. gaditana* bidirectional terminator 2 (SEQ ID NO:30), with the entire promoter-hygromycin resistance gene-terminator sequence flanked by 27 base pair identification sequences on the 5' (SEQ ID NO:41) and 3' (SEQ ID NO:42) ends to yield the DNA fragment referred to as the "Hyg Resistance Cassette Donor Fragment" (SEQ ID NO:43).

For targeted knockout of the TrifuncB locus, Cas9 Editor line GE-6791 was transformed by electroporation using 5 µg of purified chimeric guide RNA targeting the TrifuncB gene and 1 µg of the selectable donor DNA (SEQ ID NO:43) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the TrifuncB gene.

Additionally, single knockouts of three other genes involved in beta-oxidation were made (see FIG. 1): PXA1 (Peroxisomal ABC-type acyl-coenzyme A transporter, Naga_101131g2, Naga_101730g1, and Naga_102509g1 see SEQ ID NO:20 for the amino acid sequence, and SEQ ID NO:21 for the cDNA sequence), ACO1 (Acyl-CoA oxidase 1, a peroxisomal enzyme, see SEQ ID NO:22 for the amino acid sequence, and SEQ ID NO:23 for the cDNA sequence), and ICL (Isocitrate lyase, Naga_100025g12, an enzyme of the glyoxylate pathway, see SEQ ID NO:24 for the amino acid sequence, and SEQ ID NO:25 for the cDNA sequence). Proteins expressed from these genes are involved in various steps of the peroxisomal beta-oxidation and glyoxylate pathways including i) Acyl-CoA transporters that import Acyl-CoA into the peroxisome (PXA1), ii) the enzymatic steps in peroxisomal beta-oxidation (ACO1) and iii) genes down-stream of peroxisomal beta-oxidation that are part of the glyoxylate pathway and required for re-assembly of acetyl-CoA into carbon metabolism (ICL). These genes were targeted for disruption using Cas9-mediated genome editing and were generated in a manner similar to that used to disrupt TrifuncB disclosed above. For targeting these genes for disruption, DNA constructs were made (SGI-DNA, La Jolla, Calif.) for producing a guide RNA in which the DNA molecule included the sequence of a chimeric guide engineered downstream of a T7 promoter. The chimeric guide sequence included a 23 bp target sequence homologous to separate sequences within each gene sequence (SEQ ID NO:44 for PXA1; SEQ ID NO:45 for ACO1; and SEQ ID NO:46 for ICL) that was upstream of an *S. pyogenes* Cas9 PAM sequence (NGG), and also included the transactivating CRISPR (tracr) sequence. The chimeric guide sequence was synthesized by first making a DNA template made up of complementary DNA oligonucleotides that were annealed to create double-stranded DNA templates which were used in in vitro transcription reactions using the MEGAshortscript™ T7 Kit (Life Technologies #AM1354M) according to the manufacturer's instructions to synthesize the guide RNA. The resulting RNAs were purified using Zymo-Spin™ V-E columns (Zymo Research #C1024-25) according to manufacturer's protocol. The donor fragment for insertion into the targeted loci included the Hyg selectable marker cassette that included 27 base pair identification sequences on the 5' and 3' ends (SEQ ID NO:43).

For colony PCR screening, a small amount of cells from a colony to be screened was suspended into 100 µl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com; Qiagen GmbH, Germany). The primers used to detect the insertion of the donor fragment into the targeted locus of TrifuncB were SEQ ID NO:47 and SEQ ID NO:48. The primers used to detect the insertion of the donor fragment into the targeted locus of PXA1 were SEQ ID NO:49 and SEQ ID NO:50. The primers used to detect the insertion of the donor fragment into the targeted locus of ACO1 were SEQ ID NO:51 and SEQ ID NO:52. The primers used to detect the insertion of the donor fragment into the targeted locus of ICL were SEQ ID NO:53 and SEQ ID NO:54. Based on the PCR-based colony screening, three knockout strains of TrifuncB (TrifuncB-6, TrifuncB-9, and TrifuncB-42) and one knockout strain each of PXA1, ACO1, and ICL were tested in productivity assays.

The three validated TrifuncB knockout lines (TrifuncB-6, TrifuncB-9, and TrifuncB-42) were assessed in a batch productivity assay in nitrogen replete medium PM074 that included 8.8 mM nitrate as the sole nitrogen source available to the cells in the absence of any reduced carbon source that could support algal growth (i.e., the productivity assay was conducted under photoautotrophic conditions). After inoculation, engineered TrifuncB knockout strains TrifuncB-6, TrifuncB-9, and TrifuncB-42 and wild type strain WT-3730 were grown in triplicate cultures in a batch assay in 75 cm2 rectangular tissue culture flasks containing 175 ml of PM074 medium, for seven days. Under these conditions, nitrogen begins to become limiting in the culture medium on approximately Day 3, with the concentration of nitrogen in the culture medium continuing to drop throughout the remainder of the assay. The flasks were positioned with their narrowest "width" dimension against an LED light. The culture flasks were masked with an opaque white plastic to provide a 21.1 cm2 rectangular opening for irradiance to reach the cultures. Incident irradiance was programmed at a 16 h light: 8-hour dark cycle where a linear ramp up of irradiance from 0 to 1200 uE and then a linear ramp down in irradiance from 1200 to 0 uE over a 4 h period. Deionized H2O was added to the cultures daily to replace evaporative losses. The temperature of the cultures was regulated by a water bath set at 25° C. Cultures were inoculated at OD730 of 0.5 on day 0 and samples (5 mls) were removed on days 3, 5, and 7 for assessing cell density, fatty acid methyl esters (FAME) as a measure of lipid, and total organic carbon (TOC). Sampling was done 30 minutes prior to the end of the light cycle.

In these assays, the carbon partitioning to lipid phenotype which was assessed by measuring fatty acid methyl esters (FAMEs) to represent lipids and total organic carbon (TOC) to represent biomass; the ratio of FAME/TOC was used to assess whether a strain had increased carbon partitioning to lipids versus the wild type 3730 strain.

FAME analysis was performed on 2 mL culture samples that were dried using a GeneVac HT-4X. To each of the dried pellets the following were added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2K rpm and finally centrifuged for three minutes at 1K rpm. The heptane layer was sampled using a Gerstel MPS Autosampler. Quantitation used the 80 µg of C23:0 FAME internal standard. The samples were run on an Agilent 7890A gas chromatography system using a J&W Scientific 127-3212 DB-FFAP, 10 m×100 µm×100 nm column and an FID detector at 260° C. The flow rate was 500 µL/minute using H2 as a carrier with constant flow control. The oven was set at 100° C. for 0.98 min, then 15.301° C./minute to 230° C. and held for 1.66 min. The inlet contained a 4 mm glass wool packed liner (Agilent P/N 5183-4647), and was set at 250° C. and used a split ratio of 40:1. The injection volume was 900 nL. Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

Figure 3:
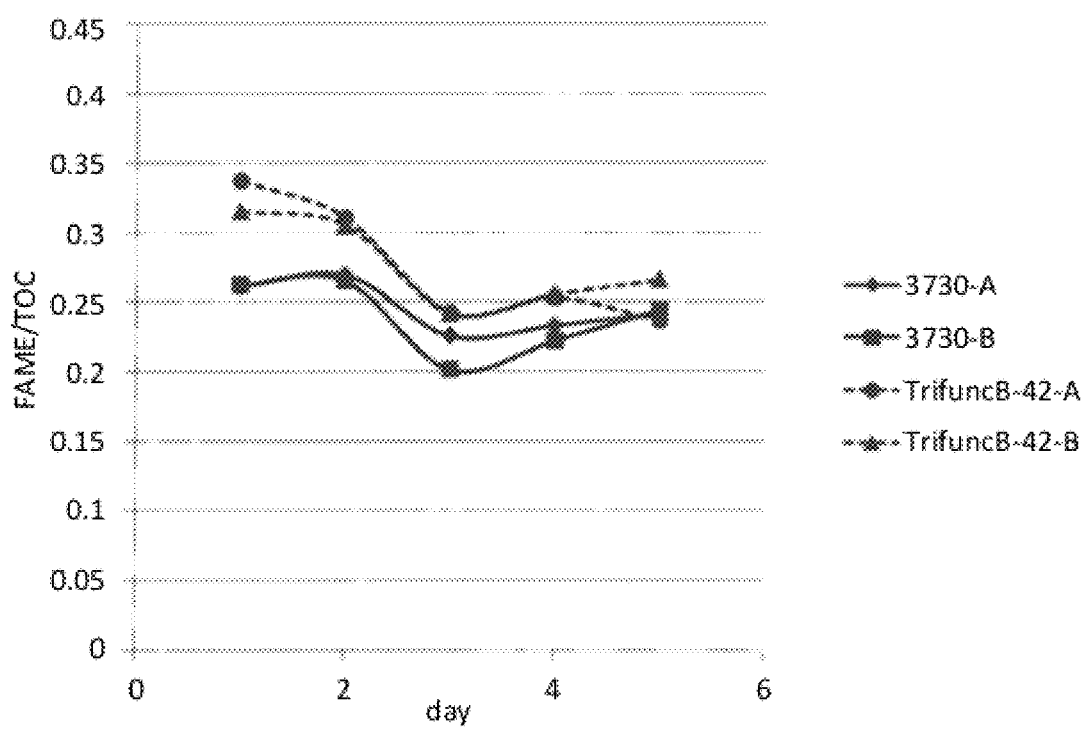
FIG. 3. Graphical representation of FAME/TOC plotted for two cultures of TrifuncB knock-out isolate #42 compared to two cultures of wild-type strain WT-3730 run in a batch productivity screen.
Figure 4:
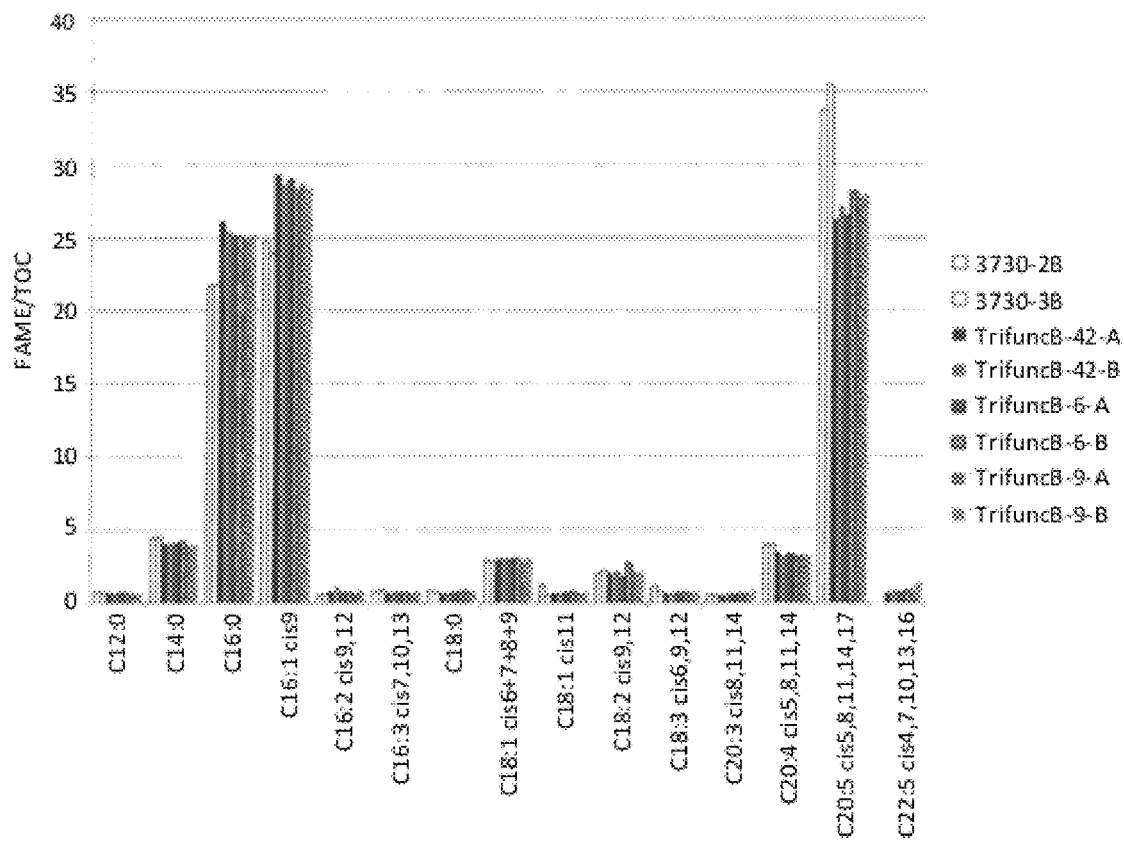
FIG. 4. Graphical representation of fatty acid profiles for three independent TrifuncB knock-out isolates as well as the wild type WT-3730 *N. gaditana* strain grown in a batch productivity screen presented on a FAME/TOC basis. Data from the $5^{th}$ day of sampling are shown.

As observed in FIG. 3, FAME/TOC values were substantially increased in the TrifuncB knockout lines when compared to wild type 3730, up to a ~30% increase at some time-points in the experiments. In addition to an increase in FAME/TOC, the fatty acid profile was also observed to be altered in the TrifuncB knockout strains, where 16:0 and 16:1 were increased when compared to wild-type but 20:4 and 20:5 fatty acids decreased (FIG. 4).

The three strains containing single knockouts of either peroxisomal transporter PXA1, peroxisomal enzyme ACO1, or glyoxylate cycle enzyme ICL were tested for increases in lipid productivity and partitioning to lipid. Notably, no distinguishable phenotypes were found in the case of individual knockouts of these genes.

Example 2

Trifuncb Knockdown Mutants in the Semi-Continuous Productivity Assay

TrifuncB-KO strain GE-8256 (transformant TrifuncB-42), wild type strain 3730, and wild type strain 3730 grown with the antibiotic kanamycin included in the culture (3730 KAN) were assayed in the semi-continuous productivity assay (SCPA), in which the assay medium, PM074, did not include a reduced carbon source for the algae.

Starter cultures were used to inoculate 225 cm2 rectangular tissue culture flasks, each of which contained a final total volume of 550 ml of culture after inoculation. The cultures were inoculated so that each 550 ml culture had an initial OD730 of 0.9. A typical inoculum volume was approximately 200 ml of scale-up culture that was added to approximately 350 ml of assay culture medium, which was PM074 (nitrogen replete medium). The culture medium did not include a source of reduced carbon ("organic carbon") that could be utilized by the algae for growth or incorporation into biomolecules, thus the assay conditions were photoautotrophic. Three cultures were initiated per strain. The flasks included stir bars and had stoppers having inserted tubing connected with syringe filters for delivering CO2 enriched air (1% CO2, flow rate, 300 ml per min) that was bubbled through the cultures. The flasks were set in a water bath programmed to maintain a constant temperature of 25° C. on stir plates set to 575 rpm during the assay period. Culture flasks were masked with an opaque white plastic to provide a 31.5 cm2 rectangular opening for irradiance to reach the culture. The flasks were aligned with the width (narrowest dimension) against an LED light bank that was programmed with a light/dark (diel) cycle and light profile that increased until "solar noon" and then declined to the end of the light period. The light profile was designed to mimic a spring day in Southern California: 14 h light:10 h dark, with the light peaking at approximately 2000 µE.

Cultures were diluted daily at mid-day, when the light intensity was at its peak, by removing 30% of the volume (165 mls) and replacing it with the same volume of the assay medium (PM074) plus an additional 10 ml of deionized water to make up for evaporation (included in the make-up medium). Semi-continuous assays were typically run for 10-14 days. Daily lipid and biomass productivities were only calculated for cultures that had reached steady state (where the increase in growth was equal to the dilution factor for the assay).

Figure 5A:
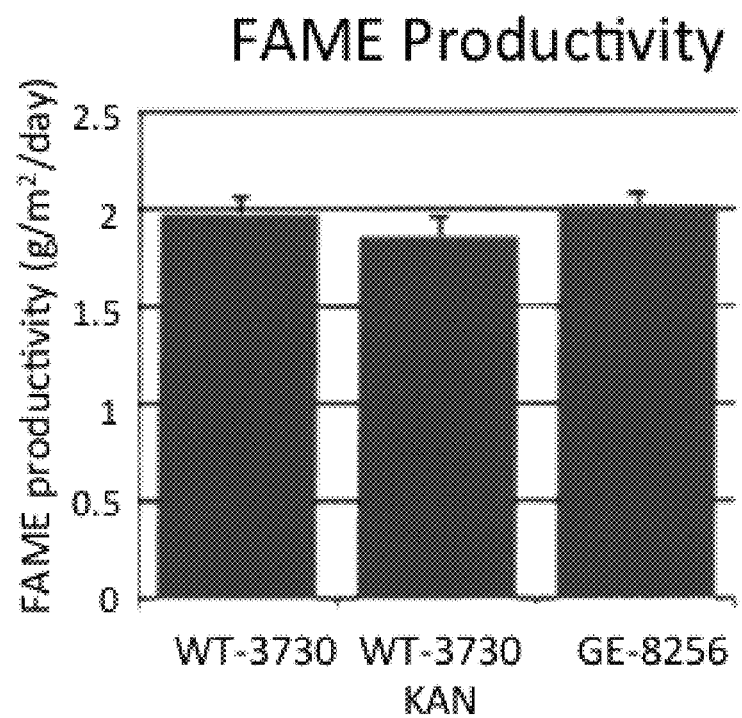
FIGS. 5A-5C. Graphical representation of Semi-Continuous Productivity Assay (SCPA) data for Trifunc-B-KO strain GE-8256, WT-3730 and WT-3730 grown in the presence of kanamycin control strains. Strains were run under a diel light regime mimicking a spring day in Southern California at a 30% daily dilution rate. A) FAME productivity, B) FAME/TOC, and C) TOC productivity averages are shown for each of the strains. GE-8256 showed a ~13% increase in FAME/TOC (B) with respect to wild type.
Figure 5B:
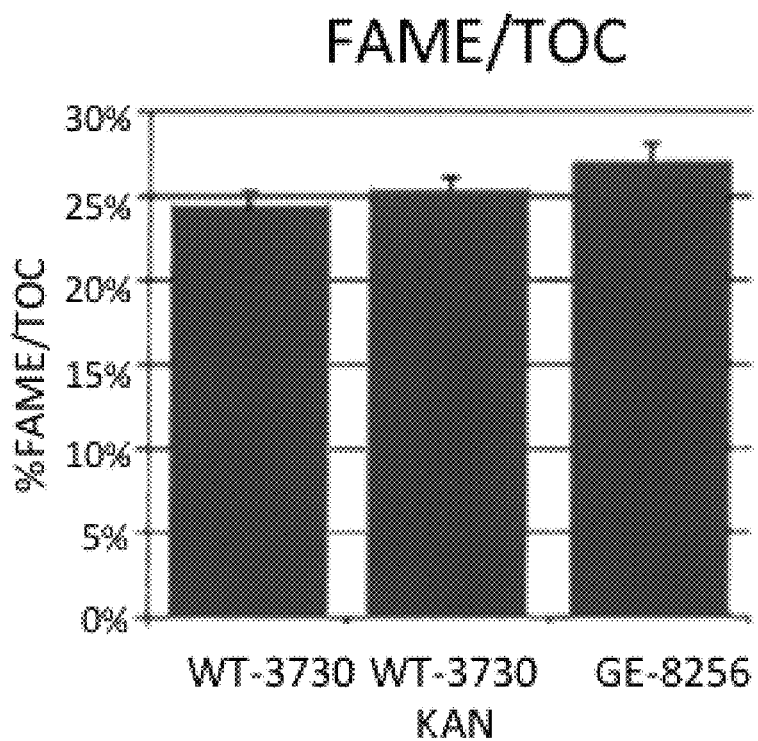
Figure 5C:
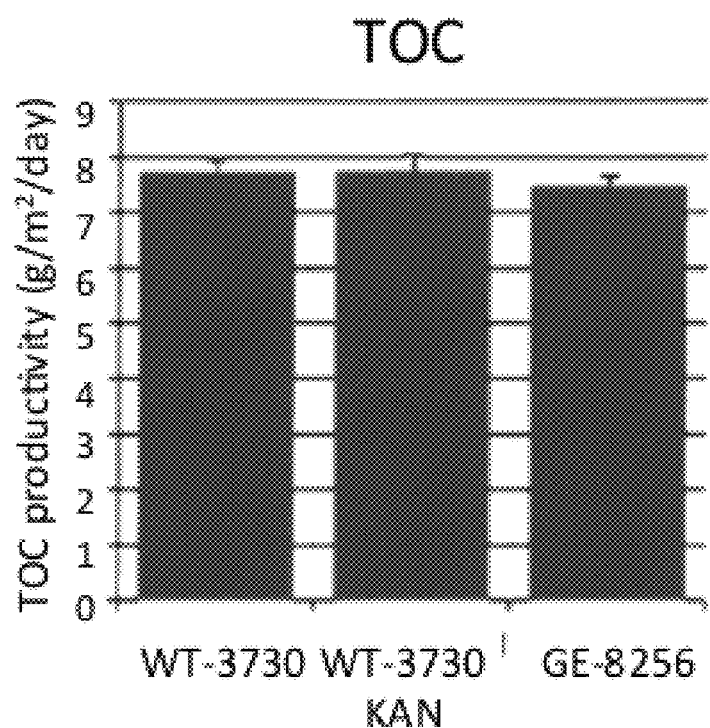

FIG. 5A provides the daily amount of FAME produced by the TrifuncB-KO strain GE-8256 in the semi-continuous assay. The amount of TOC accumulated on a daily basis by the TrifuncB-KO strain 8256 was similar to wild type cultures (FIG. 5C). In these assays, the increased FAME/TOC phenotype observed in batch assays (Example 1) was further confirmed in semi-continuous, nitrogen replete cultures, where TrifuncB-KO strain GE-8256 was observed to have an approximately 13% increase in the FAME:TOC ratio over the wild-type strain (FIG. 5B).

Example 3

Double Knockouts of TrifuncB with Genes for Peroxisomal Beta-Oxidation

Transgenic *Nannochloropsis gaditana* algal strains were created where both the mitochondrial trifunctional protein subunit B (TrifuncB) encoding gene and a second gene encoding a protein involved in either peroxisomal beta-oxidation or the glyoxylate pathway were functionally ablated or "knocked out" by targeted mutagenesis. The method of mutagenesis employed was Cas9-mediated gene editing. As provided in Example 1, the genes targeted are involved in steps of the peroxisomal beta-oxidation pathway (FIG. 1) or in post-beta-oxidation carbon pathways (e.g., the glyoxylate pathway) and included PXA1 (peroxisomal transporter), ACO1 (peroxisomal acyl-CoA oxidase enzyme), and ICL (glyoxylate pathway enzyme isocitrate lyase).

To generate double knockouts, the TrifuncB knockout mutant strain (GE-8256) was further transformed with a minimal zeocin resistance cassette comprising the Bleomycin resistance gene (BleR, SEQ ID NO:55) flanked by the GAPDH promoter from the diatom species *Phaeodactylum triconortum* (SEQ ID NO:56) and the alpha tubulin terminator from the diatom species *Thalassiosira pseudonana* (SEQ ID NO:57) and targeted for integration into the above-described genes (PXA1, ACO1, and ICL) using the chimeric guide RNAs for Cas9-mediated genome modifications as provided in Example 1. This resulted in "double knockout" strains in which the TrifuncB gene knockout was combined with a knockout in the ACO1, the PXA1, or the ICL gene. Thus, strains were produced in which the mitochondrial beta-oxidation pathway and either the peroxisomal beta-oxidation pathway or the post-beta-oxidation carbon channeling glyoxylate pathway were functionally disrupted (see FIG. 1).

Figure 6A:
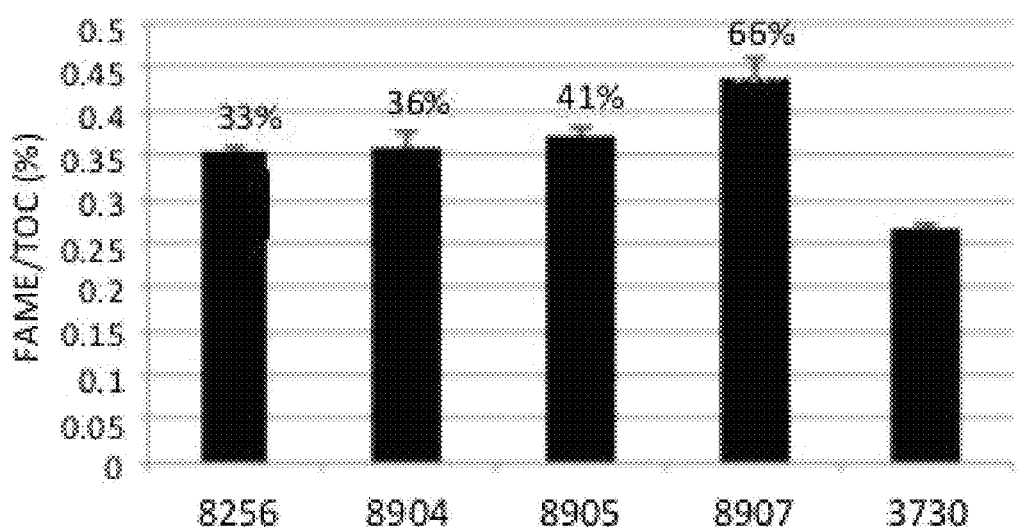
FIGS. 6A-6C. Graphical representation of SCPA productivity results for TrifuncB knock-out strain GE-8256 and double mutants generated targeting two different genes in peroxisomal beta-oxidation (PXA1 and ACO1) and a gene of the glyoxylate cycle (ICL) in the GE-8256 strain. The averages and standard deviations of biological triplicate semi-continuous cultures from data over at least 5 continuous days show the A) steady state FAME/TOC, B) FAME productivity, and C) TOC productivity. Percent change versus wildtype (WT-3730) is indicated by the text above each column. Strains are as follows: GE-8256, TrifuncB-KO; GE-8904, TrifuncB-KO/ICL-KO; GE-8905, TrifuncB-KO/PXA1-KO; GE-8907, TrifuncB-KO/ACO1-KO; WT-3730, wild-type.
Figure 6B:
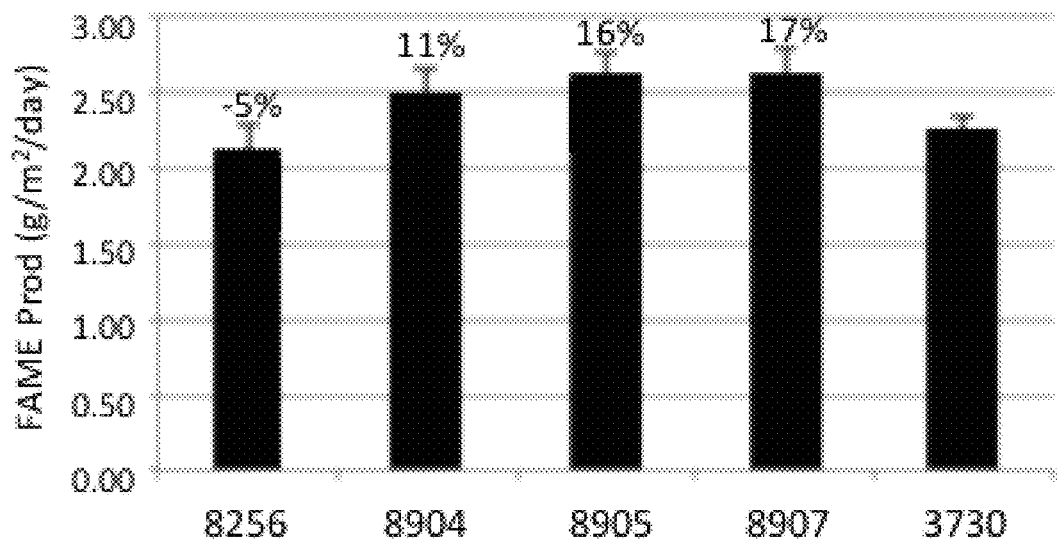
Figure 6C:
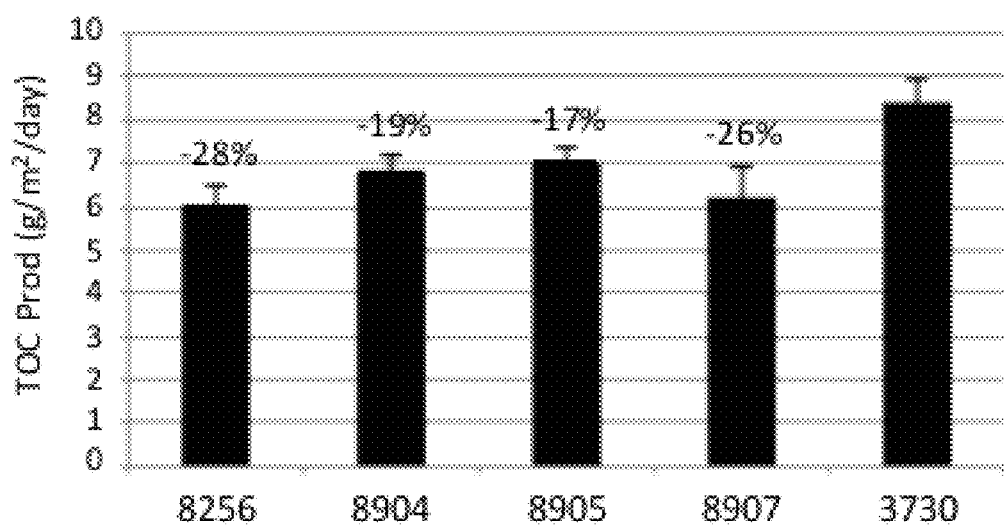

The three double mutant strains (GE-8904, TrifuncB-KO/ICL-KO; GE-8905, TrifuncB-KO/PXA1-KO; and GE-8907, TrifuncB-KO/ACO1-KO) were run in the semi-continuous assay described in Example 2 along with the TrifuncB single mutant strain (GE-8256) and the wild type strain (WT-3730). As can be seen in FIGS. 6A-C, the addition of knockouts in any of the peroxisomal pathway genes or the ICL gene to the TrifuncB knockout strain resulted in further increases in FAME/TOC (i.e., further increases in carbon partitioning to lipid) and lipid productivity with respect to the strain having only the TrifuncB gene knocked out. Combining the ACO1 knockout with the TrifuncB knockout had the greatest effect, knockout of PXA1 combined with knockout of TrifuncB had an intermediate effect, and knockout of ICL plus knockout of TrifuncB had the lowest level of observed increase.

This example details methods and strains in which the combination of knock-out mutations in mitochondrial and peroxisomal beta-oxidation genes defunctionalized or rendered non-functional both pathways of beta-oxidation. This led to increased carbon partitioning in the double mutants as evidenced by higher FAME/TOC values with respect to both wild type strains and single mutation strains assayed under either batch or semi-continuous culture conditions. In the example provided above, knockouts in two different peroxisomal beta-oxidation genes were combined with the TrifuncB knockout, but other embodiments would include any combination of a mitochondrial beta-oxidation mutation (e.g. in the TrifuncA subunit (in *N. gaditana* Naga_100466g3 and NG_scf06 (299664-304033), see SEQ ID NO:1 for the amino acid sequence, and SEQ ID NO:2 for the cDNA sequence), the mitochondrial acyl-CoA dehydrogenases, etc.) with a mutation in a peroxisomal beta-oxidation gene (see FIG. 1 for possible genes to target) such that each pathway is rendered less functional or non-functional. Further, the combination of a mutation in a mitochondrial beta-oxidation gene and a glyoxylate pathway gene is also demonstrated to increase carbon partitioning to lipid in algal strains.

Those skilled in the art can devise many modifications and other embodiments within the scope and spirit of the presently disclosed inventions. Indeed, variations in the materials, methods, drawings, experiments examples and embodiments described may be made by skilled artisans without changing the fundamental aspects of the disclosed inventions. Any of the disclosed embodiments can be used in combination with any other disclosed embodiment.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

SEQUENCES

SEQ ID NO: 1
Protein
*Nannochloropsis gaditana*
TrifuncA amino acid sequence
MLRLASARASLRLNGLGAFQGTATCPSFLKRASLSTRGQYFAPVEVKDGVAIIRIDGPGKMNTIDDNF
RQEIDALWTDKVANDASVKAAVIISAKPDNFIAGADIKFIDSVEDFASLKDVCLKGHATFQKIRKANK
PLVAAIHGPALGGGLEVALYCDYRIVTSSPKTVLGLPEVKLGLLPGFGGTQNLHPIVGLQAALDMTLT
GKNIRPDKAKKMGLADVVVDPAALETVAVETARALAEGSLKGKRKGKGLLQKVLEDTSMGRSIVYGQT
EKMVAKNTGGHYPAPTAILDTIKYGFTHSKPQALEYEATRFAELAATSVSAALRGIFTGTTALKQSKY
GKPANPVETVAVVGAGLMGAGIAQVTAEKGYRVLLKDKDLAGVSRGEKYISDNLKGKMKKKRMTKYAY
DTTTSRVVGLTDESANWGKQFGKADMVIEAVFEDLSLKHKVIQQLEEHLPPHAVFASNTSAIPIARIA
EASQRPENVIGMHYFSPVPQMPLLEIIPHKGTSKEAAAAAFEVGKKQGKTVIFVKDVPGFYVNRCLGP
YLVETGALMEAGVPLEQLDKAIKAYGFPPVGPITLADEVGVDVAAHVQAFLSKADLGVRMGGSDGPILD
ALLKAKLLGRKAGKGFYTYPAGGKKEKGPKTLNPEATSLVQKHVKGESKLTDEEVQNRLVSRFVNEAV
FALQDGVIASPVEGDIGAVFGIGFPPPFLGGPFRLIDALGAGKYCSMLEGFAGKYGEQFAPAPLLVEHA
KSGKKFHQ SEQ ID NO: 2
DNA
*Nannochloropsis gaditana*
TrifuncA cDNA
ATGCTCCGCTTGGCGTCGGCACGGGCATCGCTGCGGCTGAATGGCTTGGGTGCTTTTCAAGGCACCGC
CACGTGCCCCTCCTTCTTGAAACGCGCCAGTCTCTCCACGCGCGGGCAGTATTTCGCGCCCGTGGAAG
TGAAGGACGGGGTCGCAATCATTCGTATTGATGGGCGGGGAAGATGAACACGATTGACGACAATTTT
CGCCAAGAGATCGATGCATTGTGGACGGACAAGGTTGCAAATGACGCGAGTGTCAAGGCGGCCGTGAT
AATTTCTGCAAAGCCCGACAATTTCATCGCAGGAGCCGATATCAAATTCATCGACTCGGTGGAAGACT
TCGCGAGCCTTAAAGACGTCTGCCTCAAGGGACACGCCACCTTCCAGAAGATTCGAAAGGCCAACAAG
CCCTTGGTTGCCGCCATTCATGGGCCCGCCCTTGGCGGCGGTCTGGAAGTGGCCCTGTACTGCGACTA
CCGCATCGTCACCTCCTCCCCCAAGACGGTGCTGGGTCTCCCCGAGGTGAAGCTCGGCCTCTTGCCGG
GCTTCGGGGGCACTCAGAACCTCCACCCTATCGTCGGCTTGCAGGCGGCCCTGGACATGACGCTGACA
GGGAAGAACATCCGCCCGGACAAGGCCAAGAAGATGGGCCTGGCGGACGTGGTGGTGGACCCCGCCGC
GTTGGAGACCGTGGCGGTTGAGACGGCCCGCGCCTTGGCCGAGGGTTCGCTGAAAGGGAAGAGGAAGG
GCAAGGGGCTCCTCCAGAAGGTTCTGGAAGACACCTCGATGGGACGGTCGATCGTGTACGGGCAGACG
GAGAAGATGGTTGCCAAGAACACGGGTGGCCATTATCCCGCACCGACGGCGATATTGGATACGATCAA
GTACGGTTTCACCCACAGCAAGCCCCAAGCCCTAGAGTACGAGGCGACGCGCTTTGCGGAGCTGGCGG
CCACGAGTGTGAGCGCCGCCCTGCGAGGCATTTTCACGGGCACGACTGCCCTGAAACAAAGCAAGTAC
GGGAAGCCCGCTAATCCCGTGGAGACGGTGGCTGTGGTGGGTGCAGGATTGATGGGCGCGGGTATTGC
CCAGGTGACGGCGGAGAAAGGGTACCGGGTGCTCCTGAAGGACAAGGACCTCGCCGGGGTCAGTCGCG
GCGAGAAATACATTTCGGACAACTTAAAGGGAAAGATGAAGAAGAAGAGGATGACGAAGTACGCCTAC
GACACCACCACCAGCCGGGTGGTGGGTTTGACGGACGAGAGCGCGAACTGGGGCAAGCAATTTGGGAA
GGCGGACATGGTGATAGAGGCAGTCTTCGAGGACCTGAGCCTCAAGCATAAGGTCATTCAGCAGTTGG
AGGAGCATTTGCCTCCCCACGCCGTCTTTGCCAGCAACACCAGCGCTATCCCCATCGCTCGGATTGCC
GAGGCGAGCCAGCGACCGGAGAATGTGATTGGCATGCATTATTTCTCCCCGGTGCCCCAGATGCCTCT
TCTCGAGATCATTCCGCACAAAGGGACCAGCAAAGAGGCCGCGGCGGCTGCTTTCGAAGTGGGGAAGA
AACAGGGCAAAACGGTGATTTTCGTGAAAGACGTGCCAGGCTTTTACGTGAATCGGTGCCTGGGGCCC
TACCTGGTGGAGACGGGGGCGCTCATGGAAGCCGGCGTGCCCCTCGAACAGCTGGACAAGGCCATCAA
GGCCTACGGTTTCCCCGTGGGGCCCATCACCCTCGCCGACGAGGTCGGAGTCGACGTCGCGGCCCATG
TTCAAGCCTTCCTATCCAAAGCCGACTTGGGCGTGCGAATGGGCGGGAGCGACGGACCGATTCTGGAC
GCGTTGCTGAAGGCCAAGCTTTTGGGCCGTAAGGCCGGCAAAGGCTTCTATACGTACCCCGGCGGGGG
GAAAAAGGAGAAAGGGCCCAAGACTTTGAATCCGGAAGCCACGTCTTTGGTCCAGAAACACGTGAAAG
GGGAGAGCAAGCTCACGGACGAGGAGGTGCAGAACCGGCTGGTCTCACGCTTTGTCAACGAGGCAGTC
TTCGCCCTCCAAGATGGAGTGATCGCCTCCCCCGTCGAGGGCGACATTGGCGCCGTCTTTGGGATCGG
ATTCCCGCCTTTCCTGGGGGGTCCTTTCCGCCTGATCGACGCATTGGGAGCAGGGAAGTACTGTTCCA
TGCTGGAGGGCTTTGCCGGCAAATACGGGGAGCAATTCGCCCCCGCGCCACTCCTGGTCGAGCACGCA
AAGAGCGGGAAGAAGTTCCACCAGTAG SEQ ID NO: 3
DNA
*Nannochloropsis gaditana*
TrifuncA gDNA sequence
ATGCTCCGCTTGGCGTCGGCACGGGCATCGCTGCGGCTGAATGGCTTGGGTGCTTTTCAAGGTAAGTC
TCGCGGTTTTCCTCGAGCCCTCGCTCTCAGAGCTCAACTGCTACAAGGCATACCATTCCTTGTTCTTA
CAGGCAGGGGAGCATGAGTCGTTTGTATTGCTTTGACTTAAAGACGGCCTGATCACCGTCCATGCGTG
AATTTTATAATCGTCGGCTCGTCTTCCATTTTGATGTTGCATGTATCTTGGGTGGACCGTTTCCTGGT
CGTACTCCTCCGCTTCAACTACTTCCCCCTCCTCCCCTTGTTCTCGGTGGGCTCCCCTTGGTCCCATG
CAATGATTAGAATATGCGTCAACATTCATGTCTACCGTCTCAGGATCAGCATGCGCGCTCACATGCC
ATCATTACGTCTTCTTTTGACCCGTAACAGGCACCGCCACGTGCCCCTCCTTCTTGAAACGCGCCAGT
CTCTCCACGCGCGGGCAGTATTTCGCGCCCGTGGAAGTGAAGGACGGGGTCGCAATCATTCGTATTGA
TGGGCCGGGGAAGATGAACACGATTGACGACAATTTTCGCCAAGAGATCGATGCATTGTGGACGGTAA
TGTCATGGGAAAGACAAGGGATCGAGACGGGAAGGGGCACACTCCAGCGGTTCCTTGACCTTACGACC
CCCTGGCTGAACGATTCCTTCTCTCTTATATATACAGGACAAGGTTGCAAATGACGCGAGTGTCAAGG
CGGCCGTGATAATTTCTGCAAAGCCCGACAATTTCATCGCAGGAGCCGATATCAAATTCATCGACTCG
GTGGAAGACTTCGCGAGCCTTAAAGACGGTATGTGCGCCTGACTAGACACGTTCCCGTGCTCGAATG
TCCTTTTCCACGTCCTTGCAAGGCTGCTGCTTGTGTGCGCGTTCAGGACACGCCACCTTCCAGAAGATT
CGAAAGGCCAACAAGCCCTTGGTTGCCGCCATTCATGGGCCCGCCCTTGGCGGCGGTCTGGAAGTGGCCCTGTACTGCGACTACCGCATCGTCACCTCCTCCCCCAAGAC

| SEQUENCES |
|---|
| GGTGCTGGGTCTCCCCGAGGTGAAGCTCGGCCTCTTGCCGGGCTTCGGGGGCACTCAGAACCTCCACC<br>CTATCGTCGGCTTGCAGGCGGCCCTGGACATGACGCTGACAGGTGCGGGGGGGAGGGTGGGAAGGAA<br>GGAAGGAGGGAGGGAGGGAGGGAGGGAGGGAGGGAGGAAGGGAAAAAGGCGGGATCGTCGGACGGGAG<br>GGTCAGGAGATAACGGTGGCGGGATGCCAGCATGTGTTCCCAACGTCCAGAGCTTTCCTATCCCGTAT<br>ACCATGCAAGTCATCCTCCTTTAATGTCACTTTGTCACCTCCACATCGCAGGGAAGAACATCCGCCCG<br>GACAAGGCCAAGAAGATGGGCCTGGCGGACGTGGTGGTGGACCCCGCCGCGTTGGAGACCGTGGCGGT<br>TGAGACGGCCCGCGCCTTGGCCGAGGGTTCGCTGAAAGGGAAGAGGAAGGGCAAGGGGCTCCTCCAGA<br>AGGTTCTGGAAGACACCTCGATGGGACGGTCGATCGTGTACGGGCAGACGGAGAAGATGGTTGCCAAG<br>AACACGGGTGGCCATTATCCCGCACCGACGGCGATATTGGGTGCGTTCAGACGGGGTTTTTTAAAAAT<br>CAAAAAATAACGGATGTGTTGCGCGTGGACTCACGATTTTCCATCATCACCTCTGATTCCCTCGTGTG<br>TCCAGATACGATCAAGTACGGTTTCACCCACAGCAAGCCCCAAGCCCTAGAGTACGAGGCGACGCGCT<br>TTGCGGAGCTGGCCGGCCACGAGTGTGAGCGCCGCCCTGCGAGGCATTTTCACGGGCACGACTGCCCTG<br>AAACAAAGCAAGTACGGGAAGCCCGCTAATCCCGTGGAGACGGTGGCTGTGGTGGGTGCAGGATTGAT<br>GGGCGCGGGTATTGCCCAGGTGACGGCGGAGAAAGGGTAAGGAGGGGGAGGGAGAAAGGGAGGGAGG<br>GAGGGGAGGAGGACAAGAGCAAGAAGGCGATTATGTCGCGCATAAAGAAGAATGAGGTTGTTGATGGAC<br>AGTGTAGGGAGGGAGAGAGGGAGGAAGGGAAGGAGGAAGGGAGGGAGGAAGGGGAGGGAGGGAGGGAGG<br>GAGGGAGGGGCAGGGTTTGGGCGGAGCTTGGTGGGTTTGTTGGTGCGTGAAGGGTTATGTTTCCTGTC<br>TCTTCGTATCGGAAATCTCCCTGCTCCCTTCGAGTCACGAAATAGCGCATGACCCGCTTCCCCTCGTT<br>CAGGTACCGGGTGCTCCTGAAGGACAAGGACCTCGCCGGGGTCAGTCGCGGCGAGAAATACATTTCGG<br>ACAACTTAAAGGGAAAGATGAAGAAGAAGAGGATGACGAAGTACGCCTACGACACCACCACCAGCCGG<br>GTGGTGGGTTTGACGGACGAGAGCGCGAACTGGGGGAAGCAATTTGGGAAGGCGGACATGGTGATAGA<br>GGCAGTCTTCGAGGACCTGAGCCTCAAGCATAAGGTCATTCAGCAGTTGGAGGAGCATTTGCCTCCCC<br>ACGCCGTCTTTGCCAGCAACACCAGCGCTATCCCCATCGCTCGGATTGCCGAGGCGAGCCAGCGACCG<br>GAGAATGTGATTGGCATGCATTATTTCTCCCCGGTGCCCCAGATGCCTCTTCTCGAGATCATTCCGCA<br>CAAAGGGACCAGCAAAGAGGCCGCGGCGGCTGCTTTCGAAGTGGGGAAGAAACAGGGCAAAACGGTGA<br>TTTTCGTGAAAGACGTGCCAGGCTTTTACGTGAATCGGTGCCTGGGGCCCTACCTGGTGGAGACGGGG<br>GCGCTCATGGAAGGTGCGTTGGTTGCGAGTCTGGGGATCGGTTGTCTCGCGTGGTTACTCTCGCCACG<br>TTTGAAAATTTGAACCTTTGACAGTGCACACTTACTTACCTTTTTGATTCTCATTATTTCCTCGCGTTG<br>TTCCACCGGGACCCAGCCGGCGTGCCCCTCGAACAGCTGGACAAGGCCATCAAGGCCTACGGTTTCCC<br>CGTGGGGCCCATCACCCTCGCCGACGAGGTCGGAGTCGACGTCGCGGCCCATGTTCAAGCCTTCCTAT<br>CCAAAGCCGACTTGGGCGTGCAATGGGCGGGAGCGACGGACCGATTCTGGACGCGTTGCTGAAGGCC<br>AAGCTTTTGGGCCGTAAGGCCGGCAAAGGCTTCTATACGTACCCCGCGGGGGGAAAAAGGAGAAAGG<br>GCCCAAGACTTTGAATCCGGAAGCCACGTCTTTGGTCCAGAAACACGTGAAAGGGGAGAGCAAGCTCA<br>CGGACGAGGAGGTGCAGAACCGGCTGGTCTCACGCTTTGTCAACGAGGCAGTCTTCGCCCTCCAAGAT<br>GGAGTGATCGCCTCCCCCGTCGAGGGCGACATTGGCGCCGTCTTTGGGATCGGATTCCCGCCTTTCCT<br>GGGGGGTCCTTTCCGCCTGATCGACGCATTGGGAGCAGGGAAGTACTGTTCCATGCTGGAGGGCTTTG<br>CCGGCAAATACGGGGAGCAATTCGCCCCCGCGCCACTCCTGGTCGAGCACGCAAAGAGCGGGAAGAAG<br>TTCCACCAGTAG |

SEQ ID NO: 4
Protein
*Thalassiosira oceanica*
Trifunctional protein A
MILSSAVQRAILSQSRAAAGAARQINSLSRRPASALAACQGGASSATGVVSIGDAHAADFNNHPRRRR
AFSTAAVRDEPAPSPTPSEHTAADSSEKSFVPSPGRKYRFFRNVEVTPAGVAVIRFDNREKKVNTLSF
ELMHEAKAMWDAEVHANADVKSVVFTSAKESGFVAGADIFDISSVEDKSTLVPVIEEALDFFLHMKSK
GAPMVAAIHGPALGGGLEWALWCDYRICTDSSSTKMGLPEVKLGLLPGFGGTQNLPALVGVQGAIDIM
LTGKDIRPKKAKQMGLVDLVVAPQSLEAVAIETAEGLANGTVRKSGPKKKSLVNRLVEDTPPGRHVMW
NQVKKMVDKNTAGNYPAPYEIIDCVKYGLANPDGLGKYKHEREGFAKLAATSESESLIGIFDGMNKLK
KHDSDASPVPVRKVAVMGAGLMGAGIAQVTAEKGYDVLLKDRDDASLGRGVSYMTDNWSKKTKRRRMT
QYQNNLNQSRVTPLSDATPSWPRHFAGADLVIEAVFENLELKRKIISQVEEVTPDHCVFATNTSAIPI
ADIAAPGPEVSRPQNVVGMHYFSPVPSMPLLEIIPHEGTSEEATATAFAVGTKQGKTCVVVKDVPGFY
VNRCLGPVLVETSALVKEGVPLEKMDKAMKSFGMPVGPITLMDEVGIDVGSKVASYLSGADLDVRMTG
GDISLMSTMVDKGWLGKKSGKGFYTYSGKKGKKIGPEMRAFLTEFTGGATSDLAETDIQDRITARLVN
EAAKCLEDGIIADPVAGDIGLVFGIGFAPFRGGPFRYLDTVGVTSFVDRMNGFADAHGGQFEPCQLLK
DYAASGKRFH SEQ ID NO: 5
Protein
*Thalassiosira pseudonana*
Trifunctional protein A
MWESDVHGNDSVKSIVFTSAKETGFIAGADIFDISQVEDKAQLVPVIEEALNFFLKMKSKGVPMVAAI
HGPALGGGLEWALWCDYRICTDSSSTKLGLPEVKLGLLPGFGGTQNLPKLVGIQGGMDMMLTGKDIRP
PKAKKMGLVDLVVAPQSLESVAIQSAEGLANGTVKKSKPKEKSLMNRLIEDTPPGQYLMWDKVKKMVD
KNTGGNYPAPYAIIDCVKYGLAHPSGNDKFKHEREEFAKLAATKESEALIGIFDGMNQMKKLSSSAAP
IDVKKVAVMGAGLMGAGIAQVTAEKGYDVLLKDRDAASLGRGLSYMTENWEKKHKRKRMTTYQLNLNT
SRVTPLADDTESWKRHFAGADLVIEAVFENLDLKRKIVQQVEEVTSDHCVFATNTSAIPIADIAAPGP
DIKRPENIVGMHYFSPVPSMPLLEIIPHAGTSDEALATAFAVGTKQGKTCVVVKDVPGFYVNRCLGPI
LVEVSALVKEGVPLETLDKAMKKFGMPVGPITLIDEVGVDVAAKVSTFLSDADLGVRMGGGDLSLMTN
MVEKGWLGRKSNQGFYTYAGKKGKTIGSEVTAYLKEFTGGKVSNLSEKDIQDRIASRLVNEAAKCLED
DIIENPVAGDIGLVFGIGFAPFKGGPFRYLDAVGVSSYVDRMNGFADTLGEQFEPCQLLKDYATSGKK
FHG SEQ ID NO: 6
Protein
*Phaeodactylum tricornutum*
Trifunctional protein A

| SEQUENCES |
|---|
| MAEEAKKLWKDEIASNSDVKAVVFSSAKPDMFIAGADIFDIKAVENKQDLIPFIADGVKFFQDMRGKG<br>VPLVAAIDGPALGGGLEWALWCDYRICTDSSKTKMGLPEVKLGLLPGFGGTQNLHPVVGLQNAMDMML<br>TGKDIRPHQAKKMGLVDLVVAQASLERVAIDSAAALANGSLKAKRKSKSMFNKILEDNSIGRNVIWNQ<br>IDKMVQKNTNGKYPAPYAIIDCVKFGLDNPSQKYQHEREEFAKLAATPESEALIGIFDGMTQMKKHSF<br>GADAAIPVKTVAVMGAGLMGAGIAQVTAEKGIKVLLKDRNDEAVGRGQSYMTENWSKKLRKRKMTQYQ<br>YNLNTSNVTALTDDSPTWQRHFGNADMVIEAVFEDLDLKRKIVANVESVTKDHCIFATNTSAIPIADI<br>AQGASRPENIIGMHYFSPVPSMPLLEIIPHTGTSDTATATAFEIGSKQGKTCIVVKDVPGFYVNRCLG<br>PYLVEVSALVRDGVPLEALDKSLKNFGMPVGPITLADEVGIDVSSHVAKFLSNADLGVRMEGGDVSLM<br>EQMIGKGWLGKKSGQGFYTYKGKKKTINEEVQKYVKDFATRDLKLDEKEIQDRIVSRFVNEAAKCLED<br>EIIENPVVGDIGLVFGTGFAPFRGGPFRYLDQVGVASYVDRMNTFTDKYGPQFEPCQLLKDYAATDKK<br>FHKR<br><br>SEQ ID NO: 7<br>Protein<br>*Fragilariopsis cylindrus*<br>Trifunctional protein A<br>MTAFYSARYQSTASSAVLEEKPTDPSPSAAAASSTATNNEEGSKLFVPTADRKYEYFTNVEFTKEGVA<br>IIRFDCPNKVNTISFALSDEARQLWKGEIENNSDVKAVVFSSAKPDMFIAGADIFDIKRIENKNDLVG<br>LIEEGVTFFQHMREKKVPLVCAINGPALGGGLEWAMWCDYRVCSDSPKTKLGLPEVKLGLLPGFGGTQ<br>NLHELVGLQNAMDMMLTGKDIRPHKAKKMGLVDLVVSSQSVEKDAIQSAVDIINGKLKPKKKAKSLMN<br>RLLEDTSIGQKIIWNQINKMVQKNTNGNYPAPNAIIRCVQHGIANRSTRFENEREEFAKLAATDESEA<br>LIGIFDGMTQMKKNPFDNTVAVPVKTVAVMGAGLMGAGIAQITAEKGMSVLLKDRNDAAIERGGSYMR<br>DNWDKKLKRKRMTKFQHNLNSSNVVGLTDDNPNLVEKHFGNTDMIIEAVFEDLDLKRKIVADIEKITP<br>DHCVFATNTSAIPIGAIAEGSKRPENIIGMHYFSPVPSMPLLEIIPHEGTNEATRATAFNVGTKQGKT<br>CIVVKDVPGFYVNRCLGPFLVEVSALIRDGVSLEKLDRSVLDFGMPVGPVTLADEVGIDVTSHVATFL<br>SKADLGVRMDGGDITLMEKMIDKGWLGKKSGQGFYTYSNKKKGKTISPEVQAYVKTFVKQDLNLDKEE<br>IQNRIISRFVNEAAKCLEDEIIDNPVVGDIGLVFGTGFAPFRGGPFRYLDQIGVANYVDMMNSFADKY<br>GGQFEPCQLLKDYAATDKKFYNN<br><br>SEQ ID NO: 8<br>Protein<br>*Aureococcus anophagefferens*<br>Trifunctional protein A<br>MSSLLRYSARQVAVAGRRRLSAQPVASEGSRSWEFFAGDPEVTADGVAIVRLDAKKAKMNTLNPALQA<br>EAQEMWSELMEARGNDVKAAVFISAKPDNFIAGADISMLAAKKASGDEDSLEAICLSGHTMFAELKAT<br>NIPIVAAIHGACLGGGLEWALKCDYRVASTSPKTKLGLPEVKLGLLPGWGGTYALPKLIGLTEALPMI<br>LQGKEVKADKAKKLGLVDAVCDPAALERLAVAKAAALGNGSLKLKEKKKSWMRWATEDVSFGRDFVFK<br>KAKETVDKTTRGKYPAAYEIMDCVKHGLGKSPEEAFAFEAKAFVRLAKTPESSALIGLFDGITASKKN<br>RYGNASDPATLKALDTVAVLGAGLMGAGIAQVSAEKGLNVLLKDASPEGLAKGVDYVGGNLAKKVKRR<br>RMTDYTRNTITSKVMGYHDGPGGGGDAAWLRKAATADVVVEAVFEDLDLKHKVFQSVEPLVSEACVLA<br>TNTSAIPIAKVAAGAAKPERVLGMHYFSPVPQMLLEIIPHAGTDPKAMAAAFAVGIKQGKFCIEVKD<br>VPGFYVNRCLAPMMAELAPLFQDGVEPKQLDEAILDLGMPVGPVTLIDEVGADVGLHVQRTMLADETM<br>GGRMAGADPAMLQAVVDKGWLGRKSGKGFFVYDGKKKTPNAEANAYVESEVKRRDAGLSVETIQDRYL<br>TRFVNEAAVCLQEGILKTPADGDLGAVFGVGFLPFTGGPFRMLDAVGAATYVDKMNRLADEYGDRFAP<br>CDLLVDHANSGKKFYPSK<br><br>SEQ ID NO: 9<br>Protein<br>*Ectocarpus siliculosus*<br>Trifunctional protein A<br>MPMEDPASVESTSDKSPRFFQPVEKLDNGVAIIRIDGPEKMNTISGDFRQEIEDIWSGQIAEDPSVKA<br>VVFISGKPDNYIAGADIRMISATEDKADLKQICMDGHATFDILAKKGIPVIAAINGACLGGGLEWALH<br>CDYRLATTSPKTVLGLPEVKLGLLPGWGGTQLLHPLVGLQAALDMILTGKNIRPHKALKMGLVDQLVD<br>AASLEAVAVEAAASLADGSLKSKRKPALMNKIIEDTPMGRSIMWKKVGEKVAKSTGGNYPNATAIVD<br>CIKFGLSSSKQAALEYEAQRFSEMAATPESESLIGLFEGSTALKKNRFGKPAKKVEKVAVLGAGLMGA<br>GIAQVSAEKGMTVLLKDRDSASVGKGTSYIMDNAAAKLKKRRMTKYEMDTVGSRVIPLTDEGDLWKRH<br>FGSAEMVIEAVPENLDLKHRVIQQAEQFLPEDCVFATNTSALPIRDIAKASKRPQNVVGMHYFSPVPM<br>MPLLEIIPHDGTSDAAAAAAVDVGGRQGKTCIVVKDVPGFYVNRCLGPFLVETCALVEAGVGLEQLDK<br>VMKSYGLPVGPITLADEVGIDIGFHVQSFLSEADMGVRMTGGNVAVMGDMVEKGFLGRKSGKGFYLYP<br>KGKKGNKGGKELNPEAVSLIKAHQAAGGAGASLANDVIQDRMMCRFVNEAALCLQEGIISSPVDGDIG<br>AVFGMGFPPFRGGPFRLLDQRGAGAYADMMNRLADEHGEQFRPCQLLMDHARGDKKFHT<br><br>SEQ ID NO: 10<br>Protein<br>*Nannochloropsis gaditana*<br>TrifuncB protein sequence<br>MDTGCTIVVERMLRSSTLLRGLASKAAGAGKKPTVVFVDGARIPFAQSSTVYNDYLGVDLQKFAYKGL<br>VDKTALDPKEIDYILGGNVIQEVRTSNIAREAAMAAGLPTDIPAHTVVLACISSNVGICSAAEKVLTE<br>HASLVLALITLPKAMKKGPLGVFKHLAKLNFKDLGLETPAIANYTTGEVMGHSSDRLSAKFGVSRREQ<br>DEFAALSHQRAAKAHKDGIYKDEIIPVDGNTGENGIKGESTADTLAKLKPAFVKPHGTHTAANSSFLS<br>DGASASLIASEEKALSLGLKPKAFLRAWEFVAVDPFEQLLLGPTYATAKVLSAAGLTLADIDVIEIHE<br>AFAGQVLSNIRAMGSDKFAQEYLNRSTKVGDIDMAKTNLHGGSLSLGHPFAATGNRLVTTAANRLHRE<br>GGRYALVTACADGGLGHACIIEKYE<br><br>SEQ ID NO: 11<br>DNA<br>*Nannochloropsis gaditana* |

SEQUENCES

TrifuncB cDNA sequence
ATGCCTTCGACAGTATTTGACGCCTTTGTTGTGGCATTGAGTGCAGGATGCGCGCGGGACTTTGGCTG
CACAATTGTCGTGGAGAGAATGCTGCGGTCCTCTACGCTCCTCCGGGGCTTGGCGTCCAAAGCCGCCG
GCGCCGGGAAGAAACCCACCGTTGTATTCGTCGACGGAGCTCGCATCCCTTTCGCCCAATCCTCCACC
GTGTACAACGACTACCTGGGCGTGGACCTACAGAAATTCGCCTACAAGGGTCTGGTGGATAAAACGGC
GTTGGACCCGAAGGAAATCGACTACATCCTGGGCGGGAACGTTATCCAAGAAGTCCGTACCAGCAACA
TCGCCAGGGAAGCCGCCATGGCCGCTGGCCTCCCCACCGACATCCCCGCCCACACCGTCGTCCTGGCC
TGTATTTCCTCCAACGTGGGCATCTGCTCCGCCGCGGAGAAAGTCTTGACTGAGCACGCCAGCCTGGT
CTTGGTGGGGGGGTGGAGACCTTCTCGGACGTGCCTATCCGCCTCACCCGCCCCTCCGCCAGGCCC
TCATAACCCTGCCCAAGGCGATGAAGAAGGGCCCTCTGGGCGTCTTCAAGCACCTGGCGAAGCTCAAC
TTCAAGGATCTGGGCTTGGAGACCCCCGCCATCGCCAACTACACCACCGGGGAGGTGATGGGCCACTC
CTCGGACCGACTTTCGGCAAAATTCGGGGTTTCTCGGCGGGAACAGGACGAATTTGCGGCCCTCTCTC
ACCAACGCGCAGCCAAGGCGCACAAGGACGGCATCTACAAGGACGAGATCATCCCCGTGGACGGCAAT
ACGGGCGAGAACGGGATCAAGGGCGAGTCTACCGCAGATACCCTCGCCAAGCTCAAACCGGCCTTTGT
GAAGCCTCACGGCACCCACACCGCCGCCAACAGCTCCTTCCTCTCGGACGGCGCCTCGGCTTCCCTGG
AGTACCTGAACCGATCCACCAAGGTGGGCGACATCGACATGGCAAAGACCAATCTGCACGGAGGCTCC
CTCTCCCTCGGCCACCCCTTCGCCGCTACCGGAAACCGATTGGTGACGACGGCGGCGAATCGCCTGCA
CCGGGAGGGAGGGAGGTACGCCCTGGTCACTGCCTGCGCGGATGGCGGTTTGGGCCACGCCTGTATCA
TCGAGAAATATGAGTGA SEQ ID NO: 12
DNA
*Nannochloropsis gaditana*
TrifuncB gDNA sequence
ATGCCTTCGACAGTATTTGACGCCTTTGTTGTGGCATTGAGTGCAGGATGCGCGCGGGACTTTGGTAA
ATATGGACTTAGTTTCACCATCGTGTTCCAAGCATGAAGTGGCGGCTCTCCCCCCTCGAATACGTCGG
CTAGGACGTGGGGCCTCTTCCCCTTCCTGATCATTCGCTTTACCCCTTTCGTCTTCACACACATGGAC
ACAGGCTGCACAATTGTCGTGGAGAGAATGCTGCGGTCCTCTACGCTCCTCCGGGGCTTGGCGTCCAA
AGCCGCCGGCGCCGGGAAGAAACCCACCGTTGTATTCGTCGACGGAGCTCGCATCCCTTTCGCCCAAT
CCTCCACCGTGTACAACGACTACCTGGGCGTGGACCTACAGAAATTCGCCTACAAGGGTCTGGTGGAT
AAAACGGCGTTGGACCCGAAGGAAATCGACTACATCCTGGGCGGGAACGGTAAGCCTGAAGCAAGGGG
GGGGGGGAGATCGTGCTGGCATGTATACTCAAAGATCAAGCCCTCTCAATGATAATCACGAGTTTTCC
TGCTCGGGCCTTGTCCAATGATACTCACTAACTCCCGGCCCTTTTCTCCGCTCGAAGGATGATGGGGA
GGGAAGTGATGAGGACGGAGGAGTCTCACAACCGTGTGATGGGGAGGGACGAGAGAGGGCAACCCCCG
AGGCCTCAAGCCTCGCTCGTGCCGGTCCTGGTCCGCTTCCGCCTTCTCAAGGCTTACATCCTTTCCCT
TCCTCCCTCCCTTCTTCCCTCCCCCCTCCTTCCCTCCCTCCCCATCTCAGTTATCCAAGAAGTCCGT
ACCAGCAACATCGCCAGGGAAGCCGCCATGGCCGCTGGCCTCCCCACCGACATCCCCGCCCACACCGT
CGTCCTGGCCTGTATTTCCTCAACGTGGGCATCTGCTCCGCCGCGGGTAGGTCCTCCCTCCCCGTCC
TCCGGCCCGAAGCCCTGTCTTTGCCTGCCCTCCCTCCCTCCCTCCCTCCCTCCCTCCCTCCCTCCCTC
CCTCCCTCCCTCCCTCCCTCCCTCCCTCCCTCCCTCCCTCCCTCCCTCCCTCCCTCCCTCCCTCCCTC
CCTCCCTGCCTGCCTCGCTCCTCCCCTCCTCTCCCCCTCCAAGCTCAGAGGGAAATCTTGATTCCCCT
TCCCCCCTTCCTTTCTCCCTCGCTCCCTCCCTCCCTCCCTCCCAGAGAAAGTCTTGACTGAGCACGC
CAGCCTGGTCTTGGTGGGGGGGGTGGAGACCTTCTCGGACGTGCCTATCCGCCTCACCCGCCCCCTCC
GCCAGGCCCTCATAACCCTGCCCAAGGCGATGAAGAAGGGCCCTCTGGGCGTCTTCAAGCACCTGGCG
AAGCTCAACTTCAAGGTGCGTGTTGTCTTCTCCTTAAGCTGTTCGGGTCAGACCTCCCCCCCCTTCCT
TTCCCATCACCGATTTTGCTCAAACACATGTACCAAGGAGAGGTTGTGAAGGATGGTTACTGGAGAGG
CATATTTTTTCATGGAGTCGCCCTCCTTTCTTCCATTCTCTTCCTCCGCCTCTCCCTCCTCCCCATGC
CTTTGTTCATCTTCCCTCCCTTCCTCCCTCCTTCCCTCCTTCCCCTGCTAGGATCTGGGCTTGGAGAC
CCCCGCCATCGCCAACTACACCACCGGGGAGGTGATGGGCCACTCCTCGGACCGACTTTCGGCAAAAT
TCGGGGTTTCTCGGCGGGAACAGGGTAGGGGGGAGGGAGAGGGAAGGGAGCTAGGGAGAAGCAGAGG
GACGAGAAGAGGGCCGGGGGGGGGCGGGGTTATTACTCACCACACGTCCCTATGGATGTTTCTCGC
TTCCTCTTGACGCGCAGACGAATTTGCGGCCCTCTCTCACCAACGCGCAGCCAAGGCGCACAAGGACG
GCATCTACAAGGACGTGCGTCCTCCCTCCCTCCTTCCCTCCCTCCCTCCTACCTTCCCTTCTAC
CTTCCCTCCCTGCTTCCTATTTCGCCATTTATCGTGCAGCGCAGTCGTTCGTGCCCTCAGGTCACCTC
CTCCCTTCCTCCCTCCCTCCCTCCCTCCCTCCCTCAGGAGATCATCCCCGTGGACGGCAATACG
GGCGAGAACGGGATCAAGGGCGAGTCTACCGCAGATACCCTCGCCAAGCTCAAACCGGCCTTTGTGAA
GCCTCACGGCACCCACACCGCCGCCAACAGCTCCTTCCTCTCGGACGGCGCCTCGGCTTCCCTGGTGA
GGGANNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNN
NNNNNTCATTCCTTCAGGAGTACCTGAACCGATCCACCAAGGTGGGCGACATCGACATGGCAAAGACC
AATCTGCACGGAGGCTCCCTCTCCCTCGGCCACCCCTTCGCCGCTACCGGTAGGGAGGGAGGGAGGGA
GGGAGGGACAGATGATCCCCGACGAAATAGTTGTTGGCTTCAGCCCGTCATGGCGTATCGG
CACTTCTTGTGATTTTCTTCCACGCTCATCGTCTTTCATCGATGCGGCCATGCGCGTGCGTCCCTGC
TGTCTGTCCCCCAACCCTTCTCCCTCCGTTCTCATCACATTTGATCAAAGTATTCCCTTTGTTTATGG
AGCTTACCTTGCCATTCCTCTCTCTTTGTCGGGGAAAAATCCAAATCCTCCAAATCCATCAGGAAAC
CGATTGGTGACGACGGCGGCGAATCGCCTGCACCGGGAGGGAGGGAGGTACGCCCTGGTCACTGCCTG
CGCGGATGGCGGTTTGGGCCACGCCTGTATCATCGAGAAATATGAGTGA

| SEQUENCES |
|---|
| SEQ ID NO: 13<br>Protein<br>*Thalassiosira pseudonana* CCMP1335 TrifuncB<br>MITARLLKQGMSSPSSSSSSSRLAAITSRAATSLVTSNSFSTTSTKLKNPKTNVVIVDGIRLPFAQTT<br>TIYQDQLAVDLQRLAYQGLITKTALDKKDVDYVMAGTVIQEVRTSNLAREAAINAGFPASIGAHTVAM<br>ACISSSVAITSAAEKILSGHASIVIAGGAETFSDVPIRLTRPIRQKLITMPKAMKKGGALGAIRHLTK<br>GLKMKDISLETPAIANYTTGEVMGVSSDRLSAKFGITRLEQDEFTTDGLPRVVVSSWYDGEIVPYKGS<br>TEENGIKADSTIESVSKLKPAFVKPHGTHTAANSSFLTDGASASLIMSEERALELGYKPLAYLRDWSF<br>KACDPFEELLLGPTYCSQEVLSRNNLNLETDIGVFEIHEAFAGQILSNLTAMNSQKFADEKFGGKKVG<br>EIDMRKMNTKGGSLALGHPFGATGSRLVTTASRRLQLENQRFALIAACADGGLGHACILERYDN<br><br>SEQ ID NO: 14<br>Protein<br>*Phaeodactylum tricornutum* CCAP 1055/1 TrifuncB<br>MLSTSVRAISRGSPLVQTAARRSLASLALTPNDPVVVVSGVRLPFAMTSTIYEDQLAVDLQRLAIQGL<br>LTQTALPKSEVDYVIAGNVIQEVRTSNIAREASINAGLPLHVGAHTIAQACISANAAICAGAEKILTG<br>HASVVIAGGCETFSDVPIRLTRPIRQKLITMNKAMKKGGMVGGISHLLKGLSLKDVSVETPAIANYTT<br>GEVMGVSSDRLAAKFGVSRHDQDAFTVRSHTMAAKAHTDGFYKNEVVPYKGSTQENGIKGDSTIESVA<br>KLKPAFVKPHGTHTAANSSFLTDGAAATLIMSESKAKELGYKPLAYLRDWSFKACDPFEELLLGPTYC<br>SQEILARNKLQMSDMGVLEIHEAFAGQILANLTAMESQTFADKNEGGKIVGKVDVDKMNTKGGSLALG<br>HPFGATGSRLVSTASRRLQHEGARFALLAACADGGMGHACLLERYDNDN<br><br>SEQ ID NO: 15<br>Protein<br>*Fragilariopsis cylindrus* COMP1102 TrifuncB<br>MISSQKLVRPLLTAQRRLFSLRPIAGGRDVVIVSGVRLPFAQASTIYQDEMAVDLQRLAIKGLIDQTA<br>LPKDAIDYVVCGNVIQEVKTSNIAREAAINAGLPYNIPSHTIAQACISANAAIATGAAAIQSGHADVV<br>IAGGVETFSDVPIRLSRPIRQKLITLPKAMKKGGPIGAVRHMLKGLKMKDLSLETPAIANFTTGEVMG<br>VSSDKLSAKFGISRQEQDEFTVRSHTLAHKAHDDGFYKDEIIPYRGSIAENGIKGNSSYESVSKLKAA<br>FVKPNGTHTAANSSFLTDGAAATLIMSEEKAKELGYKPLAYLRDWSFKSCDPWEELLLGPTYCTQDIL<br>QRNSMSINDFGVFEIHEAFAGQILSNLAAMDSDIFAKEKGWSKKVGAIDFDKMNIKGGSLSIGHPFGA<br>TGSRLVTTAARRLQEEGQQFALIAACADGGLGHACLLERYDN<br><br>SEQ ID NO: 16<br>Protein<br>*Emiliania huxleyi* CCMP1516 TrifuncB<br>MLQLSTRLRAVRPAIVRARARSTAASTGQKKVVLVDGCRIPFQPSRGEYFDLMSYDLTRLAMHGLLTK<br>TAVDPKAIDYVLWGKVIQEPKTSNIARDAAFAAGIPRGVPAHTVTQACISSNQAICTGASQILSGQAE<br>VVLAGGVETFSDAPIRYSRPIRKKLIKMSKAKSPGQMASIFFKGLKMKDLAPEQPAIANFLTGEVMGH<br>NADRLSDREGVSRREQEEFALRSHLNAANAHADGFYDGEVIAGPGGKTLEDGPRADSSLEKMATLKPA<br>FVKPHGTVTAASASPFTDGASATLLMSDGKASELGLSPKAELLAYAFVACDPFEELLLGPTYGASKVL<br>RMAGLSLKDIDVIEFHEAFAGQVLSNLVAMDSDKFFAENLPGVDKVGSVDMTKLNTKGGSLSIGHPFG<br>ATGARLVTTAANRLVKEGGTYALVAACADGGLGHACILKRYGA<br><br>SEQ ID NO: 17<br>Protein<br>*Emiliania huxleyi* CCMP1516 TrifuncB<br>MLQLSTRLRAVRPAIVRARARSTAASTGQKKVVLVDGCRIPFQPSRGEYFDLMSYDLTRLAMHGLLTK<br>TAVDPKAIDYVLWGKVIQEPKTSNIARDAAFAAGIPRGVPAHTVTQACISSNQAICTGASQILSGQAE<br>VVLAGGVETFSDAPIRYSRPIRKKLIKMSKAKSPGQMASIFFKGLKMKDLAPEQPAIANFLTGEVMGH<br>NADRLSDRFGVSRREQEEFALRSHLNAANAHADGFYDGEVIAGPGGKTLEDGPRADSSLEKMATLKPA<br>FVKPHGTVTAASASPFTDGASATLLMSDGKASELGLSRKAELLAYAFVAWDPLEELLLGPTYGASKVL<br>RMPGLSLKDIDVIEFHEAFAGQVLSNLVAMDSDKFFAENLPGVDKVGSVDMTKLNTKGGSLSIGHPFG<br>ATGARLVTTAANRLVKEGGTYALVAACADGGLGHACILKRYGA<br><br>SEQ ID NO: 18<br>Protein<br>*Aureococcus anophagefferens* TrifuncB<br>MLGLKSLSSRALSSRARSLSTGGKNVVIVDGVRIPFALSQTIYQDVMAVDLAKMSLTGLMQKTGLDAS<br>LVDYVLYGTVIQESRTSNIAREAAMHAGYPIDVPAHTVTLACVSSNAAICQGAEKILAGQADVVVAGG<br>CETFSDVPIRYSRPVRKRLLGAAKALKKGPAGALGLLKGLKLKDLAPEAPSISNFTTGEVMGHSSDRL<br>AAKFGISRKDQDDYTLMSHTRAQQAHDDGLYAEELVPGVQGADLSENGIKAGSTPEKLAKLKPAFIKN<br>ETGTHTAANSSFLTDGAAATLVMSEEKALALGFKPKAYLRHWTFAAVDPFEELLLGPTYAVSKVLNDA<br>KLDLKDVGVVEMHEAFAGQVLSNFAAMNSDKFAADFLPNRTQKLGEMDFAKVNTQGGSLSLGHPFGAT<br>GSRIVTTASNRLQRSGEQFALVAACADGGIGHSCLLERYPN<br><br>SEQ ID NO: 19<br>Protein<br>*Ectocarptis siliculosus*<br>Acetyl-CoA acetyltransferase subunit, putative mitochondrial<br>presursor Acetyl-CoA<br>MVHQGVTATMRSARAAMVSSRAAAAAAARASCGRRANSSSASSSSSSSSSRKPVFVDGARIPFVLSGTT<br>YKDLLAVDLGKLALRGLLNRNPELDPKDVDYLLFGTVIQESRTSNIAREAGMGAGIPVSVPSHTVSQA<br>CISANQAMCNGAEKILAGTADVVLAGGVETFSDLPIRFSRPIRNRLLNLGKAKKKGLPGVLGLLKGLK<br>LKDIAPETPAIANYTTGEVMGHSSDRLSGREGISRQEQDEFALRSHQNAAKAHADGIYDQEIIPVDGS<br>TDENGVKGESTLEKLGSLKPAFVKPHGTHTAANSSFLSDGASAALIMSEGRALEMGLAPRSSFKSWAF |

| SEQUENCES |
|---|
| VALDPFEDLLLGPAFGAAKVLDDAGLTLSDIDVFEIHEAFAGQVLSNLAAMNSTDFAQKSMGRSAKLG<br>EVPMEKLNIHGGSLSLGHPFGATGVRLVATATNRLHREGGRYALVAACADGGLGHACIVERYDS<br><br>SEQ ID NO: 20<br>Protein<br>*Nannochloropsis gaditana*<br>PXA amino acid<br>MAPSFSHRGQKRHDNVVSAFFNSFMSAGEQKFTVVSSLFSSGLFLVALALVKQLSSLQEQEEKVAASL<br>ERQDPSKEGGSLAAPLPQPDGRCQTPQPPPPSPPPSASPSSFSATSTARTRSPNADALTRSGRDAAGH<br>GERGSGGMRRPGGPPLPQEGQRVALDDEFGRQLLSLLHKLIPSWKTREAACLGGMVFLLLARSACDLR<br>MINLVVGAEKAIVLGNRPAFRISLARFLRFMVPVACVNALLKYTTRELSLGLRQRLTEHLQSKYMKGF<br>TFYSMAVMEGHAREIEQLMTVDVDKFSLCITELASNLLKPTLDILLYATKLQTSVGPLIPLAMASYLF<br>SSGTALTRLRRPAAEYTAAIQRREGDYRFVTNRMVAHAEEIAFYDGVGREKNYLQQIFGSLLGTIRRG<br>SRFRHAMDILDSVMAKYIATALGWVLLNRAAQQQKQEALPVPSPALPPSPAASSYDSFHQSARMMFNF<br>AQALSAIVLAGREATRLAGYTSRVTRLERLIDDLEREDEARSTASEFLEKKDVIELQGVPIVAPVVGN<br>GRKDSDGGRGGRKGREGGRVRRLTSPLTLRIEPGMHVLVTGPNGSGKSSLFRMICGLWPVSEGRLIKP<br>PRSQLFYIPQRPYLPLGSLRDQVIYPHSQAEMAALGRTDADVLALLDEVQLSFLAPPRVVGPESNASD<br>ALPSLPSSLPSSLPSSLPPSFPSFSSLAQVLTRPSPTTPEEEEGREGGREGGREGGLERVCDWGETLS<br>GGEKQRLAFARLYYHRPRFAILDECTSAVSSDVEDHLYRQAQALGITLLTVAHRQALWKHHEYLLMLD<br>GKGGWSFRPMQTLEPEAAEGDGDIKYT<br><br>SEQ ID NO: 21<br>DNA<br>*Nannochloropsis gaditana*<br>PXA coding sequence<br>ATGGCCCCTTCCTTCTCCCATCGCGGTCAAAAACGGCACGACAATGTGGTTTCTGCTTTTTTCAACTC<br>CTTTATGTCCGCTGGCGAGCAAAAATTCACGGTGGTCTCATCTCTTTTCTCGAGCGGGTTGTTCCTAG<br>TTGCCTTAGCCCTCGTGAAACAGCTGTCGAGCCTACAAGAGCAAGAAGAAAAGGTTGCTGCGTCCCTA<br>GAACGCCAAGACCCAAGCAAGGAAGGAGGAAGTCTGGCGGCACCCTTGCCCCAGCCTGACGGCAGGTG<br>CCAGACCCCCAGCCTCCCCTCCCTCACCCCCACCCTCCGCCTCGCCTCCTCCTTCTCAGCGACCT<br>CCACAGCCCGGACTAGGAGTCCCAATGCCGATGCTTTGACGAGGTCGGGGAGGGATGCTGCCGGCCAT<br>GGAGAAAGAGGGAGCGGGGGCATGAGGAGACCAGGCGGCCCTCCGCTACCGCAGGAAGGGCAGAGGGT<br>GGCTCTGGACGATGAATTCGGAAGGCAGCTCTTAAGCCTTCTCCACAAATTAATCCCCAGCTGGAAGA<br>CGCGTGAAGCCGCCTGCCTAGGAGGCATGGTTTTCCTCCTCCTGGCTCGCAGCGCCTGTGACTTGCGA<br>ATGATAAACCTGGTGGTGGGGGCGGAGAAGGCGATCGTGTTGGGCAATCGGCCCGCCTTCAGGATCTC<br>TTTGGCGCGCTTTTTAAGATTCATGGTGCCTGTGGCCTGTGTGAATGCCCTGCTCAAGTACACAACGA<br>GAGAGCTCTCTCTTGGCCTCCGTCAACGACTCACAGAGCATCTTCAGTCTAAATACATGAAAGGCTTT<br>ACCTTCTACTCTATGGCGGTCATGGAAGGGCATGCGAGGGAAATCGAGCAGCTTATGACCGTGGACGT<br>GGACAAGTTCTCCCTGTGCATTACGGAGCTGGCCTCAAACCTCCTAAAGCCAACCCTTGATATTCTTC<br>TTTACGCAACAAAATTACAAACCTCGGTCGGTCCTCTGATCCCGTTAGCCATGGCTAGCTACCTCTTC<br>TCCTCTGGCACAGCCTTGACGCGCCTGCGAAGACCTGCCGCAGAGTATACGGCGCGATCCAACGGCG<br>CGAGGGCGACTACAGATTTGTGACGAATAGAATGGTCGCGCACGCCGAAGAGATCGCTTTCTACGATG<br>GAGTGGGGAGGGAAAAAAACTACCTGCAGCAGATCTTCGGTTCTTTGTTGGGAACGATCCGGCGCGGC<br>TCCCGGTTCCGCCACGCGATGGACATCCTCGATAGTGTCATGGCCAAGTACATAGCCACCGCTCTTGG<br>CTGGGTGCTTTTGAATCGCGCGGCTCAGCAACAGAAACAAGAAGCGCTTCCTGTCCCCTCTCCCGCCC<br>TCCCACCCTCCCCCGCTGCCTCTTCCTACGACTCTTTCCATCAATCCGCTCGCATGATGTTCAACTTT<br>GCACAGGCCCTCTCCGCCATCGTCCTGGCGGGCAGGGAGGCGACGCGTCTGGCAGGCTATACCTCTCG<br>GGTCACGCGCCTCGAACGCCTCATTGATGACCTGGAGCGCGAAGACGAAGCAAGATCCACCGCATCGG<br>AGTTTTTGGAGAAGAAAGATGTGATAGAGCTCCAGGGTGTGCCCATCGTCGCTCCGGTCGTCGGCAAT<br>GGCCGCAAGGACAGCGACGGCGGGAGGGGAGGGAGAAAAGGAAGGGAAGGAGGGAGGGTACGGCGATT<br>GACATCTCCTCTGACCCTGAGAATTGAGCCAGGCATGCACGTCCTCGTCACAGGACCGAATGGAAGTG<br>GGAAATCGTCTCTTTTCCGAATGATCTGTGGCCTCTGGCCTGTCTCCGAAGGGCGCCTCATCAAACCT<br>CCTCGATCCCAGCTCTTCTACATACCCCAACGACCCTACCTCCCGCTTGGAAGCTTGCGGGATCAGGT<br>GATTTACCCTCACTCCCAGGCCGAGATGGCGGCACTAGGGAGGACGGATGCAGATGTGCTGGCGCTTT<br>TGGATGAGGTTCAACTCTCCTTCCTTGCCCCCCCCCGGGTGGTAGGACCGGAGAGCAACGCCAGCGAT<br>GCTCTGCCCTCCCTCCCTTCCTCCCTCCCTTCCTCCCTCCCTTCCTCCCTTCCTCCCTCCTTTCCGTC<br>TTTCTCCTCCTTGGCCCAAGTCCTCACCCGGCCATCGCCTACGACCCCGGAAGGAGGAAGGGAGGG<br>AGGGAGGGAGGGAGGGAGGGAGGGAGGGGGTTGGAGCGAGTCTGCGACTGGGGCGAGACATTGTCG<br>GGGGGCGAGAAGCAGCGGCTGGCTTTTGCCCGTCTCTATTACCACCGACCGCGCTTTGCCATCTTGGA<br>CGAGTGCACGAGCGCCGTGTCGAGCGATGTGGAGGACCATCTGTACAGACAGGCGCAGGCACTCGGCA<br>TCACCTTGCTCACAGTGGCGCATCGGCAGGCCTTGTGGAAACATCATGAATATCTGCTGATGCTGGAT<br>GGGAAAGGGGGCTGGTCTTTTAGGCCCATGCAGACACTGGAACCGGAAGCTGCCGAAGGGGACGGAGA<br>TATAAAGTACACCTGA<br><br>SEQ ID NO: 22<br>Protein<br>*Nannochloropsis gaditana*<br>Acyl-CoA oxidase amino acid<br>MTTANARLSRLKDHLAETGAVARAPISSSAINATPFAARTTHTMERMARERAKASFPVRDMTYFLDGG<br>RSMTEVKEGMMADLAANPVFTDPEWNDLNRDQIRERTISRLRAAYKLLIRDGADVSRRNARLEIHALH<br>DLGWYVRQGVHFGLFMGALAGQGSDEQRAEWLPRTMMCEIYGCFGMTELGHGSFLRGLETTAMYDKDT<br>QEFVINSPTDTSTKWWIGAAGQTATHSVVFARLLLPSGDDMGVHNFIIPLRDMETHLPLPGIHIGDLG<br>AKMGLNGIDNGWMQFDHVRVPRDNMLCRYAQVTPEGKYIRPPRKEMAYGALIGTRAALVKTAVDFQKK<br>ALMIGIRYTALRTQGVVEEGQREETAIIDYPIHRDKLLKLLAAAYAWHFQAAYVLHLNDSLEEGLEAG<br>DLSILKDVHGTMAGLKAFGTWFTYNTIEACRQVCGGHGYSKYNGLSNTLQDFAVMCTWEGDNTVMALQ<br>TARYLVRSYEKAKRGGETLAGSVSYLQDAHPPAWRARSAEDLMNNEVQMEAWRALLAAKVSRASERVL<br>ARQAALRGNEAQAFNEHQVELFECAKTHVYFNVAARFAEAVVEAGTTHPALAPVLARLCHLFSLSSLL |

SEQUENCES

EDEASLLASGFASAGQMQLIREAVGALLLALRPDAVALVDAFNYSDEVLNSHLGTANGDIYTGYLQQV
QRLVPENKLAVAPYIMREVKPLMQGADLISTDEEED*

SEQ ID NO: 23
DNA
*Nannochloropsis gaditana*
Acyl-CoA oxidase cDNA
ATGACGACCGCCAATGCCCGTTTGTCGAGGCTCAAAGATCATTTAGCAGAGACGGGGGCTGTGGCGCG
CGCGCCGATTAGCTCCTCTGCCATCAATGCCACGCCTTTTGCGGCGAGGACGACGCATACCATGGAGC
GCATGGCAAGGGAACGAGCCAAGGCCTCCTTCCCCGTCCGAGACATGACGTACTTCTTGGACGGCGGG
AGGAGCATGACCGAGGTCAAGGAGGGCATGATGGCGGACTTGGCGGCGAATCCGGTCTTTACGGACCC
AGAATGGAACGACTTGAACAGAGATCAGATCCGTGAACGCACCATCTCTCGACTGAGAGCTGCGTACA
AGCTCCTGATCCGAGACGGTGCCGATGTCAGCCGCCGGAATGCCCGGCTTGAGATTCACGCCCTCCAT
GACTTGGGGTGGTACGTGCGGCAGGGTGTGCATTTCGGCCTCTTTATGGGCGCCTTGGCCGGGCAGGG
GAGCGACGAACAACGCGCTGAGTGGCTGCCCAGGACCATGATGTGTGAGATCTACGGGTGCTTCGGGA
TGACGGAGTTGGGGCACGGCTCATTCTTGCGGGGCCTGGAGACCACAGCGATGTACGACAAGGACACG
CAAGAATTTGTAATCAATTCCCCCACTGACACAAGCACCAAATGGTGGATCGGTGCGGCCGGGCAGAC
GGCCACACATTCGGTGGTTTTCGCCGCCTCCTCCTTCCCTCAGGGGACGACATGGGTGTGCACAACT
TCATCATACCCCTCCGGGATATGGAAACGCACTTGCCCCTCCCTGGCATCCACATTGGCGATTTGGGG
GCCAAGATGGGCTTGAATGGCATCGACAACGGGTGGATGCAATTTGACCACGTCCGCGTGCCCCGGGA
CAACATGCTTTGTCGCTACGCACAGGTCACCCCGGAGGGGAAATACATCCGTCCTCCCAGGAAGGAGA
TGGCTTACGGCGCTCTCATCGGCACTCGGGCGGCTCTGGTCAAGACAGCCGTGGACTTTCAAAAAAAG
GCCCTCATGATCGGGATCCGCTACACCGCCCTCCGGACACAGGGCGTGGTGGAGGAAGGCCAAAGGGA
AGAGACCGCCATCATCGACTACCCCATCCACCGGGACAAACTCCTGAAACTCTTGGCGGCCGCCTACG
CCTGGCACTTCCAAGCCGCCTACGTTCTCCACCTGAACGATTCCTTGGAGGAGGGGCTCGAGGCGGGG
GACCTCTCCATCCTCAAGGATGTGCATGGGACCATGGCTGGCCTCAAGGCTTTCGGAACCTGGTTCAC
GTACAACACGATCGAGGCCTGCCGGCAAGTGTGCGGGGGCCACGGGTACAGCAAGTACAACGGCCTCT
CCAACACCCTCCAGGACTTTGCTGTCATGTGCACCTGGGAGGGCGACAACACCGTGATGGCTCTACAG
ACGGCGCGGTATCTAGTTCGGTCCTACGAGAAGGCGAAGCGGGGGGGCGAGACCCTGGCAGGCTCCGT
CTCATACCTGCAGGATGCGCATCCCCGGCTTGGCGGGCGAGGTCTGCGGAGGACTTGATGAACATGG
AAGTGCAGATGGAGGCCTGGCGGGCCCTCCTAGCCGCCAAGGTCTCCAGAGCCTCAGAGCGGGTCTTG
GCAAGGCAGGCGGCGTTGCGGGGGAACGAGGCGCAGGCCTTCAACGACGCATCAGGTGGAGCTTTTCGA
GTGCGCCAAGACCCATGTCTACTTCAATGTGGCGGCGCGGTTTGCCGAGGCGGTCGTGGAGGCCGGCA
CCACCCACCCCGCCCTGGCCCCTGTCCTCGCCCGCCTCTGCCACCTCTTCTCTCTCGAGCCTTCTA
GAAGACGAAGCCTCCCTGCTCGCCAGCGGTTTCGCCTCCGCGGGCAGATGCAGCTCATTCGCGAGGC
CGTGGGCGCCCTCCTCCTCGCCCTCCGCCCGGACGCGGTTGGCCCTTGTCGACGCCTTCAACTATTCCG
ACGAAGTTTTGAACTCACATTTAGGCACCGCCAACGGCGATATTTATACGGGCTACCTCCAACAGGTG
CAGCGCCTCGTCCCTGAGAACAAGCTGGCCGTCGCCCCCTACATCATGAGGGAGGTGAAGCCTTTAAT
GCAAGGAGCAGACCTGATCTCCACGGACGAGGAGGAGGACTGA SEQ ID NO: 24
Protein
*Nannochloropsis gaditana*
Isocitrate Lyase
MYWKRTCCDCLGLHFRTLILDLFPCSAGALHSNPYRLSVRKPIKITITTRTMEETRLYHEDVAATEHF
FRNPRFAQTVRPYSAQDVVALRSSLLVEPASNRQAQKLWSLLTGLAGQGKCSYTFGALDPVQVVQMAP
HVSTIYVSGWQCSSTASTSNEPGPDFADYPMDTVPNKVHQLFSAQLFHDRRQEARARMTDASKVAEP
PVDYLRPIIADGDTGHGGLTAVMKLTKMFIERGAAGIHFEDQKPGTKKCGHMGGKVLVSVQEHIDRLT
AARLQADVMGAQTIIVARTDGEAASLLDTNIDARDHPFILGATVPGTRALNEVVAEARAQGVTGAELD
RITDQWTAAANLRRFPEAVCDALSTLPNPAPKLAVWKAQAYNLSLPQARALAKELMGREVYFDWEAPR
SREGYYRIKGGVDYCVARAVAYAPHADLIWMETAKPDLSEAREFAQGVRAAVPGKMLAYNLSPSFNWD
VAGLSPQEMEHFNSSLAAMGFVWQFITLAGFHANGLMTTMFAREYGKRGVVAYVEMIQRKEREQEVDM
LTHQKWSGAALLDKQMQTVTGGMSSTSSMGKGVTEAQFGAKGPGAAGVSSGAGAARAGAISRL SEQ ID NO: 25
DNA
*Nannochloropsis gaditana*
Isocitrate Lyase cDNA
ATGTATTGGAAGAGGACGTGTTGTGACTGTCTAGGGCTTCATTTCCGGACCCTCATTCTCGACCTCTT
CCCTTGCTCTGCTGGCGCCCTTCATTCCAACCCTTACAGACTTTCGGTGCGCAAGCCGATCAAGATCA
CAATCACCACAAGGACAATGGAGGAAACACGCCTATATCATGAAGATGTTGCTGCGACAGAGCATTTT
TTCCGCAACCCGCGCTTTGCCCAAACTGTTCGGCCCTATTCGGCGCAGGACGTCGTCGCACTCCGGTC
CAGCCTCCTGGTCGAACCTGCCTCCAATCGACAGGCCCAGAAGCTCTGGTCCCTCCTGACCGGGCTGG
CCGGTCAAGGAAAGTGCTCGTACACCTTCGGCGCCCTCGACCCCGTTCAGGTGGTGCAGATGGCCCCC
CACGTCTCCACCATTTACGTGAGTGGCTGGCAGTGCTCCTCCACGGCCTCCACTAGCAACGAGCCCGG
CCCAGACTTTGCAGATTACCCCATGGACACGGTCCCCAACAAGGTGCACCAACTCTTCTCCGCCCAAC
TCTTCCACGACCGCCGCCAGCAAGAGGCGCGAGCCCGCATGACGGACGCGAGCAAGGTGGCGGAACCC
CCTGTCGACTACCTCCGGCCCATCATCGCCGACGGCGACACGGGCCACGGCGGTCTGACCGCGGTGAT
GAAGCTGACCAAGATGTTCATTGAGCGAGGGGCGGCGGGGATTCACTTCGAGGATCAGAAACCAGGCA
CTAAGAAGTGCGGGCACATGGGCGGGAAGGTGTTGGTGTCCGTCCAAGAGCACATTGACCGGTTGACA
GCCGCACGGCTGCAGGCGGACGTGATGGGGGCGCAAACCATCATTGTGGCGCGTACTGACGGGGAGGC
GGCCAGTCTTTTGGACACCAACATCGACGCGCGCGACCATCCTTTCATCTTGGGGGCCACGGTCCCTG
GCACCCGCGCCCTGAATGAGGTGGTGGCCGAGGCGAGGGCCCAGGGGGTGACGGGCGCGAGTTGGAC
CGCATTACGGACCAATGGACGGCGGCCGCCAATTTGCGTCGCTTTCCGGAAGCTGTCTGCGACGCCTT
GTCCACGCTACCCAATCCGGCCCCGAAGCTCGCCGTCTGGAAGGCTCAGGCCTACAACCTCTCCCTGC
CGCAGGCGCGTGCGCTCGCGAAGGAACTGATGGGCCGGGAGGTGTACTTCGACTGGGAGGCGCCGCGT
TCCCGCGAGGGGTATTACCGCATCAAGGGTGGGGTGGACTACTGTGTAGCCCGGGCGGTGGCGTACGC

| SEQUENCES |
|---|
| GCCGCACGCGGATTTGATTTGGATGGAGACGGCGAAACCGGATCTTTCCGAAGCTAGGGAGTTCGCTC<br>AAGGGGTGCGGGCGGCCGTGCCTGGTAAGATGCTCGCCTACAACCTCTCTCCTTCCTTTAACTGGGAC<br>GTGGCCGGCTTGTCCCCGCAGGAGATGGAGCATTTCAACTCGTCCCTGGCGGCCATGGGCTTCGTCTG<br>GCAGTTCATTACCTTGGCGGGCTTCCACGCGAACGGGCTCATGACCACCATGTTTGCGCGCGAGTACG<br>GAAAGCGGGGGTGGTGGCCTACGTGGAGATGATCCAGCGGAAGGAGCGGGAGCAGGAGGTGGACATG<br>CTCACCCACCAGAAGTGGTCAGGAGCCGCGTTACTCGACAAGCAGATGCAGACGGTGACGGGCGGCAT<br>GTCCTCCACGTCCTCCATGGGCAAGGGCGTGACAGAGGCCCAGTTTGGCGCCAAGGGACCGGGAGCGG<br>CCGGTGTCTCATCGGGAGCAGGAGCGGCGCGTGCGGGGGCGATTTCTCGGTTGTAA |

SEQ ID NO: 26
DNA
Artificial Sequence
pSGE-6206 vector gcggccgccgtatggtcgacggttgctcggatggggggggcggggagcgatggagggaggaagatcag
gtaaggtctcgacagactagagaagcacgagtgcaggtataagaaacagcaaaaaaaagtaatgggcc
caggcctggagagggtatttgtcttgttttttcttggccaggaacttgttctccttttcttcgtttcta
ggacccgatccccgctcgcatttctctcttcctcagccgaagcgcagcggtaaagcatccattttat
cccaccgaaagggcgctcccagccttcgtcgagcggaaccggggttacagtgcctcaaccctcccaga
cgtagccagagggaagcaactccctgatgccaacccgctgtgggctgcccatcggaatctttgacaatt
gccttgatccccgggtgcaagtcaagcagcacctgccgacatcgcccgcacggagacagaatgccgcg
gttttcgttcccgatggccactatgcacgtcagatttccggcagcagccgcagcggccgttccgagga
ccacgagctccgcgcatggcccctccggtgaaatgatatacattcacgccggtaaagatccgaccgtcg
gacgagagggctgcactggccaccgagtagtcctcgctaataggtatgctgttgatggtcgcagttgc
acgttcgatcagcgtggattcctcttgggataaaggcttggccatcgagctcggtacccggggatcca
tgattgttgtattatgtacctatgtttgtgatgagacaataaatatgagaagagaacgttgcggccac
ttttttctccttccttcgcgtgctcatgttggtggtttgggaggcagaagatgcatggagcgccacac
attcggtaggacgaaacagcctcccccacaaagggaccatgggtagctaggatgacgcacaagcgagt
tcccgctctcgaagggaaaccaggcattttccttcctcttttcaagccacttgttcacgtgtcaacac
aattttggactaaaatgccctcggaactcggcaggcctccctctgctccgttgtcctggtcgccgag
aacgcgagaccgtgccgcatgccatcgatctgctcgtctgtactactaatcgtgtgcgcgtgttcgtg
cttgtttcgcacgaaattgtcctcgttcggccctcacaacggtggaaatcggtgctagaataaagtga
ggtggcttatttcaatggcggccgtcatcatgcgggatcaactgaagtacggcgggttctcgagattt
catcgtgctcgtccagagcaggtgttttgcctgcagctcttcatgtttagggctcatgatttcatct
gatatgccgtaagaaaaccaatattcacttctcaattttccatgaaaggtgaaggcctaggttgtgt
gcgaggcaacgactggggagggatcgcaacattcttgctaacctcccctctatcttggccgctgtgaa
tcggcatatttaccgggctgaattgagaaagtgttttgagggaattaaaaggtggctgtcttgcaagc
ttggcttcagtgcctgcttaattcgaaccgatccagcttgtgatgaggccttcctaagcctggtagtc
agaagcgacatggcgctataaatttcgtctcagttggagagtagaaagcatgattcgaacacggttt
tcaactgccaaagatatctccattgttccttcaatctgtacacctgcacggtgcaccagttggtacg
gcatattatggtttaataagcatacatcatatgaatacaattcagcttaaatttatcatacaaagatg
taagtgcagcgtgggtctgtaacgatcgggcgtaatttaagataatgcgagggaccggggggaggtttt
ggaacggaatgaggaatgggtcatggcccataataataatatgggtttggtcgcctcgcacagcaacc
gtacgtgcgaaaaaggaacagatccatttaataagttgaacgttattctttcctatgcaatgcgtgta
tcggaggcgagagcaagtcataggtggctgcgcacaataattgagtctcagctgagcgccgtccgcgg
gtggtgtgagtggtcatcctcctcccggcctatcgctcacatcgctcttcaatggtggtggttggggcc
tgatatgacctcaatgccgacccatattaaaacccagtaaagcattcaccaacgaacgaggggctctt
ttgtgtgtgttttgagtatgattttacacctctttgtgcatctctctggtcttccttggttccgtag
tttgggcatcatcactcacgcttccctcgaccttcgtcttcttccttttacaaccccgacacaggtcag
agttggagtaatcaaaaaggggtgcacgaatgagatacattagattttgacagatatccttttactg
gagagggttcaagggatcaaatgaacagcgggcgttggcaatctagggagggatcggaggttggcagc
gagcgaaagcgtgtccatccttttggctgtcacacctcacgaaccaactgttagcaggccagcacaga
tgacatacgagaatctttattatatcgtagacctatgtggatgacctttggtgctgtgtgtctggca
atgaacctgaaggcttgatagggaggtggctcccgtaaaccccttttgtccttttccacgctgagtctccc
ccgcactgtcctttatacaaattgttacagtcatctgcaggcggttttcttttggcaggcaaagatgc
ccaagaaaagcggaaggtcggcgactacaaggatgacgatgacaagttggagcctggagagaagccc
tacaaatgccctgagtgcgaaagagcttcagccaatctggagccttgacccggcatcaacgaacgca
tacacgagacaagaagtactccatcgggctggacatcgggacgaactccgtgggatgggccgtgatca
cagacgaatacaaggtgccttccaagaagttcaaggtgctggggaacaggacagacactccatcaag
aagaacctcatcggggccttgctcttcgactccggagaaaccgccgaagcaacgcgattgaaaagaac
cgccagaagacgatacacacgacggaagaaccgcatctgctacctccaggagatcttcagcaacgaga
tggccaaggtggacgactcgttctttcatcgcctggaggagagcttcctggtggaggaagacaagaaa
catgagcgccaccgatcttcgggaacatcgtggacgaagtggctaccacgagaaataccccacgat
ctaccacttgcgcaagaaactcgtggactccacggacaaagcggacttgcggttgatctacttggcct
tggcccacatgatcaaattcgggcccacttcctgatcgagggcgacttgaatcccgacaattccgac
gtggacaagctcttcatccagctggtgcagacctacaaccagctcttcgaggagaaccccatcaatgc
ctccggagtggacgccaaagccatcttgtccgcccgattgtccaaatccagacgcttggagaacttga
tcgcacaacttcctggcgagaagaagaacggcctcttcggcaacttgatcgcgctgtcgctgggattg
acgcctaacttcaagtccaacttcgacttggccgaggacgccaagttgcaactgtccaaggacaccta
cgacgacgacctcgacaacctgctggcccaaattggcgaccaatacgcggacttgttttttggcggcca
acttgagcgacgccatcttgttgagcgacatcttgcgcgtgaatacggagatcaccaaagcccctttg
tccgcctctatgatcaagcggtacgacgagcaccaccaagacttgaccctgttgaaagccctcgtgcg
gcaacaattgcccgagaagtacaaggagatcttcttcgaccagtccaagaacgggtacgccggctaca
tcgacgaggagcctcccaagaagagttctacaagttcatcaagcccatcctggagaagatggacggc
accgaggagttgctcgtgaagctgaaccgcgaagacttgttgcgaaaacagcggacgttcgacaatgg
cagcatccccccaaatccatttgggagagttgcacgccatcttgcgacggcaagaggacttctacc
cgttcctgaaggacaaccgcgagaaaatcgagaagatcctgacgttcagaatcccctactacgtggga
cccttggcccgaggcaattcccggtttgcatggatgacgcgcaaaagcgaagagacgatcacccctg

SEQUENCES

```
gaacttcgaagaagtggtcgacaaaggagcatccgcacagagcttcatcgagcgaatgacgaacttcg
acaagaacctgcccaacgagaaggtgttgcccaagcattcgctgctgtacgagtacttcacggtgtac
aacgagctgaccaaggtgaagtacgtgaccgagggcatgcgcaaaccgcgttcctgtcgggagagca
aaagaaggccattgtggacctgctgttcaagaccaaccggaaggtgaccgtgaaacagctgaaagagg
actacttcaagaagatcgagtgcttcgactccgtggagatctccggcgtggaggaccgattcaatgcc
tccttgggaacctaccatgacctcctgaagatcatcaaggacaaggacttcctggacaacgaggagaa
cgaggacatcctggaggacatcgtgctgaccctgaccctgttcgaggaccgagagatgatcgaggaac
ggttgaaaacgtacgcccacttgttcgacgacaaggtgatgaagcagctgaaacgccgccgctacacc
ggatggggacgattgagccgcaaactgattaatgaattcgcgacaagcaatccggaaagaccatcct
ggacttcctgaagtccgacgggttcgccaaccgcaacttcatgcagctcatccacgacgactccttga
ccttcaaggaggacatccagaaggcccaagtgtccggacaaggagactcttgcacgagcacatcgcc
aatttggccggatcccccgcaatcaaaaaaggcatcttgcaaaccgtgaaagtggtcgacgaactggt
gaaggtgatgggacggcacaagcccgagaacatcgtgatcgaaatggcccgcgagaaccaaaccaccc
aaaaaggacagaagaactcccgagagcgcatgaagcggatcgaagagggcatcaaggagttgggctcc
cagatcctgaaggagcatcccgtggagaatacccaattgcaaaacgagaagctctacctctactacct
ccagaacgggcgggacatgtacgtcgaccaagagctggacatcaaccgcctctccgactacgatgtgg
atcatattgtgcccagagcttcctcaaggacgacagcatcgacaacaaggtcctgacgcgcagcgac
aagaaccggggcaagtctgacaatgtgccttccgaagaagtcgtgaagaagatgaagaactactggcg
gcagctgctcaacgccaagctcatcacccaacggaagttcgacaacctgaccaaggccgagagaggag
gattgtccgagttggacaaagccggcttcattaaacgccaactcgtggacaccgccagatcacgaag
cacgtggcccaaatcttggactcccggatgaacacgaaatacgacgagaatgacaagctgatccgcga
ggtgaaggtgatcacgctgaagtccaagctggtgagcgacttccggaaggacttccagttctacaagg
tgcgggagatcaacaactaccatcacgcccatgacgcctacctgaacgccgtggtcggaaccgccctg
atcaagaaataccccaagctggagtccgaattcgtgtacggagattacaaggtctacgacgtgcggaa
gatgatcgcgaagtccgagcaggagatcggcaaagccaccgccaagtacttcttttactccaacatca
tgaacttcttcaagaccgagatcacgctgccaacggcgagatccgcaagcgcccctgatcgagacc
aacggcgagacgggagagattgtgtgggacaaaggaagagattttgccacagtgcgcaaggtgctgtc
catgcctcaggtgaacatcgtgaagaagaccgaggtgcaaacaggagggttttccaaagagtccattt
tgcctaagaggaattccgacaagctcatcgcccgcaagaaggactgggaccccaagaagtacggggc
ttcgactcccccacggtggcctactccgtgttggtggtggccaaagtggagaaagggaagagcaagaa
gctgaaatccgtgaaggagttgctcggaatcacgatcatggaacgatcgtcgttcgagaaaaacccca
tcgacttcctcgaagccaaagggtacaaagaggtgaagaaggacctgatcatcaagctgcccaagtac
tccctgttcgagctggagaacggccgcaagcggatgctggcctccgccggggaactgcagaaaggga
cgaattggccttgccctccaaatacgtgaacttcctctacttggcctcccattacgaaaagctcaaag
gatccctgaggacaatgagcagaagcaactcttcgtggaacaacacaagcactacctggacgagatc
atcgagcagatcagcgagttctccaagcgcgtgatcctcgccgacgccaacctggacaaggtgctctc
cgcctacaacaagcaccgcgacaagcctatccgcgagcaagccgagaatatcattcacctgttaccc
tgacgaatttgggagccctgccgcctttaaatactttgacaccaccatcgaccgcaaaagatacacc
tccaccaaggaagtcttggacgccaccctcatccaccagtccatcacgggcctctacgagacgcgcat
cgacctctcccaattgggcggcgactaaagtgatgcggcctttaggaaacaccacaaaagtaattgac
aatctcaggaacgatctgcgtgtttacagcttcccaaataacaattataccacgtaccaaaagggtt
taatgtatctcacaaattcttctaataggtacagcttctcaaatttgggtgtatgatgtgacacttcgt
ctcacacacgtcacgataattcagcgtatggcttcccttcatcacattcacgcaaacttctacacaac
cctgggcatatttcttgtgttggcaacactcccgaaatcgattctgcacacaatggttcattcaatga
ttcaagtacgttttagacggactaggcagttttaattaaaaacatctatcctccagatcaccagggcca
gtgagaggccggcataaaggacggcaaggaaagaaaagaaagaaagaaaaggacacttatagcatagt
ttgaagttataagtagtcgcaatctgtgtgcagccagacagatgcttttttttttccgtttggcaggag
gtgtagggatgtcgaagaccagtccagctagtattctatcctacaagtcaatcatgctgcgacaaaaa
tttctcgcacgaggcctctcgataaacaaaactttaaaagcacacttcattgtcatgcagagtaataa
ctcttccgcgtcgatcaatttatcaatctctatcatttccgcccctttccttgcatagagcaagaaaa
gcgacccggatgaggataacatgtcctgcgccagtagtgtggcattgcctgtctctcatttacacgta
ctgaaagcataatgcacgcgcataccaatattttcgtgtacggagatgaagagacgcgacacgtaag
atcacgagaaggcgagcacggttgccaatggcagacgcgctagtctccattatcgcgttgttcggtag
cttgctgcatgtcttcagtggcactatatccactctgcctcgtcttctacacgagggccacatcggtg
caagttcgaaaaatcatatctcaatcttcagatccttttccagaaacggtgctcaggcgggaaagtgaa
ggtttttctactctagtggctaccccaattctctccgactgtcgcagacggtccttcgttgcgcacgca
ccgcgcactacctctgaaattcgacaaccgaagttcaattttacatctaacttctttcccattctctc
accaaaagcctagcttacatgttggagagcgacgagagcggcctgcccgccatggagatcgagtgccg
catcaccggcaccctgaacggcgtggagttcgagctggtgggcggcggagagggcaccccccgagcagg
gccgcatgaccaacaagatgaagagcaccaaaggcgccctgaccttcagcccctacctgctgagccac
gtgatgggctacggcttctaccacttcggcacctaccccagcggctacgagaacccctcctgcacgc
catcaacaacggcggctacaccaacacccgcatcgagaagtacggaggcgtgctgcacgtga
gcttcagctaccgctacgaggccggccgcgtgatcggcgacttcaaggtgatgggcaccggcttcccc
gaggacagcgtgatcttcaccgacaagatcatccgcagcaacgccaccgtggagcacctgcacccat
gggcgataacgatctggatggcagcttcacccgcaccttcagcctgcgcgacggcggctactacagct
ccgtggtggacagccacatgcacttcaagagcgccatccaccccagcatcctgcagaacgggggcccc
atgttcgccttccgccgcgtggagggagatcacagcaacaccgagctggcgatcgtggagtaccagac
gccttcaagaccccggatgcagatgccggtgaagaataagggtgggaaggagtcggggagggtcctgg
cagagcggcgtcctcatgatgtgttggagacctggagagtcgagagcttcctcgtcacctgattgtca
tgtgtgtataggttaaggggggcccactcaaagccataaagacgaacacaaacactaatctcaacaaag
tctactagcatgccgtctgtccatctttattcctggcgcgcctatgcttgtaaaccgttttgtgaaa
aaattttaaaataaaaaggggacctctagggtccccaattaattagtaatataatctattaaaggt
cattcaaaaggtcatccagacgaaagggcctcgtgatacgcctatttttataggttaatgtcatgata
ataatggtttcttagacgtcaggtggcacttttcggggaaatgtgcgcggaaccccctatttgtttatt
tttctaaatacattcaaatatgtatccgctcatgagacaataaccctgataaatgcttcaataatatt
gaaaaggaagagtatgagtattcaacatttccgtgtcgcccttattccctttttttgcgcattttgc
cttcctgttttgctcacccagaaacgctggtgaaagtaaaagatgctgaagatcagttgggtgcacg
```

-continued

SEQUENCES agtgggttacatcgaactggatctcaacagcggtaagatccttgagagttttcgccccgaagaacgtt
ttccaatgatgagcacttttaaagttctgctatgtggcgcggtattatcccgtattgacgccgggcaa
gagcaactcggtcgccgcatacactattctcagaatgacttggttgagtactcaccagtcacagaaaa
gcatcttacggatggcatgacagtaagagaattatgcagtgctgccataaccatgagtgataacactg
cggcaacttacttctgacaacgatcggaggaccgaaggagctaaccgcttttttgcacaacatgggg
gatcatgtaactcgccttgatcgttgggaaccggagctgaatgaagccataccaaacgacgagcgtga
caccacgatgcctgtagcaatggcaacaacgttgcgcaaactattaactggcgaactacttactctag
cttcccggcaacaattaatagactggatggaggcggataaagttgcaggaccacttctgcgctcggcc
cttccggctggctggtttattgctgataaatctggagccggtgagcgtgggtctcgcggtatcattgc
agcactggggccagatggtaagccctcccgtatcgtagttatctacacgacggggagtcaggcaacta
tggatgaacgaaatagacagatcgctgagataggtgcctcactgattaagcattggtaactgtcagac
caagtttactcatatatactttagattgatttaaaacttcatttttaatttaaaaggatctaggtgaa
gatccttttttgataatctcatgaccaaaatcccttaacgtgagttttcgttccactgagcgtcagacc
ccgtagaaaagatcaaaggatcttcttgagatcctttttttctgcgcgtaatctgctgcttgcaaaca
aaaaaaccaccgctaccagcggtggtttgtttgccggatcaagagctaccaactcttttccgaaggt
aactggcttcagcagagcgcagataccaaatactgtccttctagtgtagccgtagttaggccaccact
tcaagaactctgtagcaccgcctacatacctcgctctgctaatcctgttaccagtggctgctgccagt
ggcgataagtcgtgtcttaccgggttggactcaagacgatagttaccggataaggcgcagcggtcggg
ctgaacggggggttcgtgcacacagcccagcttggagcgaacgacctacaccgaactgagatacctac
agcgtgagctatgagaaagcgccacgcttcccgaagggagaaaggcggacaggtatccggtaagcggc
agggtcggaacaggagagcgcacgagggagcttccaggggaaacgcctggtatctttatagtcctgt
cgggtttcgccacctctgacttgagcgtcgatttttgtgatgctcgtcaggggggcggagcctatgga
aaaacgccagcaacgcggcctttttacggttcctggccttttgctggccttttgctcacatgttcttt
cctgcgttatcccctgattctgtggataaccgtattaccgcctttgagtgagctgataccgctcgccg
cagccgaacgaccgagcgcagcgagtcagtgagcgaggaagcggaaga SEQ ID NO: 27
DNA
Artificial Sequence
S. pyogenes CAS9 gene codon optimized for Nannochloropsis
gacaagaagtactccatcgggctggacatcgggacgaactccgtgggatgggccgtgatcacagacga
atacaaggtgccttccaagaagttcaaggtgctggggaacacggacagacactccatcaagaagaacc
tcatcgggcccttgctcttcgactccggagaaaccgccgaagcaacgcgattgaaaagaaccgccaga
agacgatacacacgacggaagaaccgcatctgctacctccaggagatcttcagcaacgagatggccaa
ggtggacgactcgttctttcatcgcctggaggagagcttcctggtggaggaagacaagaaacatgagc
gccacccgatcttcgggaacatcgtggacgaagtggcctaccacgagaaataccccacgatctaccac
ttgcgcaagaaactcgtggactccacggacaaagcggacttgcggttgatctacttggccttggccca
catgatcaaatttcggggccacttcctgatcgaggcgacttgaatcccgacaattccgacgtggaca
agctcttcatccagctggtgcagacctacaaccagctcttcgaggagaaccccatcaatgcctccgga
gtggacgccaaagccatcttgtccgccgattgtccaaatccagacgcttggagaacttgatcgcaca
acttcctggcgagaagaagaacggcctcttcggcaacttgatcgcgctgtcgctgggattgacgccta
acttcaagtccaacttcgacttggccgaggacgccaagttgcaactgtccaaggacacctacgacgac
gacctcgacaacctgctggcccaaattggcgaccaatacgcggacttgttttggcggccaagaactt
gagcgacgccatcttgttgagcgacatcttgcgcgtgaatacggagatcaccaaagccccttttgtccg
cctctatgatcaagcggtacgacgagcaccaccaagacttgacccctgttgaaagccctcgtgcggcaa
caattgcccgagaagtacaaggagatcttcttcgaccagtccaagaacgggtacgccggctacatcga
cggaggagcctcccaagaagagttctacaagttcatcaagcccatcctggagaagatggacggcaccg
aggagttgctcgtgaagctgaaccgcgaagacttgttgcgaaaacagcggacgttcgacaatggcagc
atccccaccaaatccatttgggagagttgcacgccatcttgcgactgtactcaagaggacttctacccgtt
cctgaaggacaaccgcgagaaaatcgagaagatcctgacgttcagaatcccctactacgtgggaccct
tggcccgaggcaattcccggtttgcatggatgacgcgcaaaagcgaagaacgatcaccccctggaac
ttcgaagaagtggtcgacaaaggagcatccgcacagagcttcatcgagcgaatgacgaacttcgacaa
gaacctgcccaacgagaaggtgttgcccaagcattcgctgctgtacgagtacttcacggtgtacaacg
agctgaccaaggtgaagtacgtgaccgagggcatgcgcaaacccgcgttcctgtcgggagagcaaaag
aaggccattgtggacctgctgttcaagaccaaccggaaggtgaccgtgaaacagcgaaagaggacta
cttcaagaagatcgagtgcttcgactccgtggagatctccggcgtggaggaccgattcaatgcctcct
tgggaacctaccatgacctcctgaagatcatcaaggacaaggacttcctggacaacgaggagaacgag
gacatcctggaggacatcgtgctgaccctgaccctgttcgaggaccgagagatgatcgaggaacggtt
gaaaacgtacgcccacttgttcgacgacaaggtgatgaagcagctgaaacgccgccgctacaccggat
ggggacgattgagccgcaaactgattaatggaattcgcgacaagcaatccggaaagaccatcctggac
ttcctgaagtccgacggggttcgccaaccgcaacttcatgcagctcatccacgacgactccttgaccttt
caaggaggacatccagaaggcccaagtgtccggacaagagacctccttgcacgacacatcgccaatt
tggccggatcccccgcaatcaaaaaaggcatcttgcaaaccgtgaaagtggtcgacgaactggtgaag
gtgatgggacggcacaagcccgagaacatcgtgatcgaaatggcccgcgagaacaaaccaccaaaa
aggacagaagaactcccgagagcgcatgaagcggatcgaagagggcatcaaggagtgggctcccaga
tcctgaaggagcatccgtggagaatacccaattgcaaaacgagaagctctacctctactacctccag
aacgggcgggacatgtacgtcgaccaagagctggacatcaaccgcctctccgactacgatgtggatca
tattgtgccccagagcttcctcaaggacgacagcatcgacaacaaggtcctgacgcgcagcgacaaga
accgggcaagtctgacaatgtgccttccgaagaagtcgtgaagaagatgaagaactactggcggcag
ctgctcaacgccaagctcatcacccaacgaagttcgacaacctgaccaaggccgagagaggaggatt
gtccgagttggacaaagccggcttcattaaacgccaactcgtggagacccgccagatcacgaagcacg
tggcccaaatcttggactcccggatgaacacgaaatacgacgagaatgacaagctgatccgcgaggtg
aaggtgatcacgctgaagtccaagctggtgagcgacttccggaaggacttccagttctacaaggtgcg
ggagatcaacaactaccatcacgcccatgacgcctacctgaacgccgtggtcggaaccgcctgatca
agaaatacccccaagctggagtccgaattcgtgtacggagattacaaggtctacgacgtgcggaagatg
atcgcgaagtccgagcaggagatcggcaaagccaccgccaagtacttcttttactccaacatcatgaa
cttcttcaagaccgagatcacgctcgccaacggcgagatccgcaagcgcccctgatcgagaccaacg -continued

| SEQUENCES |
|---|
| gcgagacgggagagattgtgtgggacaaaggaagagattttgccacagtgcgcaaggtgctgtccatg
cctcaggtgaacatcgtgaagaagaccgaggtgcaaacaggagggttttccaaagagtccattttgcc
taagaggaattccgacaagctcatcgcccgcaagaaggactgggaccccaagaagtacggggcttcg
actccccacggtggcctactccgtgttggtggtggccaaagtggagaaagggaagagcaagaagctg
aaatccgtgaaggagttgctcggaatcacgatcatggaacgatcgtcgttcgagaaaaacccatcga
cttcctcgaagccaaagggtacaaagaggtgaagaaggacctgatcatcaagctgcccaagtactcc
tgttcgagctggagaacggccgcaagcggatgctggcctccgccggggaactgcagaaagggaacgaa
ttggccttgccctccaaatacgtgaacttcctctacttggcctcccattacgaaaagctcaaaggatc
ccctgaggacaatgagcagaagcaactcttcgtggaacaacacaagcactacctggacgagatcatcg
agcagatcagcgagttctccaagcgcgtgatcctcgccgacgccaacctggacaaggtgctctccgcc
tacaacaagcaccgcgacaagcctatccgcgagcaagccgagaatatcattcacctgtttaccctgac
gaatttgggagcccctgccgcctttaaatactttgacaccaccatcgaccgcaaaagatacacctcca
ccaaggaagtcttggacgccaccctcatccaccagtccatcacgggcctctacgagacgcgcatcgac
ctctcccaattgggcggcgac |

SEQ ID NO: 28
DNA
Artificial Sequence
Encodes NLS, FLAG tag, linker
atgcccaagaaaaagcggaaggtcggcgactacaaggatgacgatgacaagttggagcctggagagaa
gccctacaaatgccctgagtgcggaaagagcttcagccaatctggagccttgacccggcatcaacgaa
cgcatacacga SEQ ID NO: 29
DNA
N. gaditana
RPL24 promoter
aataagcatacatcatatgaatacaaattcagcttaaatttatcatacaaagatgtaagtgcagcgtgg
gtctgtaacgatcgggcgtaatttaagataatgcgagggaccggggggaggttttggaacggaatgagg
aatgggtcatggcccataataataatatgggtttggtcgcctcgcacagcaaccgtacgtgcgaaaaa
ggaacagatccatttaataagttgaacgttattctttcctatgcaatgcgtgtatcggaggcgagagc
aagtcataggtggctgcgcacaataattgagtctcagctgagcgccgtccgcgggtggtgtgagtggt
catcctcctcccggcctatcgctcacatcgcctctcaatggtggtggtggggcctgatatgacctcaa
tgccgacccatattaaaacccagtaaagcattcaccaacgaacgaggggctcttttgtgtgtgttttg
agtatgattttacacctctttgtgcatctctctggtcttccttggttcccgtagtttgggcatcatca
ctcacgcttccctcgaccttcgttcttccttttacaaccccgacacaggtcagagttggagtaatcaaa
aaagggggtgcacgaatgagatacattagattttgacagatatcctttttactggagagggttcaaggga
tcaaatgaacagcgggcgttggcaatctagggagggatcggaggttggcagcgagcgaaagcgtgtcc
atcctttttggctgtcacacctcacgaaccaactgttagcaggccagcacagatgacatacgagaatct
ttattatatcgtagaccttatgtggatgacctttggtgctgtgtgtctggcaatgaacctgaaggctt
gatagggaggtggctcccgtaaacccttttgtccttttccacgctgagtctccccgcactgtcctttat
acaaattgttacagtcatctgcaggcggttttttctttggcaggcaaag SEQ ID NO: 30
DNA
Nannochloropsis gaditana
Bidirectional terminator 2
agtgatgcggcctttaggaaacaccacaaaagtaattgacaatctcaggaacgatctgcgtgtttaca
gcttcccaaataacaattataccacgtaccaaaaggggtttaatgtatctcacaaattcttctaatag
gtacagcttctcaaattgggtgtatgatgtgacacttcgtctcacacacgtcacgataattcagcgta
tggcttcccttcatcacattcacgcaaacttctacacaaaccctgggcatatttcttgtgttggcaaca
ctcccgaaatcgattctgcacacaatggttcattcaatgattcaa SEQ ID NO: 31
DNA
Artificial Sequence
Aspergillus terreus BLAST gene codon optimized for N. gaditana
atggccaagcctttatcccaagaggaatccacgctgatcgaacgtgcaactgcgaccatcaacagcat
acctattagcgaggactactcggtggccagtgcagccctctgtccgacggtcggatctttaccggcgt
gaatgtatatcatttcaccggaggggccatgcgcggagctcgtggtcctcggaacggccgctgcggctg
ctgccggaaatctgacgtgcatagtggccatcgggaacgaaaaccgcggcattctgtctccgtgcggg
cgatgtcggcaggtgctgcttgacttgcacccggggatcaaggcaattgtcaaagattccgatgggca
gcccacagcggttggcatcagggagttgcttccctctggctacgtctgggagggttga SEQ ID NO: 32
DNA
Nannochloropsis gaditana
TCTP promoter
cgtgcaggtgtacagattgaaggaaacaatggagatatctttggcagttgaaaaccgtgttcgaatca
tgcttttctactctccaactgagacgaaatttatagcgccatgtcgcttctgactaccaggcttagga
aggcctcatcacaagctggatcggttcgaattaagcaggcactgaagccaagcttgcaagacagccac
cttttaattccctcaaaaacactttctcaattcagcccggtaaatatgccgattcacgcggccaagat
agaggggaggttagcaagaatgttgcgatccctccccagtcgttgcctcgcacacaacctaggcctttc
acctttccatggaaaattgagaagtgaatattggttttcttacggcatatcagatgaaatcatgaccc
ctaaacatgaagagctgcaggcaaaacacctgctctggacgagcacgatgaaatctcgaacccgcc
gtacttcagttgatcccgcatgatgacggccgccattgaaataagccacctcactttattctagcacc
gatttccaccgttgtgagggccgaacgaggacaatttcgtgcgaaacaagcacgaacacgcacacgat |

|SEQUENCES|
|---|
|tagtagtacagacgagcagatcgatggcatgcggcacggtctcgcgttctcggcgaccaggacaacgg
agcagagggaggcctgccgagttccgaggggcattttagtccaaaattgtgttgacacgtgaacaagt
ggcttgaaaagaggaaggaaatgcctgggtttccttcgagagcgggaactcgcttgtgcgtcatcct
agctacccatggtccctttgtggggggaggctgtttcgtcctaccgaatgtgtggcgctccatgcatct
tctgcctcccaaaccaccaacatgagcacgcgaaggaaggagaaaaaagtggccgcaacgttctcttc
tcatatttattgtctcatcacaaacataggtacataatacaacaatc SEQ ID NO: 33
DNA
*Nannochloropsis gaditana*
EIF3 terminator
Ggcactgtaacccccggttccgctcgacgaaggctgggagcgccctttcggtgggataaaatggatgct
ttaccgctgcgcttcggctgaggaagagagaaatgcgagcggggatcggggtcctagaaacgaagaaa
ggagaacaagttcctggccaaagaaaaacaagacaaataccctctccaggcctgggcccattactttt
ttttgctgtttcttatacctgcactcgtgcttctctagtctgtcgagaccttacctgatcttcctccc
tccatcgctccccgccccccccatccgagcaaccgtcgaccatacg SEQ ID NO: 34
DNA
Artificial Sequence
TurboGFP gene codon optimized for *N. gaditana*
atgttggagagcgacgagagcggcctgcccgccatggagatcgagtgccgcatcaccggcaccctgaa
cggcgtggagttcgagctggtgggcggcgagagggcaccccgagcagggccgcatgaccaacaaga
tgaagagccaccaaaggcgccctgaccttcagccccctacctgctgacgcacgtgatgggctacggcttc
taccacttcggcacctaccccagcggctacgagaaccccttcctgcacgccatcaacaacggcggcta
caccaacacccgcatcgagaagtacgaggacggcggcgtgctgcacgtgagcttcagctaccgctacg
aggccggccgcgtgatcggcgacttcaaggtgatgggcaccggcttccccgaggacagcgtgatcttc
accgacaagatcatccgcagcaacgccaccgtggagcacctgcacccccatgggcgataacgatctgga
tggcagcttcacccgcaccttcagcctgcgcgacggcggctactacagctccgtggtggacagccaca
tgcacttcaagagcgccatccaccccagcatcctgcagaacggggccccatgttcgccttccgccgc
gtggaggaggatcacagcaacaccgagctgggcatcgtggagtaccagcacgccttcaagaccccgga
tgcagatgccggtgaagaataa SEQ ID NO: 35
DNA
*Nannochloropsis gaditana*
4A-III promoter
ggcataaaggacggcaaggaaagaaaagaaagaaagaaaaggacacttatagcatagtttgaagttat
aagtagtcgcaatctgtgtgcagccgacagatgcttttttttccgtttggcaggaggtgtagggatg
tcgaagaccagtccagctagtatctatcctacaagtcaatcatgctgcgacaaaaatttctcgcacga
ggcctctcgataaacaaaacttaaaagcacacttcattgtcatgcagagtaataactcttccgcgtc
gatcaatttatcaatctctatcatttccgccccttttccttgcatagagcaagaaaagcgacccggatg
aggataacatgtcctgcgccagtagtgtggcattgcctgtctctcatttacacgtactgaaagcataa
tgcacgcgcataccaatattttcgtgtacggagatgaagagacgcgacacgtaagatcacgagaagg
cgagcacggttgccaatggcagacgcgctagtctccattatcgcgttgttcggtagcttgctgcatgt
cttcagtggcactatatccactctgcctcgtcttctacacgagggccacatcggtgcaagttcgaaaa
atcatatctcaatcttcagatcctttccagaaacggtgctcaggcgggaaagtgaaggttttctactc
tagtggctaccccaattctctccgactgtcgcagacggtccttcgttgcgcacgcaccgcgcactacc
tctgaaattcgacaaccgaagttcaattttacatctaacttctttcccattctctccaccaaaagccta
gcttac SEQ ID NO: 36
DNA
*Nannochloropsis gaditana*
bidirectional terminator 5
gggtgggaaggagtcggggagggtcctggcagagcggcgtcctcatgatgtgttggagacctggagag
tcgagagcttcctcgtcacctgattgtcatgtgtataggttaaggggcccactcaaagccataaaga
cgaacacaaacactaatctcaacaaagtctactagcatgccgtctgtccatctttatttcct SEQ ID NO: 37
DNA
Artificial Sequence
HygR Cassette
tcataatcaaagatgagccagccacgaagctaccggagaattctgtaagaaaaatgtttaaagttgaa
aatgctaacagtgaagtgatatcctttttttaatggagtgttgaggtgaagtctagcatcgtagggga
aacaggattctgtgtcttccattctactccttgataaagcgaagaaatccgacaaaaccaaagagatt
gttcaagtttaagatttgtaagcgtacaactatgaacttcttctctttgtaggcctgagtggtcgtat
gcatacgattcatgaagtgaatcagtatcgctggattttgcttaggagtaaagcacaactaagaaaat
atgctgcctggcaggcatcctgagacatgaggcaagcgacgtagcaattgaatcctaatttaagccag
ggcatctgtatgactctgttagttaattgatgaaccaatgagcttaaaaaaaaatcgttgcgcgtaa
tgtagttttaattctccgccttgaggtgcgggcatttcggacaaggttctttggacggagatggca
gcatgtgtccctctccaaattggtccgtgtggtagttgagatgctgccttaaaattctgctcggtca
tcctgccttcgcattcactccttcgagctgtcgggttcctcacgaggcctccgggagcggattgcgc
agaaaggcgacccggagacacagagaccatacaccgactaaattgcactggacgatacgcatggcga
cgacgatggccaagcattgctacgtgattattcgccttgtcattcagggagaaatgatgacatgtgtg
ggacggtctttacatgggaagagggcatgaaaataacatggcctggcgggatggagcgtcacacctgt
gtatgcgttcgatccacaagcaactcaccatttgcgtcggggcctgtctccaatctgctttaggctac|

-continued

SEQUENCES ttttctctaatttagcctattctatacagacagagacacacagggatcatggggaagaaaccggaact
gaccgctacgtccgtggagaaattccttattgagaagttcgactctgtctccgacttgatgcaactga
gcgagggagaggagagtagggcgttctcgtttgacgtaggggggtcggggatacgtgttgagggttaat
agttgtgcggacgggttctacaaggatcggtatgtctaccgtcatttcgcctccgccgctctcccat
accagaggtactggacattggggagtttagcgaatctctcacgtactgcatctcgcgccgagcccagg
gagtgacgttgcaagatctgcccgaaactgaattgcctgccgttttgcaacccgtggccgaggccatg
gacgcgatcgctgccgcagatctgtctcagacgtccggcttttggaccttttgggccccagggcatcgg
gcagtacacgacctggcgagacttcatctgcgccattgccgatcctcacgtctatcattggcagacag
tcatggatgacaccgtgtctgcatccgtggcccaagcactggacgaactcatgttgtgggccgaggat
tgccctgaggtcaggcacctggtgcacgcggatttcggcagcaataacgtacttacagacaatggtcg
gattactgctgtcatcgactggtccgaagcgatgtttggtgatagccaatacgaagtggcgaacatat
tcttctggcgtccctggttggcgtgcatggagcagcagacacgctactttgaacggaggcacccggag
ctggccggctcccacgactccgcgcctatatgttgcgtatcggactcgatcagctttaccagtctct
cgtcgacggcaacttcgacgacgccgcgtgggcgcagggccgctgcgacgcgatagtccgcagcgggg
ctgggacggtgggtcggacccaaatcgcacgccggtcggctgcggtgtggacagacggctgtgttgag
gtgcttgcggactcgggcaaccgtaggccgagcacccgaccgcgtgcaaaggagtgattgaatcattg
aatgaaccattgtgtgcagaatcgatttcgggagtgttgccaacacaagaaatatgcccagggttgtg
tagaagtttgcgtaatgtgatgaagggaagccatacgctgaattatcgtgacgtgtgtgagacgaag
tgtcacatcatacacccaatttgagaagctgtacctattagaagaatttgtgagatacattaaacccc
ttttggtacgtggtataattgttatttgggaagctgtaaacacgcagatcgttcctgagattgtcaat
tacttttgtggtgtttcctaaaggccgcatcact SEQ ID NO: 38
DNA
*Nannochloropsis gaditana*
Target sequence of guide targeting TrifuncB (PAM sequence underlined)
GGCTTGGCGTCCAAAGCCGCCGG SEQ ID NO: 39
DNA
Artificial Sequence
Hygromycin resistance gene, codon optimized for *Nannochloropsis*
atggggaagaaaccggaactgaccgctacgtccgtggagaaattccttattgagaagttcgactctgt
ctccgacttgatgcaactgagcgagggagaggagagtagggcgttctcgtttgacgtaggggggtcggg
gatacgtgttgagggttaatagttgtgcggacgggttctacaaggatcggtatgtctaccgtcatttc
gcctccgccgctctccccataccagaggtactggacattggggagtttagcgaatctctcacgtactg
catctcgcgccgagcccagggagtgacgttgcaagatctgcccgaaactgaattgcctgccgttttgc
aacccgtggccgaggccatggacgcgatcgctgccgcagatctgtctcagacgtccggcttttggacct
tttgggccccagggcatcgggcagtacacgacctggcgagacttcatctgcgccattgccgatcctca
cgtctatcattggcagacagtcatggatgacaccgtgtctgcatccgtggcccaagcactggacgaac
tcatgttgtgggccgaggattgccctgaggtcaggcacctggtgcacgcggatttcggcagcaataac
gtacttacagacaatggtcggattactgctgtcatcgactggtccgaagcgatgtttggtgatagcca
atacgaagtggcgaacatattcttctggcgtccctggttggcgtgcatggagcagcagacacgctact
ttgaacggaggcacccggagctggccggctcccacgactccgcgcctatatgttgcgtatcggactc
gatcagctttaccagtctctcgtcgacggcaacttcgacgacgccgcgtgggcgcagggccgctgcga
cgcgatagtccgcagcggggctgggacggtgggtcggacccaaatcgcacgccggtcggctgcggtgt
ggacagacggctgtgttgaggtgcttgcggactcgggcaaccgtaggccgagcacccgaccgcgtgca
aaggagtga SEQ ID NO: 40
DNA
*N. gaditana*
EIF3 promoter
tcataatcaaagatgagccagccacgaagctaccggagaattctgtaagaaaaatgtttaaagttgaa
aatgctaacagtgaagtgatatcctttttttaatggagtgttgaggtgaagtctagcatcgtaggggaa
aacaggattctgtgtcttccattctactccttgataaagcgaagaaatccgacaaaaccaaagagatt
gttcaagtttaagatttgtaagcgtacaactatgaacttcttctctttgtaggcctgagtggtcgtat
gcatacgattcatgaagtgaatcagtatcgctggattttgcttaggagtaaagcacaactaagaaaat
atgctgcctggcaggcatcctgagacatgaggcaagcgacgtagcaattgaatcctaatttaagccag
ggcatctgtatgactctgttagttaattgatgaaccaatgagctttaaaaaaaaatcgttgcgcgtaa
tgtagttttaattctccgccttgaggtgcggggccatttcggacaaggttctttggacggagatggca
gcatgtgtcccttctccaaattggtccgtgtggtagttgagatgctgccttaaaattctgctcggtca
tcctgccttcgcattcactccttttcgagctgtcgggttcctcacgaggcctccgggagcggattgcgc
agaaaggcgacccggagacacagagaccatacaccgactaaattgcactggacgatacggcatggcga
cgacgatggccaagcattgctacgtgattattcgccttgtcattcagggagaaatgatgacatgtgtg
ggacggtctttacatgggaagagggcatgaaaataacatggcctgcgggatggagcgtcacacctgt
gtatgcgttcgatccacaagcaactcaccatttgcgtcggggcctgtctccaatctgctttaggctac
ttttctctaatttagcctattctatacagacagagacacacagggatc SEQ ID NO: 41
DNA
Synthetic
5'ID sequence
tccacagcccgaacccatgagagagaa

SEQUENCES

SEQ ID NO: 42
DNA
Synthetic
3'ID sequence
gcccgaatcgagttgatggcccgcaaa

SEQ ID NO: 43
DNA
Artificial Sequence
HygR Cassette with flanking ID sequences
tccacagcccgaacccatgagagagaatcataatcaaagatgagccagccacgaagctaccggagaat
tctgtaagaaaaatgtttaaagttgaaaatgctaacagtgaagtgatatccttttttaatggagtgtt
gaggtgaagtctagcatcgtagggaaaacaggattctgtgtcttccattctactccttgataaagcg
aagaaatccgacaaaaccaaagagattgttcaagtttaagatttgtaagcgtacaactatgaacttct
tctctttgtaggcctgagtggtcgtatgcatacgattcatgaagtgaatcagtatcgctggattttgc
ttaggagtaaagcacaactaagaaaatatgctgcctggcaggcatcctgagacatgaggcaagcgacg
tagcaattgaatcctaatttaagccagggcatctgtatgactctgttagttaattgatgaaccaatga
gctttaaaaaaaaatcgttgcgcgtaatgtagttttaattctccgccttgaggtgcggggccatttcg
gacaaggttctttggacggagatggcagcatgtgtcccttctccaaattggtccgtgtggtagttgag
atgctgccttaaaattctgctcggtcatcctgccttcgcattcactcctttcgagctgtcgggttcct
cacgaggcctccgggagcggattgcgcagaaaggcgacccggagacacagagaccatacaccgactaa
attgcactggacgatacggcatggcgacgacgatggccaagcattgctacgtgattattcgccttgtc
attcagggagaaatgatgacatgtgtgggacggtctttacatgggaagagggcatgaaaataacatgg
cctggcgggatggagcgtcacacctgtgtatgcgttcgatccacaagcaactcaccatttgcgtcggg
gcctgtctccaatctgctttaggctacttttctctaatttagcctattctatacagacagagacacac
agggatcatggggaagaaaccggaactgaccgctacgtccgtggagaaattccttattgagaagttcg
actctgtctccgacttgatgcaactgagcgagggagaggagagtagggcgttctcgtttgacgtaggg
ggtcggggatacgtgttgagggttaatagttgtgcggacgggttctacaaggatcggtatgtctaccg
tcatttcgcctccgccgctctcccataccagaggtactggacattggggagtttagcgaatctctca
cgtactgcatctcgcgccgagcccagggagtgacgttgcaagatctgcccgaaactgaattgcctgcc
gttttgcaacccgtggccgaggccatggacgcgatcgctgccgcagatctgtctcagacgtccggctt
tggaccttttgggccccagggcatcgggcagtacacgacctggcgagactttcatctgcgccattgccg
atcctcacgtctatcattggcagacagtcatggatgacaccgtgtctgcatccgtgggcccaagcactg
gacgaactcatgttgtgggccgaggattgccctgaggtcaggcacctggtgcacgcggatttcggcag
caataacgtacttacagacaatggtcggattactgctgtcatcgactggtccgaagcgatgtttggtg
atagccaatacgaagtggcgaacatattcttctggcgtccctggttggcgtgcatggagcagcagaca
cgctactttgaacggaggcacccggagctggccggctccccacgactccgcgcctatatgttgcgtat
cggactcgatcagctttaccagtctctcgtcgacggcaacttcgacgacgccgcgtgggcgcagggcc
gctgcgacgcgatagtccgcagcggggctgggacggtgggtcggacccaaatcgcacgccggtcggct
gcggtgtggacagacggctgtgttgaggtgcttgcggactcgggcaaccgtaggccgagcacccgacc
gcgtgcaaaggagtgattgaatcattgaatgaaccattgtgtgcagaatcgatttcgggagtgttgcc
aacacaagaaatatgcccagggttgtgtagaagtttgcgtgaatgtgatgaagggaagccatacgctg
aattatcgtgacgtgtgtgagacgaagtgtcacatcatacacccaatttgagaagctgtacctattag
aagaatttgtgagatacattaaacccctttggtacgtggtataattgttatttgggaagctgtaaaca
cgcagatcgttcctgagattgtcaattacttttgtggtgtttcctaaaggccgcatcactgcccgaat
cgagttgatggcccgcaaa SEQ ID NO: 44
DNA
*Nannochloropsis gaditana*
Target sequence of guide targeting PXA1 (on non-coding strand of gene, PAM is underlined)
GGGGTCTGGCACCTGCCGTC<u>AGG</u>

SEQ ID NO: 45
DNA
*Nannochloropsis gaditana*
Target sequence of guide targeting ACO1(PAM is underlined)
GGCGAGGACGACGCATACCA<u>TGG</u>

SEQ ID NO: 46
DNA
*Nannochloropsis gaditana*
Target sequence of guide targeting ICL (on non-coding strand of gene, PAM is underlined)
GGCAGGTTCGACCAGGAGGC<u>TGG</u>

SEQ ID NO: 47
DNA
*Nannochloropsis gaditana*
Forward primer to detect donor fragment insertion at TrifuncB locus
GGCTTGGCGTCCAAAGCCGCCGG SEQ ID NO: 48
DNA
*Nannochloropsis gaditana*

| SEQUENCES |
| --- |

Reverse primer to detect donor fragment insertion at TrifuncB locus
GGCGAATTTCTGTAGGTCCACG SEQ ID NO: 49
DNA
*Nannochloropsis gaditana*
Forward primer to detect donor fragment insertion at PXA1 locus
GCTTGTGTAGGTCGTGACCTGGAAGGC SEQ ID NO: 50
DNA
*Nannochloropsis gaditana*
Reverse primer to detect donor fragment insertion at PXA1 locus
CCGACCTCGTCAAAGCATCGGC SEQ ID NO: 51
DNA
*Nannochloropsis gaditana*
Forward primer to detect donor fragment insertion at AOC1 locus
TCAAAGATCATTTAGCAGAGA SEQ ID NO: 52
DNA
*Nannochloropsis gaditana*
Reverse primer to detect donor fragment insertion at AOC1 locus
AGTCGAGAGATGGTGCGTTCA SEQ ID NO: 53
DNA
*Nannochloropsis gaditana*
Forward primer to detect donor fragment insertion at ICL locus
GGACTTTCCATGCGACATAGCTTTC SEQ ID NO: 54
DNA
*Nannochloropsis gaditana*
Reverse primer to detect donor fragment insertion at ICL locus
CATCTGCACCACCTGAACGG SEQ ID NO: 55
DNA
Artificial
Bleomycin resistance gene, codon optimized for *Nannochloropsis*
ATGGCCAAGCTGACCAGCGCCGTTCCGGTGCTCACCGCGCGCGACGTCGCCGGAGCGGTCGAGTTCTG
GACCGACCGGCTCGGGTTCTCCCGGGACTTCGTGGAGGACGACTTCGCCGGTGTGGTCCGGGACGACG
TGACCCTGTTCATCAGCGCGGTCCAGGACCAGGTGGTGCCGGACAACACCCTGGCCTGGGTGTGGGTG
CGCGGCCTGGACGAGCTGTACGCCGAGTGGTCGGAGGTCGTGTCCACGAACTTCCGGGACGCCTCCGG
GCCGGCCATGACCGAGATCGGCGAGCAGCCGTGGGGCGGGAGTTCGCCCTGCGCGACCCGGCCGGCA
ACTGCGTGCACTTCGTGGCCGAGGAGCAGGACTAA SEQ ID NO: 56
DNA
*Phaeodactylum tricornutum*
GAPDH promoter
GGATTTGCCTCCCATGCGCGGAAAGTTTGCACAGAGCCAGCTACAGCAATGTCAATTTCTTTTGCAGT
GGTTGGCACGGGTTGATGGGCTGCACTATCGATATTGCTGTCAATGGCTGTGCTTTGGTTTGACATCG
GTGCTGTGCGACGTTTGGCCATGCGCTCGGCCATTCTGTTTTTTCGAATATGCAAAGTTGTCTCTTCC
CGAGATCGACGACCGTCTTCAGCTGACACGGTCTTCTTAAATGACGCATCACGACGAGGAACTAAAGC
CGCCCAGGTATACAATTGTGGCATTAGAGACTGAATACAATGCCTCGAATAGCGGAGATACTAAGGGC
CGTTATTTCGTACCTGCGGCGACTAGGGTCATGATTGTATCTCTAAGAACAACAAGGGAAATTTCTGA
TCAAGGTCGACGGGTAAAAGGCGGAACAAGAATAAAAGGATGGTGATACGGAACAGAGCAACGCTACA
GAAAAGTGAGGATCGCCAACCATCAAGTTGTGGCGATGCGATACTTTTTGCGATAACGTCTCGCGCTC
TATGATTTTCTTTGTTATATTAATTTGTTCAACATGAGCTAATTAACCGAAACCTTATGCCTCAACTG
CCGACTCAGCACAAGTACCTAACTTTGCAAGGTTTTGTCGTATACGTCTGTCCATAGAACGTTGACTA
ATGTAAGAGGAAGATTTTTGTGGACGTTGTGCGCTTGACATCCATTGGTTGATGTGGTTTTGCTGATG
TCACGGCATCCTGAGTCCCCTAACGTTTCACTTGGCGCCTCGCAGCTGTTTGCCTCCGGTATC
TTTTTCTAGGATCTTCCGCAGATTTGAAGTTCGCATCGAAACCATTCCTGTCGTGGAAAAAAGGCCTG
GATCGCATCTTGCAGGTGCAACGCTAATTCTTCTCCATTCATAAAAACAGAACTCGTAGAAAACGATT
CAAATCTTTTTTCGCCTTTCTAAACATCAGTAATTCTATCAAATTCTA SEQ ID NO: 57
DNA
*Thalassiosira pseudonana*
alpha tubulin terminator
TCACTCTGTCGCGCTGTTGGCGCCACTACTTTGGGGGTACGAGTTTAGGCTGCCTTGGCTGGGATAAA
GAATGATAAGTTTACATAATTTGTATTGGAAATCCATCGAGTTTTGGATTCAGTTGACGTCTCCTGCG
TTACTATGTCTTCATTCTCTCCAGTATCAATGCCTATGGTTCGTCGACATTGAGCACATTTCTTTCAT

```
CAGCGCGATGCATGCAATCATCACTTCGCAATCTTGACAAACATCCTCAATGATTCCTCCACCTCTCC
CAACAAAGTCAATGCATTCATCCTTGGATCTTCTCCTCCACCGAACGGCCGTGAAGCCGACTCCATTA
GTGCATCCAGTCCATCAAAATACCGTATGAATTCCCGAAAAGATTCACTTGCCAAGTACTGTTTGTCA
TCCTCCTCTTCAGGTATCTCATCAATGAGTGCATTTGCAGCTATACGAATCTTTGACTCGGAAATCAA
TCC
```

What is claimed is:

1. A Eustigmatophyte algal microorganism comprising a disruption in a gene encoding a mitochondrial trifunctional protein subunit B (TrifuncB) having at least 90% sequence identity to SEQ ID NO: 10 and/or mitochondrial trifunctional protein subunit A (TrifuncA) having at least 90% sequence identity to SEQ ID NO: 1, wherein the microorganism produces more fatty acid methyl ester-derivatizable lipids (FAME lipids) on a per volume per day basis than a control microorganism of the same species.

2. The algal microorganism of claim 1 wherein the microorganism exhibits a fatty acid methyl ester-derivatizable lipids to total organic carbon (FAME/TOC) ratio at least 15% higher than a FAME/TOC ratio of a wild type microorganism of the same species cultured under the same conditions.

3. The algal microorganism of claim 2, wherein the algal microorganism exhibits a FAME/TOC ratio at least 30% higher than the FAME/TOC ratio of the control microorganism.

4. The algal microorganism of claim 1 wherein the algal microorganism has increased volumetric lipid productivity as compared to a control microorganism.

5. The algal microorganism of claim 1 wherein the disruption is a knockout mutation.

6. The algal microorganism of claim 1 wherein the disruption is a knockdown mutation.

7. The algal microorganism of claim 5 wherein the microorganism comprises a disruption in mitochondrial trifunctional protein subunit B (TrifuncB).

8. The algal microorganism of claim 1, further comprising a disruption in a gene encoding a peroxisomal beta-oxidation pathway protein Acyl-CoA oxidase 1 (ACO1) having at least 90% sequence identity to SEQ ID NO: 22.

9. The algal microorganism of claim 8, wherein the algal microorganism exhibits a FAME/TOC ratio at least 30% higher than the FAME/TOC ratio of the control microorganism.

10. The algal microorganism of claim 1, wherein the disruption is present in a gene encoding a peroxisomal beta-oxidation pathway protein peroxisomal ABC-type acyl-coenzyme A transporter (PXA1) having at least 90% sequence identity to SEQ ID NO: 20.

11. The algal microorganism of claim 1, further comprising a disruption in a gene encoding a glyoxylate pathway protein isocitrate lyase (ICL) having at least 90% sequence identity to SEQ ID NO: 24.

12. The algal microorganism of claim 1, wherein disruption comprises insertion of exogenous DNA into the TrifuncB or TrifuncA gene thereby attenuating expression of the gene.

13. The algal microorganism of claim 1, wherein the mutant algal microorganism is a species of *Elipsoidon, Eustigmatos, Nannochloropsis*, and *Vischeria*.

14. The algal microorganism of claim 13, wherein the mutant algal microorganism is a species of *Nannochloropsis*.

15. A biomass comprising an algal microorganism according to claim 1.

16. A biomass comprising an algal microorganism according to claim 8.

17. A method of producing lipid, comprising culturing an algal microorganism of claim 1 in a culture medium and isolating lipid from the microorganism, the culture medium, or both.

18. A method of producing lipid comprising culturing an algal microorganism of claim 8 in a culture medium and isolating lipid from the microorganism, the culture medium, or both.

19. A method according to claim 18, wherein the culture conditions are nitrogen replete.

20. A method according to claim 18, wherein the culture conditions are photoautotrophic.

21. The Eustigmatophyte algal organism of claim 1 wherein the disruption is present in a gene encoding a polypeptide having the sequence of SEQ ID NO: 1.

22. The Eustigmatophyte algal organism of claim 1 wherein the disruption is present in a gene encoding a polypeptide having the sequence of SEQ ID NO: 10.

23. The algal microorganism of claim 7 further comprising a disruption in a gene encoding a peroxisomal beta-oxidation pathway protein Acyl-CoA oxidase 1 (ACO1) having at least 90% sequence identity to SEQ ID NO: 22.

* * * * *